United States Patent
Cutler et al.

(10) Patent No.: US 11,730,736 B2
(45) Date of Patent: *Aug. 22, 2023

(54) ANTICANCER AGENTS

(71) Applicant: RAPT THERAPEUTICS, INC., South San Francisco, CA (US)

(72) Inventors: Gene Cutler, San Francisco, CA (US); William Yew-Wai Ho, San Francisco, CA (US); Paul David Kassner, San Mateo, CA (US); Silpa Suthram, San Jose, CA (US); Brian Russell Wong, Los Altos, CA (US)

(73) Assignee: RAPT Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,200

(22) Filed: Nov. 5, 2018

(65) Prior Publication Data

US 2019/0134031 A1  May 9, 2019

Related U.S. Application Data

(60) Provisional application No. 62/723,415, filed on Aug. 27, 2018, provisional application No. 62/582,284, filed on Nov. 6, 2017.

(51) Int. Cl.

| | | |
|---|---|---|
| *A61K 31/4985* | (2006.01) | |
| *A61P 35/02* | (2006.01) | |
| *A61K 31/506* | (2006.01) | |
| *A61K 31/497* | (2006.01) | |
| *A61K 31/519* | (2006.01) | |
| *A61K 31/5377* | (2006.01) | |
| *A61K 45/06* | (2006.01) | |

(52) U.S. Cl.
CPC ........ *A61K 31/4985* (2013.01); *A61K 31/497* (2013.01); *A61K 31/506* (2013.01); *A61K 31/519* (2013.01); *A61K 31/5377* (2013.01); *A61K 45/06* (2013.01)

(58) Field of Classification Search
CPC ............................ A61P 35/02; A61K 31/4985
See application file for complete search history.

(56) References Cited

U.S. PATENT DOCUMENTS

| | | | |
|---|---|---|---|
| 5,300,498 A | 4/1994 | Shutske | |
| 6,509,357 B1 | 1/2003 | Zhou et al. | |
| 10,179,787 B2 | 1/2019 | Beck et al. | |
| 10,246,462 B2 | 4/2019 | Beck et al. | |
| 2002/0132836 A1 | 9/2002 | Dairaghi et al. | |
| 2002/0173524 A1 | 11/2002 | Collins et al. | |
| 2003/0018022 A1 | 1/2003 | Collins et al. | |
| 2003/0149018 A1 | 8/2003 | Zhou et al. | |
| 2004/0039035 A1 | 2/2004 | Collins et al. | |
| 2005/0287138 A1 | 12/2005 | Iida et al. | |
| 2006/0004010 A1 | 1/2006 | Habashita et al. | |
| 2006/0122195 A1 | 6/2006 | Harrison et al. | |
| 2006/0128723 A1 | 6/2006 | Mete et al. | |
| 2006/0189613 A1 | 8/2006 | Cheshire | |
| 2007/0020263 A1 | 1/2007 | Shitara et al. | |
| 2007/0031896 A1 | 2/2007 | Wu et al. | |
| 2008/0293742 A1 | 11/2008 | Cheshire et al. | |
| 2010/0144759 A1 | 6/2010 | Cheshire et al. | |
| 2012/0015932 A1 | 1/2012 | Hobbs et al. | |
| 2013/0295045 A1 | 11/2013 | Shitara et al. | |
| 2015/0147321 A1 | 5/2015 | Ishii et al. | |
| 2016/0185865 A1 | 6/2016 | Marasco et al. | |
| 2017/0088627 A1 | 3/2017 | Lin et al. | |
| 2017/0290911 A1 | 10/2017 | Marasco et al. | |

FOREIGN PATENT DOCUMENTS

| | | |
|---|---|---|
| WO | WO-97/42174 A1 | 11/1997 |
| WO | WO-01/05758 A2 | 1/2001 |
| WO | WO-01/05758 A3 | 1/2001 |
| WO | WO-03/051876 A1 | 6/2003 |
| WO | WO-2006/101456 A1 | 9/2006 |
| WO | WO-2007/065683 A1 | 6/2007 |
| WO | WO-2007/065924 A1 | 6/2007 |
| WO | WO-2007/115231 A2 | 10/2007 |
| WO | WO-2007/115231 A3 | 10/2007 |
| WO | WO-2008/045529 A1 | 4/2008 |
| WO | WO-2008/094575 A2 | 8/2008 |
| WO | WO-2008/094575 A3 | 8/2008 |
| WO | WO-2008/094602 A2 | 8/2008 |
| WO | WO-2008/094602 A3 | 8/2008 |
| WO | WO-2010/118367 A2 | 10/2010 |
| WO | WO-2010/118367 A3 | 10/2010 |
| WO | WO-2013/082429 A1 | 6/2013 |
| WO | WO-2018/022992 A1 | 2/2018 |
| WO | WO-2018/049271 A1 | 3/2018 |

(Continued)

OTHER PUBLICATIONS

Gura (Science, vol. 278, pp. 1041-1042 (1997) (Year: 1997).*
Johnson et al., British Journal of Cancer, vol. 84(10), pp. 1424-1431 (2001). (Year: 2001).*
Gupta et al., Postgrad. Med. J., vol. 81, pp. 236-242 (2005). (Year: 2005).*
Maeda et al. (Cancer Immunol Res (Jul. 1, 2019);7(7): 1175-1187; DOI:10.1158/2326-6066.CIR-18-0751) (Year: 2019).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
Marshall et al. (J Immunother Cancer 2020;8(2)). (Year: 2020).*

(Continued)

*Primary Examiner* — Jeffrey S Lundgren
*Assistant Examiner* — Chris E Simmons
(74) *Attorney, Agent, or Firm* — Irina E. Britva; Mintz, Levin, Cohn, Ferris, Glovsky and Popeo, P.C.

(57) ABSTRACT

Disclosed herein are therapeutic methods of administering compounds that modulate the C—C chemokine receptor type 4 (CCR4) for the treatment of Epstein Bar virus (EBV) positive cancers and malignancies.

15 Claims, No Drawings

(56) References Cited

FOREIGN PATENT DOCUMENTS

WO     WO-2018/187509 A1     10/2018
WO     WO-2019/090272 A1     5/2019

OTHER PUBLICATIONS

Yoshimitsu et al. ("Mogamulizumab for the treatment of adult T-cell leukemia/lymphoma." Blood and Lymphatic Cancer: Targets and Therapy (Dec. 18, 2014); 2015(5): p. 17-23. http://dx.doi.org/10.2147/BLCTT.S32468). (Year: 2014).*
Bates, G.J. et al. (Dec. 1, 2006). "Quantification of regulatory T cells enables the identification of high-risk breast cancer patients and those at risk of late relapse," *J Clin Oncol* 24(34):5373-5380.
Curiel, T.J. et al. (Sep. 2004, e-published Aug. 22, 2004). "Specific recruitment of regulatory T cells in ovarian carcinoma fosters immune privilege and predicts reduced survival," *Nat Med* 10(9):942-949.
Fridman, W.H. et al. (Sep. 1, 2011, e-published Aug. 16, 2011). "Prognostic and predictive impact of intra- and peritumoral immune infiltrates," *Cancer Res* 71(17):5601-5605.
Fridman, W.H. et al. (Dec. 2017, e-published Jul. 25, 2017). "The immune contexture in cancer prognosis and treatment," *Nat Rev Clin Oncol* 14(12):717-734.
Gobert, M. et al. (Mar. 1, 2009, e-published Feb. 24, 2009). "Regulatory T cells recruited through CCL22/CCR4 are selectively activated in lymphoid infiltrates surrounding primary breast tumors and lead to an adverse clinical outcome," *Cancer Res* 69(5):2000-2009.
Hjalgrim, H. et al. (2007). "The epidemiology of EBV and its association with malignant disease," Chapter 53 in *Human Herpesviruses: Biology, Therapy, and Immunoprophylaxis*, Cambridge University Press.
International Search Report dated Mar. 21, 2019, for PCT Application No. PCT/US2018/059284, 6 pages.

Kanazawa, T. et al. (Oct. 1, 2014, e-published Aug. 12, 2014). "Anti-CCR4 monoclonal antibody mogamulizumab for the treatment of EBV-associated T- and NK-cell lymphoproliferative diseases," *Clin Cancer Res* 20(19):5075-5084.
Nakayama, T. et al. (Feb. 2004). "Selective induction of Th2-attracting chemokines CCL17 and CCL22 in human B cells by latent membrane protein 1 of Epstein-Barr virus," *J Virol* 78(4):1665-1674.
Neparidze, N. et al. (Jun. 2014). "Malignancies associated with epstein-barr virus: pathobiology, clinical features, and evolving treatments," *Clin Adv Hematol Oncol* 12(6):358-371.
Pardoll, D.M. et al. (Mar. 22, 2012). "The blockade of immune checkpoints in cancer immunotherapy," *Nat Rev Cancer* 12(4):262-264.
Ren, Y.-X. et al. (Aug. 5, 2011). "Correlation between $CD4^+CD25^+$ $T_{reg}$ cells and CCR4 in nasopharyngeal carcinoma," *Clinical Oncology and Cancer Research* 8:106.
Sharma, P. et al. (Apr. 3, 2015). "The future of immune checkpoint therapy," *Science* 348(6230):56-61.
Shin, D.S. et al. (Apr. 2015, e-published Jan. 23, 2015). "The evolution of checkpoint blockade as a cancer therapy: what's here, what's next?," *Curr Opin Immunol* 33:23-35.
Takegawa, S. et al. (Feb. 2008). "Expression of CCL17 and CCL22 by latent membrane protein 1-positive tumor cells in age-related Epstein-Barr virus-associated B-cell lymphoproliferative disorder," *Cancer Sci* 99(2):296-302.
Talay, O. et al. (Apr. 17, 2018). "EBV associated tumors have increased regulatory T cell recruitment and are therefore a potential indication for treatment with potent and selective small molecule CCR4 antagonists," located at <http://www.abstractonline.com/pp8/#!/4562/presentation/3761> 1 page.
Written Opinion dated Mar. 21, 2019, for PCT Application No. PCT/US2018/059284, 9 pages.
Zhang, N.N. et al. (Dec. 17, 2015). "Accumulation Mechanisms of CD4(+)CD25(+)FOXP3(+) Regulatory T Cells in EBV-associated Gastric Carcinoma," *Sci Rep* 5:18057.
PubChem R1T69T65FJ, FLX-475 (Jun. 23, 2018), 15 pages.

* cited by examiner

ANTICANCER AGENTS

This application claims the benefit of U.S. Provisional Application No. 62/723,415, filed Aug. 27, 2018 and U.S. Provisional Application No. 62/582,284, filed Nov. 6, 2017, the contents of which are incorporated herein by reference in their entireties and for all purposes.

I. FIELD

Provided herein, inter alia, are methods for treating or managing certain cancers and malignancies using compounds that modulate the C—C chemokine receptor type 4 (CCR4), or pharmaceutically acceptable salts thereof. For example, provided herein are methods in which a CCR4 modulator is administered alone or in combination with one or more anti-cancer agents to treat certain cancers and malignancies. In addition, provided herein are pharmaceutical compositions for use in such methods.

II. BACKGROUND

Cancer is a major worldwide public health problem; in the United States alone, approximately 570,000 cancer-related deaths were expected in 2005. See, e.g., Jemal et al., CA Cancer J. Clin. 55(1):10-30 (2005). The incidence of cancer continues to climb as the general population ages and new forms of cancer develop.

The Epstein-Barr virus (EBV) is a ubiquitous herpesvirus first discovered as the causative agent of Burkitt's Lymphoma. EBV was subsequently found to have a very high prevalence, with over 95% of the adult population infected. Infections are generally asymptomatic, but EBV can be the cause of infectious mononucleosis. EBV-positivity has also been associated with a variety of cancers, including various lymphomas, nasopharyngeal carcinoma (NPC), and gastric carcinoma (Hjalgrim, H., Friborg, J. and Melbye, M. 2007. *Human Herpesviruses*).

For many years researchers have tried to boost the immune response to fight cancer. Though earlier interventions had limited success, the recent use of antibodies such as anti-CTLA-4 and anti-PD-1/PD-L1, also known as immune checkpoint inhibitors (CPIs), has resulted in meaningful antitumor immune responses in multiple types of cancer (Pardoll, 2012; Sharma, 2015; Shin, 2015).

Tumors are capable of adapting, co-opting natural immune suppressive mechanisms to evade detection by the immune system (Hanahan, 2011; Dunn, 2002). An important way that cancers do this is by recruiting and subverting immune suppressive lymphocytes known as regulatory T cells ($T_{reg}$). While these suppressive cells help keep immune responses to foreign antigens such as viruses, commensal bacteria, and foreign bodies in check and limit autoimmune disease, $T_{reg}$ can also interfere with immune surveillance and allow tumors to evade eradication by the immune system (Chaudrhy, 2013; Nishikawa, 2014; Tanaka, 2017).

Numerous studies of human cancers have found $T_{reg}$ accumulation in and around tumors, which can preclude cytotoxic (effector) T cells ($T_{eff}$) from or inhibit killing tumor cells (Fridman, 2017). Increased $T_{reg}$ numbers in tumors, or a reduced ratio of $T_{eff}$ to $T_{reg}$, correlates with poor patient prognosis in many cancers, including melanoma, lung and breast cancers (Fridman, 2011; Gobert, 2009; Bates, 2006; Curiel, 2004). Data such as these have triggered research into curbing $T_{reg}$ cell activity in an effort to initiate or amplify a therapeutic antitumor immune response. By removing their suppressive effects on an otherwise effective antitumor response, a therapy targeting $T_{reg}$ cells may help eradicate tumors.

Strategies to suppress $T_{reg}$ cells have included modulating cytokine signaling, depletion with antibodies, or treatment with cytotoxic agents. However, these approaches frequently impact other cell populations required for robust immune responses and can trigger side effects due to interference with the normal role of $T_{reg}$ cells in healthy tissues (Kurose, 2015). An alternative approach is to suppress the recruitment of $T_{reg}$ to the tumor microenvironment (TME).

Systemic circulation of leukocytes is an important factor enabling immune surveillance. Chemokines are small secreted proteins which form gradients to attract subsets of leukocytes from the circulation in a tissue-specific manner (Solari, 2015). To enable recruitment to various tissues, $T_{reg}$ express a number of chemokine receptors, though predominantly the C—C chemokine receptor type 4 (CCR4) (Lellem, 2001; Hirahara, 2006). CCR4 is a G-protein coupled receptor (GPCR) that selectively binds the chemokine ligands CCL17 (TARC) and CCL22 (MDC), and this ligand binding plays a key role in the recruitment of $T_{reg}$ and their accumulation in the TME (Curiel, 2004; Gobert, 2009; Li, 2013). As such, CCR4 may be an ideal target to selectively block $T_{reg}$ cell recruitment into the TME. CCR4 antagonism may enable the immune system to elicit a more robust antitumor response, particularly when combined with other immunomodulatory agents.

The EBV latent protein LMP1 may lead to expression of CCL17 and CCL22 (Nakayama et. al. J Virol, 2004; Takegawa et al Cancer Sci 2008). $T_{reg}$ are increased in EBV-associated gastric carcinoma as compared to EBV-negative gastric carcinoma (Zhang et al Sci. Reports, 2015), and is correlated with higher production of CCL22 in EBV+ gastric carcinoma. Nasopharyngeal carcinoma is associated with EBV (Neparidze, N. and Lacy, J. 2014. Malignancies associated with Epstein-Barr Virus: Pathobiology, Clinical Features, and Evolving Treatments. *Clinical advances in hematology & oncology: H&O.* 12, 6 (2014), 358-71), and there is an increasing number of $T_{reg}$ in NPC with increasing stage (Ren et al, Clinical Onc and Cancer Res, 2011).

III. SUMMARY

In one aspect, provided herein are methods for treating or managing EBV-associated cancers using compounds having formulae (I), (II), (III), (IV), or (V), or a salt, solvate, or hydrate thereof.

In embodiments, the compounds used in the methods disclosed herein, are disclosed in U.S. patent application Ser. No. 15/662,861 filed Jul. 28, 2017 of Beck et al. (e.g., for example, compounds of Formulae I through VII), which are incorporated herein by reference in its entirety for all purposes. In embodiments, the compounds have the chemical structure according to Formula I herein.

In embodiments, the compounds used in the methods disclosed herein, are disclosed in U.S. patent application Ser. No. 15/700,040 filed Sep. 8, 2017 of Beck et al. (e.g., for example, compounds of Formulae I through X), which are incorporated herein by reference in its entirety for all purposes. In embodiments, the compounds have the chemical structure according to Formula II herein.

In embodiments, the compounds used in the methods disclosed herein, are disclosed in U.S. Patent Application 62/481,515 filed Apr. 4, 2017 of Beck et al. (e.g., for example, compounds of Formulae I through VI), which are incorporated herein by reference in its entirety for all purposes. In embodiments, the compounds have the chemical structure according to Formula III herein.

In embodiments, compounds used in the methods disclosed herein, are disclosed in U.S. Patent Application 62/622,774 filed Jan. 26, 2018, of Robles-Resendiz et al. (e.g., for example, compounds of Formulae I through VII), which are incorporated herein by reference in its entirety for all purposes. In embodiments, the compounds have the chemical structure according to Formula IV herein.

In embodiments, compounds used in the methods disclosed herein, are disclosed in U.S. Patent Application 62/622,771 filed Jan. 26, 2018, of Jackson et al. (e.g., for example, compounds of Formula I), which are incorporated herein by reference in its entirety for all purposes. In embodiments, the compound have the chemical structure according to Formula V herein.

In embodiments, the CCR4 modulator is a compound disclosed in one of the following published patent applications: Hobbs et al, US 2012/0015932; Cheshire et al, US 2010/0144759; Cheshire et al, US 2008/0293742; Cheshire US 2006/0189613; Mete et al, US 2006/0128723; Harrison et al, US 2006/0122195; Habashita et al, US 2006/0004010; Collins et al, US 2004/0039035; Collins et al, US 2003/0018022; Collins et al, US 2002/0173524; Dairaghi et al, US 2002/0132836; U.S. Pat. Nos. 5,300,498; 6,509,357; US 2003/149018; WO 01/005758; WO 03/051876; WO 97/042174; WO 2006/101456; WO 2007/065683; WO 2007/065924; WO 2007/115231; WO 2008/045529; WO 2008/094575; WO 2008/094602; WO 2010/118367; and WO 2013/082429, the CCR4 modulating compounds disclosed in which are incorporated herein by reference.

In embodiments, the CCR4 modulator is an antibody disclosed in one of the following published patent applications: Marasco et al. US 2017/0290911; Lin et al. US 2017/0088627; Marasco et al. US 2016/0185865; Ishii et al. US 2015/0147321; shiara et al. US 2013/0295045; Wu et al. US 2007/0031896; shiara et al. US 2007/0020263; and Iida et al. US 2005/0287138, the CCR4 binding antibodies disclosed in which are incorporated herein by reference.

In embodiments, the EBV-associated cancer is a solid tumor. In one embodiment, the EBV-associated cancer is relapsed or refractory. In another embodiment, the methods of the invention are for treating EBV-associated cancers. In one embodiment, the EBV-associated cancer is nasopharyngeal carcinoma. In one embodiment, the EBV-associated cancer is gastric carcinoma. In embodiments, the EBV-associated cancer is a lymphoproliferative disorder (e.g. Burkitt's lymphoma, Hodgkin lymphoma, diffuse large B-cell lymphoma, NK/T cell leukemia or lymphoma, etc.).

In embodiments, a compound of formulae (I), (II), (III), (IV), or (V), or a salt, solvate, or hydrate thereof is administered orally or parenterally. In one embodiment, a compound of formulae (I), (II), (III), (IV), or (V), or a salt, solvate, or hydrate thereof is administered orally. In embodiments, a compound of formulae (I), (II), (III), (IV), or (V), or a salt, solvate, or hydrate thereof is administered to a subject in need thereof for a sustained period of time. In embodiments, a compound of formulae (I), (II), (III), (IV), or (V), or a salt, solvate, or hydrate thereof is administered to a subject in need thereof cyclically (e.g., dosing for one or more days, followed by a resting period). In embodiments, a compound of formulae (I), (II), (III), (IV), or (V), or a salt, solvate, or hydrate thereof is administered to a subject in need thereof over multiple dosing cycles. In one embodiment, the additional anti-cancer agent is administered orally or parenterally. In one embodiment, a compound of formulae (I), (II), (III), (IV), or (V), or a salt, solvate, or hydrate thereof is administered via the same route as the one or more additional anti-cancer agent(s). In one embodiment, a compound of formulae (I), (II), (III), (IV), or (V), or a salt, solvate, or hydrate thereof is administered via a different route as the one or more additional anti-cancer agent(s) (e.g., one administered orally and the other administered parenterally).

In embodiments, a compound of formulae (I), (II), (III), (IV), or (V), or a salt, solvate, or hydrate thereof is administered in a particular dosing cycle. In one embodiment, a compound of formulae (I), (II), (III), (IV), or (V), or a salt, solvate, or hydrate thereof and the one or more additional anti-cancer agent(s) (including, but not limited to, romidepsin, carboplatin, paclitaxel, or Abraxane®) are co-administered in a particular dosing cycle. In particular embodiments, a compound of formulae (I), (II), (III), (IV), or (V), or a salt, solvate, or hydrate thereof is first administered to a subject in need thereof for one or more days (e.g., for 7 days or more), and the one or more additional anti-cancer agent(s) is/are administered to the subject (e.g., starting on Day 8 or later of the treatment cycle). In particular embodiments, when one or more additional anti-cancer agent(s) is/are administered to the subject, a compound of formulae (I), (II), (III), (IV), or (V), or a salt, solvate, or hydrate thereof is also administered to the subject. In particular embodiments, when one or more additional anti-cancer agent(s) is/are administered to the subject, a compound of formulae (I), (II), (III), (IV), or (V), or a salt, solvate, or hydrate thereof is not administered to the subject simultaneously.

In embodiments, a compound of formulae (I), (II), (III), (IV), or (V), or a salt, solvate, or hydrate thereof is administered alone as a single agent to a subject in need thereof. In one embodiment, a compound of formulae (I), (II), (III), (IV), or (V), or a salt, solvate, or hydrate thereof is administered in combination with one or more additional anti-cancer agent(s), including, but not limited to, romidepsin, carboplatin, paclitaxel, or Abraxane® (paclitaxel protein-bound particles), among others. In one embodiment, the additional anti-cancer agent is an alkylating agent, a cytotoxic agent, an anti-angiogenic agent, an anti-tubulin agent, an anti-metabolite, a kinase inhibitor, a biologics agent, or any other known anti-cancer agent (e.g., an anti-cancer agent provided herein elsewhere). In certain embodiments, in addition to a compound of formulae (I), (II), (III), (IV), or (V), or a salt, solvate, or hydrate thereof or one or more additional anti-cancer agent(s), an anti-emetic is administered to a subject in need thereof. In a particular embodiment, a compound of formulae (I), (II), (III), (IV), or (V), or a salt, solvate, or hydrate thereof is administered in combination with carboplatin. In another embodiment, a compound of formulae (I), (II), (III), (IV), or (V), or a salt, solvate, or hydrate thereof is administered in combination with Abraxane®. In another embodiment, a compound of formulae (I), (II), (III), (IV), or (V), or a salt, solvate, or hydrate thereof is administered in combination with romidepsin. In one embodiment, a compound of formulae (I), (II), (III), (IV), or (V), or a salt, solvate, or hydrate thereof is administered in combination with one or more additional immunomodulatory agent(s) including, but not limited to, (1) antibodies targeting PD-1, PD-L1, CTLA-4, CD40, GITR, LAG3 and/or CD137; (2) inhibitors of IDO, TDO, A2AR, A2BR, CD39, CD73, USP7, GCN2 and/or HPK1 (3) activators of innate immunity including TLRs, STING, cGAS, etc.; (4) cellular immunotherapies including adoptive T cell transfer, Chimeric Antigen Receptor (CAR)-T cell transfer, NK cell therapies, etc.; (5) vaccine strategies including bacterial, viral, or synthetic vaccination; (6) oncolytic viral therapies and/or (7) bi-specific/tri-specific T cell engagers.

In one aspect, provided herein is a pharmaceutical composition comprising a compound of formulae (I), (II), (III), (IV), or (V), or a salt, solvate, or hydrate thereof for use in any of the methods described herein.

In embodiments, a compound of formulae (I), (II), (III), (IV), or (V), or a salt, solvate, or hydrate thereof is formulated in an oral dosage form provided herein (e.g., a tablet or a capsule).

In embodiments, provided herein are pharmaceutical compositions comprising a compound of formulae (I), (II), (III), (IV), or (V), or a salt, solvate, or hydrate thereof, wherein the composition releases the active pharmaceutical ingredient (API) substantially in the stomach upon oral administration. In one embodiment, provided herein are pharmaceutical compositions comprising a compound of formulae (I), (II), (III), (IV), or (V), or a salt, solvate, or hydrate thereof, wherein the composition releases the API substantially in the stomach and/or the upper intestine upon oral administration. In one embodiment, provided herein are pharmaceutical compositions comprising a compound of formulae (I), (II), (III), (IV), or (V), or a salt, solvate, or hydrate thereof, wherein the composition releases the API substantially in the stomach, the upper intestine and/or the lower intestine upon oral administration. Also provided are methods for making the compositions, and methods for using the compositions to treat or manage diseases and disorders including EBV-associated cancer, disorders related to abnormal cell proliferation, solid tumors, and hematologic disorders.

In one aspect, provided herein is a kit comprising a compound of formulae (I), (II), (III), (IV), or (V), or a salt, solvate, or hydrate thereof for use in any of the methods described herein.

IV. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

V. DEFINITIONS

As used in the specification, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

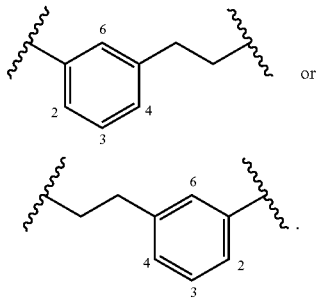

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, □$NHNH_2$, □$ONH_2$, □NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', □NR'NR"R'", □ONR'R", □NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', □NR'NR"R'", □ONR'R", □NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, ☐NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In some embodiments, the compound is a chemical species set forth in the Examples section, FIGURES, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)-for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the onset of symptoms of the particular disease.

In some embodiments, the terms refer to the prevention of the onset, recurrence or spread of a disease or disorder, or of one or more symptoms thereof. In certain embodiments, the terms refer to treatment prior to the onset of symptoms, particularly to subjects at risk of disease or disorders provided herein. The terms encompass the inhibition or reduction of a symptom of the particular disease. Subjects with familial history of a disease are potential candidates for preventive regimens in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, "amelioration" of the symptoms of a particular disorder by administration of a particular pharmaceutical composition refers to any lessening, whether permanent or temporary, lasting or transient, that can be attributed to or associated with administration of the composition.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

As used herein, and unless otherwise specified, the term "tumor" refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the terms "cancer" and "cancerous" refer to or describe the physiological condition in mammals that is typically characterized by unregulated cell growth. Examples of cancer include, but are not limited to blood-borne (e.g., lymphoma, leukemia) and solid tumors.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, the terms "Epstein-Barr virus" and "EBV" are used interchangeably herein and refer to a virus that is also sometimes called human herpesvirus 4 (HHV-4). This virus is one of eight known human herpesvirus types in the herpes family, and is one of the most common viruses in humans. The virus is best known as the cause of infectious mononucleosis (glandular fever). It is also associated with particular forms of cancer, such as Hodgkin's lymphoma, Burkitt's lymphoma, gastric cancer, nasopharyngeal carcinoma, and conditions associated with human immunodeficiency virus (HIV), such as hairy leukoplakia and central nervous system lymphomas.

As used herein, and unless otherwise specified, the terms "EBV-associated", "EBV positive" and "EBV+", when use in describing a cancer or malignancy, refers to a cancer or malignancy that has been linked to the Epstein-Barr virus (EBV), namely a cancer that contains the EBV genome, or expresses one or more genes from the EBV genome in the form of miRNA, mRNA or protein.

As used herein, and unless otherwise specified, the terms "C—C chemokine receptor type 4" and "CCR4" refer to a protein (including homologs, isoforms, and functional fragments thereof) and is a high affinity receptor for the C—C type chemokines (e.g., CCL2 (MCP-1), CCL4 (MIP-1), CCL5 (RANTES), CCL17 (TARC), and CCL22 (MDC)). It is referred to by a number of different names in the scientific literature, including "CC—CKR-4", "C—C CKR-4", "K5-5", "CD194", "CMKBR4", "ChemR13", "HGCN", and "14099". The term includes any recombinant or naturally-occurring form of CCR4 variants thereof that maintain CCR4 activity (e.g. within at least 30%, 40%, 50%, 60%, 70%, 80%, 90%, 95%, or 100% activity compared to wildtype CCR4). The term includes any mutant form of CCR4 variants (e.g., frameshift mutations) thereof that maintain CCR4 activity (e.g. within at least 30%, 40%, 50%, 60%, 70%, 80%, 90%, 95%, or 100% activity compared to wildtype CCR4). In embodiments, the CCR4 protein encoded by the CCR4 gene has the amino acid sequence set forth in or corresponding to Entrez 1233, UniProt P51679, or RefSeq (protein) NP 005499.1. In embodiments, the CCR4 gene has the nucleic acid sequence set forth in RefSeq (mRNA) NM 005508. In embodiments, the amino acid sequence or nucleic acid sequence is the sequence known at the time of filing of the present application. In embodiments, the sequence corresponds to GI:5031627. In embodiments, the sequence corresponds to NP_005499.1. In embodiments, the sequence corresponds to NM_005508.4. In embodiments, the sequence corresponds to GI:48762930. In embodiments, the CCR4 is a human CCR4, such as a human cancer causing CCR4. Though frequently found on dendritic cells, macrophages, NK cells, platelets, and basophils, CCR4 is predominantly associated with T cells. It plays a role in the progression of multiple inflammation-related disorders, and, as described herein, has also been implicated in a number of other conditions. The genomic sequence of CCR4 is present on chromosome 3 (NC_000003.12), and the CCR4 gene is conserved in a number of species, including chimpanzee, Rhesus monkey, dog, cow, mouse, rat, chicken, and zebrafish. The CCR4 polypeptide comprises 360 amino acid residues (NP_005499.1), and, like other chemokine receptors, CCR4 is a G protein-coupled receptor found on the surface of leukocytes (see Horuk (1994) Trends Pharm. Sci. 15:159-165).

As used herein, and unless otherwise specified, the term "anti-cancer agent," "anticancer agent" or "cancer therapeutic agent" is meant to include anti-proliferative agents and chemotherapeutic agents, including, but not limited to, anti-metabolites (e.g., 5-fluoro uracil, methotrexate, azacitidine, decitabine, fludarabine, cytarabine (also known as cytosine arabinoside or Ara-C), and high dose cytarabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, carmustine, lomustine, ifosfamide, carmustine, busulfan, cyclophosphamide, dacarbazine, ifosfamide, and nitrosoureas, such as bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), and, topoisomerase inhibitors (e.g., etoposide, mitoxantrone and camptothecins), purine antagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat and romidepsin), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monoclonal antibodies (e.g., gemtuzumab ozogamicin, alemtuzumab, rituximab, and yttrium-90-ibritumomab tiuxetan), immuno-modulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, immune system modulating agents, and agents to attenuate any adverse effects (e.g., antiemetics) and other approved chemotherapeutic drugs, including, but not limited to, alkylating drugs (mechlorethamine, chlorambucil, cyclophosphamide, melphalan, and ifosfamide), antimetabolites (cytarabine, high dose cytarabine, and methotrexate), purine antagonists and pyrimidine antagonists (6-mercaptopurine, 5-fluorouracil, cytarabine, and gemcitabine), spindle poisons (vinblastine, vincristine, vinorelbine, docetaxel, and paclitaxel, e.g., Abraxane®), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For additional available cancer therapies, see, e.g., http://www.nci.nih-.gov/; for a list of FDA approved oncology drugs, see, e.g., http://www.fda.gov/, The Merck Manual, 18th Ed. 2006, and PDR: Physician Desk Reference 2010, 64th Ed. 2009; the contents of each of which are hereby incorporated by reference in their entireties.

As used herein, and unless otherwise specified, the terms "co-administration" and "in combination with" include the administration of two or more therapeutic agents simultaneously, concurrently, or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The terms "composition," "formulation," and "dosage form," as used herein are intended to encompass compositions comprising the specified ingredient(s) (in the specified amounts, if indicated), as well as any product(s) which result, directly or indirectly, from combination of the specified ingredient(s) in the specified amount(s). By "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof.

Unless indicated otherwise, the terms "composition," "formulation," and "dosage form" are used herein interchangeably.

As used herein, and unless otherwise specified, the term "immediate release," when used in reference to a composition, formulation, or dosage form provided herein, means that the composition, formulation, or dosage form does not comprise a component (e.g., a coating) that serves to delay the spatial and/or temporal release of some or all of the API from the composition, formulation, or dosage form following oral administration. In certain embodiments, an immediate release composition, formulation, or dosage form is one that releases the API substantially in the stomach following oral administration. In certain embodiments, an immediate release composition, formulation, or dosage form is one that releases the API substantially in the stomach or the upper intestine following oral administration. In specific embodiments, an immediate release composition, formulation, or dosage form is one that is not delayed-release. In specific embodiments, an immediate release composition, formulation, or dosage form is one that does not comprise an enteric coating.

As used herein, and unless otherwise specified, the term "non-enteric-coated," refers to a pharmaceutical composition, formulation, or dosage form that does not comprise a coating intended to release the active ingredient(s) beyond the stomach (e.g., in the intestine). In certain embodiments, a non-enteric-coated composition, formulation, or dosage form is designed to release the active ingredient(s) substantially in the stomach. In certain embodiments, a non-enteric-coated composition, formulation, or dosage form is designed to release the active ingredient(s) substantially in the stomach and the upper intestine.

As used herein, and unless otherwise specified, the term "substantially in the stomach," when used herein in reference to a composition, formulation, or dosage form provided herein, means that at least about 99%, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, or at least about 10% of a CCR4 modulator is released in the stomach. The term "released in the stomach" and related terms as used herein refer to the process whereby a CCR4 modulator is made available for uptake by or transport across cells lining the stomach and then made available to the body.

Certain compounds disclosed herein possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)-for amino acids, and individual isomers are encompassed within the scope of the present disclosure. The compounds of the present disclosure do not include those that are known in art to be too unstable to synthesize and/or isolate. The presently disclosed compounds include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

It will be apparent to one skilled in the art that certain compounds may exist in tautomeric forms, all such tautomeric forms of the compounds being within the scope hereof.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope hereof.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope hereof.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as, e.g., a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington, The Science and Practice of Pharmacy, 21st Edition; Lippincott Williams & Wilkins: Philadelphia, Pa., 2005; Handbook of Pharmaceutical Excipients, 5th Edition; Rowe et al., ed., The Pharmaceutical Press and the American Pharmaceutical Association: 2005; and Handbook of Pharmaceutical Additives, 3rd Edition; Ash and Ash ed., Gower Publishing Company: 2007; Pharmaceutical Preformulation and Formulation, Gibson ed., CRC Press LLC: Boca Raton, Fla., 2004.

As used herein, and unless otherwise specified, the term "hydrate" means a compound provided herein or a salt thereof, which further includes a stoichiometric or non-stoichiometric amount of water bound by non-covalent intermolecular forces.

As used herein, and unless otherwise specified, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

As used herein, and unless otherwise specified, the term "contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, and unless otherwise specified, the term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As used herein, and unless otherwise specified, the term "CCR4 modulator" refers to a compound or a composition that increases or decreases the level of CCR4 in a cell or a tissue, increases or decreases the function of CCR4 or its physical state.

As defined herein, and unless otherwise specified, the term "activation", "activate", "activating" and the like in reference to a target-inhibitor interaction means positively affecting (e.g. increasing) the activity or function of the target (e.g., protein) relative to the activity or function of the target (e.g., protein) in the absence of the inhibitor. The terms reference activation, or activating, sensitizing, or up-regulating signal transduction or enzymatic activity or the amount of a protein decreased in a disease.

As defined herein, and unless otherwise specified, the terms "agonist," "activator," "upregulator," etc. refer to a substance capable of detectably increasing the expression or activity of a given gene or protein relative to a control (e.g., in the absence of the agonist). The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, and unless otherwise specified, the term "inhibition," "inhibit", "inhibiting," and the like, in reference to a target-inhibitor interaction means negatively affecting (e.g. decreasing) the activity or function of the target (e.g., protein) relative to the activity or function of the target (e.g., protein) in the absence of the inhibitor. In embodiments inhibition means negatively affecting (e.g. decreasing) the concentration or levels of the target (e.g., protein) relative to the concentration or level of the target (e.g., protein) in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a target (e.g., protein). In embodiments, inhibition refers to a reduction of activity of a target (e.g., protein) resulting from a direct interaction (e.g. an inhibitor binds to the target (e.g., protein)). In embodiments, inhibition refers to a reduction of activity of a target (e.g., protein) from an indirect interaction (e.g. an inhibitor binds to a protein that activates the target (e.g., protein), thereby preventing target (e.g., protein) activation).

As defined herein, and unless otherwise specified, the terms "inhibitor," "repressor" or "antagonist" or "downregulator" interchangeably refer to a substance capable of detectably decreasing the expression or activity of a given gene or protein relative to a control (e.g., in the absence of the inhibitor). The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

As defined herein, and unless otherwise specified, the term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

As defined herein, and unless otherwise specified, the terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As defined herein, and unless otherwise specified, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., CCR4 inhibitor) described herein may be particularly efficacious (due to, for example, limitations of current therapies) are described in more detail hereafter. Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As defined herein, and unless otherwise specified, the term "cancer" refers to all types of cancer, neoplasm or malignant tumors found in mammals (e.g. humans), including leukemia, lymphoma, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As defined herein, and unless otherwise specified, the term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As defined herein, and unless otherwise specified, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

As defined herein, and unless otherwise specified, the term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

As defined herein, and unless otherwise specified, the term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

As defined herein, and unless otherwise specified, the term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As defined herein, and unless otherwise specified, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As defined herein, and unless otherwise specified, the terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, the treating or treatment is no prophylactic treatment.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

As defined herein, and unless otherwise specified, the term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

As defined herein, and unless otherwise specified, the term "Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

As defined herein, and unless otherwise specified, an "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

As defined herein, and unless otherwise specified, the term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As defined herein, and unless otherwise specified, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). In embodiments, the administering does not include administration of any active agent other than the recited active agent. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles. In embodiments, the administering does not include administration of any active agent other than the recited active agent.

As defined herein, and unless otherwise specified, "co-administer" means that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. colon cancer), cardiovascular disease, metabolic disease, immune or inflammatory disease or disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. colon cancer), cardiovascular disease, metabolic disease, immune or inflammatory disease or disorder.

As defined herein, and unless otherwise specified, "Cardiovascular agent" is used in accordance with its plain ordinary meaning and refers to a composition (e.g. compound, drug, antagonist, inhibitor, modulator) used in any way to treat conditions of the heart or the circulatory or vascular system relative to a control. In some embodiments, a cardiovascular agent is an agent identified herein having utility in methods of treating cardiovascular disease or disorder. In some embodiments, a cardiovascular agent is an agent approved by the FDA or similar regulatory agency of a country other than the USA, for treating cardiovascular disease or disorder.

As defined herein, and unless otherwise specified, [0001] "anti-inflammatory agent" is used in accordance with its plain ordinary meaning and refers to a composition (e.g. compound, drug, antagonist, inhibitor, modulator) used in any way to reduce inflammation or swelling relative to a control (e.g., the absence of the agent). In some embodiments, an anti-inflammatory agent is an agent identified herein having utility in methods of treating an inflammatory disease or disorder. In some embodiments, an anti-inflammatory agent is an agent approved by the FDA or similar regulatory agency of a country other than the USA, for reducing swelling and inflammation.

The compounds described herein can be administered to treat an immune or inflammatory disease or disorder, a cardiovascular or metabolic disease or disorder and/or cancer. In this regard, the compounds disclosed herein may be administered either alone to treat such diseases or disorders or may be co-administered with another therapeutic agent to treat such diseases or disorders.

The compounds disclosed herein may be co-administered with a cytokine or agonist or antagonist of cytokine function, (including agents which act on cytokine signaling pathways such as modulators of the SOCS system) including alpha-, beta-, and gamma-interferons; insulin-like growth factor type I (IGF-1); interleukins (IL) including IL1 to 17, and interleukin antagonists or inhibitors such as analcinra; tumour necrosis factor alpha (TNF-.alpha.) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxifylline.

The compounds disclosed herein may be co-administered with an anti-inflammatory agent, such as thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds disclosed herein may be co-administered with a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxifylline; thrombolytic, or an anticoagulant such as a platelet aggregation inhibitor.

As defined herein, and unless otherwise specified, "Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli-n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli-n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin .alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in anti sense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

VI. CCR4 MODULATORS

Any known CCR4 modulator can be used in performing the presently disclosed treatment methods. In certain embodiments, the CCR4 modulator is one that is suitable for oral administration. In other embodiments, the CCR4 modulator is one that is suitable for parental administration. In other embodiments, the CCR4 modulator is a CCR4-binding antibody.

Orally-Administered CCR4 Modulators

Provided are compounds useful for the treatment of EPV+ malignancies. One group of CCR4 modulators are compounds disclosed in U.S. patent application Ser. No. 15/662,861 filed Jul. 28, 2017 of Beck et al. (e.g., for example, compounds of Formulae I through VII), which are incorporated herein by reference in its entirety for all purposes. In embodiments, the compounds having Formula I:

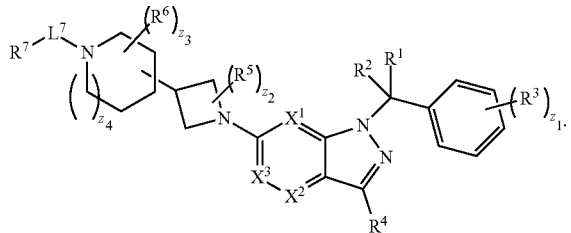

(I)

or a pharmaceutically acceptable salt thereof,
wherein:
$X^1$ is $CR^8$ or N;
$X^2$ is $CR^9$ or N;
$X^3$ is $CR^{10}$ or N;
n1, n2, n3, n4, n5, n6, n7, n8, n9 and n10 are independently an integer from 0 to 4;
m1, m2, m3, m4, m5, m6, m7, m8, m9, m10, v1, v2, v3, v4, v5, v6, v7, v8, v9 and v10 are independently 1 or 2;
z1 is an integer from 0 to 5;
z2 is an integer from 0 to 2;
z3 is an integer from 0 to 11;
z4 is an integer from 0 to 2;
$L^7$ is a bond, —O—, —S—, —$NR^{7.2B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NHNR^{2B}R^{2C}$, —$ONR^{2B}R^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}_3$, —OCHX$^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, —$CX^{3.1}_3$, —$CHX^{3.1}_2$, —$CH_2X^{3.1}$, —CN, —$N_3$, —$SO_{n3}R^{3A}$, —$SO_{v3}NR^{3B}R^{3C}$, —$NHNR^{3B}R^{3C}$, —$ONR^{3B}R^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^4$ is hydrogen, halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —$NHNR^{4B}R^{4C}$, —$ONR^{4B}R^{4C}$, —NHC(O)NHNR$^{4B}$R$^{4C}$, —NHC(O)NR$^{4B}$R$^{4C}$, —N(O)$_{m4}$, —NR$^{4B}$R$^{4C}$, —C(O)R$^{4D}$, —C(O)OR$^{4D}$, —C(O)NR$^{4B}$R$^{4C}$, —OR$^{4A}$, —NR$^{4B}$SO$_2$R$^{4A}$, —NR$^{4B}$C(O)R$^{4D}$, —NR$^{4B}$C(O)OR$^{4D}$, —NR$^{4B}$OR$^{4D}$, —OCX$^{4.1}_3$, —OCHX$^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^5$ is independently hydrogen, halogen, oxo, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^{5.1}_3$, —OCHX$^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^6$ is independently hydrogen, halogen, oxo, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —$NHNR^{6B}R^{6C}$, —$ONR^{6B}R^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^7$ is hydrogen, halogen, —$CX^{7.1}_3$, —$CHX^{7.1}_2$, —$CH_2X^{7.1}$, —CN, —$N_3$, —$SO_{n7}R^{7A}$, —$SO_{v7}NR^{7B}R^{7C}$, —$NHNR^{7B}R^{7C}$, —$ONR^{7B}R^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7B}$C(O)R$^{7D}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^8$ is hydrogen, halogen, —$CX^{8.1}_3$, —$CHX^{8.1}_2$, —$CH_2X^{8.1}$, —CN, —$N_3$, —$SO_{n8}R^{8A}$, —$SO_{v8}NR^{8B}R^{8C}$, —$NHNR^{8B}R^{8C}$, —$ONR^{8B}R^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, halogen, —CX⁹·¹₃, —CHX⁹·¹₂, —CH₂X⁹·¹, —CN, —N₃, —SO$_{n9}$R⁹ᴬ, —SO$_{v9}$NR⁹ᴮR⁹ᶜ, —NHNR⁹ᴮR⁹ᶜ, —ONR⁹ᴮR⁹ᶜ, —NHC(O)NHNR⁹ᴮR⁹ᶜ, —NHC(O)NR⁹ᴮR⁹ᶜ, —N(O)$_{m9}$, —NR⁹ᴮR⁹ᶜ, —C(O)R⁹ᴰ, —C(O)OR⁹ᴰ, —C(O)NR⁹ᴮR⁹ᶜ, —OR⁹ᴬ, —NR⁹ᴮSO₂R⁹ᴬ, —NR⁹ᴮC(O)R⁹ᴰ, —NR⁹ᴮC(O)OR⁹ᴰ, —NR⁹ᴮOR⁹ᴰ, —OCX⁹·¹₃, —OCHX⁹·¹₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹⁰ is hydrogen, halogen, —CX¹⁰·¹₃, —CHX¹⁰·¹₂, —CH₂X¹⁰·¹, —CN, —N₃, —SO$_{n10}$R¹⁰ᴬ, —SO$_{v10}$NR¹⁰ᴮR¹⁰ᶜ, —NHNR¹⁰ᴮR¹⁰ᶜ, —ONR¹⁰ᴮR¹⁰ᶜ, —NHC(O)NHNR¹⁰ᴮR¹⁰ᶜ, —NHC(O)NR¹⁰ᴮR¹⁰ᶜ, —N(O)$_{m10}$, —NR¹⁰ᴮR¹⁰ᶜ, —C(O)R¹⁰ᴰ, —C(O)OR¹⁰ᴰ, —C(O)NR¹⁰ᴮR¹⁰ᶜ, —OR¹⁰ᴬ, —NR¹⁰ᴮSO₂R¹⁰ᴬ, —NR¹⁰ᴮC(O)R¹⁰ᴰ, —NR¹⁰ᴮC(O)OR¹⁰ᴰ, —NR¹⁰ᴮOR¹⁰ᴰ, —OCX¹⁰·¹₃, —OCHX¹⁰·¹₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹ᴬ, R¹ᴮ, R¹ᶜ, R¹ᴰ, R²ᴬ, R²ᴮ, R²ᶜ, R²ᴰ, R³ᴬ, R³ᴮ, R³ᶜ, R³ᴰ, R⁴ᴬ, R⁴ᴮ, R⁴ᶜ, R⁴ᴰ, R⁵ᴬ, R⁵ᴮ, R⁵ᶜ, R⁵ᴰ, R⁶ᴬ, R⁶ᴮ, R⁶ᶜ, R⁶ᴰ, R⁷ᴬ, R⁷ᴮ, R⁷ᶜ, R⁷ᴰ, R⁸ᴬ, R⁸ᴮ, R⁸ᶜ, R⁸ᴰ, R⁹ᴬ, R⁹ᴮ, R⁹ᶜ, R⁹ᴰ, R¹⁰ᴬ, R¹⁰ᴮ, R¹⁰ᶜ and R¹⁰ᴰ are independently hydrogen, halogen, —CF₃, —CCl₃, —CBr₃, —CI₃, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R¹ᴮ, R¹ᶜ, R²ᴮ, R²ᶜ, R³ᴮ, R³ᶜ, R⁴ᴮ, R⁴ᶜ, R⁵ᴮ, R⁵ᶜ, R⁶ᴮ, R⁶ᶜ, R⁷ᴮ, R⁷ᶜ, R⁸ᴮ, R⁸ᶜ, R⁹ᴮ, R⁹ᶜ, R¹⁰ᴮ and R¹⁰ᶜ substituents bonded to the same nitrogen atom may optionally be joined to form a substituted or unsubstituted heterocycloalkyl or substituted or unsubstituted heteroaryl; and X¹·¹, X²·¹, X³·¹, X⁴·¹, X⁵·¹, X⁶·¹, X⁷·¹, X⁸·¹, X⁹·¹ and X¹⁰·¹ are independently —Cl, —Br, —I or —F, wherein at least one of X¹, X² and X³ is N.

In embodiments, the compounds of formula (I) are modulators of CCR4 activity. In embodiments, the compounds of formula (I) are CCR4 antagonists.

In embodiments, pharmaceutically acceptable salts of the compounds disclosed in U.S. patent application Ser. No. 15/662,861 filed Jul. 28, 2017 of Beck et al. (e.g., for example, compounds of Formulae I through VII) are used as CCR4 modulators. In embodiments, the CCR4 modulators are the compounds selected from the group consisting of:

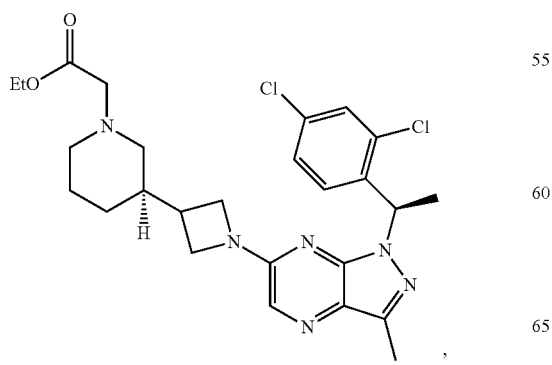

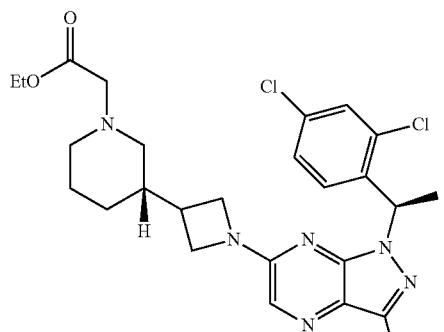

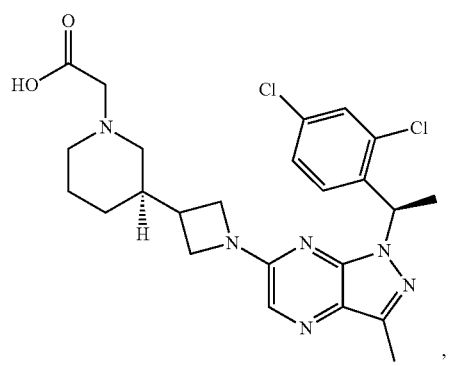

-continued

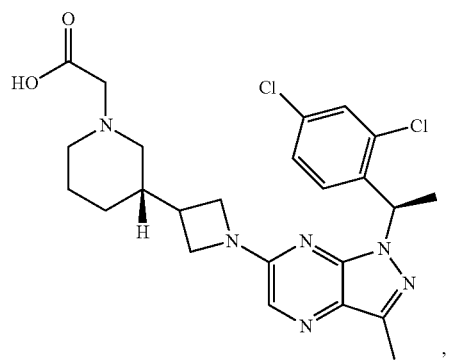

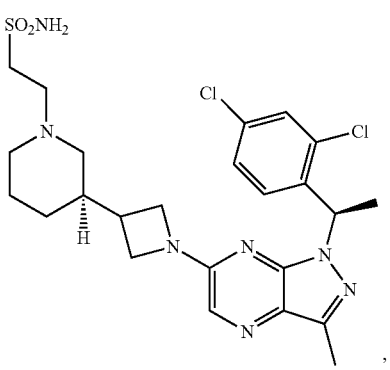

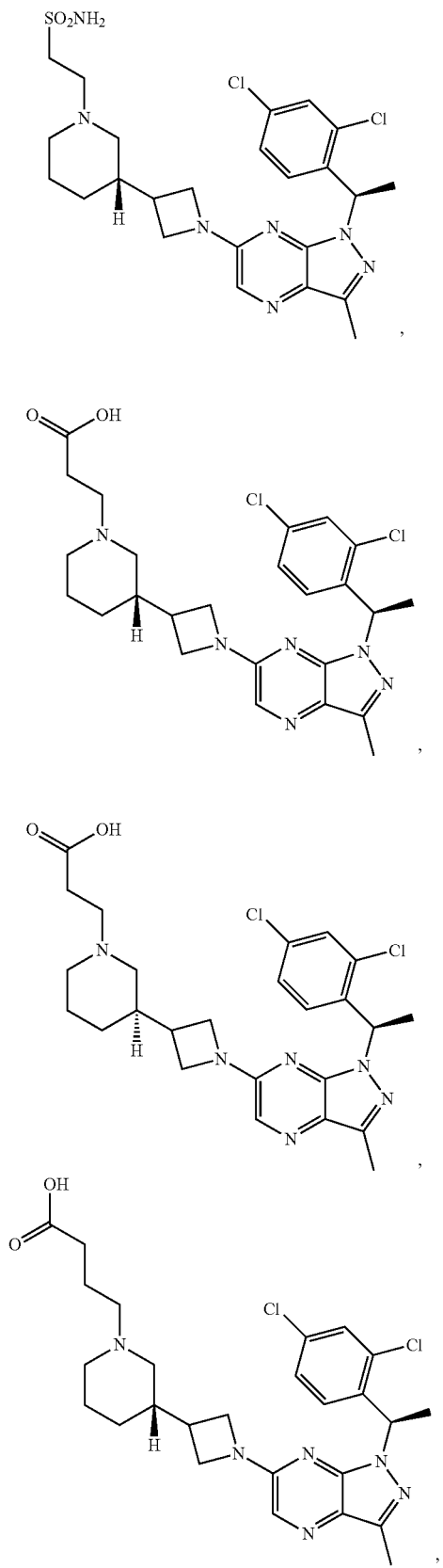
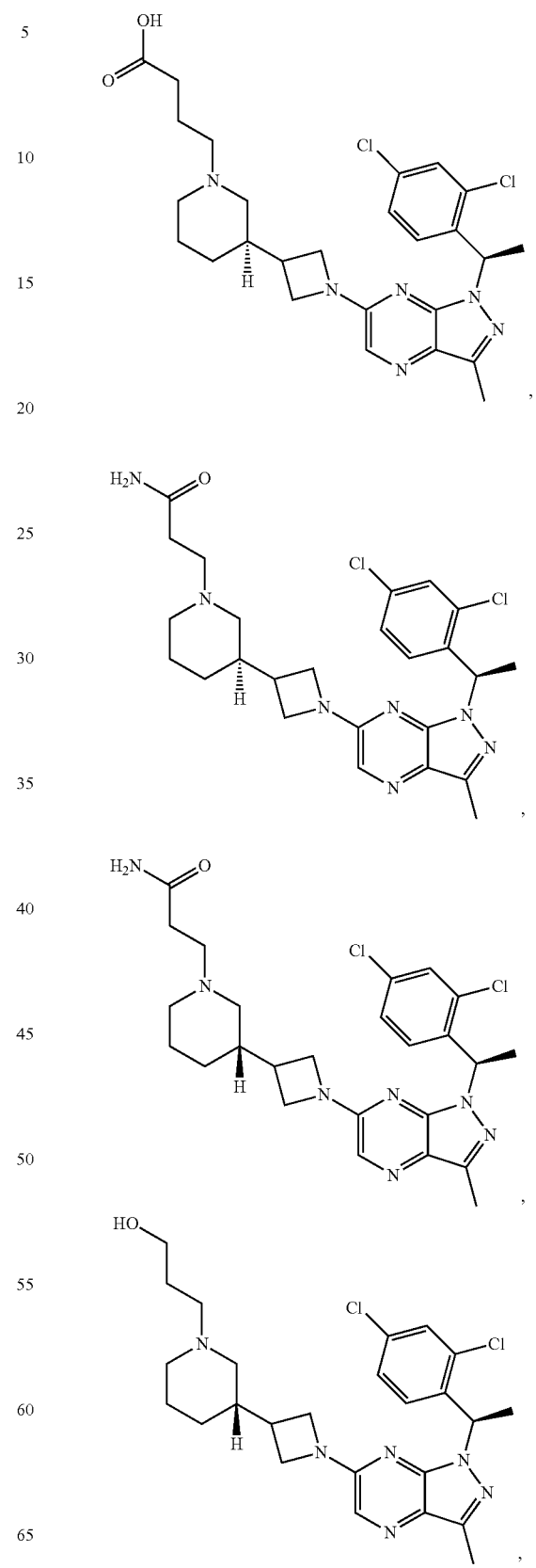

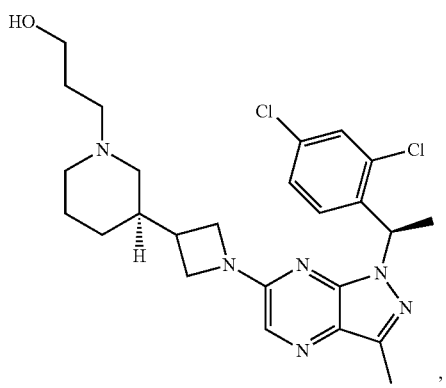
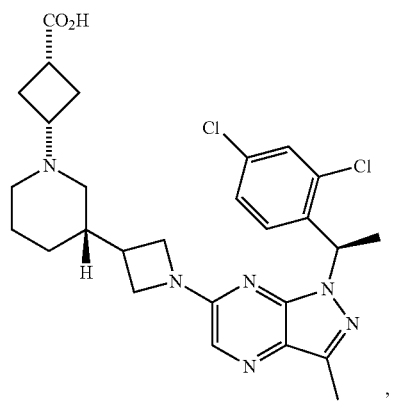
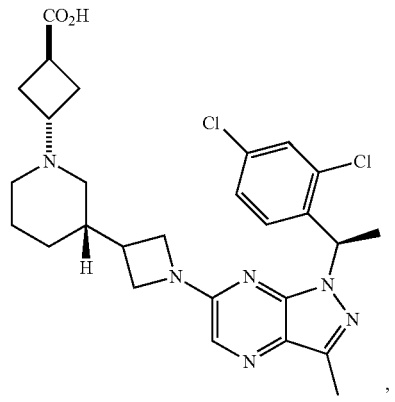
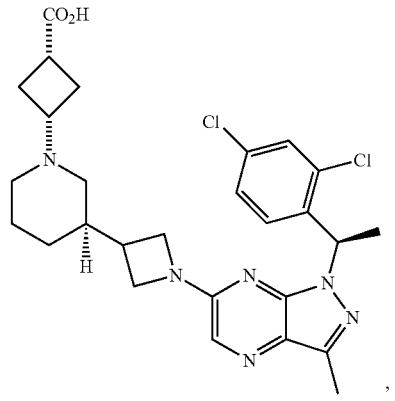
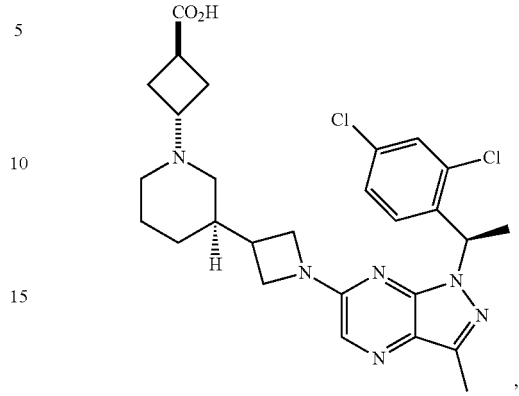
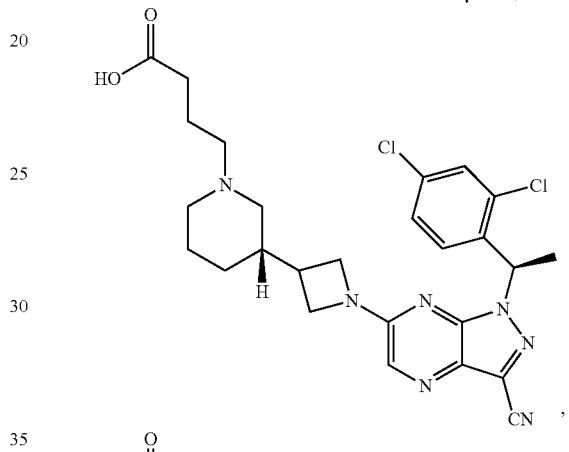
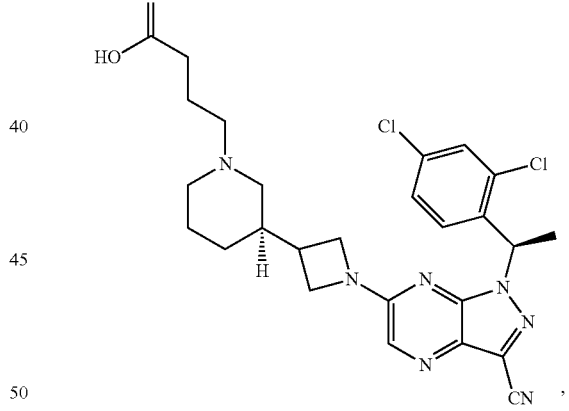
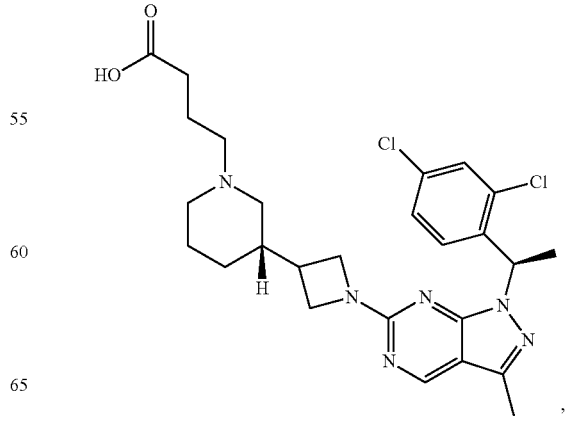

49
-continued
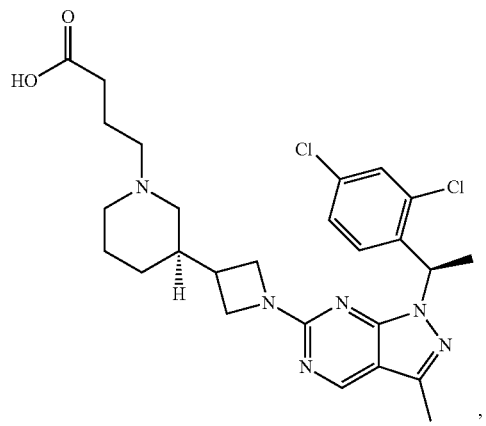
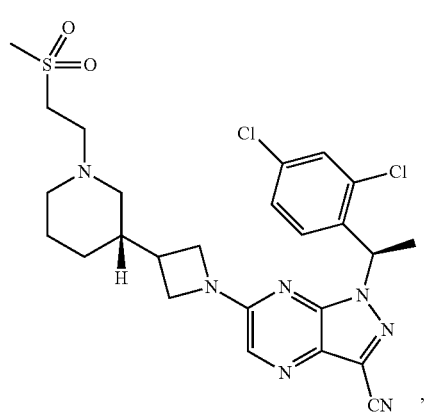
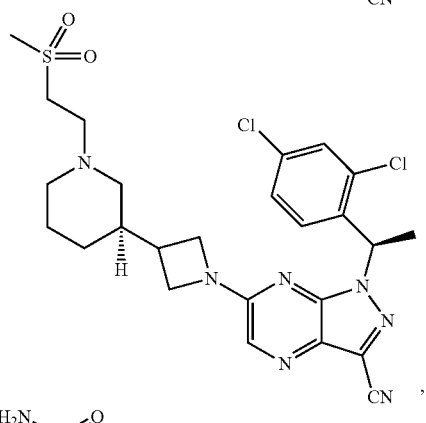
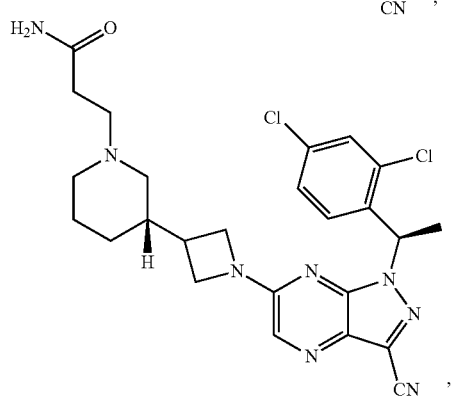
50
-continued
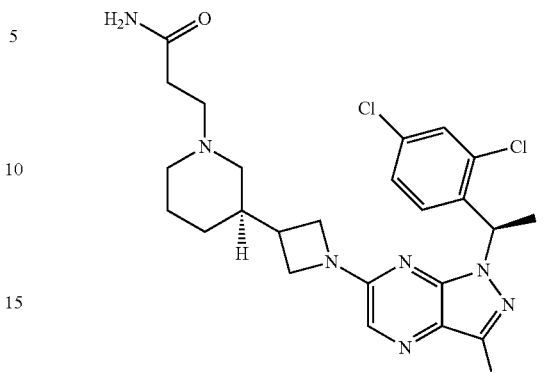
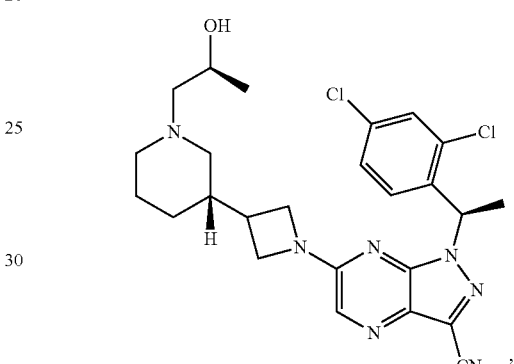
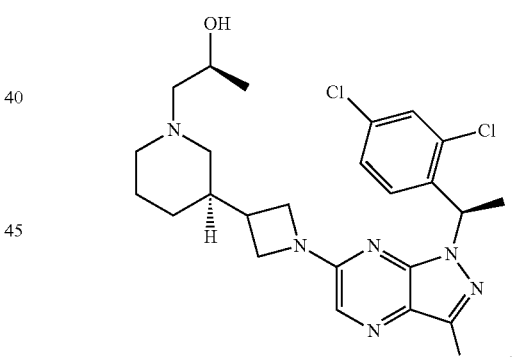
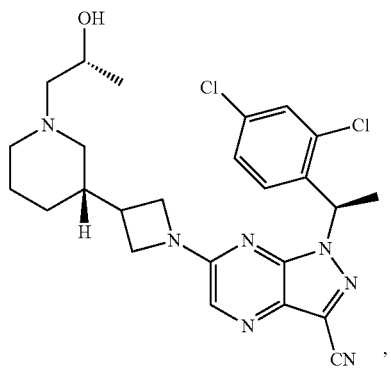

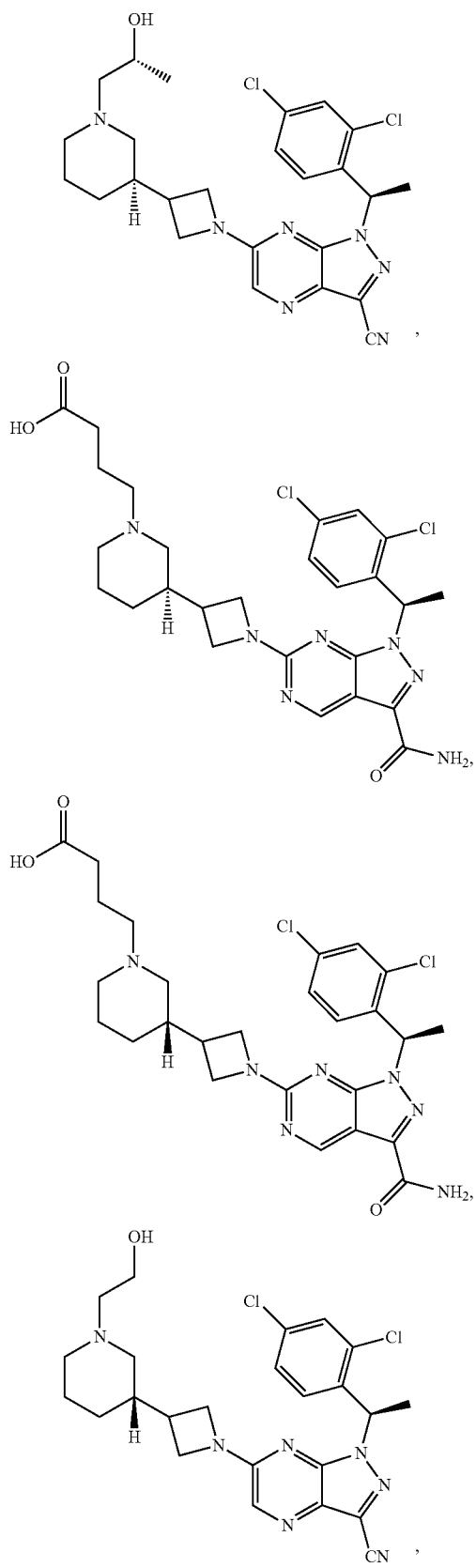
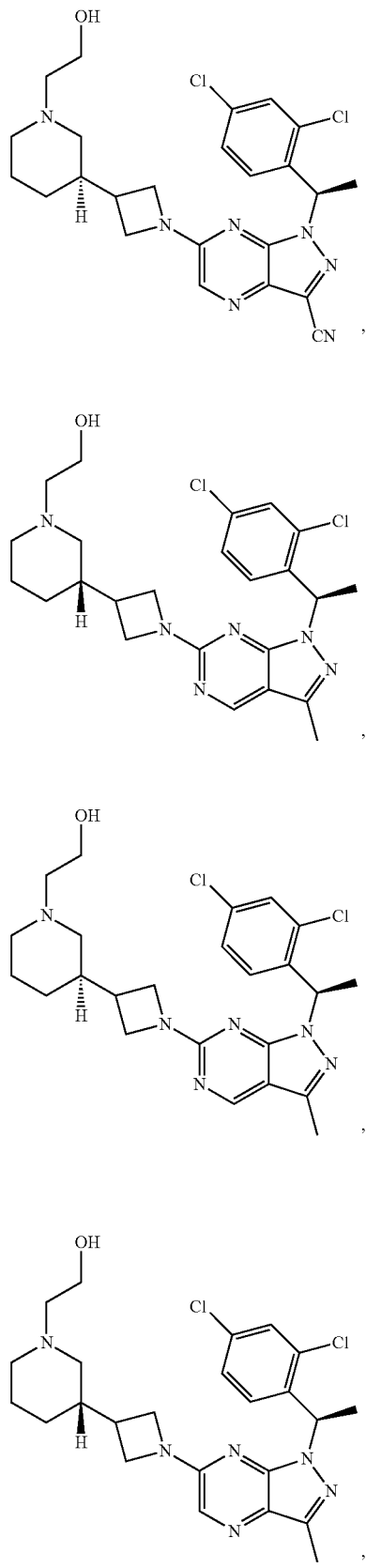

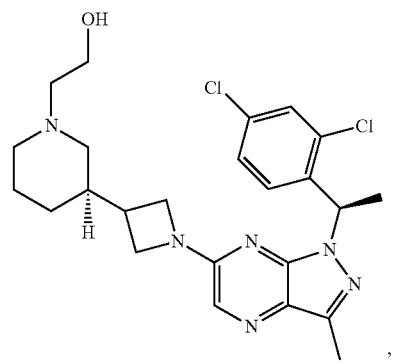
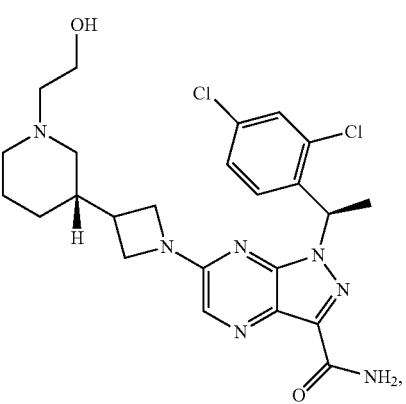
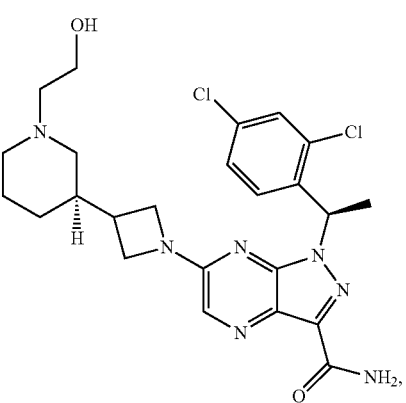
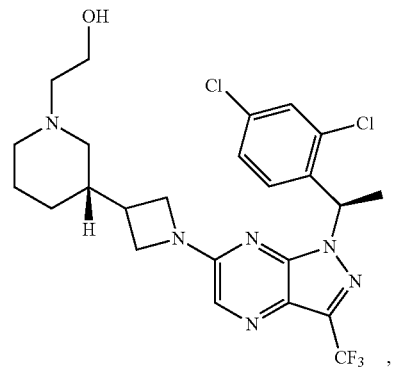
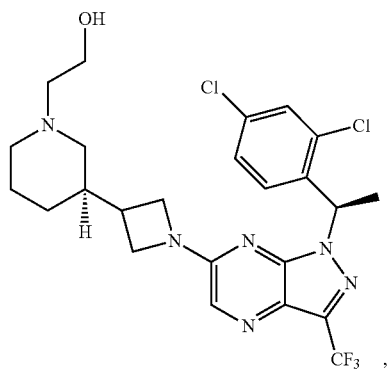
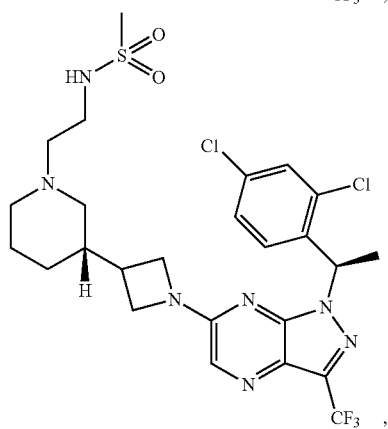
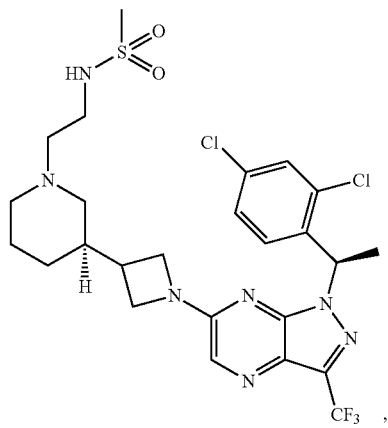
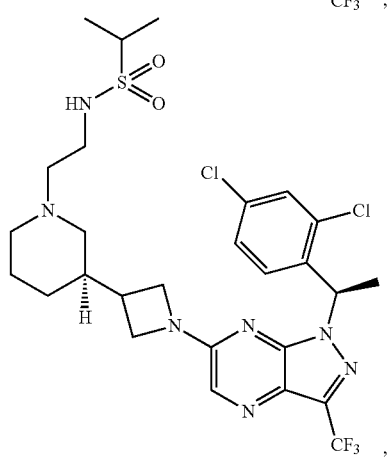

55
-continued
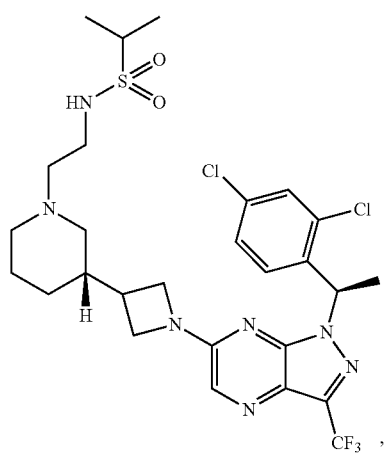
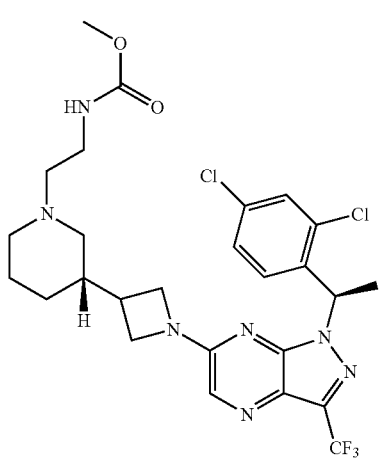
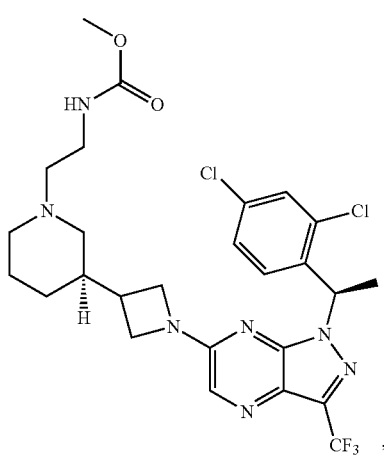
56
-continued
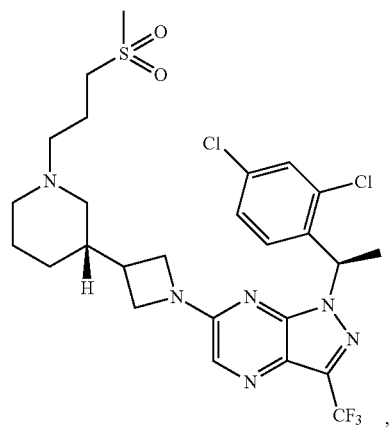
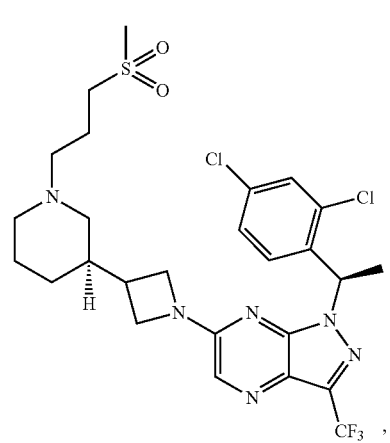
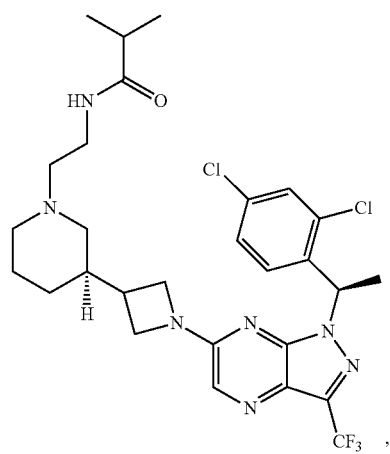

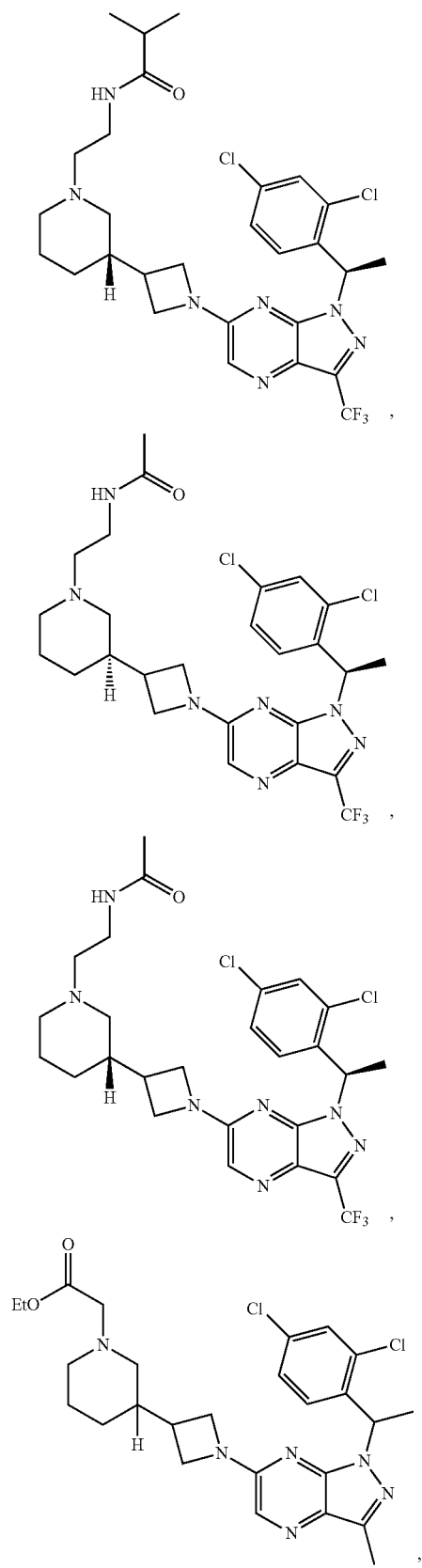 [SMILES: CC(C)C(=O)NCCN1CCC[C@@H](C2CN(c3cnc4c(C(F)(F)F)nn([C@H](C)c5ccc(Cl)cc5Cl)c4n3)C2)C1 ; CC(=O)NCCN1CCC[C@H](C2CN(c3cnc4c(C(F)(F)F)nn([C@H](C)c5ccc(Cl)cc5Cl)c4n3)C2)C1 ; CC(=O)NCCN1CCC[C@@H](C2CN(c3cnc4c(C(F)(F)F)nn([C@H](C)c5ccc(Cl)cc5Cl)c4n3)C2)C1 ; CCOC(=O)CN1CCCC(C2CN(c3cnc4c(C)nn(C(C)c5ccc(Cl)cc5Cl)c4n3)C2)C1]
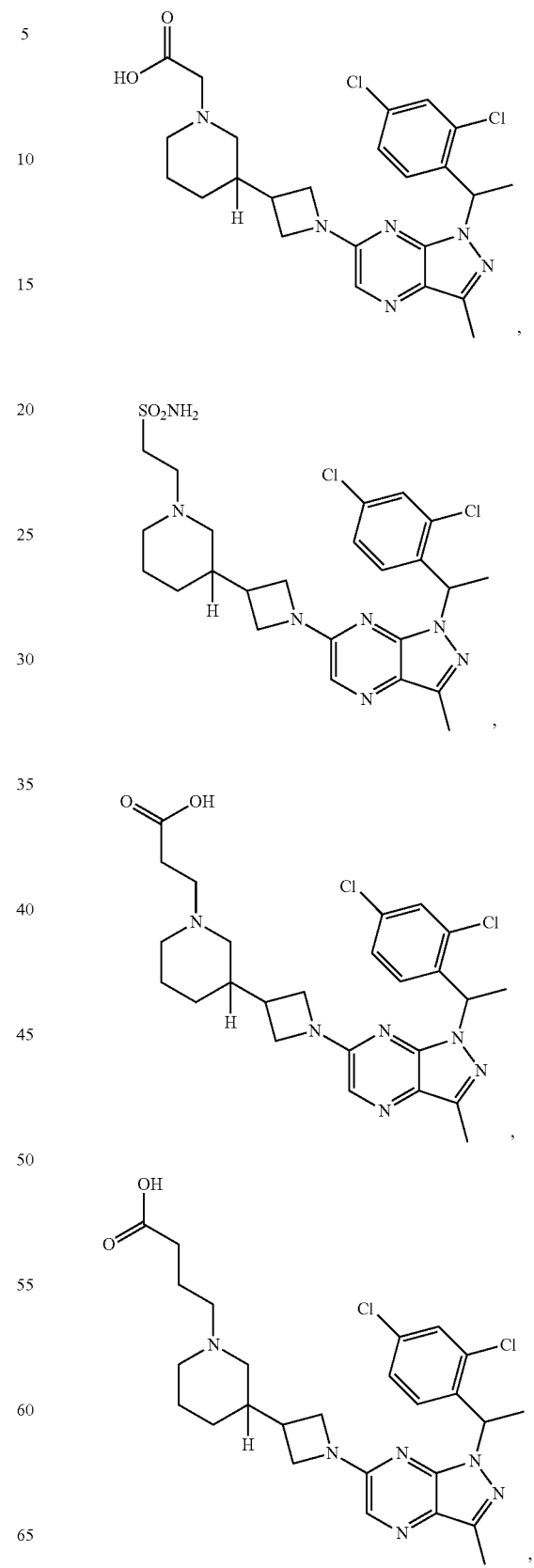

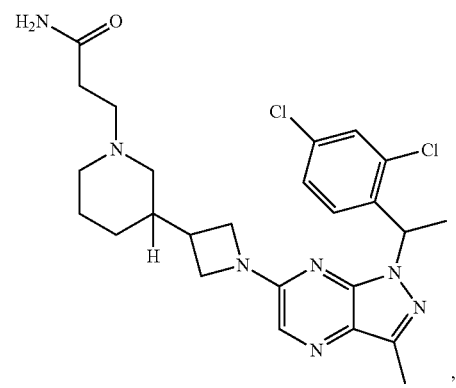
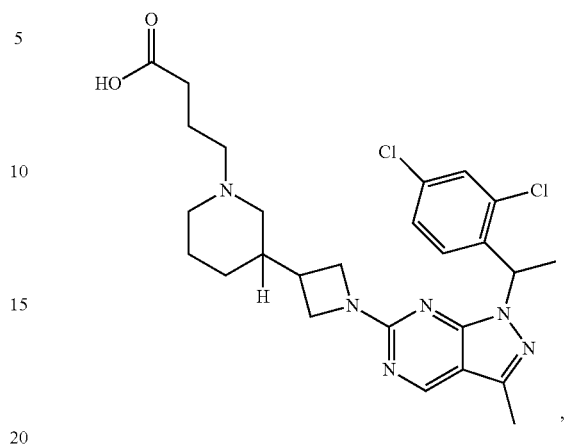
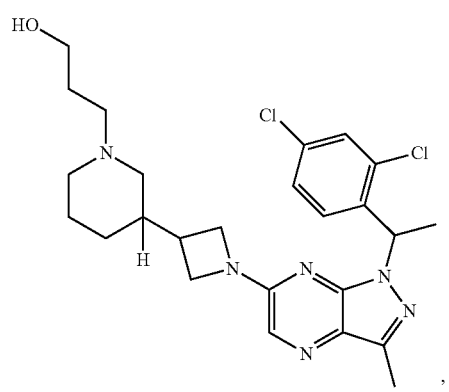
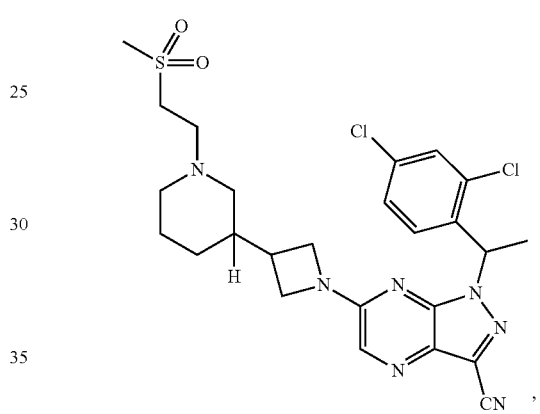
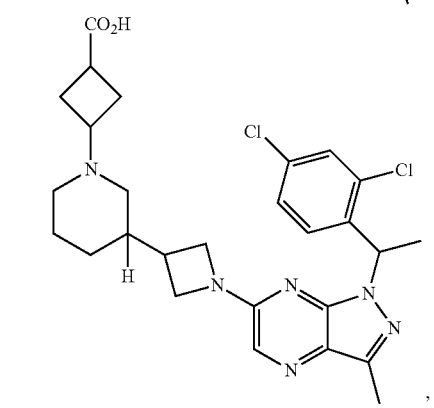
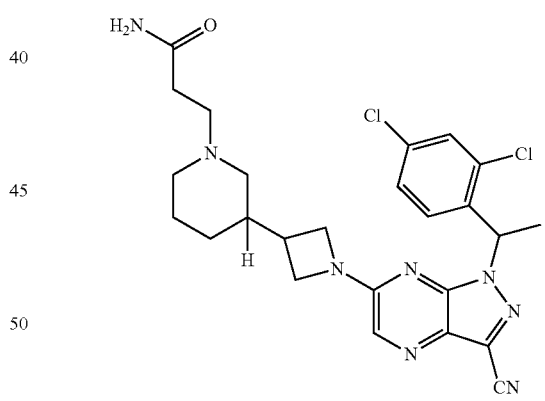
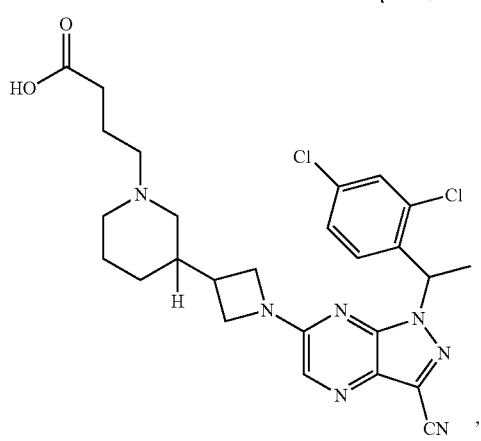
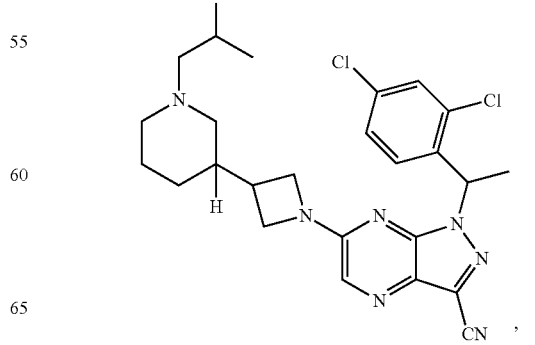

-continued
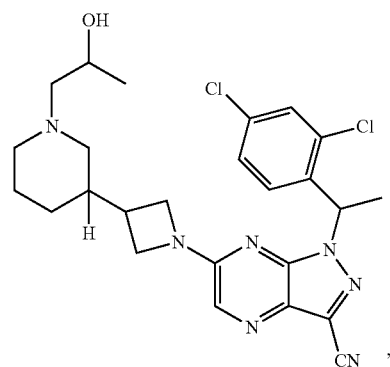
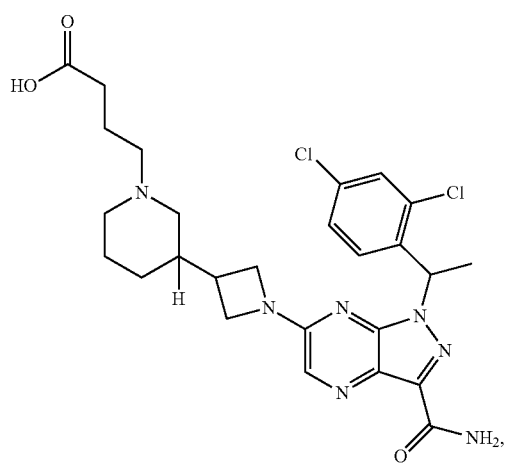
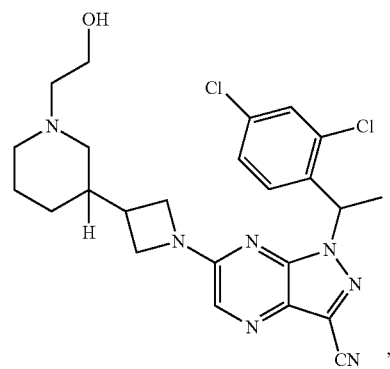
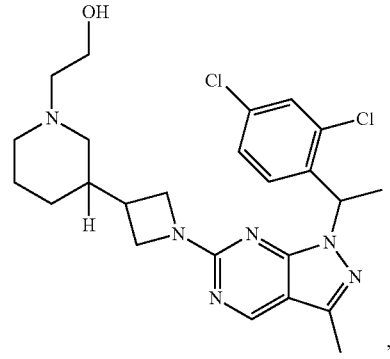
-continued
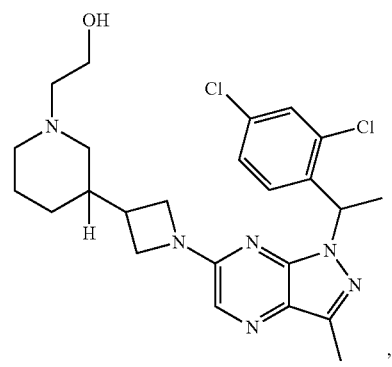
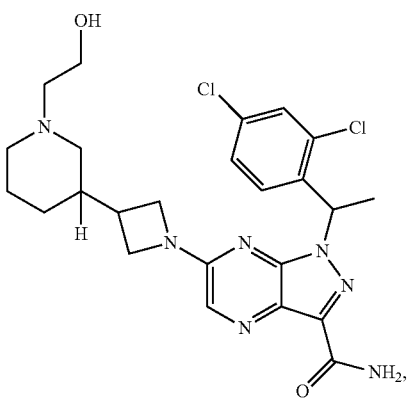
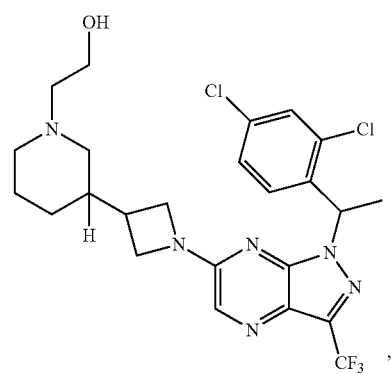
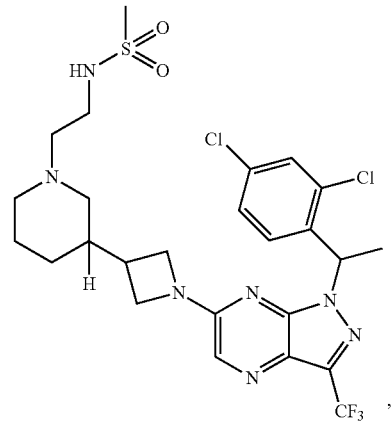

63
-continued
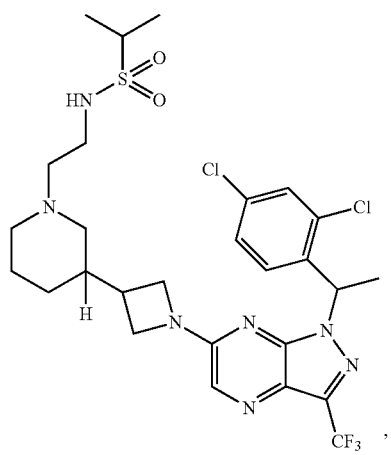
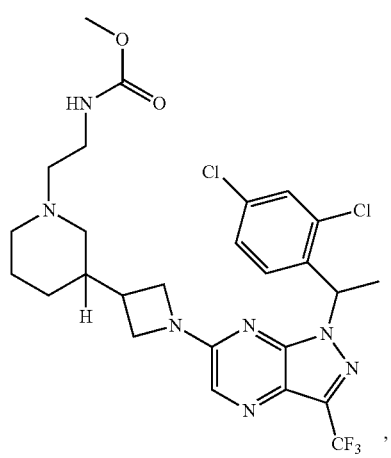
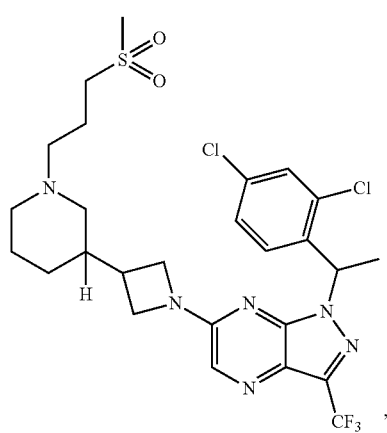
64
-continued
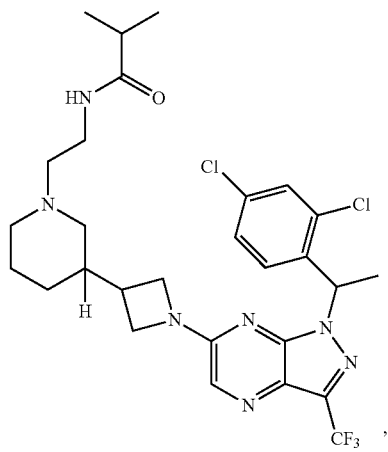
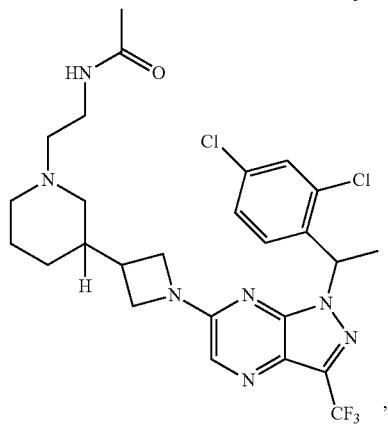
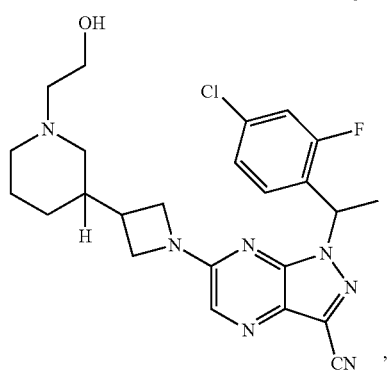
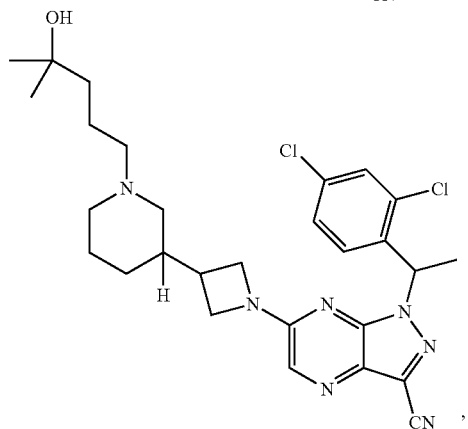

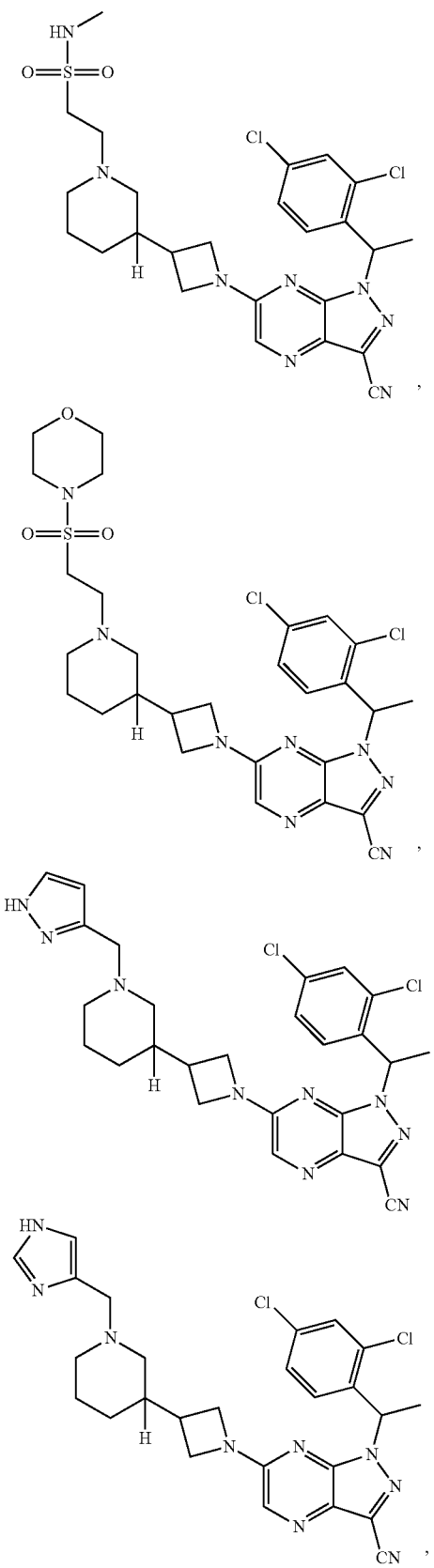
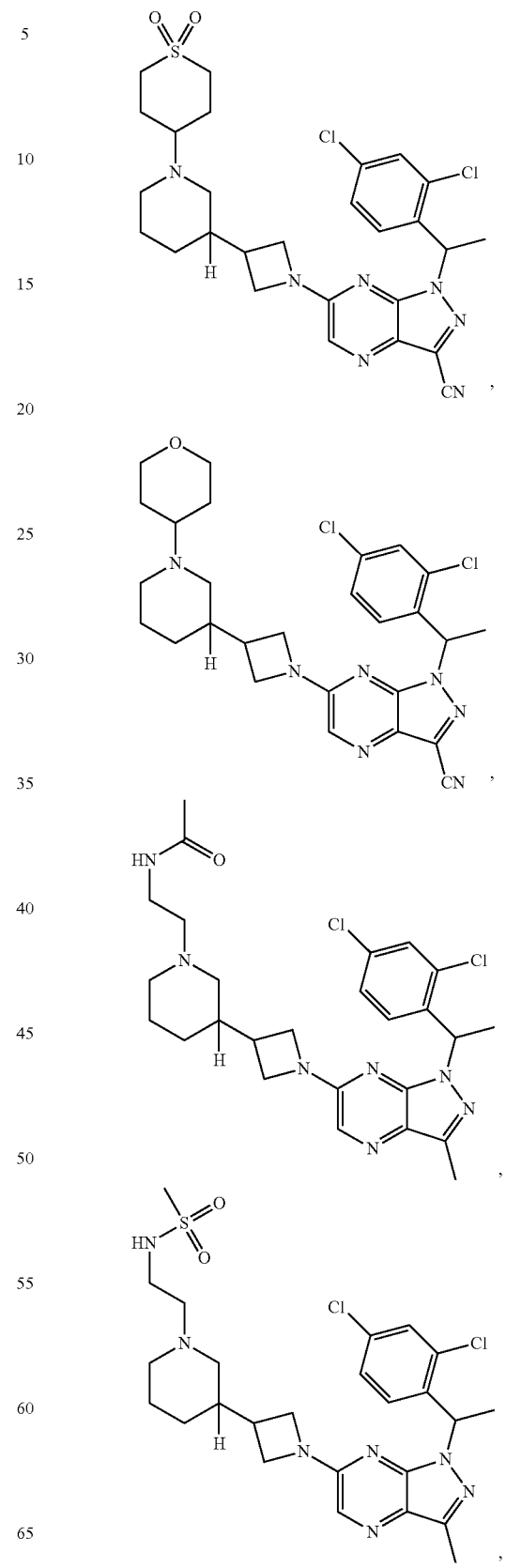

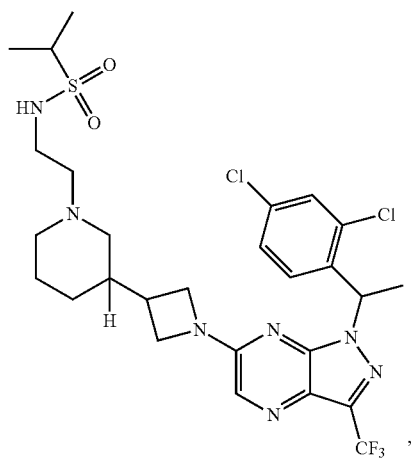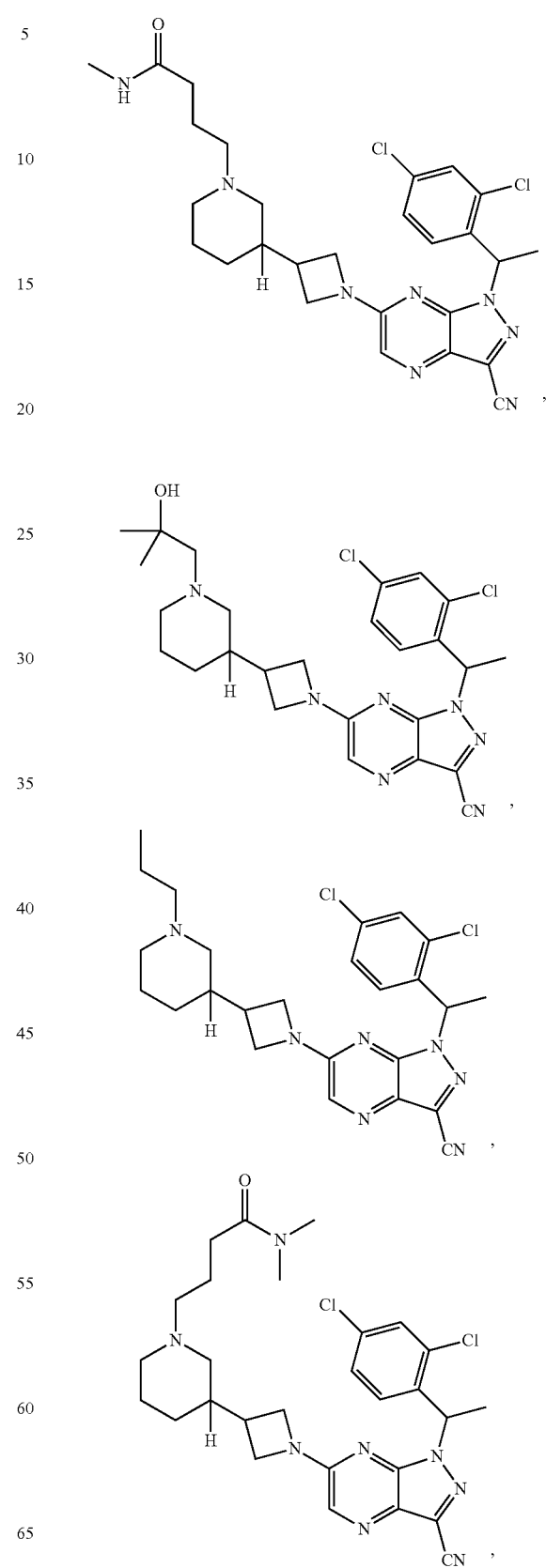

69
-continued
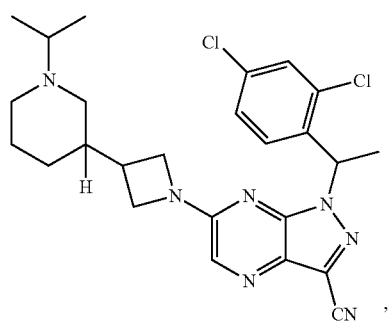
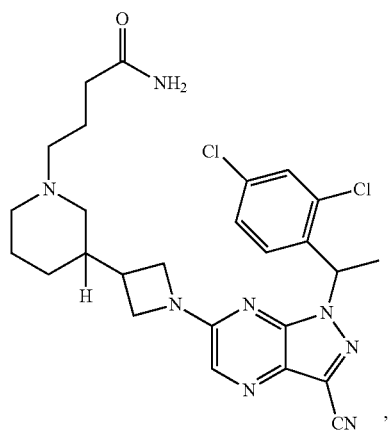
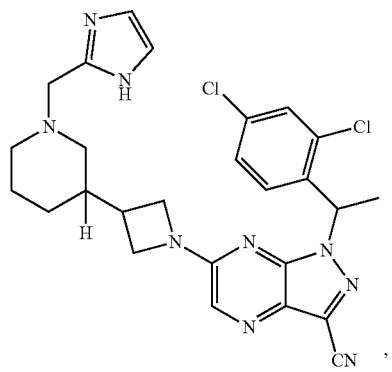
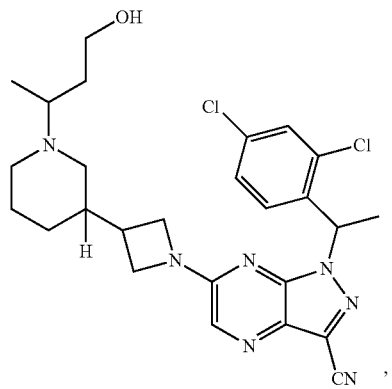
70
-continued
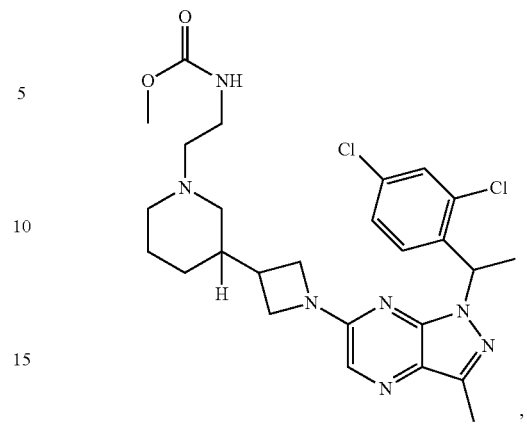
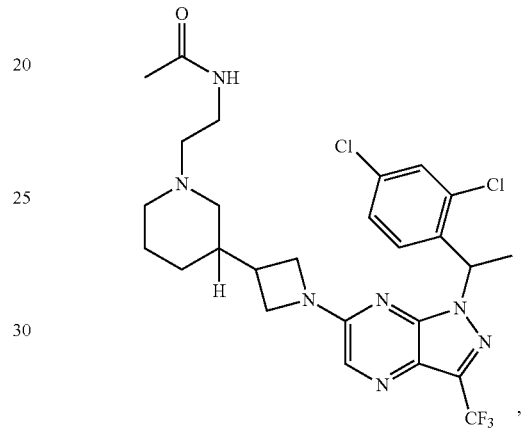
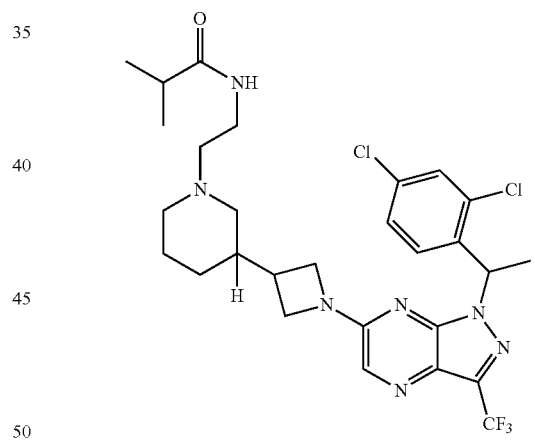
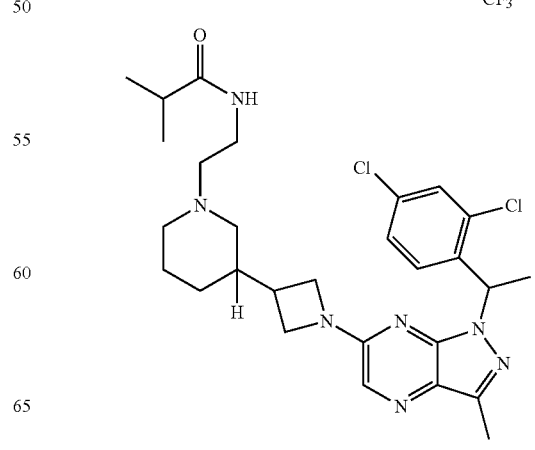

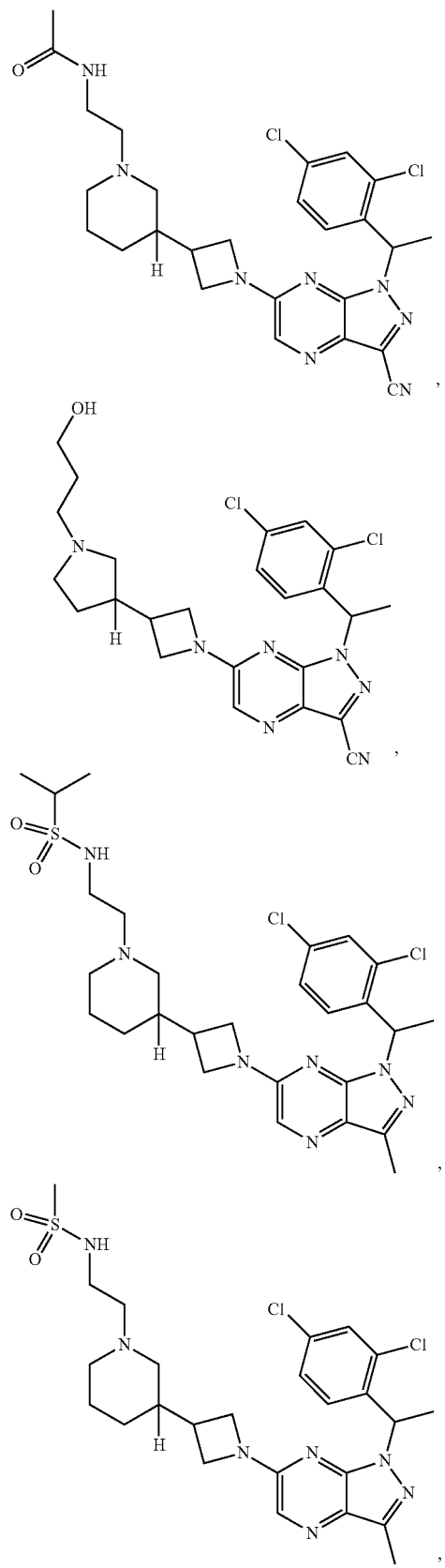
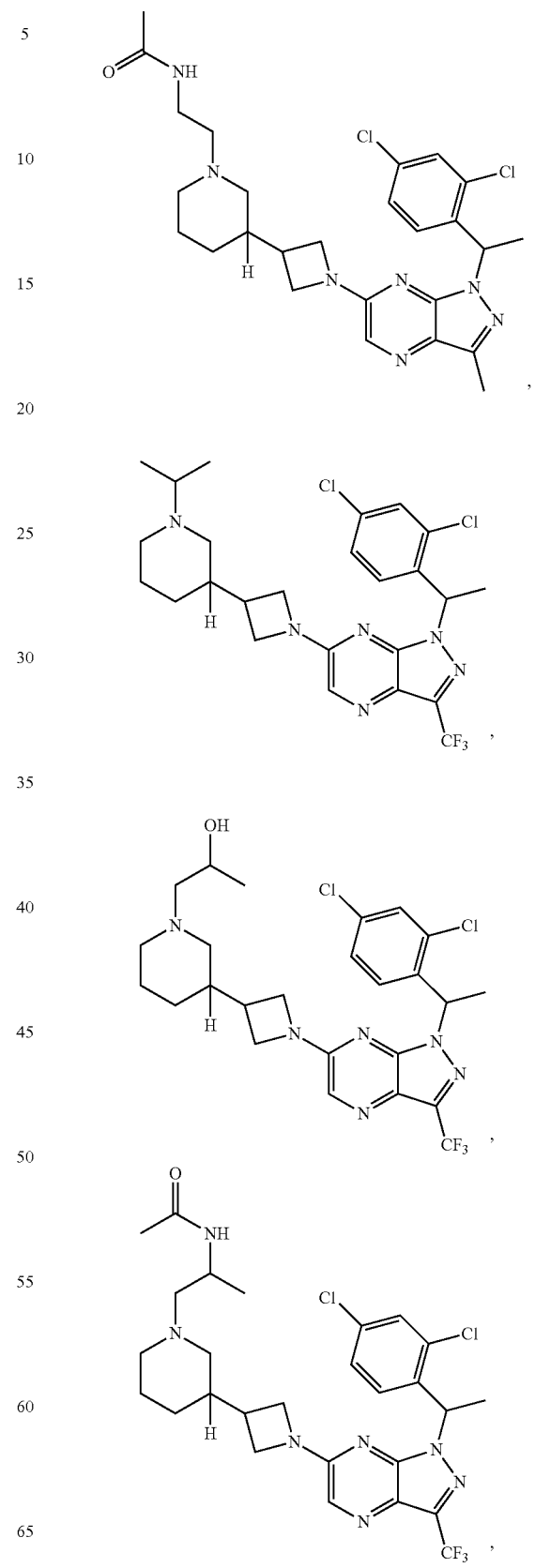

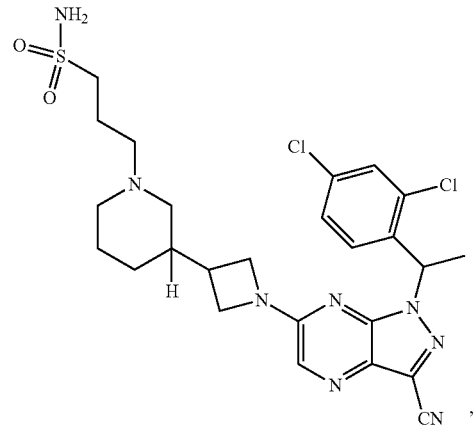

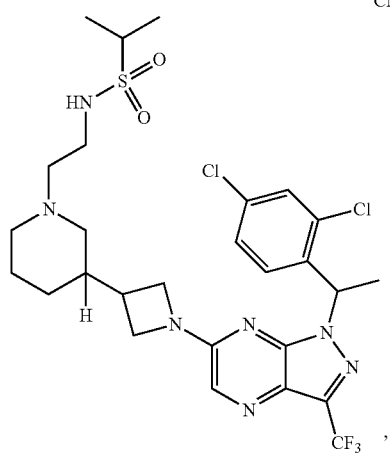

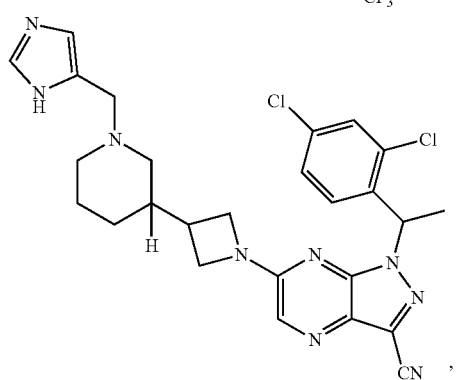

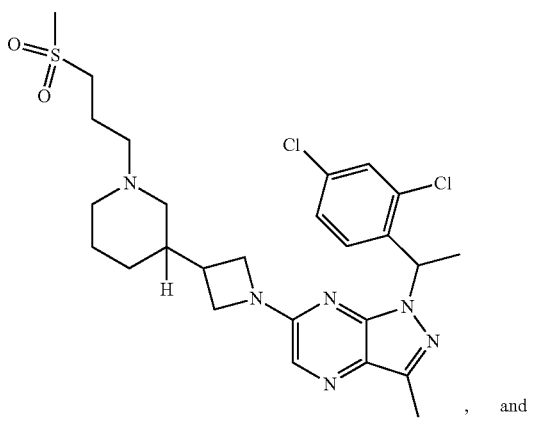

, and

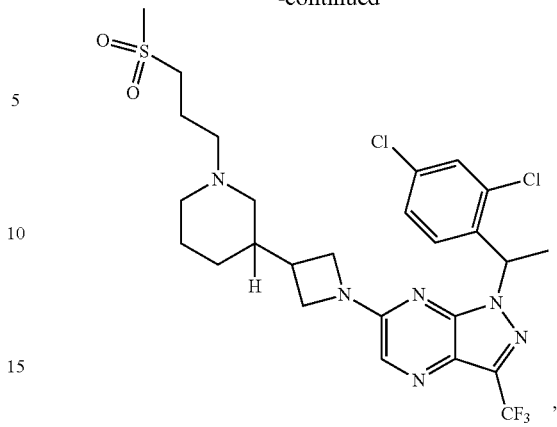

or a pharmaceutically acceptable salt of any of the foregoing compounds.

Another group of CCR4 modulators are compounds disclosed in U.S. patent application Ser. No. 15/700,040 filed Sep. 8, 2017 of Beck et al (e.g., for example, compounds of Formulae I through X), which are incorporated herein by reference in its entirety for all purposes. In embodiments, the compounds having Formula II:

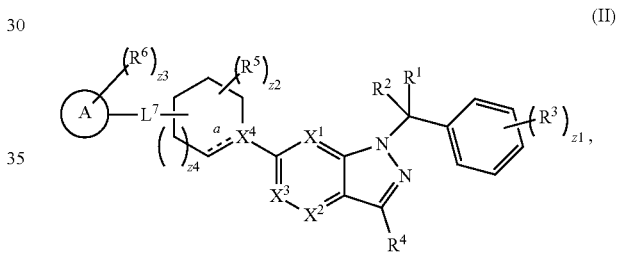

(II)

or a pharmaceutically acceptable salt thereof,
wherein:
A is a substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
z1 is an integer from 0 to 5;
z2 is an integer from 0 to 13;
z3 is an integer from 0 to 12;
z4 is an integer from 0 to 3;
⸺ is a single bond or double bond, wherein if ⸺ is a single bond, then $X^4$ is $CR^{11}$ or N, and if ⸺ is a double bond, then $X^4$ is C;
$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}{}_3$, —$CHX^{1.1}{}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}{}_3$, —$OCHX^{1.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CX^{2.1}_3$, $-CHX^{2.1}_2$, $-CH_2X^{2.1}$, $-CN$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $-CX^{3.1}_3$, $-CHX^{3.1}_2$, $-CH_2X^{3.1}$, $-CN$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, $-CX^{4.1}_3$, $-CHX^{4.1}_2$, $-CH_2X^{4.1}$, $-CN$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, $-CX^{5.1}_3$, $-CHX^{5.1}_2$, $-CH_2X^{5.1}$, $-CN$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}_3$, $-OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, $-CX^{6.1}_3$, $-CHX^{6.1}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}_3$, $-CHX^{9.1}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10.1}_3$, $-CHX^{10.1}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11.1}_3$, $-CHX^{11.1}_2$, $-CH_2X^{11.1}$, $-CN$, $-SO_{n11}R^{11A}$, $-SO_{v11}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m11}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl;

n1, n2, n3, n4, n5, n6, n8, n9, n10 and n11 are independently an integer from 0 to 4;

m1, m2, m3, m4, m5, m6, m8, m9, m10, m11, v1, v2, v3, v4, v5, v6, v8, v9, v10, and v11 are independently 1 or 2; and $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, and $X^{11.1}$ are independently $-Cl$, $-Br$, $-I$ or $-F$, wherein at least one of $X^1$, $X^2$, and $X^3$ is N.

In embodiments, the compounds of formula (II) are modulators of CCR4 activity. In embodiments, the compounds of formula (II) are CCR4 antagonists.

In embodiments, pharmaceutically acceptable salts of the compounds disclosed in U.S. patent application Ser. No. 15/700,040 filed Sep. 8, 2017 of Beck et al. (e.g., for example, compounds of Formulae I through X) are used as CCR4 modulators. In embodiments, the CCR4 modulators are the compounds selected from the group consisting of:
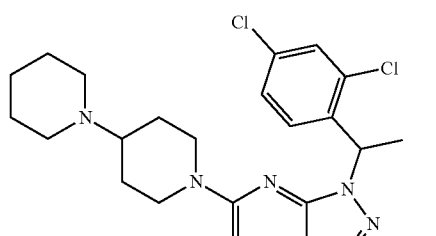
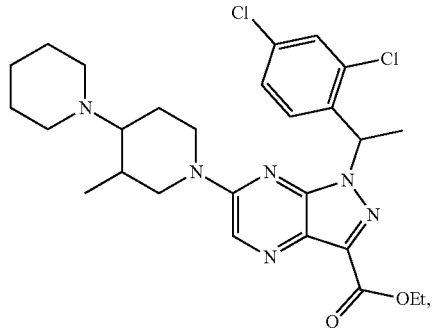
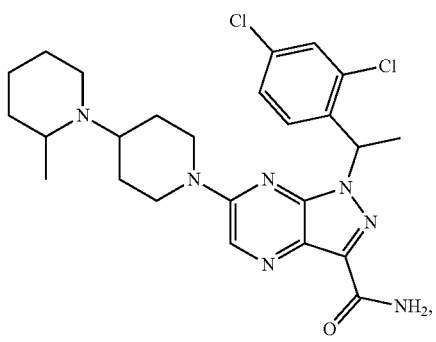
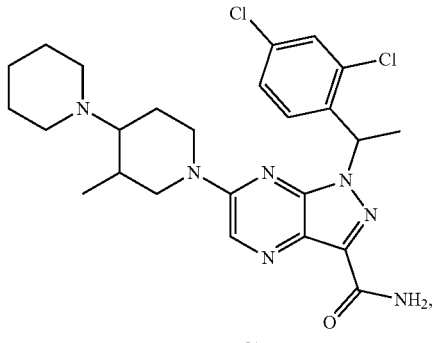
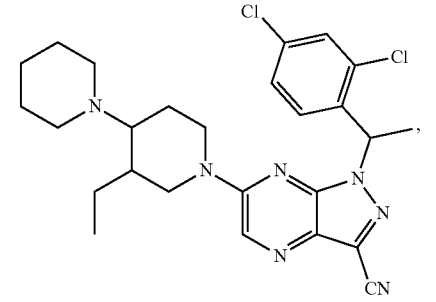
-continued
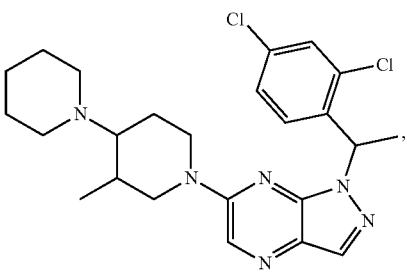
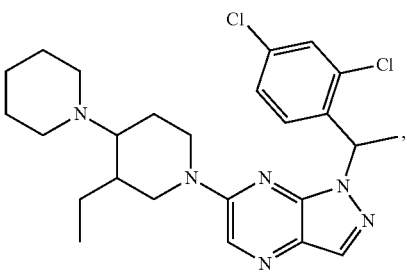
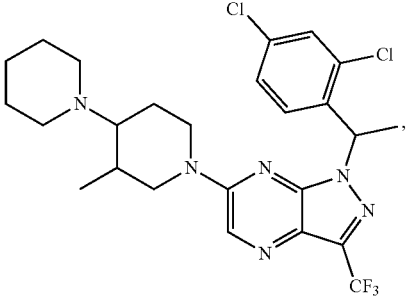
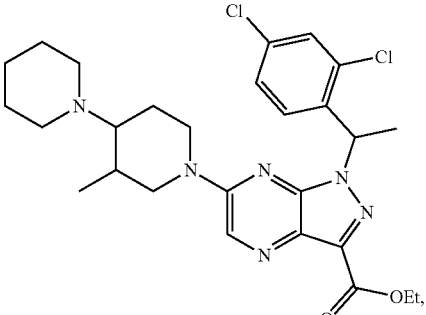
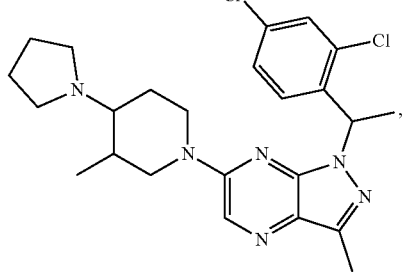

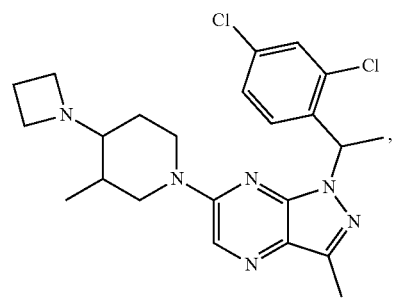
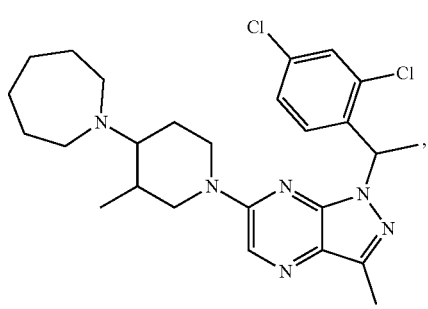
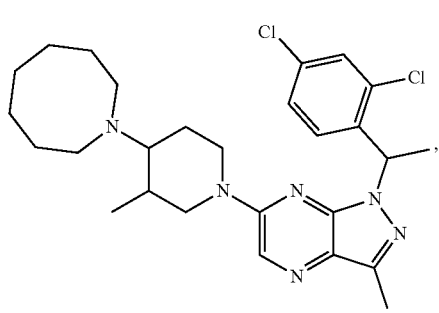
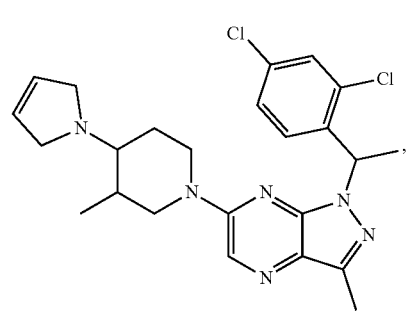
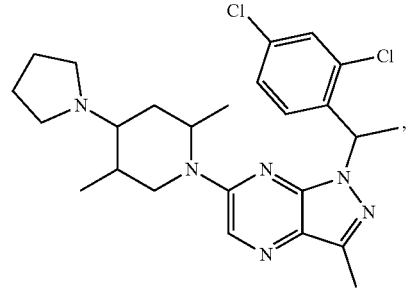
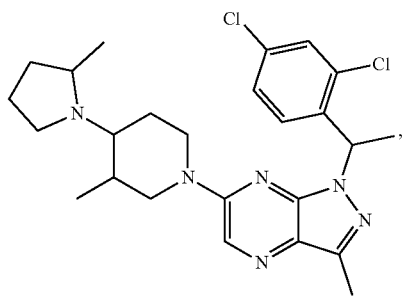
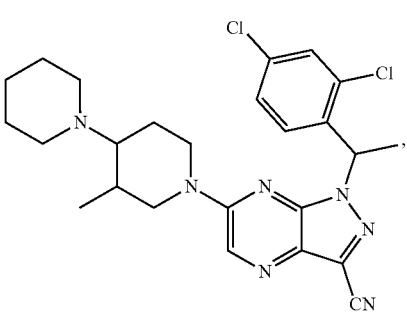
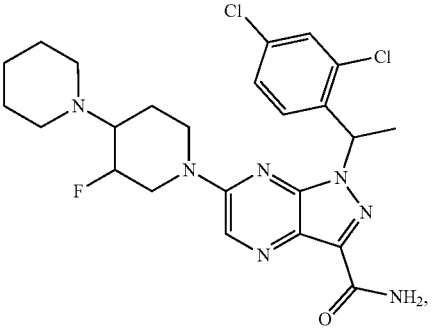
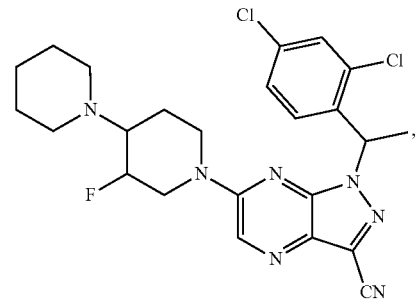
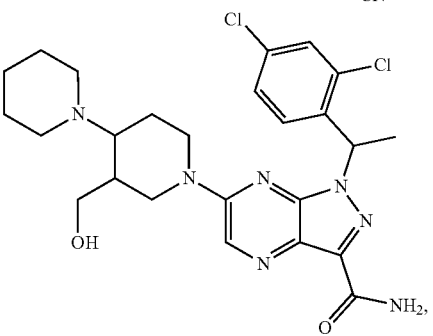

81
-continued
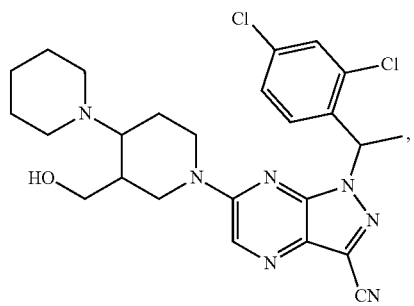
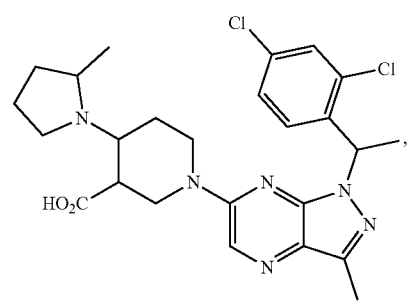
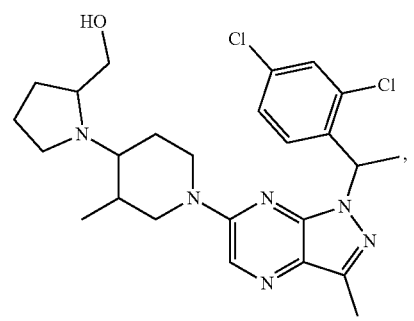
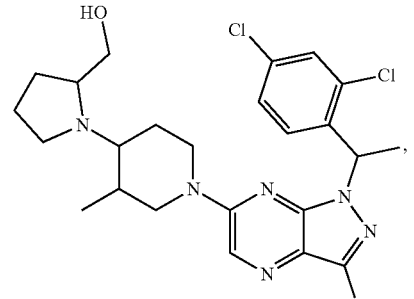
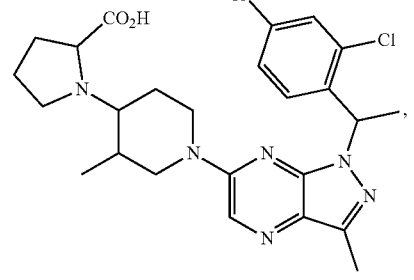
82
-continued
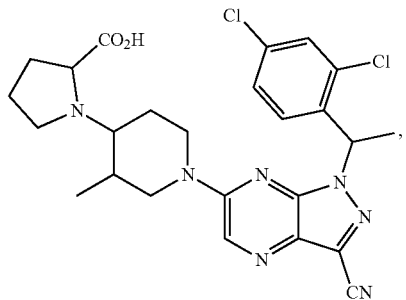
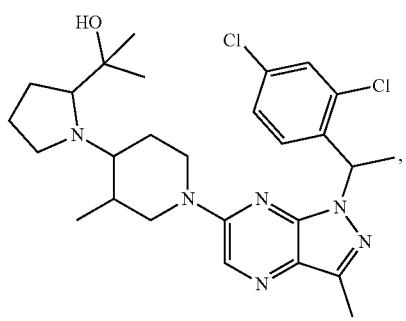
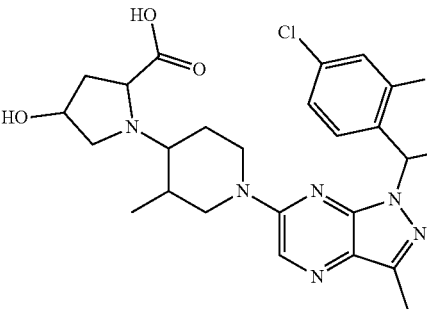
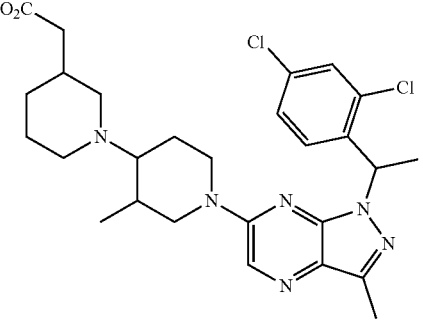
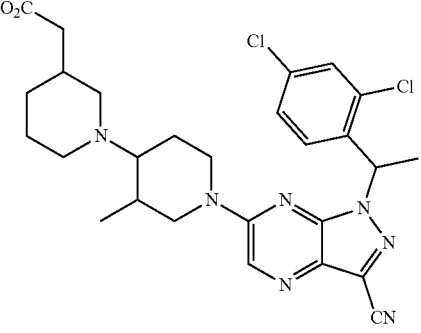

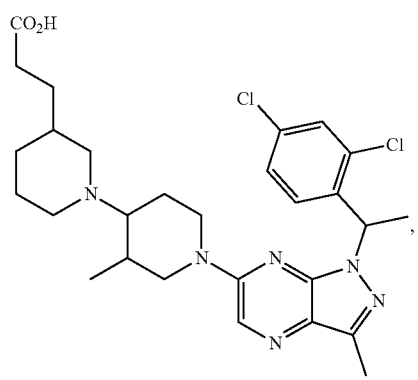
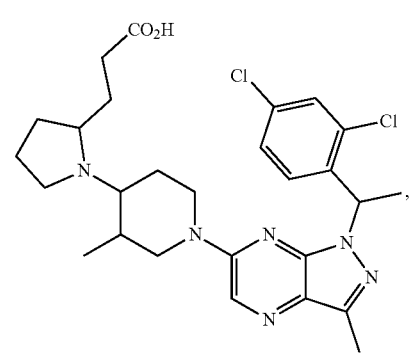
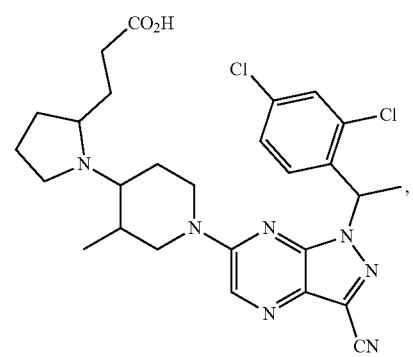
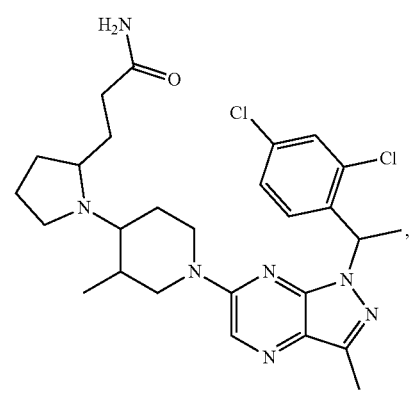
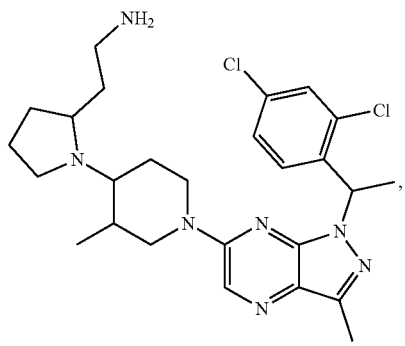
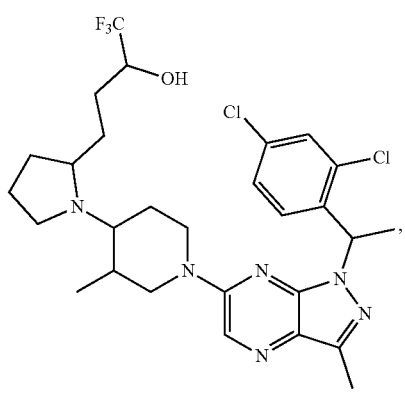
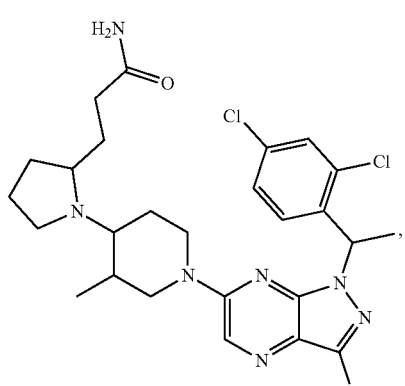
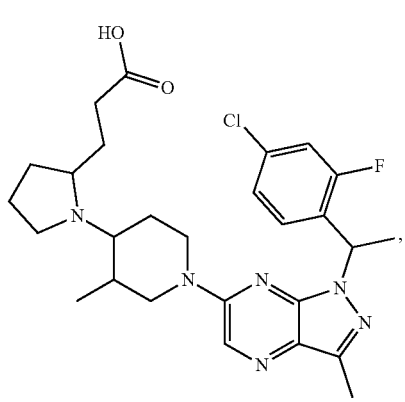

85
-continued
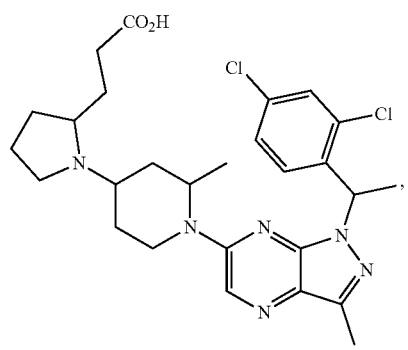
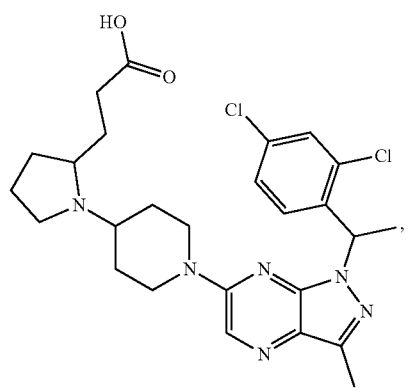
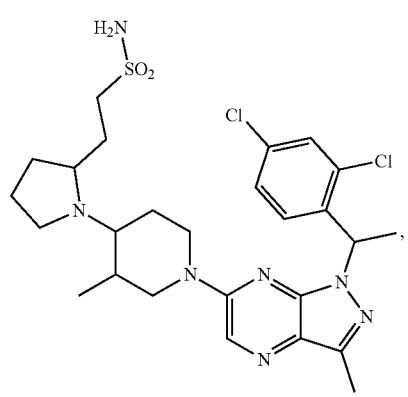
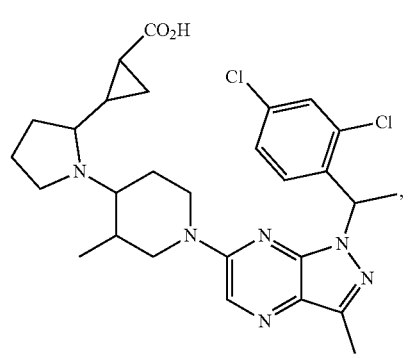
86
-continued
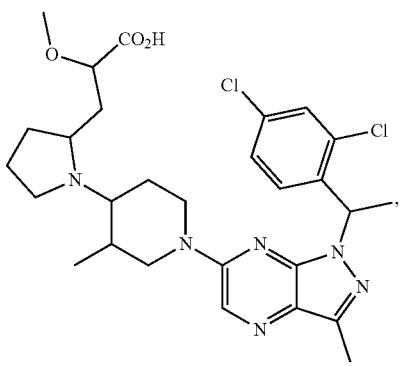
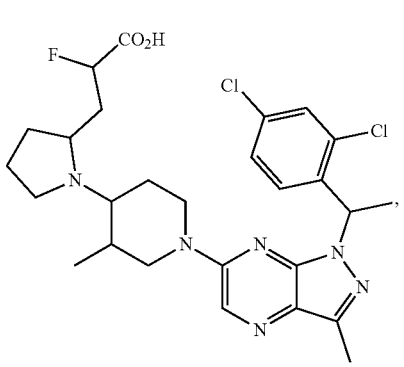
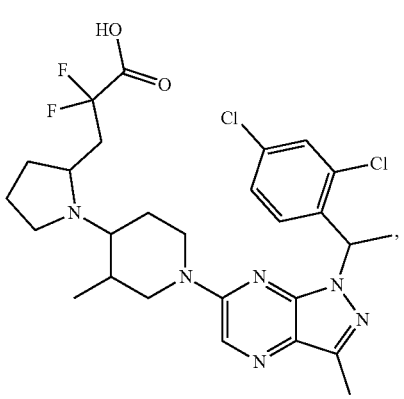
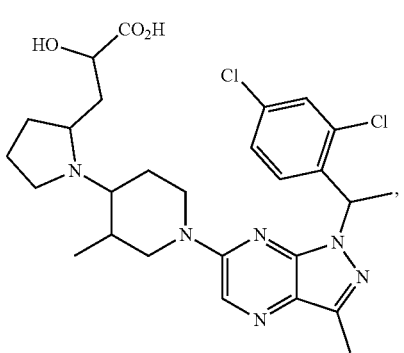

87
-continued
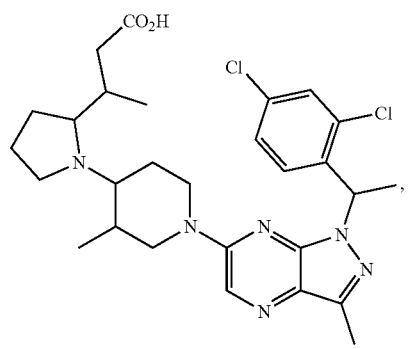
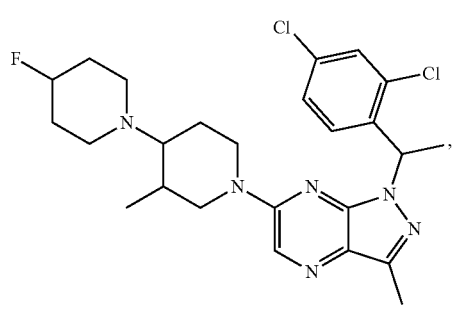
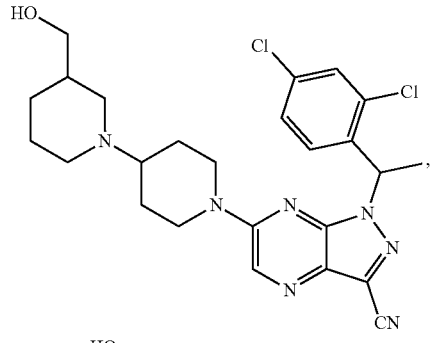
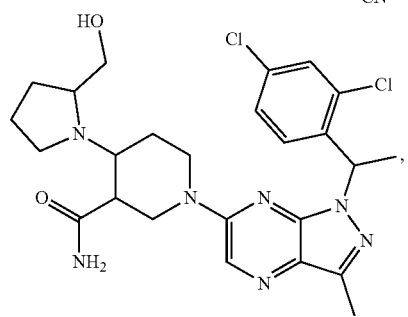
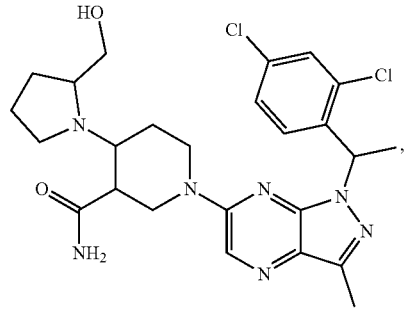
88
-continued
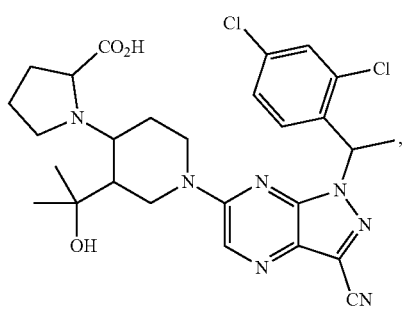
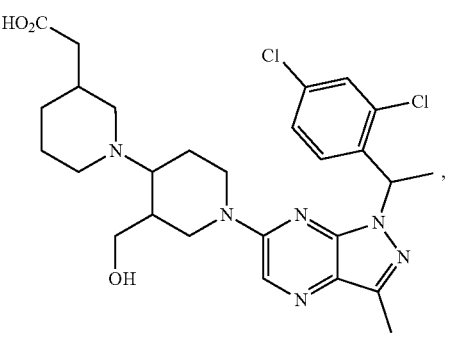
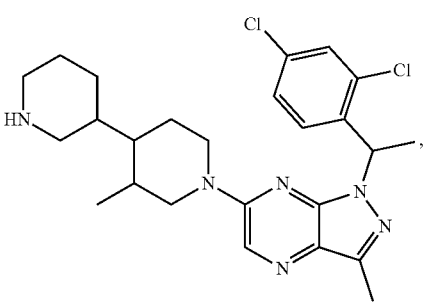
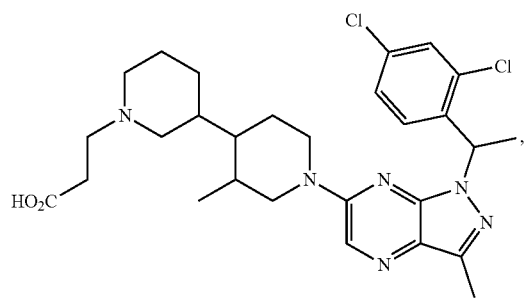
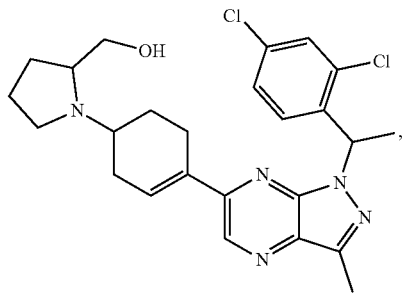

-continued
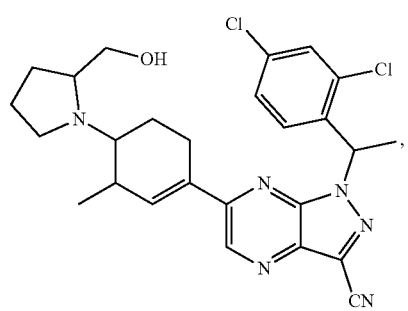
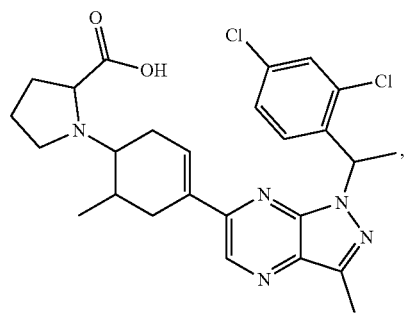
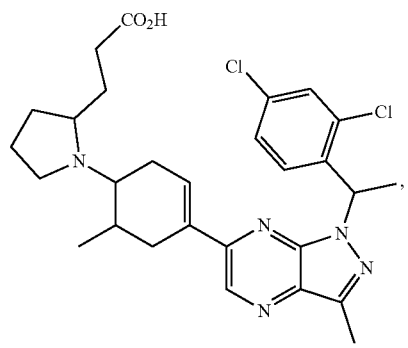
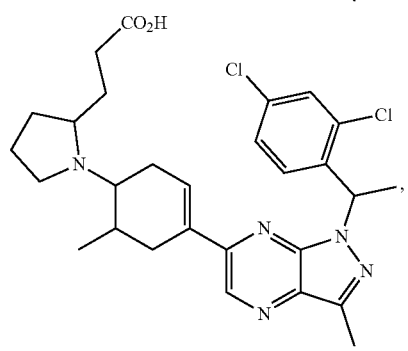
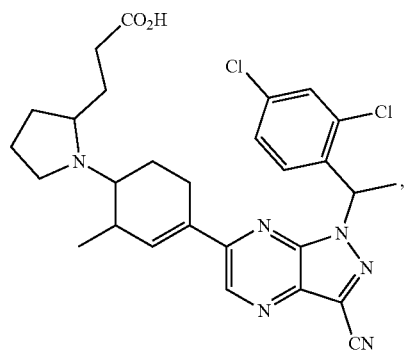
-continued
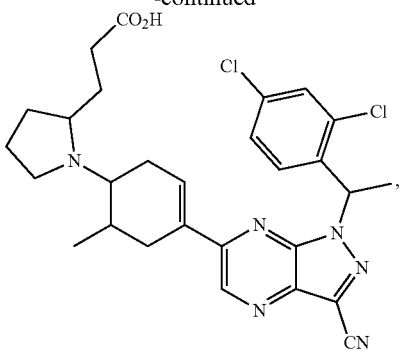
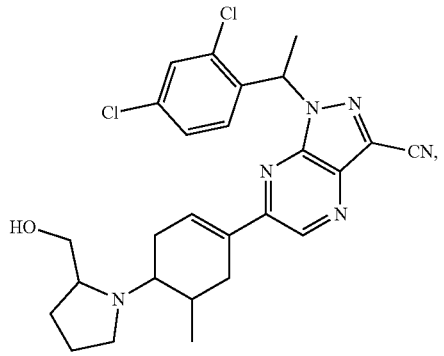
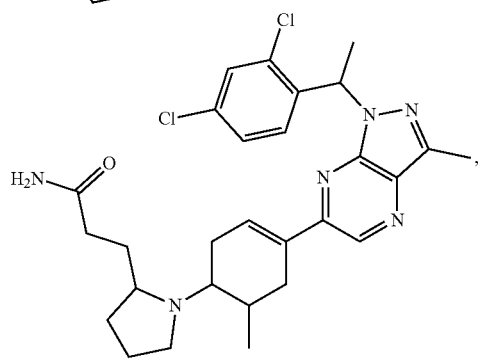
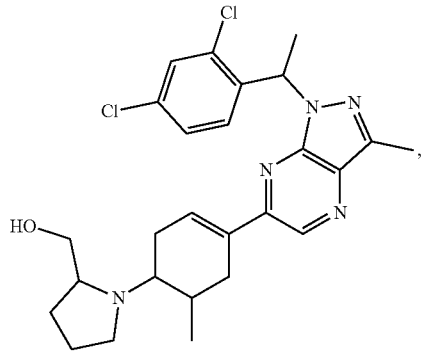
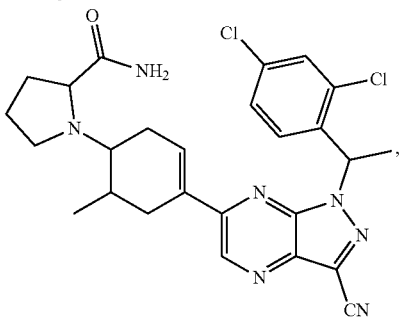

-continued
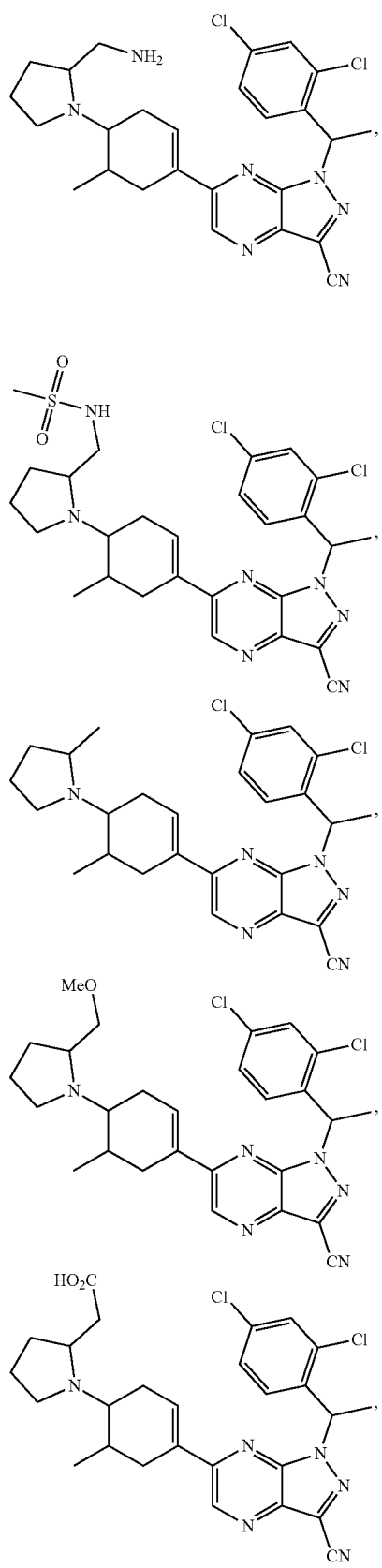
-continued
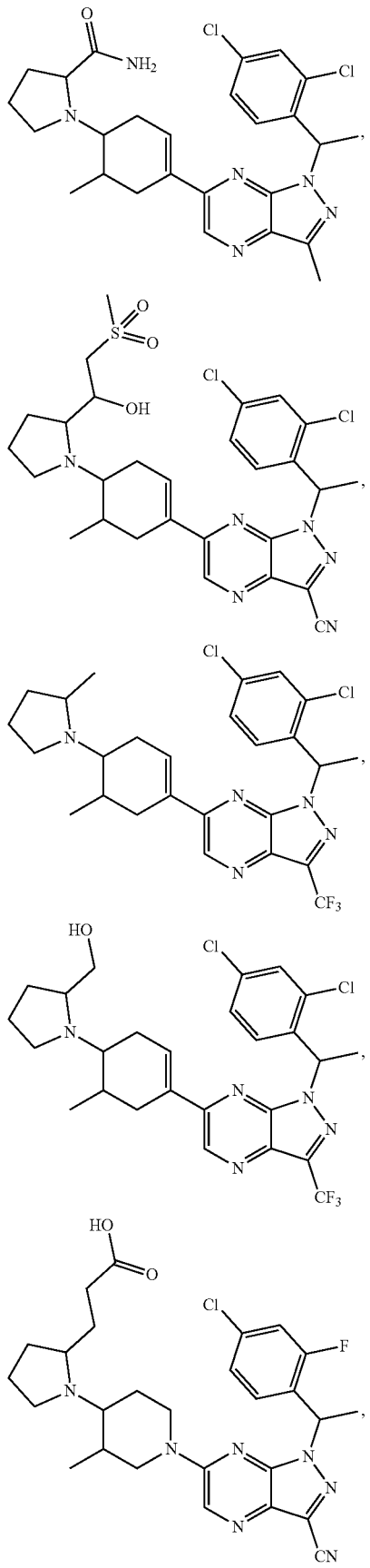

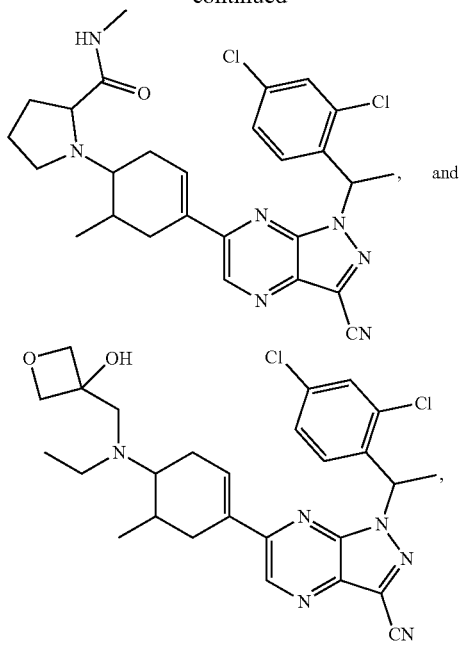

or a pharmaceutically acceptable salt of any of the foregoing compounds.

Another group of CCR4 modulators are compounds disclosed in U.S. Patent Application 62/481,515 filed Apr. 4, 2017, of Beck et al. (e.g., for example, compounds of Formulae I through VI), which are incorporated herein by reference in its entirety for all purposes. In embodiments, the compounds having Formula III:

(III)

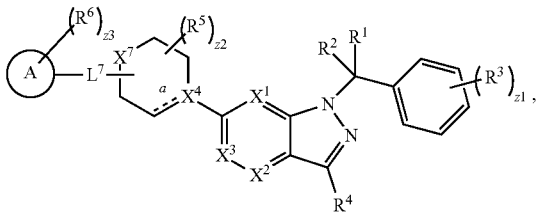

or a pharmaceutically acceptable salt thereof, wherein:

A is substituted or unsubstituted cycloalkyl or substituted or unsubstituted heterocycloalkyl;

$X^1$ is $CR^8$ or N;
$X^2$ is $CR^9$ or N;
$X^3$ is $CR^{10}$ or N;
$X^4$ is C, $CR^{11}$ or N;
$X^7$ is $NR^{17}$ or N, wherein when $L^7$ is covalently bound to $X^7$, then $X^7$ is N;

n1, n2, n3, n4, n5, n6, n8, n9, n10, n11, and n17 are independently an integer from 0 to 4;

m1, m2, m3, m4, m5, m6, m8, m9, m10, m11, m17, v1, v2, v3, v4, v5, v6, v8, v9, v10, v11, and v17 are independently 1 or 2;

z1 is an integer from 0 to 5;
z2 is an integer from 0 to 8;
z3 is an integer from 0 to 12;

 is a single bond or double bond, wherein if  is a single bond, then $X^4$ is $CR^{11}$ or N, and if  is a double bond, then $X^4$ is C;

$L^7$ is a bond, —O—, —S—, $—NR^{7B}$—, —C(O)—, —C(O)O—, —S(O)—, $—S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, $—CX^{1.1}_3$, $—CHX^{1.1}_2$, $—CH_2X^{1.1}$, —CN, $—SO_{n1}R^{1A}$, $—SO_{v1}NR^{1B}R^{1C}$, $—NHNR^{1B}R^{1C}$, $—ONR^{1B}R^{1C}$, $—NHC(O)NHNR^{1B}R^{1C}$, $—NHC(O)NR^{1B}R^{1C}$, $—N(O)_{m1}$, $—NR^{1B}R^{1C}$, $—C(O)R^{1D}$, $—C(O)OR^{1D}$, $—C(O)NR^{1B}R^{1C}$, $—OR^{1A}$, $—NR^{1B}SO_2R^{1A}$, $—NR^{1B}C(O)R^{1D}$, $—NR^{1B}C(O)OR^{1D}$, $—NR^{1B}OR^{1D}$, $—OCX^{1.1}_3$, $—OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $—CX^{2.1}_3$, $—CHX^{2.1}_2$, $—CH_2X^{2.1}$, —CN, $—SO_{n2}R^{2A}$, $—SO_{v2}NR^{2B}R^{2C}$, $—NHNR^{2B}R^{2C}$, $—ONR^{2B}R^{2C}$, $—NHC(O)NHNR^{2B}R^{2C}$, $—NHC(O)NR^{2B}R^{2C}$, $—N(O)_{m2}$, $—NR^{2B}R^{2C}$, $—C(O)R^{2D}$, $—C(O)OR^{2D}$, $—C(O)NR^{2B}R^{2C}$, $—OR^{2A}$, $—NR^{2B}SO_2R^{2A}$, $—NR^{2B}C(O)R^{2D}$, $—NR^{2B}C(O)OR^{2D}$, $—NR^{2B}OR^{2D}$, $—OCX^{2.1}_3$, $—OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, $—CX^{3.1}_3$, $—CHX^{3.1}_2$, $—CH_2X^{3.1}$, —CN, $—SO_{n3}R^{3A}$, $—SO_{v3}NR^{3B}R^{3C}$, $—NHNR^{3B}R^{3C}$, $—ONR^{3B}R^{3C}$, —NHC(O)NHNR^{3B}R^{3C}$, $—NHC(O)NR^{3B}R^{3C}$, $—N(O)_{m3}$, $—NR^{3B}R^{3C}$, $—C(O)R^{3D}$, $—C(O)OR^{3D}$, $—C(O)NR^{3B}R^{3C}$, $—OR^{3A}$, $—NR^{3B}SO_2R^{3A}$, $—NR^{3B}C(O)R^{3D}$, $—NR^{3B}C(O)OR^{3D}$, $—NR^{3B}OR^{3D}$, $—OCX^{3.1}_3$, $—OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, $—CX^{4.1}_3$, $—CHX^{4.1}_2$, $—CH_2X^{4.1}$, —CN, $—SO_{n4}R^{4A}$, $—SO_{v4}NR^{4B}R^{4C}$, $—NHNR^{4B}R^{4C}$, $—ONR^{4B}R^{4C}$, $—NHC(O)NHNR^{4B}R^{4C}$, $—NHC(O)NR^{4B}R^{4C}$, $—N(O)_{m4}$, $—NR^{4B}R^{4C}$, $—C(O)R^{4D}$, $—C(O)OR^{4D}$, $—C(O)NR^{4B}R^{4C}$, $—OR^{4A}$, $—NR^{4B}SO_2R^{4A}$, $—NR^{4B}C(O)R^{4D}$, $—NR^{4B}C(O)OR^{4D}$, $—NR^{4B}OR^{4D}$, $—OCX^{4.1}_3$, $—OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, $—CX^{5.1}_3$, $—CHX^{5.1}_2$, $—CH_2X^{5.1}$, —CN, $—SO_{n5}R^{5A}$, $—SO_{v5}NR^{5B}R^{5C}$, $—NHNR^{5B}R^{5C}$, $—ONR^{5B}R^{5C}$, —NHC(O)NHNR^{5B}R^{5C}$, $—NHC(O)NR^{5B}R^{5C}$, $—N(O)_{m5}$, $—NR^{5B}R^{5C}$, $—C(O)R^{5D}$, $—C(O)OR^{5D}$, $—C(O)NR^{5B}R^{5C}$, $—OR^{5A}$, $—NR^{5B}SO_2R^{5A}$, $—NR^{5B}C(O)R^{5D}$, $—NR^{5B}C(O)OR^{5D}$, $—NR^{5B}OR^{5D}$, $—OCX^{5.1}_3$, $—OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, $—CX^{6.1}_3$, $—CHX^{6.1}_2$, $—CH_2X^{6.1}$, —CN, $—SO_{n6}R^{6A}$, $—SO_{v6}NR^{6B}R^{6C}$, $—NHNR^{6B}R^{6C}$, $—ONR^{6B}R^{6C}$, —NHC (O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}$$_3$, —OCHX$^{6.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^8$ is hydrogen, halogen, —CX$^{8.1}$$_3$, —CHX$^{8.1}$$_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}$$_3$, —OCHX$^{8.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}$$_3$, —CHX$^{9.1}$$_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}$$_3$, —OCHX$^{9.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10.1}$$_3$, —CHX$^{10.1}$$_2$, —CH$_2$X$^{10.1}$, —CN, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}$$_3$, —OCHX$^{10.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11.1}$$_3$, —CHX$^{11.1}$$_2$, —CH$_2$X$^{11.1}$, —CN, —SO$_{n11}$R$^{11A}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m11}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}$$_3$, —OCHX$^{11.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17.1}$$_3$, —CHX$^{17.1}$$_2$, —CH$_2$X$^{17.1}$, —CN, —SO$_{n17}$R$^{17A}$, —SO$_{v17}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m17}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}$$_3$, —OCHX$^{1.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{17A}$, R$^{17B}$, R$^{17C}$ and R$^{17D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$, R$^{4B}$ and R$^{4C}$, R$^{5B}$ and R$^{5C}$, R$^{6B}$ and R$^{6C}$, R$^{8B}$ and R$^{8C}$, R$^{9B}$ and R$^{9C}$, R$^{10B}$ and R$^{10C}$ R$^{11B}$ and R$^{11C}$ and R$^{17B}$ and R$^{17C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{8.1}$, X$^{9.1}$, X$^{10.1}$, X$^{11.1}$ and X$^{17.1}$ are independently —Cl, —Br, —I or —F, wherein at least one of X$^1$, X$^2$ and X$^3$ is N.

In embodiments, the compounds of formula (III) are modulators of CCR4 activity. In embodiments, the compounds of formula (III) are CCR4 antagonists.

In embodiments, pharmaceutically acceptable salts of the compounds disclosed in U.S. Patent Application 62/481,515 filed Apr. 4, 2017 of Beck et al (e.g., for example, compounds of Formulae I through VI) are used as CCR4 modulators. In embodiments, the CCR4 modulators are the compounds selected from the group consisting of:

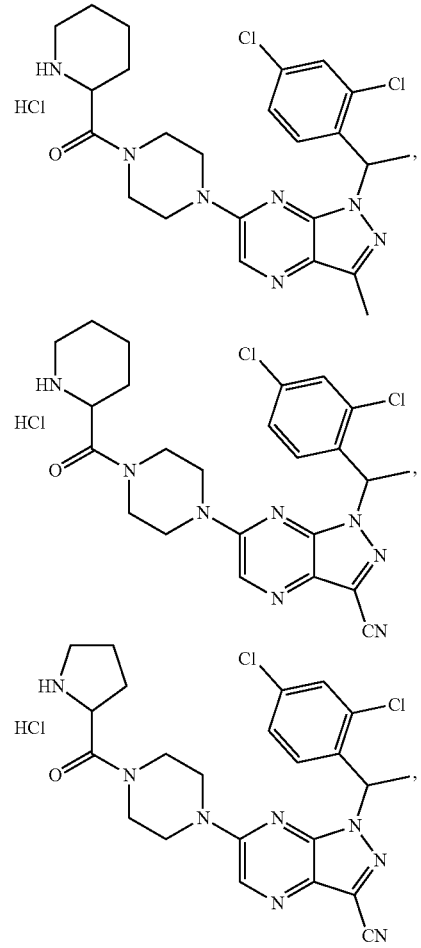

97
-continued
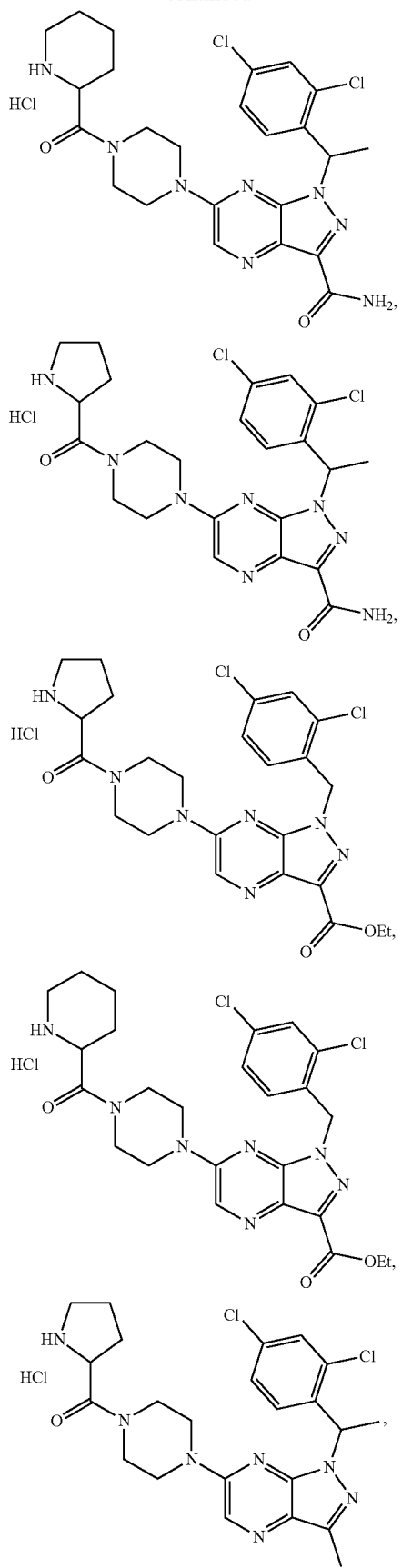
98
-continued
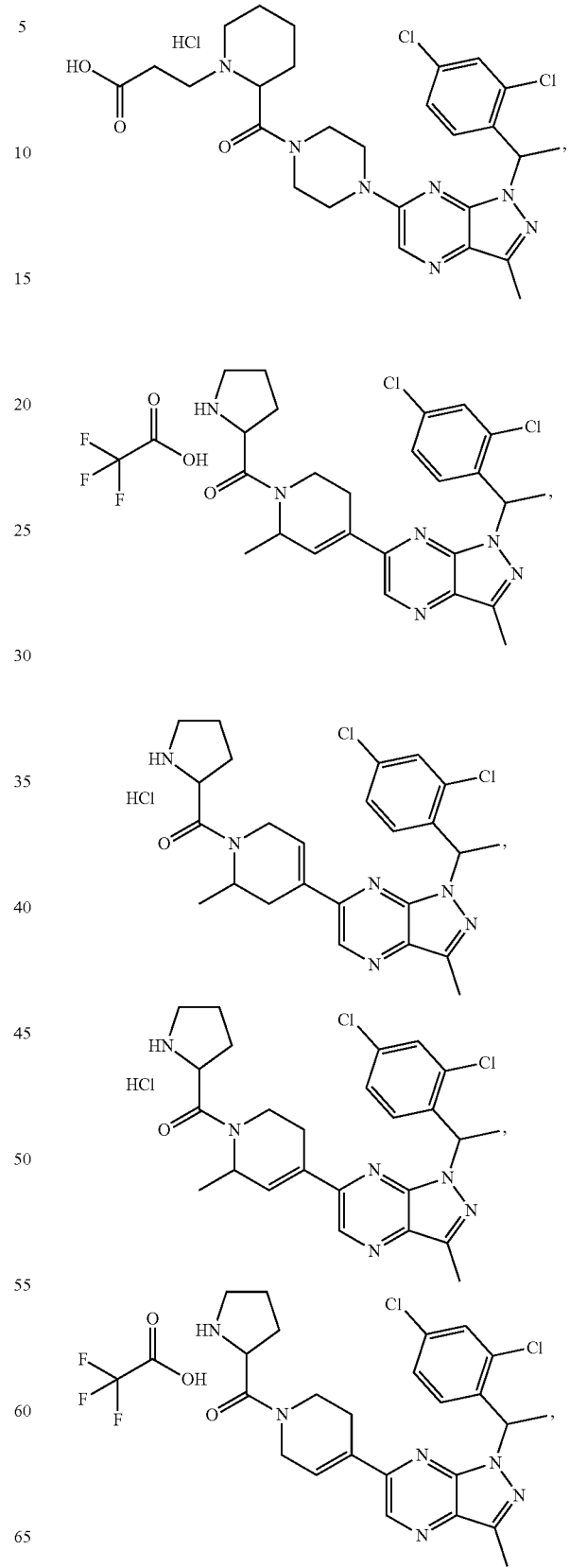

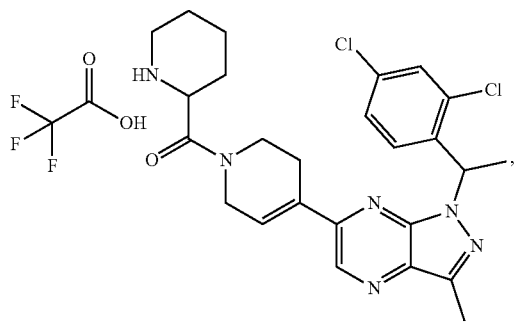
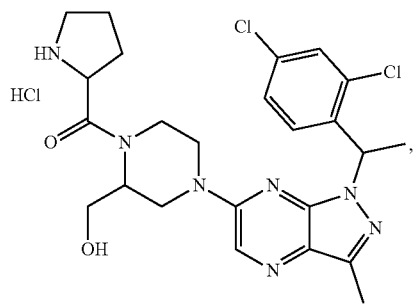
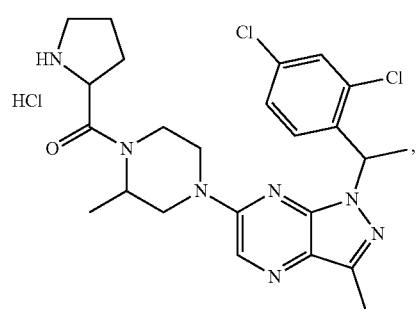
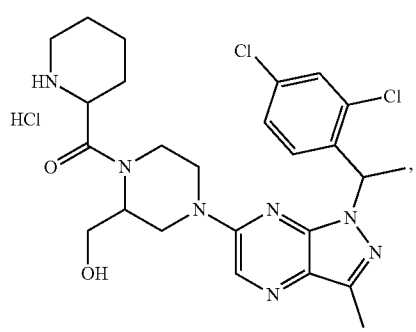
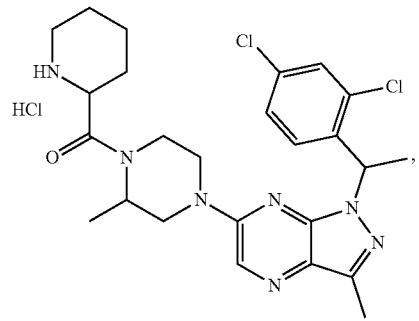
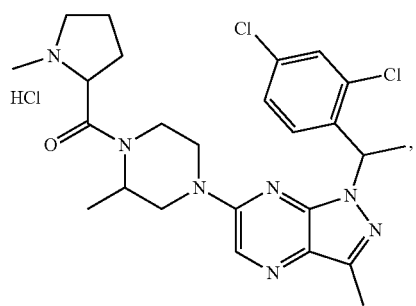
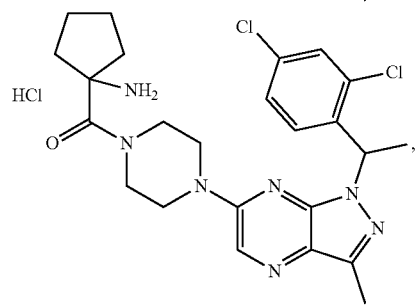
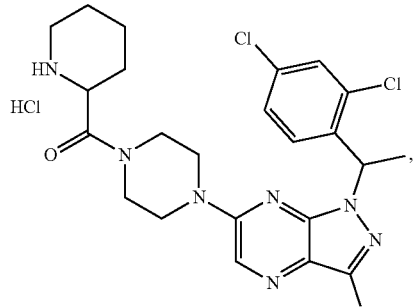
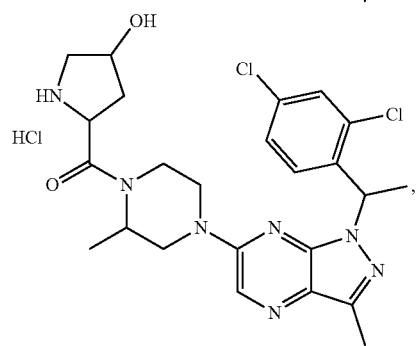
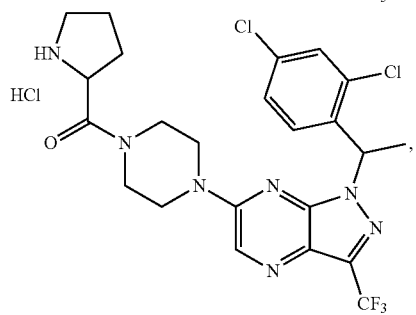

-continued

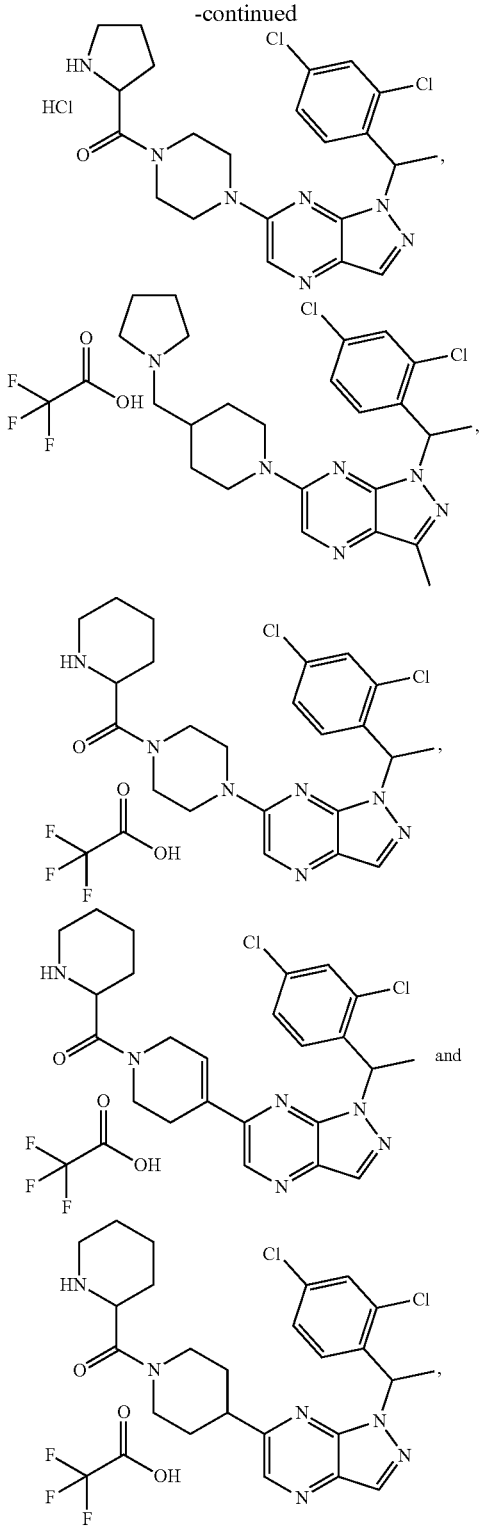

or a pharmaceutically acceptable salt of any of the foregoing compounds.

Another group of CCR4 modulators are compounds disclosed in U.S. Patent Application 62/622,774 filed Jan. 26, 2018, of Robles-Resendiz et al. (e.g., for example, compounds of Formulae I through VII), which are incorporated herein by reference in its entirety for all purposes. In embodiments, the compounds having Formula IV:

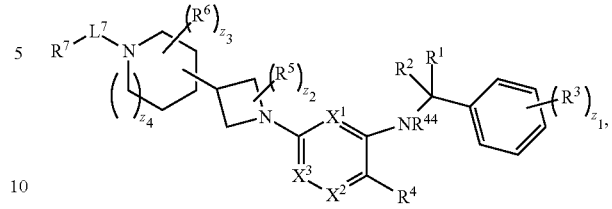

(IV)

or a pharmaceutically acceptable salt thereof,
wherein:
$X^1$ is $CR^8$ or N;
$X^2$ is $CR^9$ or N;
$X^3$ is $CR^{10}$ or N;
n1, n2, n3, n4, n5, n6, n7, n8, n9, n10, and n44 are independently an integer from 0 to 4;
m1, m2, m3, m4, m5, m6, m7, m8, m9, m10, v1, v2, v3, v4, v5, v6, v7, v8, v9, v10, and v44 are independently 1 or 2;
z1 is an integer from 0 to 5;
z2 is an integer from 0 to 4;
z3 is an integer from 0 to 11;
z4 is an integer from 0 to 2;
$L^7$ is a bond, —O—, —S—, —$NR^{7.2B}$—, —C(O)—, —C(O)O—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, —$OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, —$OCH_2X^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently halogen, —$CX^{3.1}_3$, —$CHX^{3.1}_2$, —$CH_2X^{3.1}$, —CN, —$N_3$, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.2}$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^4$ is hydrogen, halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —NHNR$^{4B}$R$^{4C}$, —ONR$^{4B}$R$^{4C}$, —NHC(O)NHNR$^{4B}$R$^{4C}$, —NHC(O)NR$^{4B}$R$^{4C}$, —N(O)$_{m4}$, —NR$^{4B}$R$^{4C}$, —C(O)R$^{4D}$, —C(O)OR$^{4D}$, —C(O)NR$^{4B}$R$^{4C}$, —OR$^{4A}$, —NR$^{4B}$SO$_2$R$^{4A}$, —NR$^{4B}$C(O)R$^{4D}$, —NR$^{4B}$C(O)OR$^{4D}$, —NR$^{4B}$OR$^{4D}$, —OCX$^{4.1}_3$, —OCHX$^{4.1}_2$, —OCH$_2$X$^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or when X$^2$ is CR$^9$, then R$^4$ and R$^9$ may optionally be joined to form a substituted or unsubstituted cycloalkyl, substituted or unsubstituted heterocycloalkyl, substituted or unsubstituted aryl, or substituted or unsubstituted heteroaryl;

R$^5$ is independently halogen, oxo, —CX$^{5.1}_3$, —CHX$^{5.1}_2$, —CH$_2$X$^{5.1}$, —CN, —N$_3$, —SO$_{n5}$R$^{5A}$, —SO$_{v5}$NR$^{5B}$R$^{5C}$, —NHNR$^{5B}$R$^{5C}$, —ONR$^{5B}$R$^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^{5.1}_3$, —OCHX$^{5.1}_2$, —OCH$_2$X$^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^6$ is independently halogen, oxo, —CX$^{6.1}_3$, —CHX$^{6.1}_2$, —CH$_2$X$^{6.1}$, —CN, —N$_3$, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, —OCH$_2$X$^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^7$ is hydrogen, halogen, —CX$^{7.1}_3$, —CHX$^{7.1}_2$, —CH$_2$X$^{7.1}$, —CN, —N$_3$, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7B}$C(O)R$^{7D}$, —NR$^{7B}$C(O)OR$^{7D}$, —NR$^{7B}$OR$^{7D}$, —OCX$^{7.1}_3$, —OCHX$^{7.1}_2$, —OCH$_2$X$^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^8$ is hydrogen, halogen, —CX$^{8.1}_3$, —CHX$^{8.1}_2$, —CH$_2$X$^{8.1}$, —CN, —N$_3$, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, —OCH$_2$X$^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}_3$, —CHX$^{9.1}_2$, —CH$_2$X$^{9.1}$, —CN, —N$_3$, —SO$_9$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, —OCH$_2$X$^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or when X$^2$ is CR$^9$, then R$^4$ and R$^9$ may optionally be joined to form a substituted or unsubstituted cycloalkyl, substituted or unsubstituted heterocycloalkyl, substituted or unsubstituted aryl, or substituted or unsubstituted heteroaryl; or when X$^2$ is CR$^9$ and X$^3$ is CR$^{10}$, then R$^9$ and R$^{10}$ may optionally be joined to form a substituted or unsubstituted cycloalkyl, substituted or unsubstituted heterocycloalkyl, or unsubstituted aryl, or substituted or unsubstituted heteroaryl;

R$^{10}$ is hydrogen, halogen, —CX$^{10.1}_3$, —CHX$^{10.1}_2$, —CH$_2$X$^{10.1}$, —CN, —N$_3$, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, —OCH$_2$X$^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or when X$^2$ is CR$^9$ and X$^3$ is CR$^{10}$, then R$^9$ and R$^{10}$ may optionally be joined to form a substituted or unsubstituted cycloalkyl, substituted or unsubstituted heterocycloalkyl, or unsubstituted aryl, or substituted or unsubstituted heteroaryl;

R$^{44}$ is hydrogen, —CX$^{44.1}_3$, —CHX$^{44.1}_2$, —CH$_2$X$^{44.1}$, —SO$_{n44}$R$^{44A}$, —SO$_{v44}$NR$^{44B}$R$^{44C}$, —C(O)R$^{44D}$, —C(O)OR$^{44D}$, —C(O)NR$^{44B}$R$^{44C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{7.2B}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{44A}$, R$^{44B}$, R$^{44C}$, and R$^{44D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{44B}$, and R$^{44C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, and X$^{44.1}$ are independently —Cl, —Br, —I or —F;

wherein at least one of X$^1$, X$^2$ and X$^3$ is N.

In embodiments, the compounds of formula (IV) are modulators of CCR4 activity. In embodiments, the compounds of formula (IV) are CCR4 antagonists.

In embodiments, pharmaceutically acceptable salts of the compounds disclosed in U.S. Patent Application 62/622,774 filed Jan. 26, 2018, of Robles-Resendiz et al. (e.g., for example, compounds of Formulae I through VII) are used as CCR4 modulators. In embodiments, the CCR4 modulators are the compounds selected from the group consisting of:

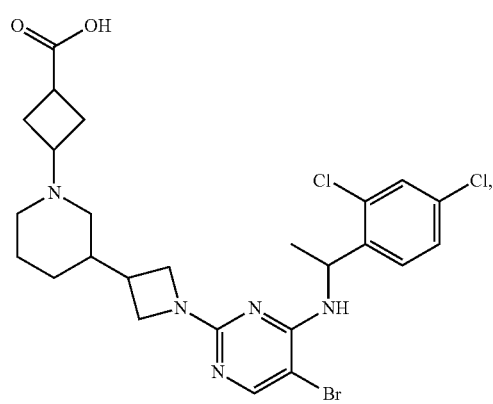
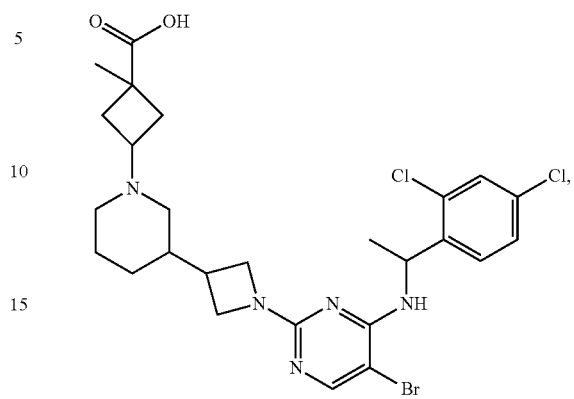
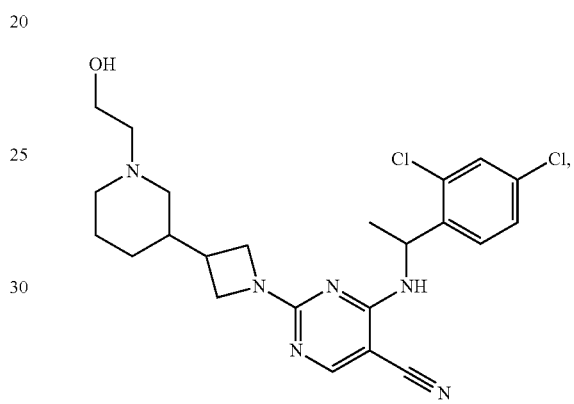
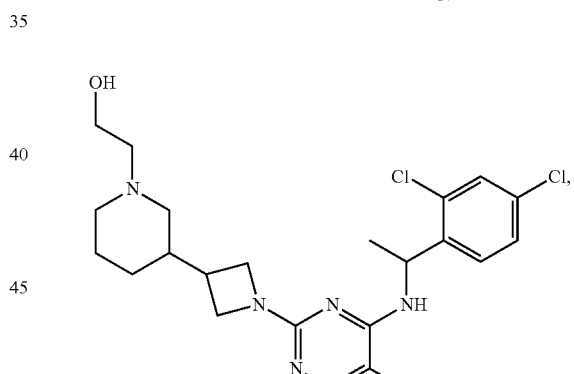
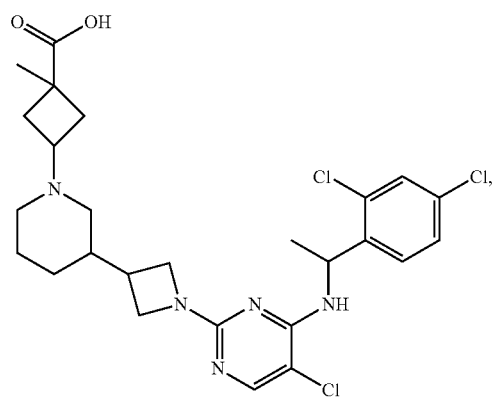
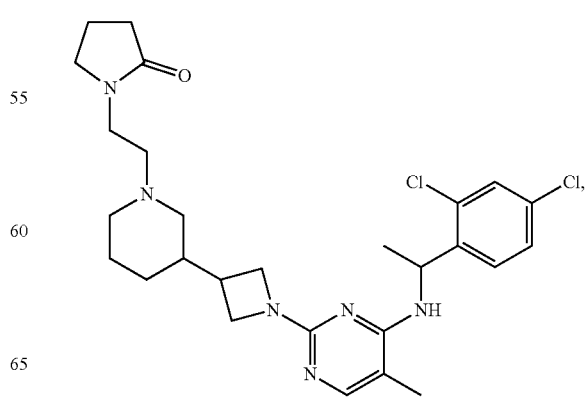

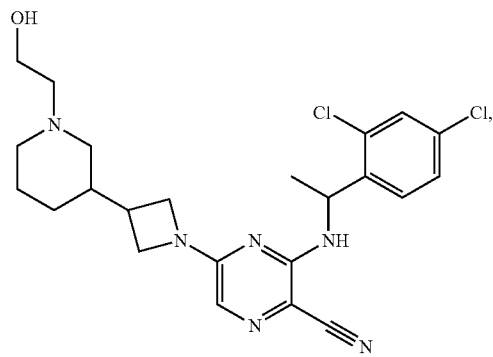
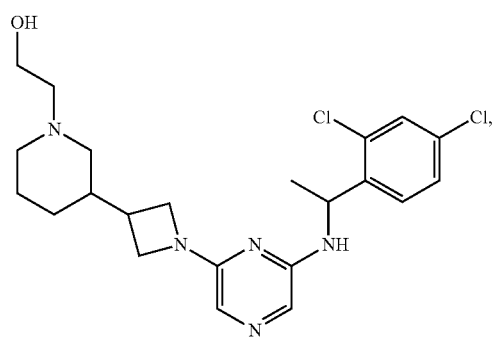
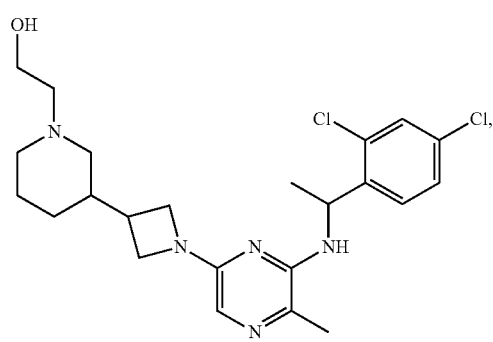
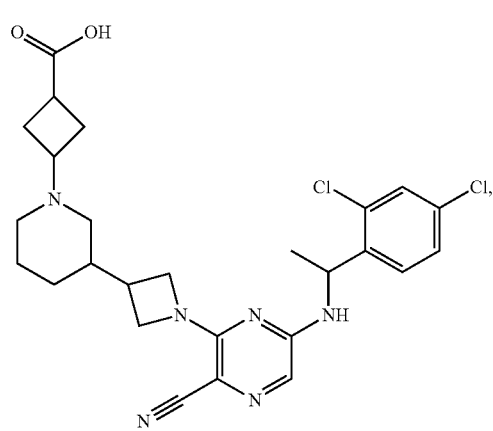
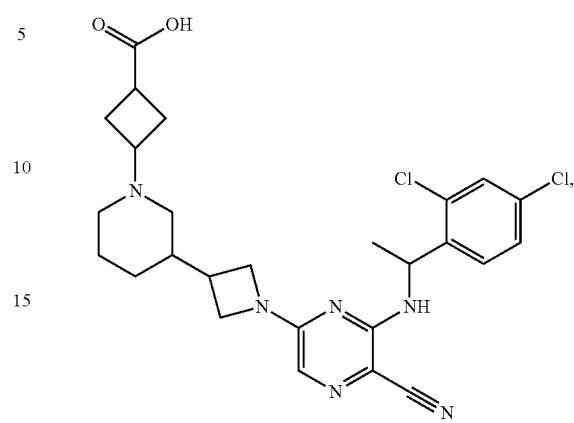
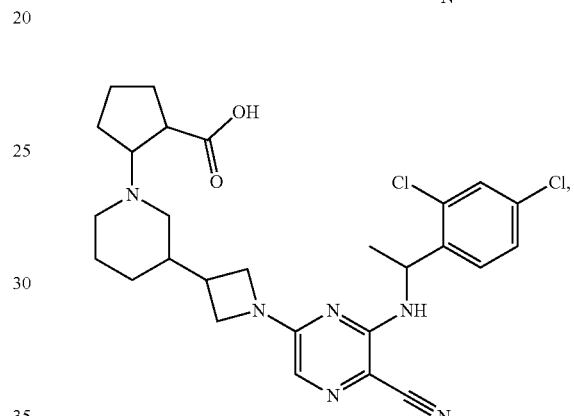
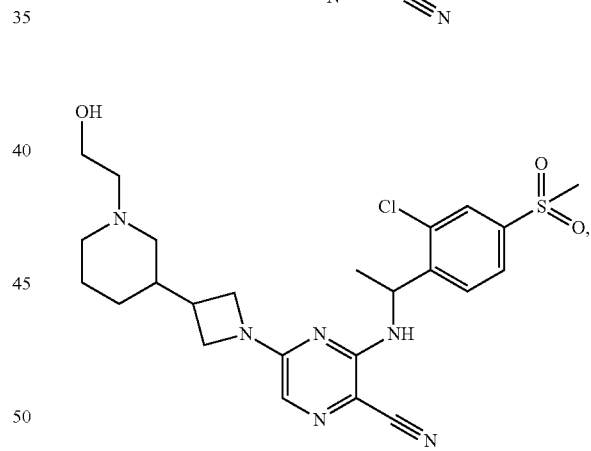
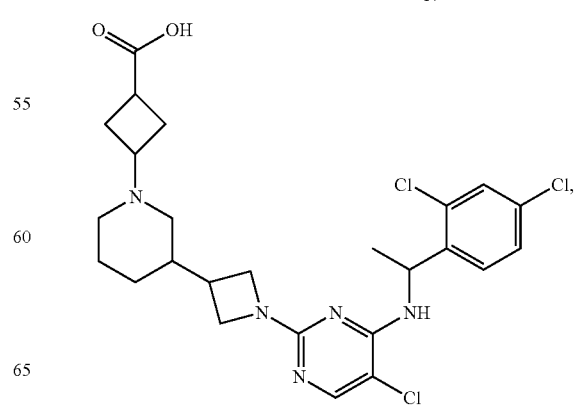

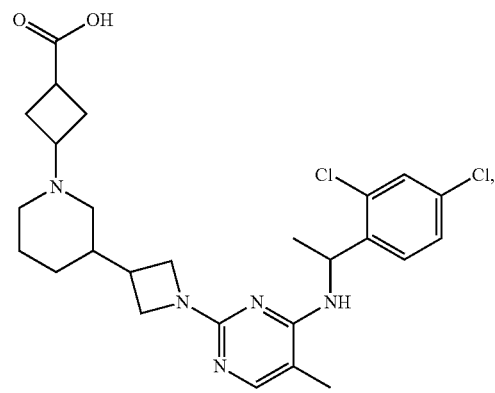
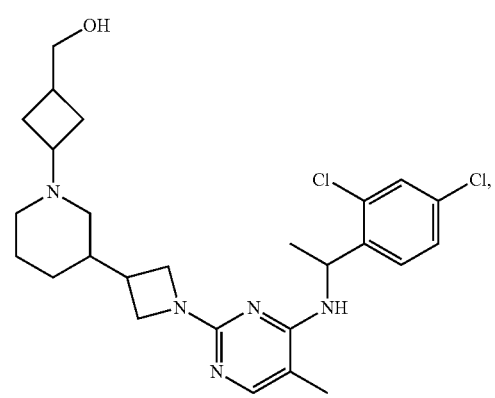
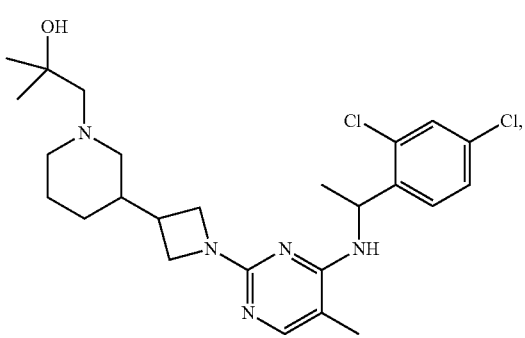
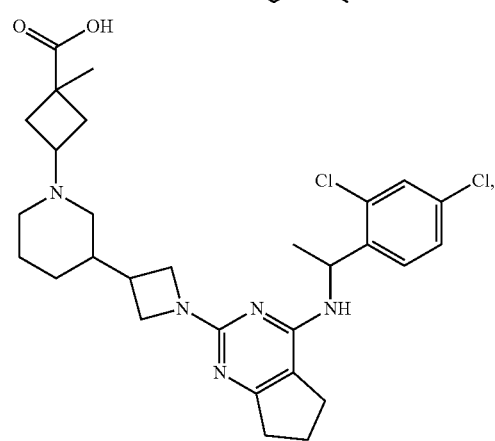
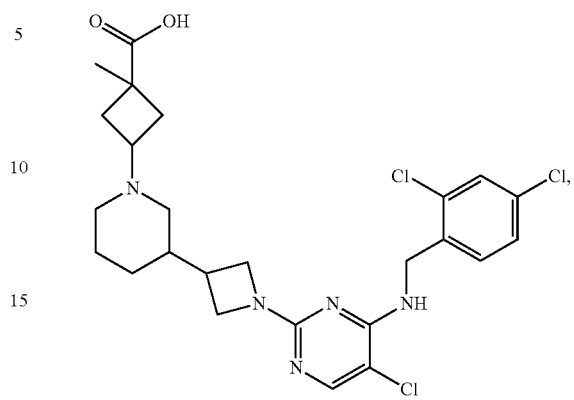
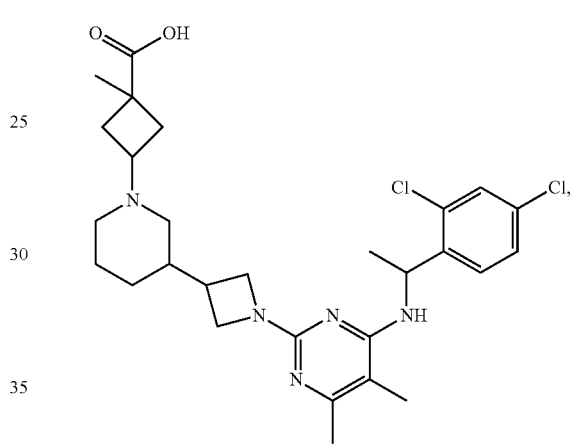
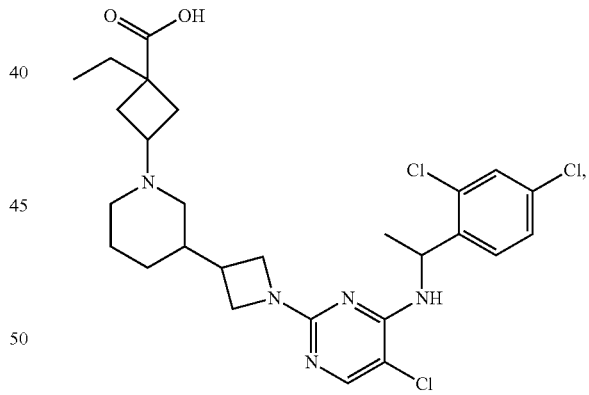
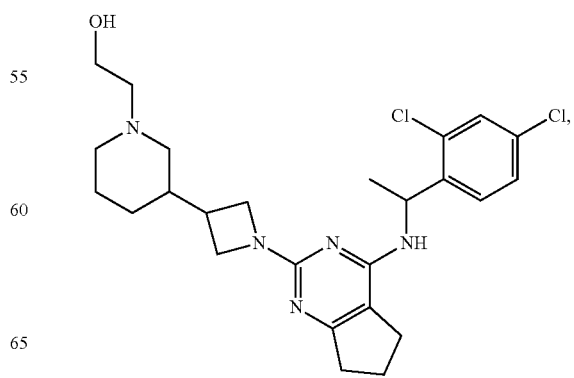

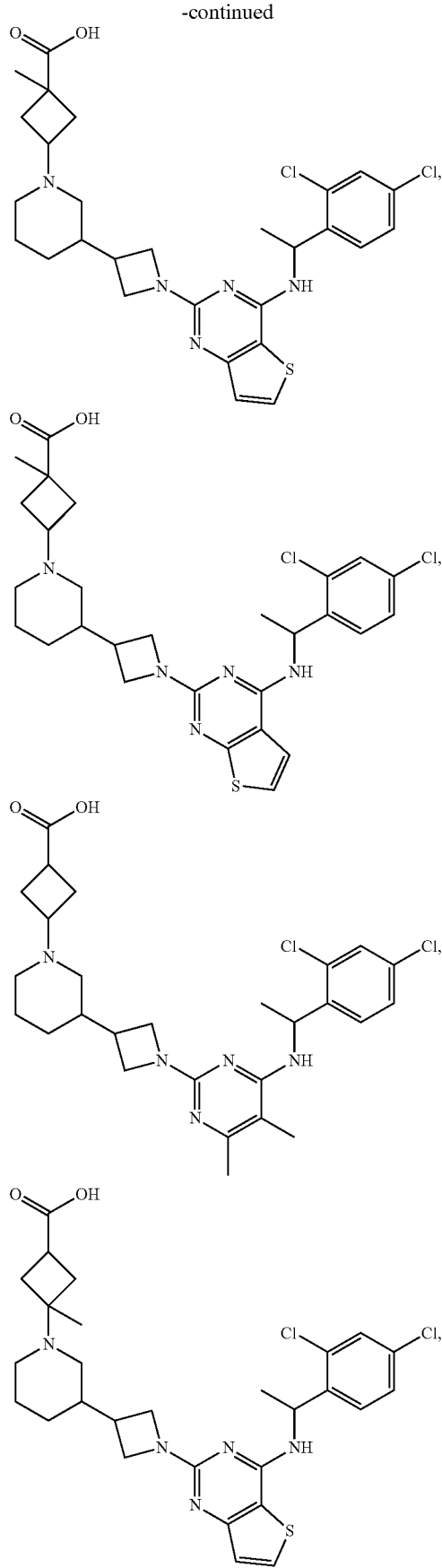
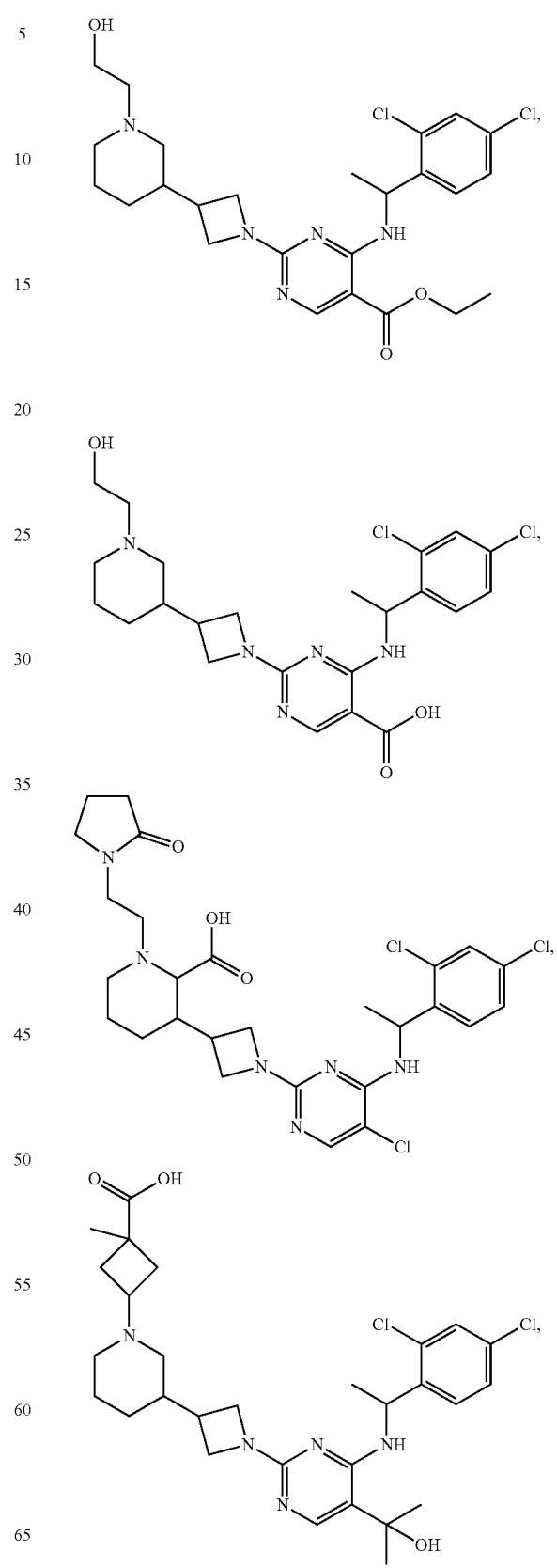

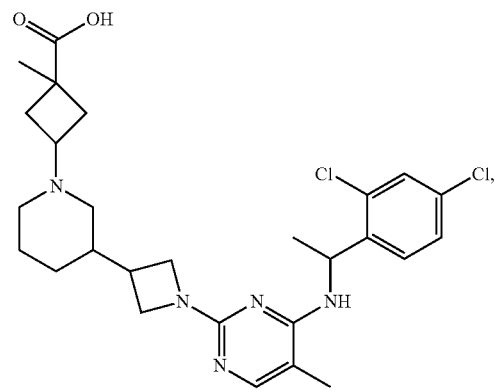
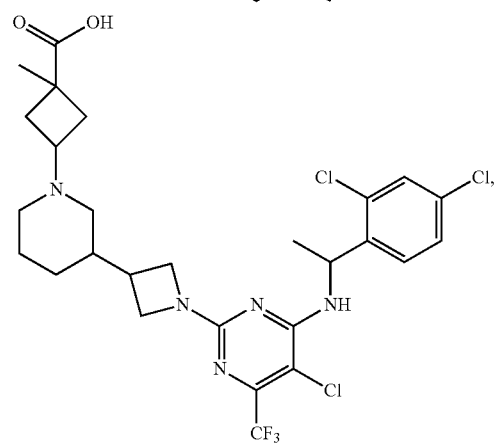
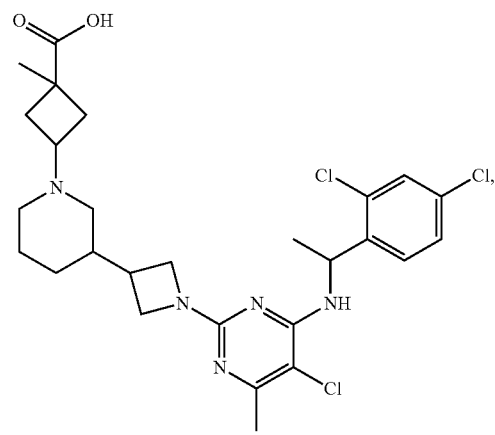
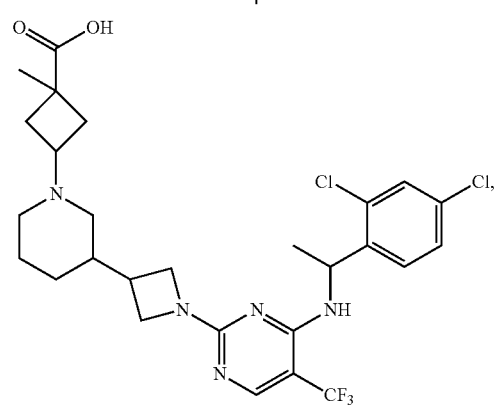
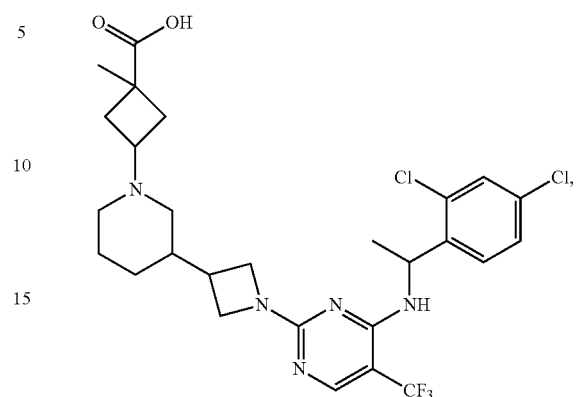
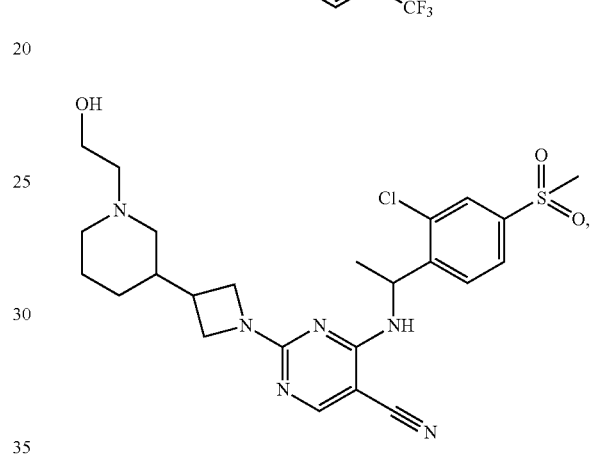
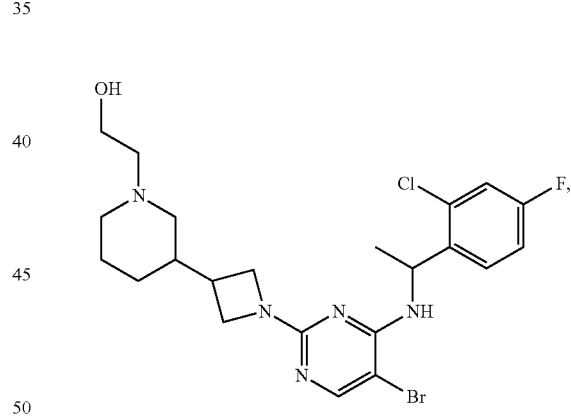
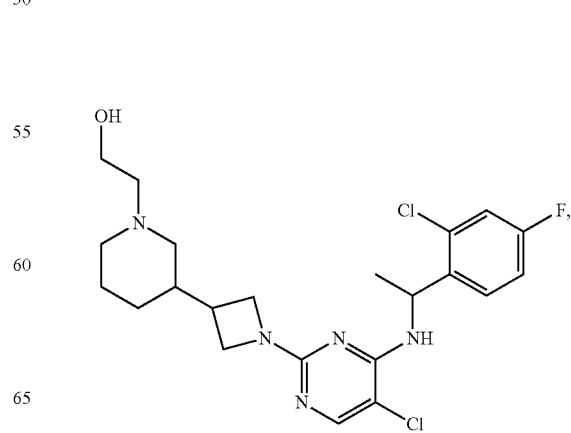

-continued
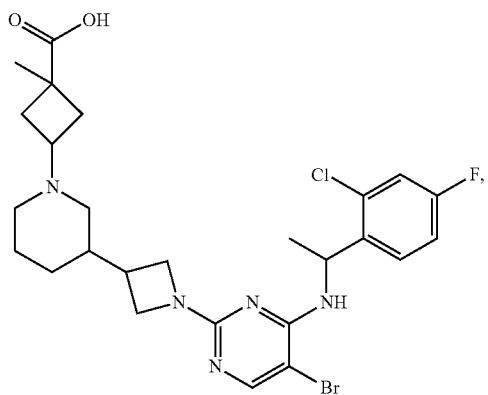
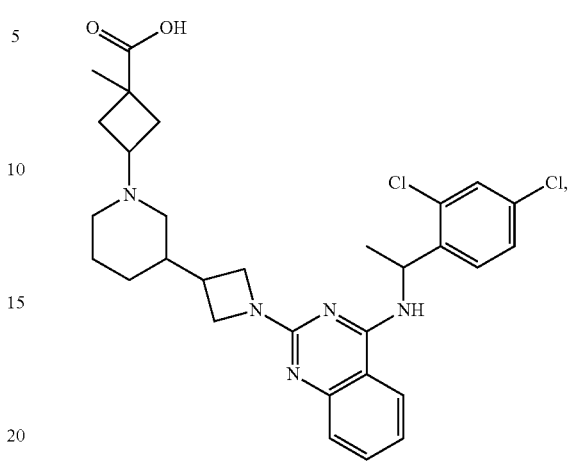
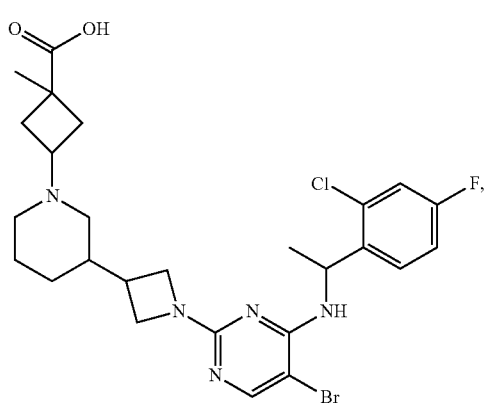
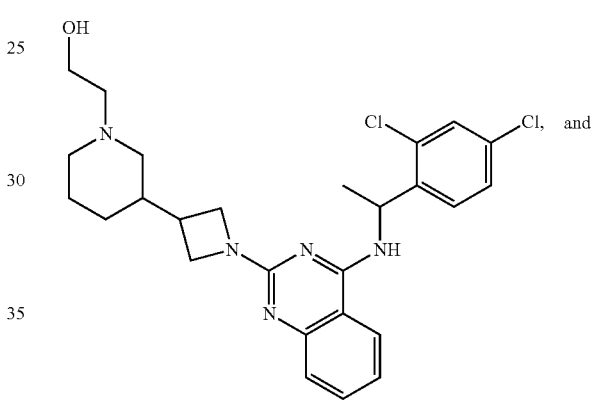
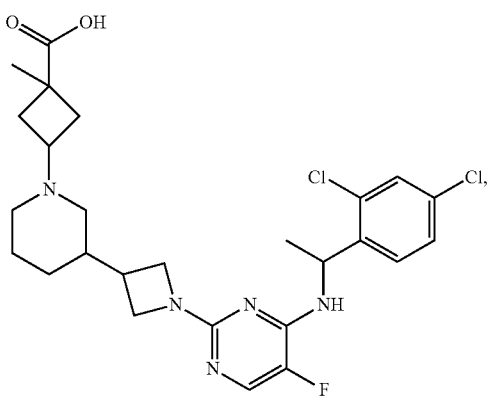
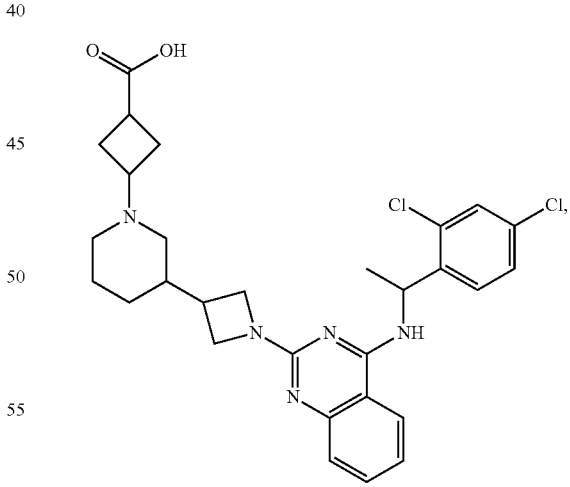
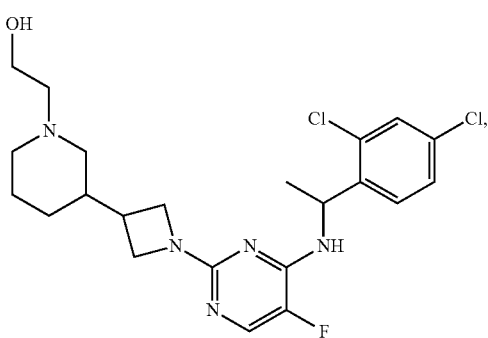
or a pharmaceutically acceptable salt of any of the foregoing compounds.
Another group of CCR4 modulators are compounds disclosed in U.S. Patent Application 62/622,771 filed Jan. 26, 2018, of Jackson et al., which are incorporated herein by reference in its entirety for all purposes. In embodiments, the compound having Formula V:

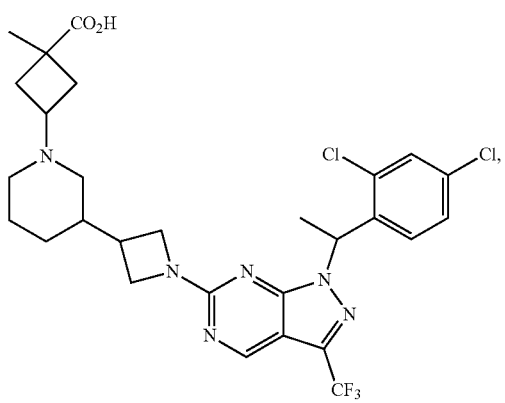

(V)

or a pharmaceutically acceptable salt thereof.

In embodiments, the compounds of formula (V) are modulators of CCR4 activity. In embodiments, the compounds of formula (V) are CCR4 antagonists.

In embodiments, pharmaceutically acceptable salts of the compounds disclosed in U.S. Patent Application 62/622,771 filed Jan. 26, 2018, of Jackson et al. are used as CCR4 modulators. In embodiments, the CCR4 modulator is the compound of formula V:

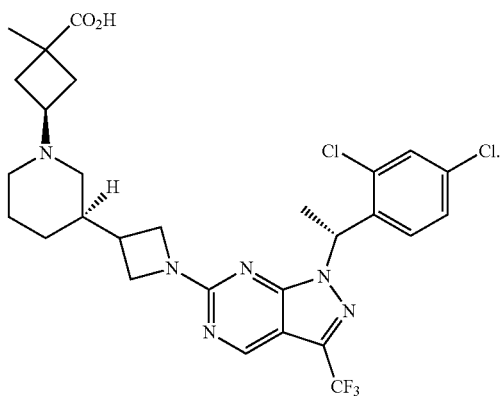

Additional orally administered CCR4 modulators include the compounds disclosed in the following published patent applications: US 2012/0015932 (Hobbs et al); US 2010/0144759 (Cheshire et al); US 2008/0293742 (Cheshire et al); US 2006/0189613 (Cheshire); US 2006/0128723 (Mete et al); US 2006/0122195 (Harrison et al); US 2006/0004010 (Habashita et al); US 2004/0039035 (Collins et al); US 2003/0018022 (Collins et al); US 2002/0173524 (Collins et al); US 2002/0132836 (Dairaghi et al); U.S. Pat. Nos. 5,300,498; 6,509,357; US 2003/149018; WO 01/005758; WO 03/051876; WO 97/042174; WO 2006/101456; WO 2007/065683; WO 2007/065924; WO 2007/115231; WO 2008/045529; WO 2008/094575; WO 2008/094602; WO 2010/118367; and WO 2013/082429, all of which are incorporated herein by reference in their entireties.

Parenterally Administered CCR4 Modulators

The CCR4 modulator used in the presently disclosed therapeutic methods can also be a CCR4-binding antibody. Such antibodies are disclosed in the following published patent applications: US 2017/0290911 (Marasco et al); US 2017/0088627 (Lin et al); US 2016/0185865 (Marasco et al); US 2015/0147321 (Ishii et al); US 2013/0295045 (Shitara et al); US 2007/0031896 (Wu et al); US 2007/0020263 (Shitara et al); and US 2005/0287138 (Lida et al), all of which are incorporated herein by reference in their entireties.

In certain embodiments herein provide salts, cocrystals, solvates (e.g., hydrates), complexes, prodrugs, precursors, metabolites, and/or other derivatives of a CCR4 modulator provided herein. For example, particular embodiments provide salts, cocrystals, solvates (e.g., hydrates), complexes, precursors, metabolites, and/or other derivatives of a CCR4 modulator. Certain embodiments provide a CCR4 modulator that is not salts, cocrystals, solvates (e.g., hydrates), or complexes of a CCR4 modulator provided herein. For example, particular embodiments provide a CCR4 modulator in a non-ionized, non-solvated (e.g., anhydrous), non-complexed form.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers. Where the compound provided herein contains an alkenyl or alkenylene group, the compound may exist as one geometric (i.e., cis/trans or E/Z) isomer or a mixture of geometric (i.e., cis/trans or E/Z) isomers. Unless otherwise specified, a compound provided herein is intended to encompass all geometric isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism. It will be understood that unless otherwise specified, a compound provided herein is intended to encompass all possible tautomers. Similarly, unless otherwise specified, a compound provided herein is intended to encompass all possible stereoisomers.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation. In some instances, for compounds that undergo epimerization in vivo, one of skill in the art will recognize that administration of a compound in its (R) form is equivalent to administration of the compound in its (S) form, and vice versa.

When the compound provided herein contains an acidic or basic moiety, it may also be provided as a pharmaceutically acceptable salt (See, Berge et al., J. Pharm. Sci. 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, .alpha.-oxoglutaric acid, glycolic acid, hippuric acid, hydrobromic acid, hydrochloric acid, hydroiodic acid, (+)-L-lactic acid, (.+−.)-DL-lactic acid, lactobionic acid, lauric acid, maleic acid, (−)-L-malic acid, malonic acid, (.+−.)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound provided herein, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., Curr. Pharm. Design 1999, 5, 265-287; Pauletti et al., Adv. Drug. Delivery Rev. 1997, 27, 235-256; Mizen et al., Pharm. Biotech. 1998, 11, 345-365; Gaignault et al., Pract. Med. Chem. 1996, 671-696; Asgharnejad in "Transport Processes in Pharmaceutical Systems," Amidon et al., Ed., Marcell Dekker, 185-218, 2000; Balant et al., Eur. J. Drug Metab. Pharmacokinet. 1990, 15, 143-53; Balimane and Sinko, Adv. Drug Delivery Rev. 1999, 39, 183-209; Browne, Clin. Neuropharmacol. 1997, 20, 1-12; Bundgaard, Arch. Pharm. Chem. 1979, 86, 1-39; Bundgaard, Controlled Drug Delivery 1987, 17, 179-96; Bundgaard, Adv. Drug Delivery Rev. 1992, 8, 1-38; Fleisher et al., Adv. Drug Delivery Rev. 1996, 19, 115-130; Fleisher et al., Methods Enzymol. 1985, 112, 360-381; Farquhar et al., J. Pharm. Sci. 1983, 72, 324-325; Freeman et al., J. Chem. Soc., Chem. Commun. 1991, 875-877; Friis and Bundgaard, Eur. J. Pharm. Sci. 1996, 4, 49-59; Gangwar et al., Des. Biopharm. Prop. Prodrugs Analogs, 1977, 409-421; Nathwani and Wood, Drugs 1993, 45, 866-94; Sinhababu and Thakker, Adv. Drug Delivery Rev. 1996, 19, 241-273; Stella et al., Drugs 1985, 29, 455-73; Tan et al., Adv. Drug Delivery Rev. 1999, 39, 117-151; Taylor, Adv. Drug Delivery Rev. 1996, 19, 131-148; Valentino and Borchardt, Drug Discovery Today 1997, 2, 148-155; Wiebe and Knaus, Adv. Drug Delivery Rev. 1999, 39, 63-80; and Waller et al., Br. J. Clin. Pharmac. 1989, 28, 497-507.

Pharmaceutical Compositions

In an aspect, provided are compositions for treatment of EBV+ malignancies. The compounds (the compound of formulae (I), (II), (III), (IV), or (V)) of the present disclosure may be in the form of compositions suitable for administration to a subject. In general, such compositions are "pharmaceutical compositions" comprising a compound (e.g., the compound of formulae (I), (II), (III), (IV), or (V)) and one or more pharmaceutically acceptable or physiologically acceptable diluents, carriers or excipients. In certain embodiments, the compound (e.g., the compound of formulae (I), (II), (III), (IV), or (V)) is present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., the compound of formulae (I), (II), (III), (IV), or (V) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrylate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethyl cellulose, methylcellulose, hydroxy-propylmethyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a CCR4 modulator contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a CCR4 modulator, including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., CCR4 modulator) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compound (e.g., CCR4 modulator) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compound (e.g., CCR4 modulator) contemplated by the present disclosure may be in the form of any other suitable pharmaceutical composition (e.g., sprays for nasal or inhalation use) currently known or developed in the future.

Additional Therapeutic Agents

In some embodiments, provided herein is a pharmaceutical composition comprising one, two, three, or more other pharmacologically active substances (also termed herein "additional therapeutic agents," "second active agents," or the like) (e.g., other than a CCR4 modulator). In some embodiments, the formulations of the compound of formulae (I), (II), (III), (IV), or (V) provided herein further comprise one, two, three, or more other pharmacologically active substances (also termed herein "additional therapeutic agents," "second active agents," or the like). In other embodiments, the formulation of the compound of formulae (I), (II), (III), (IV), or (V) provided herein is co-administered with one, two, three, or more other pharmacologically active substances. In particular embodiments, the oral formulations provided herein comprise the additional therapeutic agent(s) in a therapeutically effective amount. In particular embodiments, the formulations of the compound of formulae (I), (II), (III), (IV), or (V) and the additional therapeutic agent(s) are co-formulated together in the same dosage form using methods of co-formulating active pharmaceutical ingredients, including methods disclosed herein and methods known in the art. In other embodiments, the formulations of the compound of formulae (I), (II), (III), (IV), or (V) and the additional therapeutic agent(s) are co-administered in separate dosage forms. It is believed that certain combinations work synergistically in the treatment of particular diseases or disorders, including, e.g., types of EBV-associated cancer and certain diseases and conditions associated with, or characterized by, undesired angiogenesis or abnormal cell proliferation, for example, solid tumors. The formulations of the compound of formulae (I), (II), (III), (IV), or (V) provided herein can also work to alleviate adverse effects associated with certain second active agents, and some second active agents can be used to alleviate adverse effects associated with a CCR4 modulator dosage forms provided herein. In certain embodiments, the formulations of a CCR4 modulator provided herein are co-administered with one or more therapeutic agents to provide a resensitization effect in subjects in need thereof. Additional therapeutic agents can be, e.g., large molecules (e.g., proteins) or small molecules (e.g., synthetic inorganic, organometallic, or organic molecules).

Examples of particular additional therapeutic agents useful in the compositions and methods disclosed herein include, but are not limited to, e.g., cytotoxic agents, antimetabolites, antifolates, HDAC inhibitors (e.g., entinostat, also known as SNDX-275 or MS-275; or vorinostat, also known as suberoylanilide hydroxamic acid (SAHA) or N-hydroxy-N-phenyl-octanediamide), DNA intercalating agents, DNA cross-linking agents, DNA alkylating agents, DNA cleaving agents, topoisomerase inhibitors, HDAC inhibitors such as MGCD0103 (a.k.a. N-(2-aminophenyl)-4-((4-(pyridin-3-yl)pyrimidin-2-ylamino)methyl)benzamide), CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiments, the co-administered therapeutic agent is an immunomodulator. In specific embodiments, the immunomodulatory compound is thalidomide, lenalidomide, or pomalidomide. In particular embodiments, the co-administered therapeutic agent is carboplatin. In particular embodiments, the co-administered therapeutic agent is paclitaxel (e.g., Abraxane®). See, e.g., U.S. Pat. Nos. 7,758,891, 7,771,751, 7,820,788, 7,923,536, 8,034,375; US Patent Publication Nos. 2007/0082838 and 2010/0048499; U.S. Pat. Nos. 5,916,596; 6,506,405; 6,749,868, and 6,537,579; PCT Publication Nos. WO08/057562, WO09/126938, WO09/126401, and WO09/126175; all of which are incorporated herein by reference in their entireties.

In embodiments, the co-administered agent may be dosed orally. In another embodiment, the co-administered agent may be dosed by injection. In one embodiment, the route of the administration of the compound of formulae (I), (II), (III), (IV), or (V) is independent of the route of the administration of the second/co-administered therapy. In one embodiment, the compound of formulae (I), (II), (III), (IV), or (V) is administered orally. In another embodiment, the compound of formulae (I), (II), (III), (IV), or (V) is administered intravenously or subcutaneously. In certain embodiments, the compound of formulae (I), (II), (III), (IV), or (V) is administered orally, and the second therapy is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound of formulae (I), (II), (III), (IV), or (V) and a second therapy agent are administered by the same mode of administration, e.g., orally, intravenously, or subcutaneously. In another embodiment, the compound of formulae (I), (II), (III), (IV), or (V) is administered by one mode of administration, e.g., orally, whereas the second agent (e.g., an anticancer agent) is administered by another mode of administration, e.g., intravenously or subcutaneously. In yet another embodiment, the compound of formulae (I), (II), (III), (IV), or (V) is administered by one mode of administration, e.g., intravenously or subcutaneously, whereas the second agent (e.g., an anticancer agent) is administered by another mode of administration, e.g., orally.

Other examples of additional therapeutic agents include, but are not limited to, hematopoietic growth factor, a cytokine, granulocyte colony-stimulating factor (G-CSF), granulocyte-macrophage colony-stimulating factor (GM-CSF), erythropoietin (EPO), interleukin (IL), interferon (IFN), oblimersen, melphalan, topotecan, pentoxifylline, taxotere, irinotecan, ciprofloxacin, doxorubicin, vincristine, dacarbazine, Ara-C, vinorelbine, prednisone, cyclophosphamide, bortezomib, arsenic trioxide. Such additional therapeutic agents are particularly useful in methods and compositions disclosed herein including, but not limited to, those relating to treatment of Burkitt lymphoma, Hodgkin lymphoma, diffuse large B-cell lymphoma, NK/T-cell lymphoma, cutaneous T-cell lymphoma, nasopharyngeal carcinoma and gastric cancer.

Other examples of additional therapeutic agents include, but are not limited to, an antibody (e.g., rituximab, anti-CD33), hematopoietic growth factor, cytokine, antibiotic, cox-2 inhibitor, immunomodulatory agent, immunosuppressive agent, corticosteroid, or a pharmacologically active mutant or derivative thereof. See, e.g., S. Nand et al., Leukemia and Lymphoma, 2008, 49(11):2141-47 (describing a Phase II study involving the administration of a combination of hydroxyurea, azacitidine and low dose gemtuzumab ozogamicin to elderly patients with AML and high-risk MDS, and concluding that this combination appears to be a safe and effective regimen in the treatment of AML and high risk MDS in this group of patients). Such additional therapeutic agents are particularly useful in methods and compositions disclosed herein including, but not limited to, those relating to treatment of the diseases and disorders disclosed herein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name Neupogen®. (Amgen, Thousand Oaks, Calif.); sargramostim, which is sold in the United States under the trade name Leukine®. (Immunex, Seattle, Wash.); and recombinant EPO, which is sold in the United States under the trade name Epogen®. (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Embodiments herein encompass the use of native, naturally occurring, and recombinant proteins. Particular embodiments encompass mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be co-administered with the compound of formulae (I), (II), (III), (IV), or (V) include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), nivolumab (Opdivo™), pembrolizumab (Keytruda™), avelumab (Bavencio™) atezolizumab (Tecentriq™), durvalumab (Imfinzi™) and ipilimumab (Yervoy™) and G250. Oral formulations disclosed herein can also comprise, be combined with, or used in combination with anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., Curr. Opinion Mol. Ther. 3(1):77-84 (2001).

In embodiments, the additional therapeutic agent (e.g., large-molecule compound or small-molecule compound) reduces, eliminates, or prevents an adverse effect associated with the administration (e.g., oral administration) of the compound of formulae (I), (II), (III), (IV), or (V) as described herein. Depending on the disease or disorder begin treated, adverse effects of the compound of formulae (I), (II), (III), (IV), or (V) can include, but are not limited to, anemia, neutropenia, febrile neutropenia, thrombocytopenia, hepatotoxicity (e.g., including, but not limited to, hepatoxicity in patients with preexisting hepatic impairment), elevated serum creatinine, renal failure, renal tubular acidosis, hypokalemia, hepatic coma, nausea, vomiting, dyspepsia, abdominal pain, pyrexia, leukopenia, diarrhea, constipation, ecchymosis, petechiae, rigors, weakness, pneumonia, anxiety, insomnia, lethargy, and decrease in weight, among others known in the art to be associated with administration of a CCR4 modulator.

Like some large molecules, many small-molecule compounds are believed to be capable of providing a synergistic effect when administered with (e.g., before, after or simultaneously) the compound of formulae (I), (II), (III), (IV), or (V) as disclosed herein. Examples of small molecule second active agents include, but are not limited to, anti-cancer agents, antibiotics, immunosuppressive agents, immunostimulatory agents and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-a CCR4 modulator; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron;

oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional therapeutic agents include, but are not limited to, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil), paclitaxel, ganciclovir, adriamycin, estramustine sodium phosphate (Emcyt®), sulindac, and etoposide.

Methods of Use

In an aspect, provided herein are methods for treating or managing EBV-associated cancer by administering the compound of formulae (I), (II), (III), (IV), or (V), or a pharmaceutically acceptable salt thereof, to a subject having the cancer. In one embodiment, the methods comprise treating EBV-associated cancer with the compound of formulae (I), (II), (III), (IV), or (V), or a pharmaceutically acceptable salt thereof. In one embodiment, the methods comprise managing EBV-associated cancer with the compound of formulae (I), (II), (III), (IV), or (V), or a pharmaceutically acceptable salt thereof. In certain embodiments, the methods comprise co-administering one or more additional active agents (e.g., an anti-cancer agent as disclosed herein). In certain embodiments, the subject is a mammal. In certain embodiments, the subject is a human. In particular embodiments, the EBV-associated cancer is a solid tumor (e.g., a relapsed or refractory solid tumor).

In embodiments, provided herein is the use of the compound of formulae (I), (II), (III), (IV), or (V), or a pharmaceutically acceptable salt thereof, in the manufacture of a medicament for the treatment and/or management of EBV-associated cancer (e.g., a relapsed or refractory solid tumor).

In embodiments, provided herein is the compound of formulae (I), (II), (III), (IV), or (V), or a pharmaceutically acceptable salt thereof, for use in the treatment and/or management of EBV-associated cancer (e.g., a relapsed or refractory solid tumor).

In embodiments, provided herein are methods of treating or managing certain types of EBV-associated cancers, including but not limited to, an EBV-associated solid tumor; a refractory EBV-associated cancer or a relapsed EBV-associated cancer; or a refractory EBV-associated solid tumor or a relapsed EBV-associated solid tumor. In one embodiment, provided herein are methods of treating or managing certain types of EBV-associated cancer, including, but not limited to, Burkitt lymphoma, Hodgkin lymphoma, diffuse large B-cell lymphoma, NK/T-cell lymphoma, cutaneous T-cell lymphoma, nasopharyngeal carcinoma, gastric cancer, vulvar squamous cell carcinoma, salivary gland cancer, orbit choroidal melanoma, and adenocarcinoma consistent with pancreaticobiliary.

In embodiments, provided herein are methods of treating or managing EBV-associated cancers, including Burkitt's lymphoma, Hodgkin lymphoma, diffuse large B-cell lymphoma, NK/T-cell lymphoma, cutaneous T-cell lymphoma, nasopharyngeal carcinoma, gastric cancer, vulvar squamous cell carcinoma, salivary gland cancer, orbit choroidal melanoma, and adenocarcinoma consistent with pancreaticobiliary. In embodiments, provided herein are methods of treating or managing adenocarcinoma consistent with pancreatiocobilary.

In embodiments, provided herein are methods of treating or managing lymphoma. In embodiments, provided herein are methods of treating or managing Burkitt's lymphoma.

In embodiments, provided herein are methods of treating or managing nasopharyngeal carcinoma. In one embodiment, the nasopharyngeal carcinoma is keratinizing squaous-cell carcinoma (formerly WHO type I). In one embodiment, the nasopharyngeal carcinoma is non-keratinizing carcinoma. In one embodiment, the nasopharyngeal carcinoma is basaloid squamous cell carcinoma. In one embodiment, the non-keratinizing carcinoma is differentiated non-keratinizing carcinoma (formerly WHO type II). In one embodiment, the non-keratinizing carcinoma is undifferentiated non-keratinizing carcinoma (formerly WHO type III).

In embodiments, the methods comprise treating or managing certain stages of EBV-associated cancer, e.g., Stage 0, Stage I, Stage II, Stage III, and Stage IV, by administering the compound of formulae (I), (II), (III), (IV), or (V), or a pharmaceutically acceptable salt thereof, to a subject having such a cancer. The staging of cancer may be defined according to methods known in the art, for example, according to the guidelines provided by the American Joint Committee on Cancer (AJCC). In one embodiment, the staging of cancer is designated and grouped based on the TNM classification, i.e., a classification based on the status of primary tumor (e.g., TX, T0, Tis, T1, T2, T3, T4), regional lymph nodes (e.g., NX, N0, N1, N2, N3), and/or distant metastasis (e.g., MX, M0, M1), in a subject having EBV-associated cancer.

Particular embodiments provide treating a subject having EBV-associated cancer using one or more of the methods provided herein, together with surgery. Particular embodiments provide treating a subject having EBV-associated cancer using one or more of the methods provided herein, together with chemotherapy. Particular embodiments provide treating a subject having EBV-associated cancer using one or more of the methods provided herein, together with immunotherapy. Particular embodiments provide treating a subject having EBV-associated cancer using one or more of the methods provided herein, together with targeted therapy. Particular embodiments provide treating a subject having EBV-associated cancer using one or more of the methods provided herein, together with radiation therapy. Particular embodiments provide treating a subject having EBV-associated cancer using one or more of the methods provided herein, together with cellular therapy. Particular embodiments provide treating a subject having EBV-associated cancer using one or more of the methods provided herein, together with vaccination therapy. Particular embodiments provide treating a subject having EBV-associated cancer using one or more of the methods provided herein, together with gene therapy. Particular embodiments provide treating a subject having EBV-associated cancer using one or more of the methods provided herein, together with two or more of the treatments selected from surgery, chemotherapy, immunotherapy, targeted therapy, radiation therapy, cellular therapy, vaccination therapy or gene therapy. Particular embodiments provide treating a subject having EBV-associated cancer using one or more of the methods provided herein, together with two or more of the treatments selected from surgery, chemotherapy, immunotherapy and radiation therapy.

In embodiments, the subject to be treated with one of the methods provided herein has not been treated with anticancer therapy prior to the administration of the compound of formulae (I), (II), (III), (IV), or (V). In certain embodiments, the subject to be treated with one of the methods provided herein has been treated with one or more anticancer therapies prior to the administration of the compound of formulae (I), (II), (III), (IV), or (V). In certain embodiments, the subject to be treated with one of the methods provided herein has been treated with a cancer therapeutic agent, as described herein. In certain embodiments, the subject to be treated with one of the methods provided herein has developed drug resistance to anticancer therapy. In certain embodiments, the subject to be treated with the methods provided herein has a relapsed EBV-associated cancer. In certain embodiments, the subject to be treated with the methods provided herein has a refractory EBV-associated cancer. In certain embodiments, the subject to be treated with the methods provided herein has a metastatic EBV-associated cancer. In certain embodiments, the subject to be treated with the methods provided herein has EBV-associated lymphoma. In certain embodiments, the subject to be treated with the methods provided herein has Burkitt's lymphoma.

In embodiments, the methods provided herein encompass treating a subject regardless of patient's age, although some diseases or disorders are more common in certain age groups. Further provided herein is a method for treating a subject who has undergone surgery in an attempt to treat the disease or condition at issue. Further provided herein is a method for treating a subject who has not undergone surgery as an attempt to treat the disease or condition at issue. Because the subjects with EBV-associated cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with EBV-associated cancer.

In embodiments provided herein, the method may further comprise one or more diagnostic steps, to determine, e.g., the type of EBV-associated cancer, the presence of particular cell types, the genetic profile of a subject, and/or the staging of the disease in a subject.

In embodiments provided herein, the method may further comprise a disease evaluation step after the compound of formulae (I), (II), (III), (IV), or (V) has been administered to the subject, to determine, e.g., changes in one or more molecular markers as described herein elsewhere, changes in tumor size and location, and/or other benchmarks used by those skilled in the art to determine the prognosis of EBV-associated cancer in a subject.

Embodiments herein provide administration of the compound of formulae (I), (II), (III), (IV), or (V) by, e.g., intravenous (IV), subcutaneous (SC) or oral routes of administration. Certain methods herein provide administration of the compound of formulae (I), (II), (III), (IV), or (V) by oral route of administration. Certain embodiments herein provide co-administration of the compound of formulae (I), (II), (III), (IV), or (V) with one or more additional active agents to provide a synergistic therapeutic effect in subjects in need thereof. The co-administered agent(s) may be a cancer therapeutic agent, as described herein. In certain embodiments, the co-administered agent(s) may be dosed, e.g., orally or by injection (e.g., IV or SC).

Embodiments herein provide methods for treating disorders of abnormal cell proliferation comprising administering the compound of formulae (I), (II), (III), (IV), or (V) using, e.g., IV, SC and/or oral administration methods. Certain embodiments herein provide methods for treating disorders of abnormal cell proliferation comprising administering the compound of formulae (I), (II), (III), (IV), or (V) using oral administration methods. In certain embodiments, treatment cycles comprise multiple doses administered to a subject in need thereof over multiple days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). Suitable dosage amounts for the methods provided herein include, e.g., therapeutically effective amounts and prophylactically effective amounts. In specific embodiments, a treatment cycle comprises multiple doses administered to a subject in need thereof once a day or more than once a day, for 3 days, for 5 days, for 7 days, for 14 days, for 21 days, or for 28 days. In specific embodiments, a treatment cycle comprises a resting period of 1 day, 2 days, 3 days, 4 days, 5 days, 7 days, 14 days, 21 days, or 28 days. In specific embodiments, a subject is treated with multiple treatment cycles, for example, multiple 7-day, 14-day, 21-day, 28-day, 35-day, or 42-day treatment cycles for a total period of treatment of about 1, 2, 3, 4, 5, 6, 7, 8, 9, 10, 11, 12, 13, 14, 15, 16, 17, 18, 19, 20, 21, 22, 23, or 24 months, or greater than 24 months. In specific embodiments, a subject is treated with multiple treatment cycles, that may be the same or different (e.g., a 7-day treatment cycle followed by a 14-day, 21-day, or 28-day treatment cycle).

In embodiments, the amount of the compound of formulae (I), (II), (III), (IV), or (V) administered in the methods provided herein may range, e.g., between about 1 mg/day and about 2,000 mg/day, between about 1 mg/day and about 1,000 mg/day, between about 50 mg/day and about 500 mg/day, or between about 100 mg/day and about 400 mg/day. In certain embodiments, particular dosages are, e.g., about 50 mg/day, about 75 mg/day, about 100 mg/day, about 120 mg/day, about 140 mg/day, about 160 mg/day, about 180 mg/day, about 200 mg/day, about 220 mg/day, about 240 mg/day, about 240 mg/day, about 260 mg/day, about 280 mg/day, about 300 mg/day, about 320 mg/day, about 340 mg/day, about 360 mg/day, about 380 mg/day, about 400 mg/day, about 420 mg/day, about 440 mg/day, about 460 mg/day, about 480 mg/day, or about 500 mg/day. In certain embodiments, particular dosages are, e.g., up to about 50 mg/day, up to about 75 mg/day, up to about 100 mg/day, up to about 125 mg/day, up to about 150 mg/day, up to about 175 mg/day, up to about 200 mg/day, up to about 225 mg/day, up to about 250 mg/day, up to about 275 mg/day, up to about 300 mg/day, up to about 325 mg/day, up to about 350 mg/day, up to about 325 mg/day, up to about 350 mg/day, up to about 375 mg/day, up to about 400 mg/day, up to about 425 mg/day, up to about 450 mg/day, up to about 475 mg/day, up to about 500 mg/day, up to about 750 mg/day, or up to about 1000 mg/day.

In embodiments, depending on the disease to be treated and the subject's condition, the compound of formulae (I), (II), (III), (IV), or (V) may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. In some embodiments, the compound of formulae (I), (II), (III), (IV), or (V) may be formulated, alone or together with one or more active agent(s), in suitable dosage unit with pharmaceutically acceptable excipients, carriers, adjuvants and vehicles, appropriate for each route of administration. In one embodiment, the compound of formulae (I), (II), (III), (IV), or (V) is administered orally. In another embodiment, the compound of formulae (I), (II), (III), (IV), or (V) is administered parenterally. In yet another embodiment, the compound of formulae (I), (II), (III), (IV), or (V) is administered intravenously. In yet another embodiment, the compound of formulae (I), (II), (III), (IV), or (V) is administered subcutaneously.

In embodiments the compound of formulae (I), (II), (III), (IV), or (V) is delivered as a single dose such as, e.g., a single bolus injection, or oral tablets or pills; or over time such as, e.g., continuous infusion over time or divided bolus doses over time. In embodiments, the compound of formulae (I), (II), (III), (IV), or (V) is administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. See, e.g., Response Evaluation Criteria in Solid Tumors (RECIST) Guidelines, Journal of the National Cancer Institute 92(3): 205-216 (2000). Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In embodiments, the compound of formulae (I), (II), (III), (IV), or (V) is administered once daily (QD), or divided into multiple daily doses such as twice daily (BID), three times daily (TID), and four times daily (QID). In embodiments, the administration is continuous (i.e., daily for consecutive days or every day), or intermittent, e.g., in cycles (i.e., including days, weeks, or months of rest when no drug is administered). In embodiments, the compound of formulae (I), (II), (III), (IV), or (V) is administered daily, for example, once or more than once each day for a period of time. In embodiments, the compound of formulae (I), (II), (III), (IV), or (V) is administered daily for an uninterrupted period of at least 7 days, in some embodiments, up to 52 weeks. In embodiments, the compound of formulae (I), (II), (III), (IV), or (V) is administered intermittently, i.e., stopping and starting at either regular or irregular intervals. In embodiments, the compound of formulae (I), (II), (III), (IV), or (V) is administered for one to six days per week. In embodiments, the compound of formulae (I), (II), (III), (IV), or (V) is administered in cycles (e.g., daily administration for about one, two, three, four, five, six, seven, or eight consecutive weeks, then a rest period with no administration for about one, two, three, or four weeks). In embodiments, the compound of formulae (I), (II), (III), (IV), or (V) is administered on alternate days. In embodiments, the compound of formulae (I), (II), (III), (IV), or (V) is administered in cycles (e.g., administered daily or continuously for a certain period interrupted with a rest period).

In embodiments, the frequency of administration ranges from about daily to about monthly. In certain embodiments, the compound of formulae (I), (II), (III), (IV), or (V) is administered once a day, twice a day, three times a day, four times a day, once every other day, twice a week, once every week, once every two weeks, once every three weeks, or once every four weeks. In embodiments, the compound of formulae (I), (II), (III), (IV), or (V) is administered once a day. In embodiments, the compound of formulae (I), (II), (III), (IV), or (V) is administered twice a day. In embodiments, the compound of formulae (I), (II), (III), (IV), or (V) is administered three times a day. In embodiments, the compound of formulae (I), (II), (III), (IV), or (V) is administered four times a day.

In embodiments, the compound of formulae (I), (II), (III), (IV), or (V) is administered once per day from one day to six months, from one week to three months, from one week to four weeks, from one week to three weeks, or from one week to two weeks. In certain embodiments, the compound of formulae (I), (II), (III), (IV), or (V) is administered once per day for one week, two weeks, three weeks, or four weeks. In embodiments, the compound of formulae (I), (II), (III), (IV), or (V) is administered once per day for one week. In embodiments, the compound of formulae (I), (II), (III), (IV), or (V) is administered once per day for two weeks. In embodiments, the compound of formulae (I), (II), (III), (IV), or (V) is administered once per day for three weeks. In embodiments, the compound of formulae (I), (II), (III), (IV), or (V) is administered once per day for four weeks.

In embodiments, the compound of formulae (I), (II), (III), (IV), or (V) is administered once per day for about 1 week, about 2 weeks, about 3 weeks, about 4 weeks, about 6 weeks, about 9 weeks, about 12 weeks, about 15 weeks, about 18 weeks, about 21 weeks, or about 26 weeks. In certain embodiments, the compound of formulae (I), (II), (III), (IV), or (V) is administered intermittently. In certain embodiments, the compound of formulae (I), (II), (III), (IV), or (V) is administered intermittently in the amount of between about 50 mg/day and about 1,000 mg/day. In certain embodiments, the compound of formulae (I), (II), (III), (IV), or (V) is administered intermittently in the amount of between about 100 mg/day and about 500 mg/day. In certain embodiments, the compound of formulae (I), (II), (III), (IV), or (V) is administered continuously. In certain embodiments, the compound of formulae (I), (II), (III), (IV), or (V) is administered continuously in the amount of between about 50 mg/day and about 1,000 mg/day. In certain embodiments, the compound of formulae (I), (II), (III), (IV), or (V) is administered continuously in the amount of between about 100 mg/day and about 500 mg/day.

In certain embodiments, the compound of formulae (I), (II), (III), (IV), or (V) is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

Kits

In another aspect, provided herein is a kit including the compound of formulae (I), (II), (III), (IV), or (V) as described herein or pharmaceutical compositions thereof. The kits are generally in the form of a physical structure housing various components, as described below, and may be utilized, for example, in practicing the methods described herein.

In embodiments, a kit includes one or more of the compound of formulae (I), (II), (III), (IV), or (V) disclosed herein (e.g., provided in a sterile container), which may be in the form of a pharmaceutical composition suitable for administration to a subject. The compounds described herein can be provided in a form that is ready for use (e.g., an oral formulation such as a tablet or capsule or an injectable form such as a sterile solution) or in a form requiring, for example, reconstitution or dilution (e.g., a powder) prior to administration. In embodiments, when the compound of formulae (I), (II), (III), (IV), or (V) is in a form that needs to be reconstituted or diluted by a user, the kit also includes diluents (e.g., sterile water), buffers, pharmaceutically acceptable excipients, and the like, packaged with, or separately from, the compound. In embodiments, each component of the kit may be enclosed within an individual container, and all of the various containers may be within a single package. In embodiments, a kit of the present disclosure may be designed for conditions necessary to properly maintain the components housed therein (e.g., refrigeration or freezing).

In embodiments, a kit contains a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts include manufacturer information such as lot numbers and expiration dates. In embodiments, the label or packaging insert is integrated into the physical structure housing the components, contained separately within the physical structure, or affixed to a component of the kit (e.g., an ampule, tube or vial).

In embodiments, labels or inserts additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

P EMBODIMENTS

Embodiment P1

A method of treating a malignancy that is positive for Epstein Barr Virus (EBV), the method comprising administering to a subject in need thereof a therapeutically effective amount of a compound of formula (I):

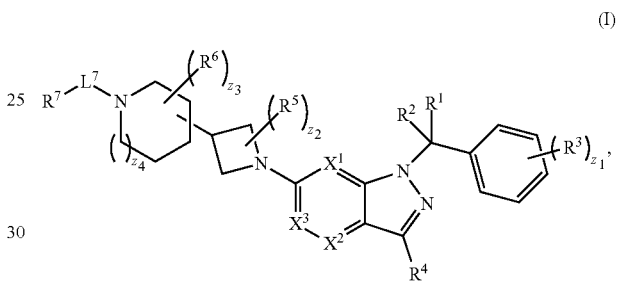

or a pharmaceutically acceptable salt thereof, wherein:

$X^1$ is $CR^8$ or N;

$X^2$ is $CR^9$ or N;

$X^3$ is $CR^{10}$ or N;

n1, n2, n3, n4, n5, n6, n7, n8, n9 and n10 are independently an integer from 0 to 4;

m1, m2, m3, m4, m5, m6, m7, m8, m9, m10, v1, v2, v3, v4, v5, v6, v7, v8, v9 and v10 are independently 1 or 2;

z1 is an integer from 0 to 5;

z2 is an integer from 0 to 2;

z3 is an integer from 0 to 11;

z4 is an integer from 0 to 2;

$L^7$ is a bond, —O—, —S—, —NR$^{7.2B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —CX$^{1.1}_3$, —CHX$^{1.1}_2$, —CH$_2$X$^{1.1}$, —CN, —N$_3$, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —CX$^{2.1}_3$, —CHX$^{2.1}_2$, —CH$_2$X$^{2.1}$, —CN, —N$_3$, —SO$_{n2}$R$^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —$CN$, —$N_3$, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —$CN$, —$N_3$, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —$CN$, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —$CN$, —$N_3$, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^7$ is hydrogen, halogen, —$CX^{7.1}_3$, —$CHX^{7.1}_2$, —$CH_2X^{7.1}$, —$CN$, —$N_3$, —$SO_{n7}R^{7A}$, —$SO_{v7}NR^{7B}R^{7C}$, —$NHNR^{7B}R^{7C}$, —$ONR^{7B}R^{7C}$, —$NHC(O)NHNR^{7B}R^{7C}$, —$NHC(O)NR^{7B}R^{7C}$, —$N(O)_{m7}$, —$NR^{7B}R^{7C}$, —$C(O)R^{7D}$, —$C(O)OR^{7D}$, —$C(O)NR^{7B}R^{7C}$, —$OR^{7A}$, —$NR^{7B}SO_2R^{7A}$, —$NR^{7B}C(O)R^{7D}$, —$NR^{7B}C(O)OR^{7D}$, —$NR^{7B}OR^{7D}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}_3$, —$CHX^{8.1}_2$, —$CH_2X^{8.1}$, —$CN$, —$N_3$, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —$CN$, —$N_3$, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10.1}_3$, —$CHX^{10.1}_2$, —$CH_2X^{10.1}$, —$CN$, —$N_3$, —$SO_{n10}R^{10A}$, —$SO_{v10}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m10}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$ and $R^{10D}$ are independently hydrogen, halogen, —$CF_3$, —$CCl_3$, —$CBr_3$, —$CI_3$, —$COOH$, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$ and $R^{10C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$ and $X^{10.1}$ are independently —Cl, —Br, —I or —F, wherein at least one of $X^1$, $X^2$ and $X^3$ is N.

Embodiment P2
The method of embodiment P1, wherein the compound is:
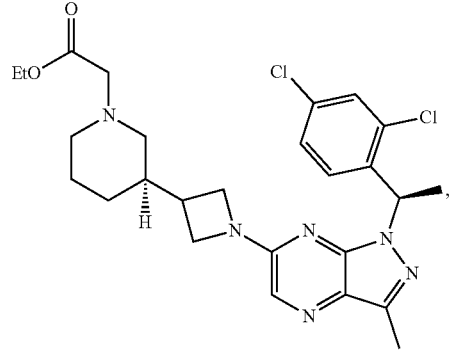
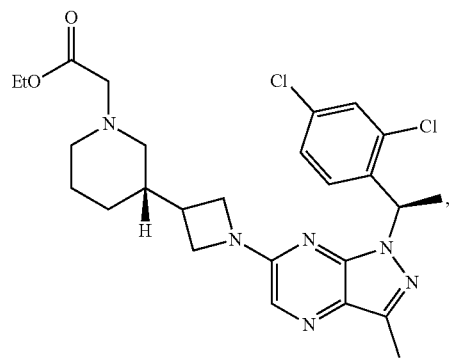
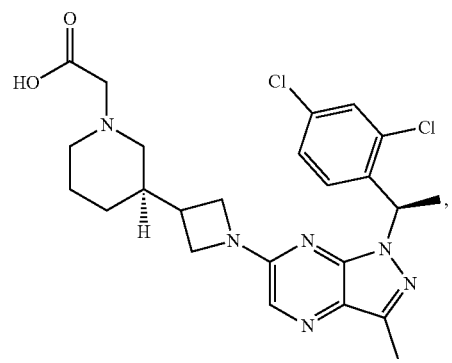
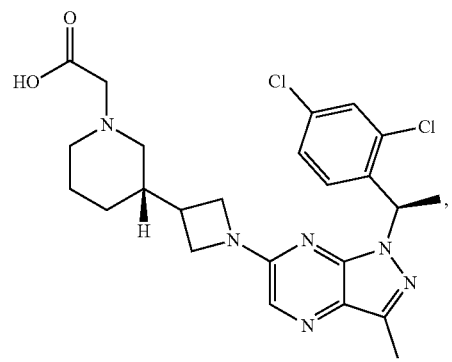
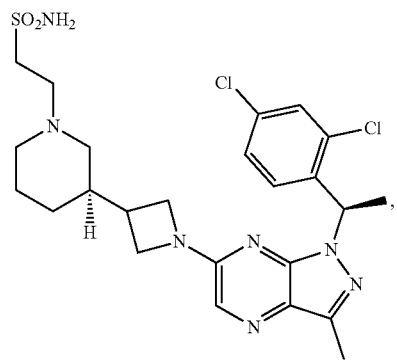
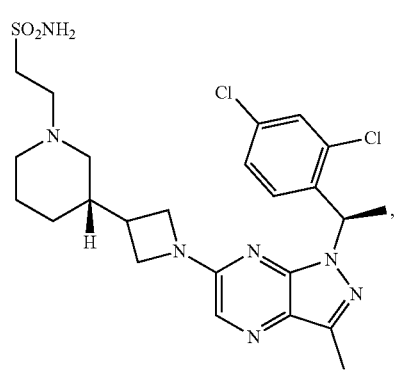
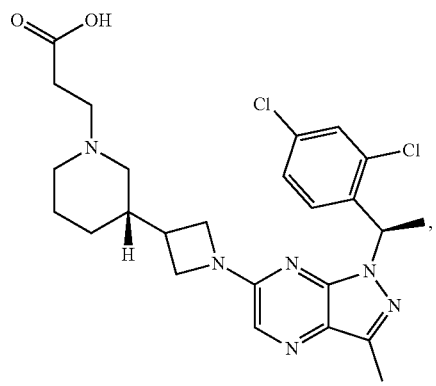
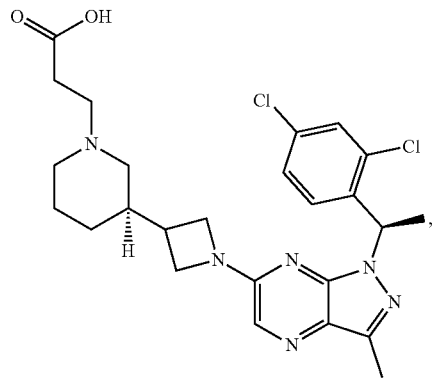

141
-continued
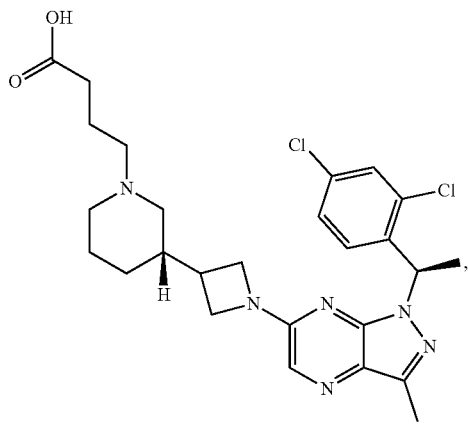
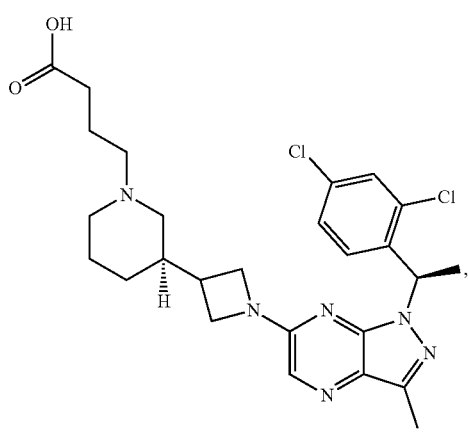
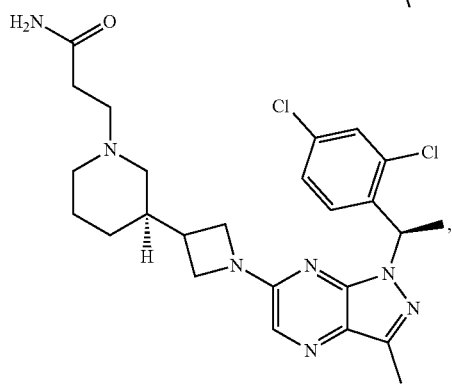
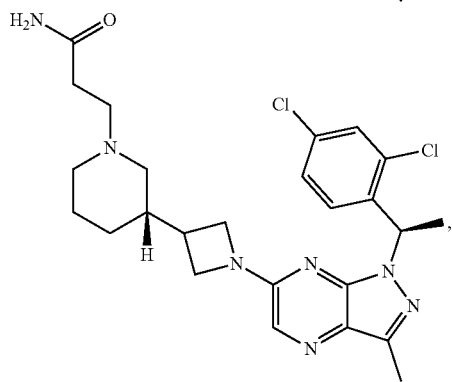
142
-continued
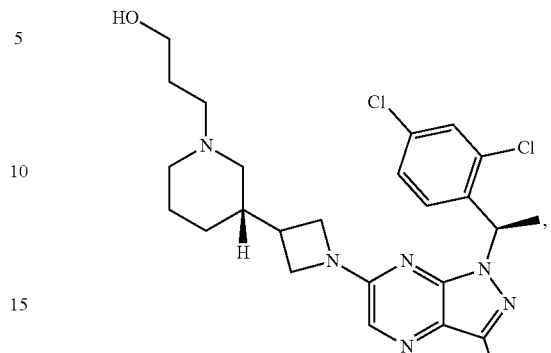
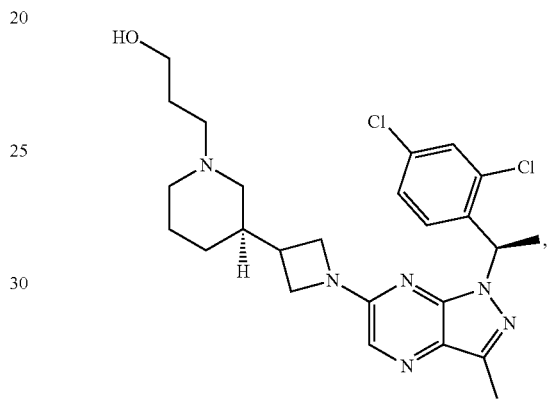
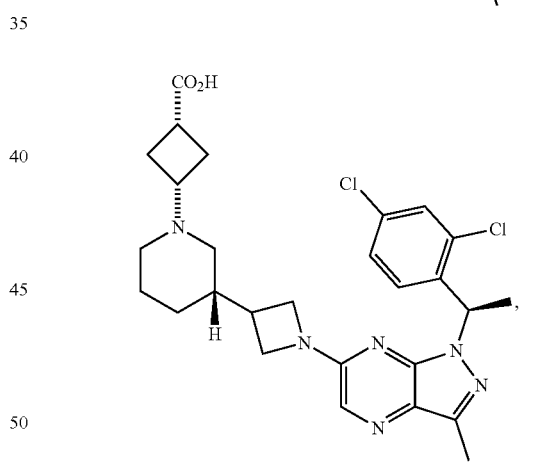
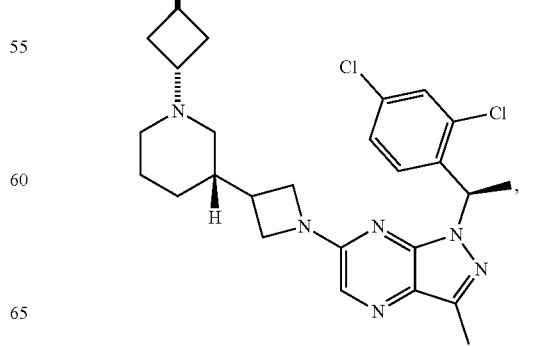

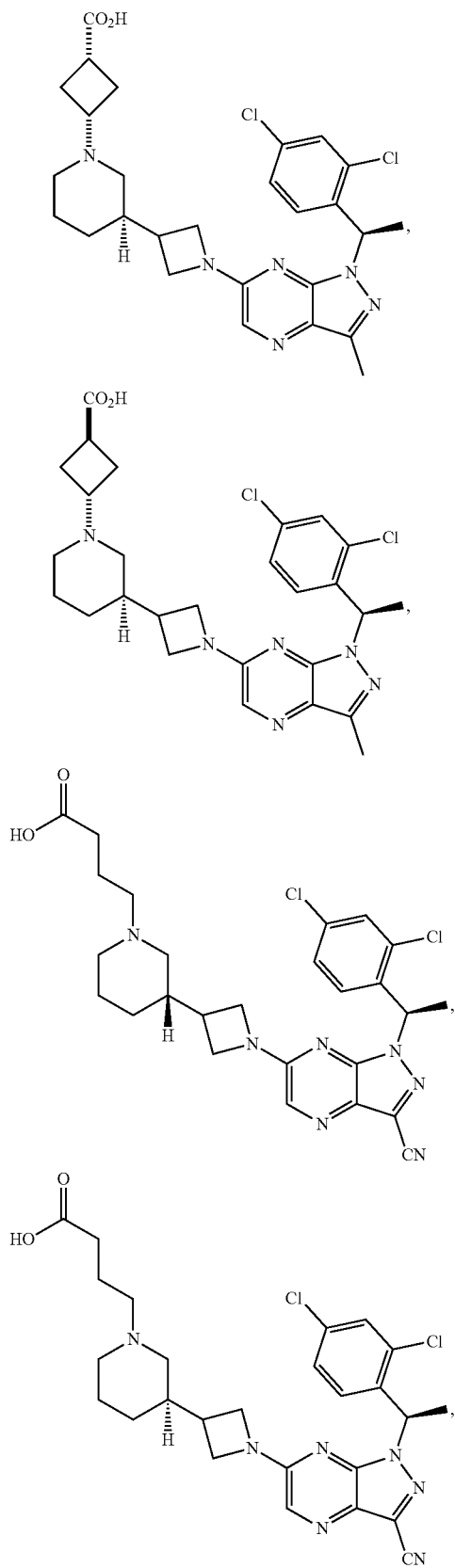
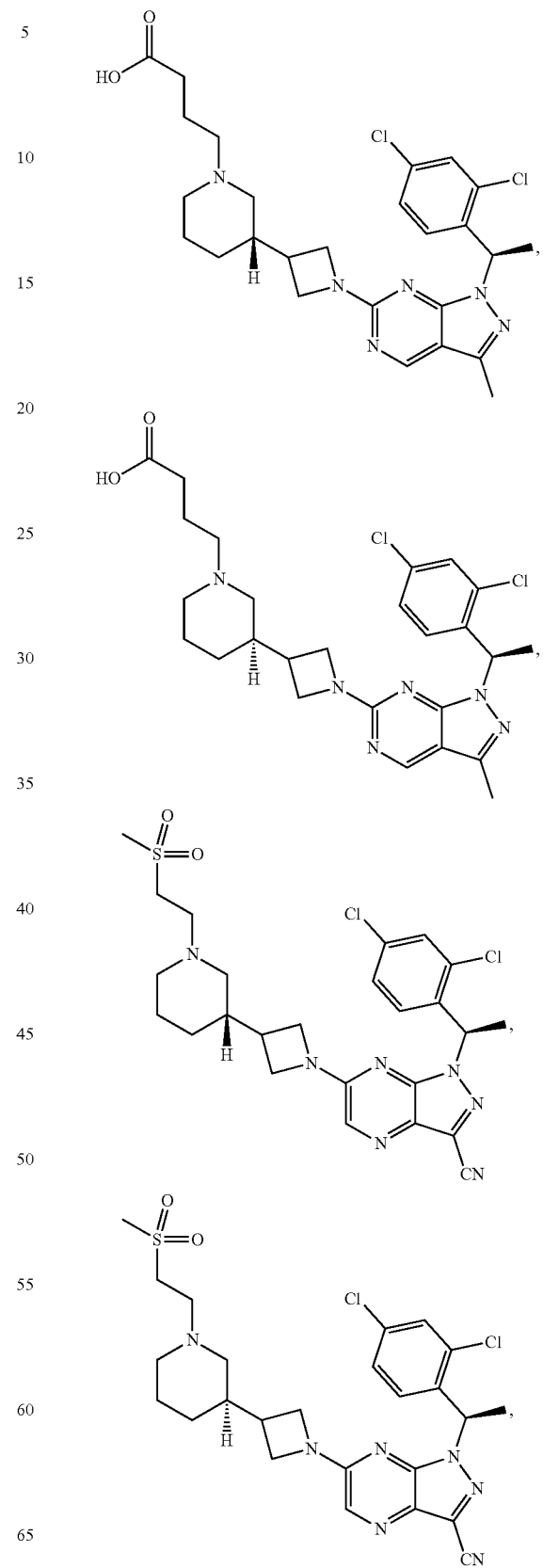

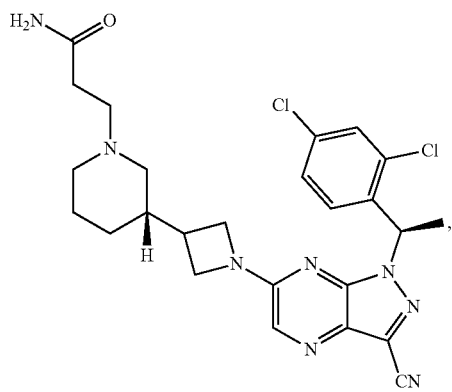
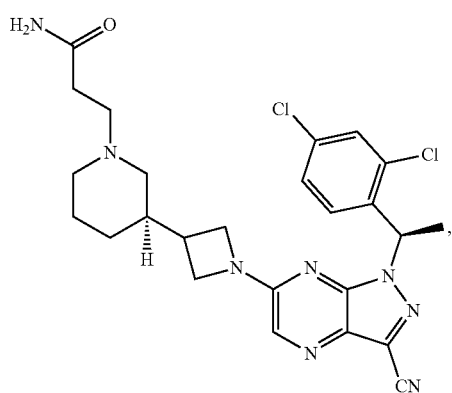
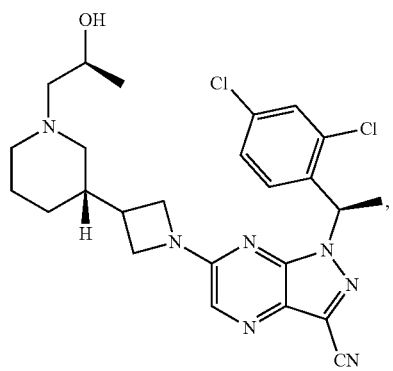
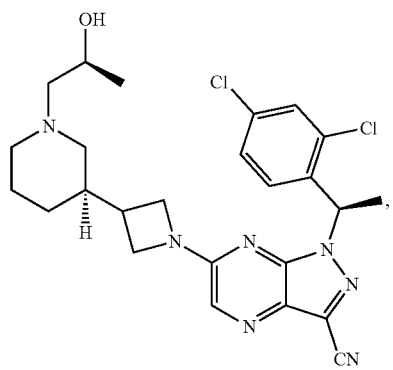
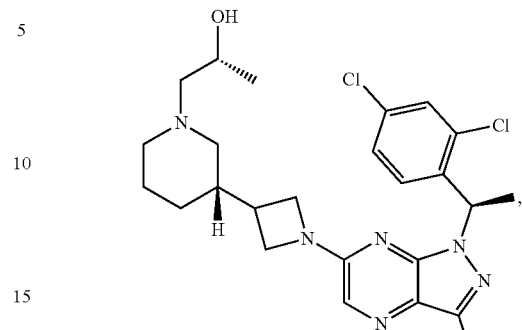
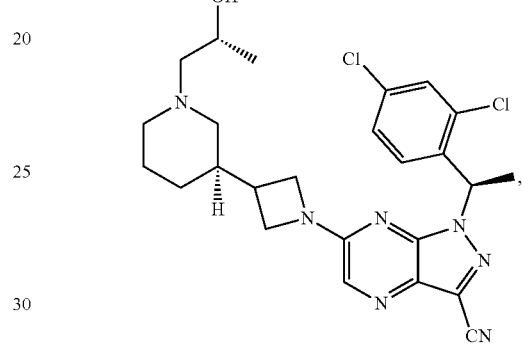
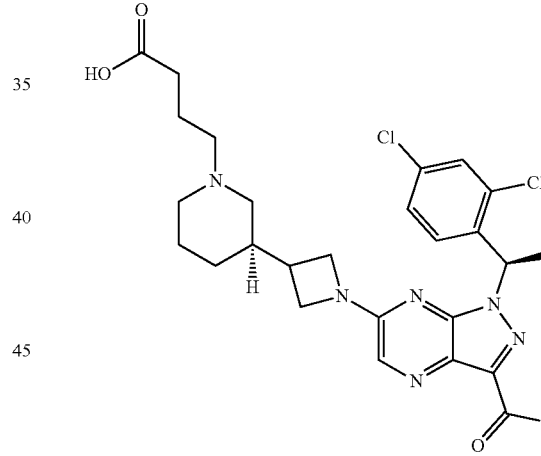
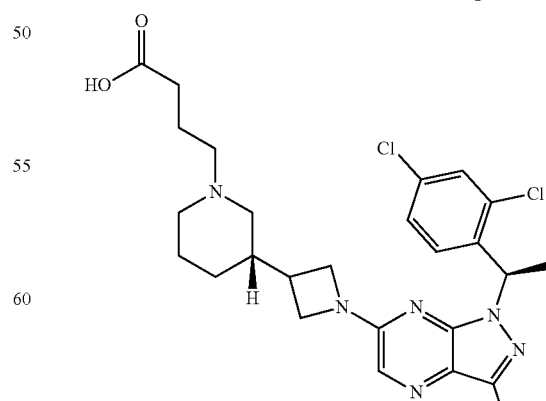

-continued
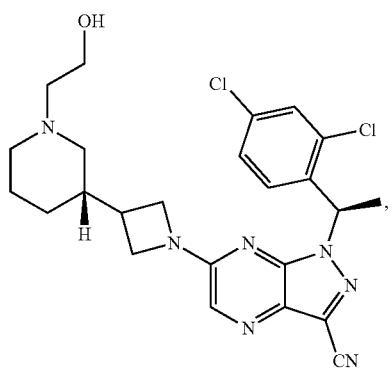
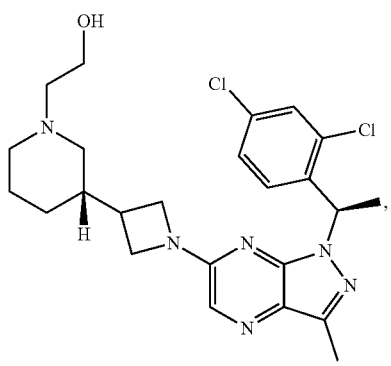
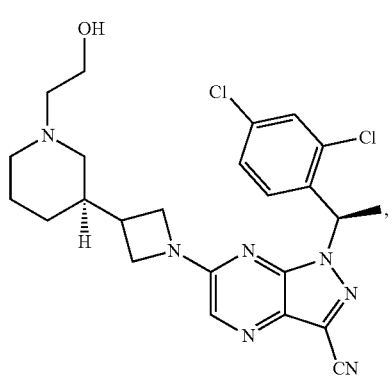
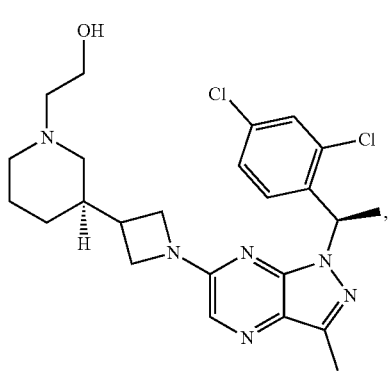
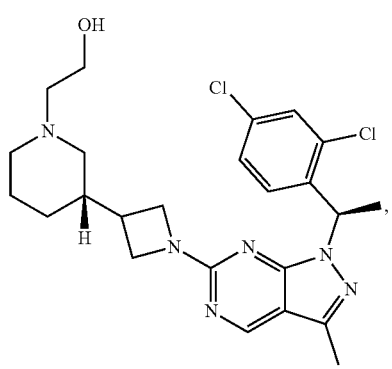
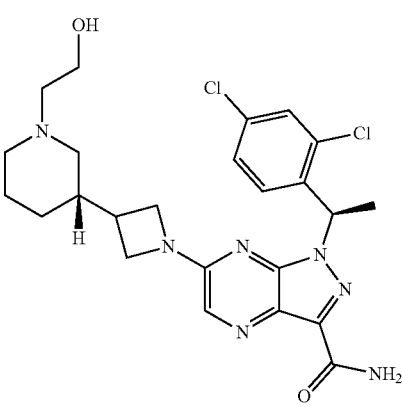
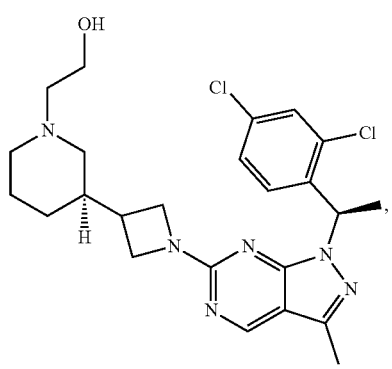
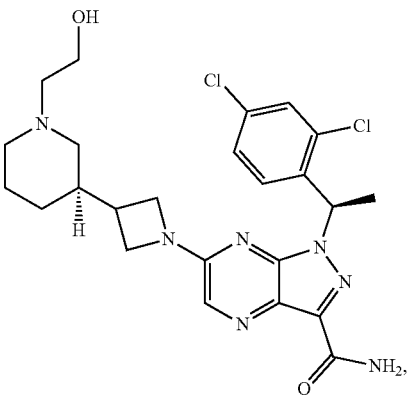

149
-continued
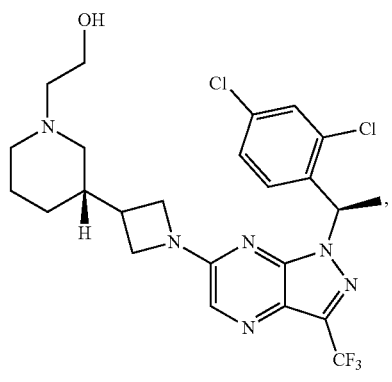
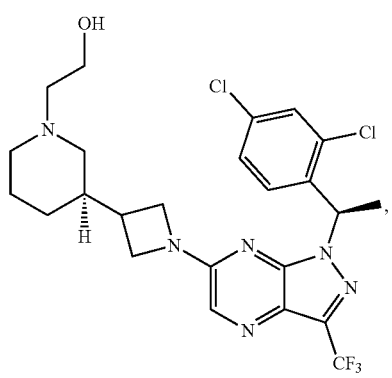
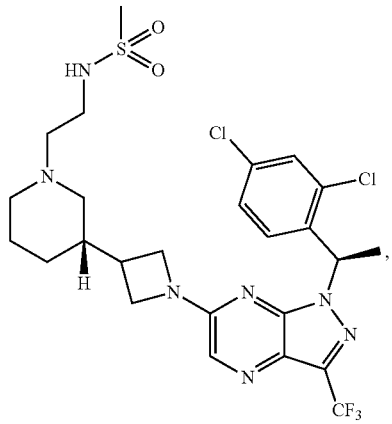
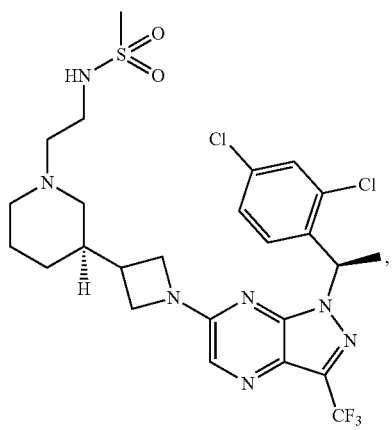
150
-continued
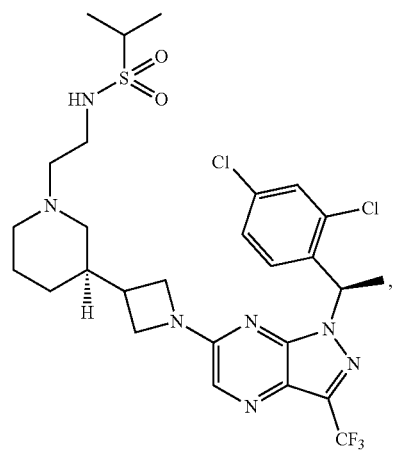
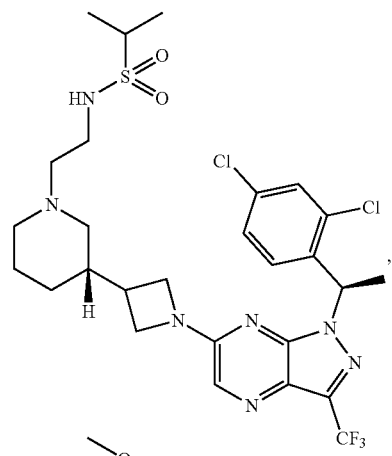
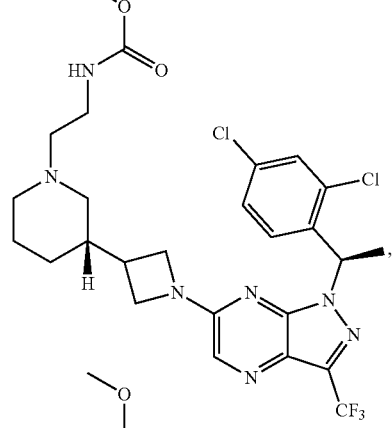
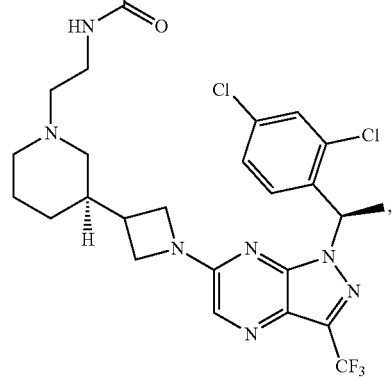

151
-continued
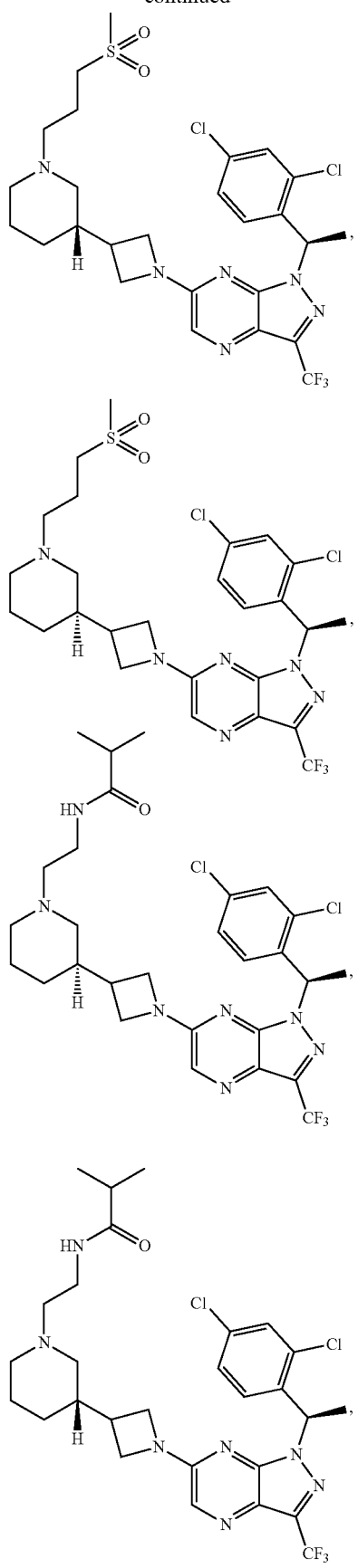
152
-continued
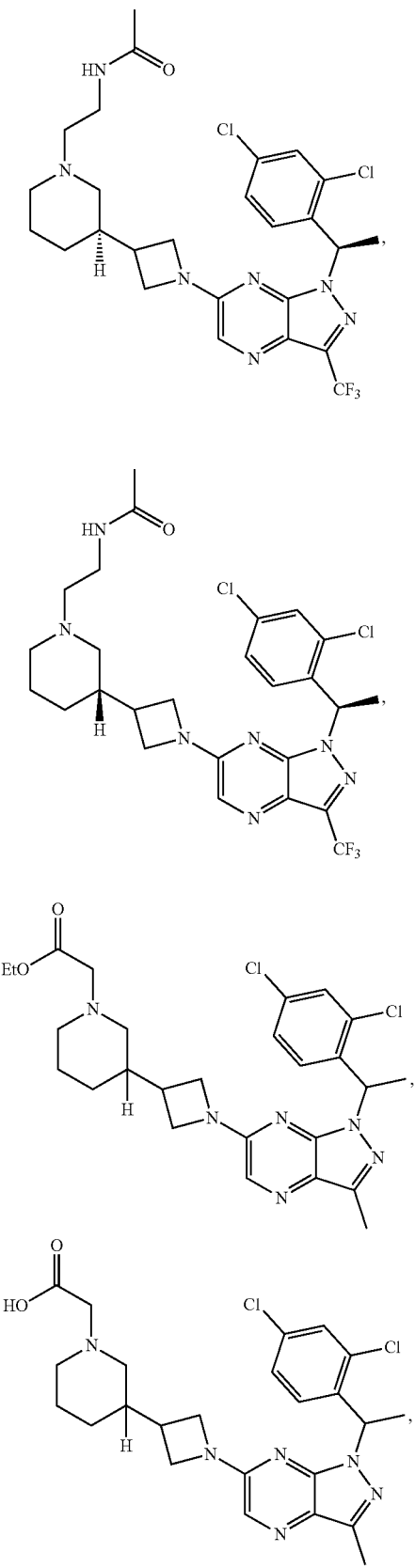

153
-continued
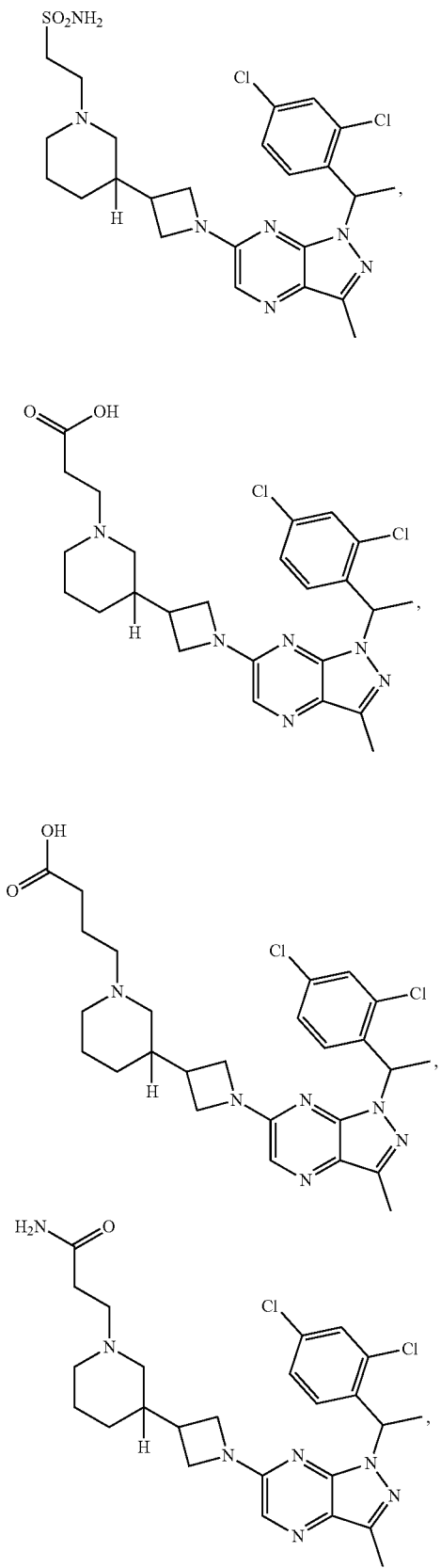
154
-continued
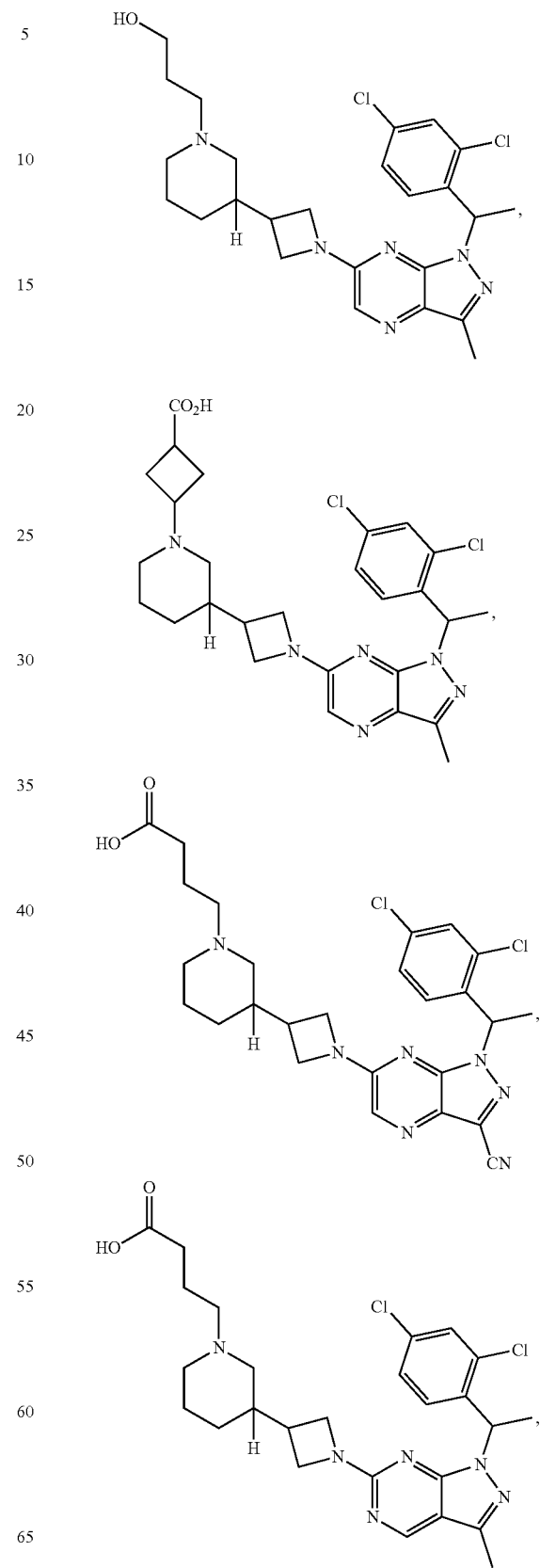

-continued
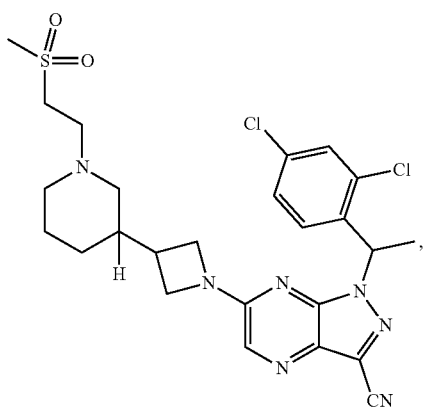
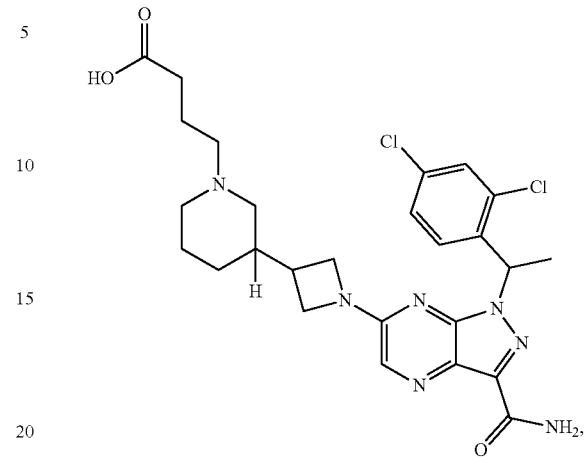
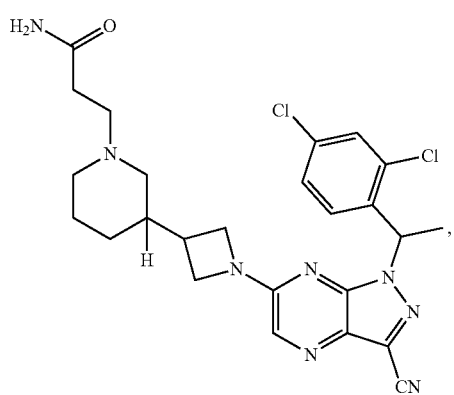
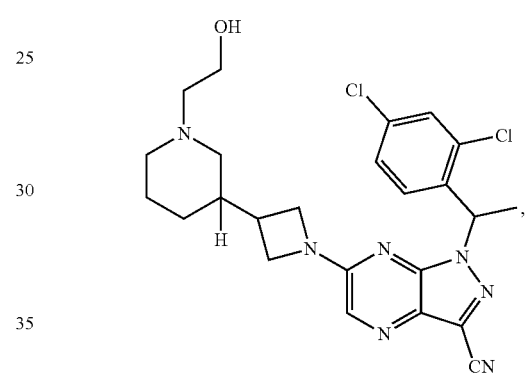
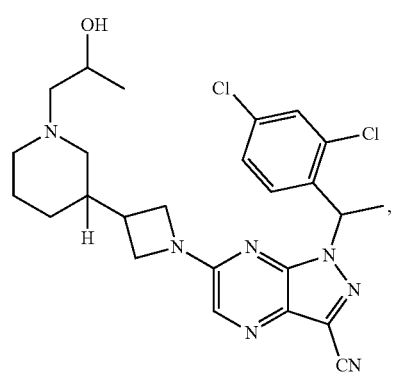
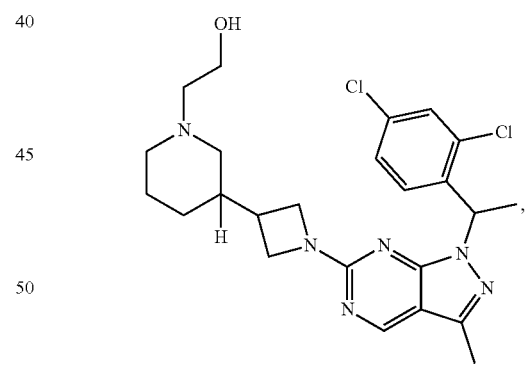
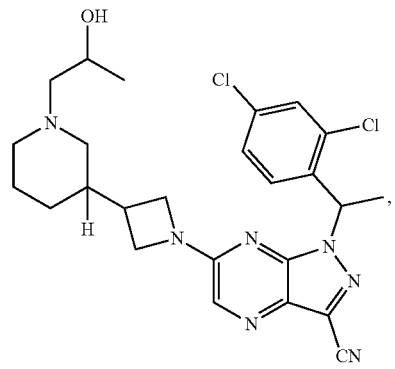
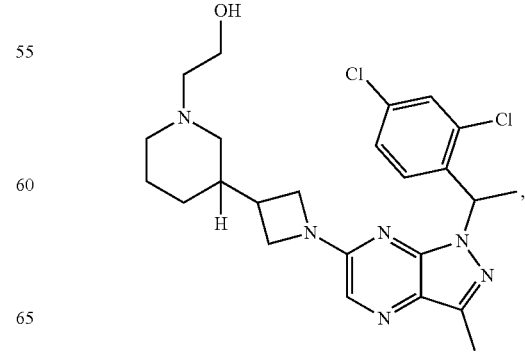

157
-continued
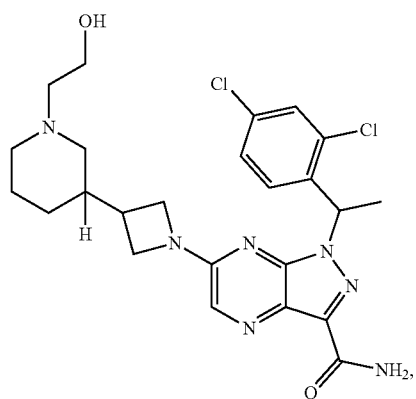
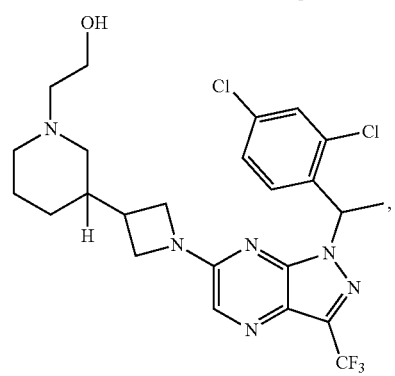
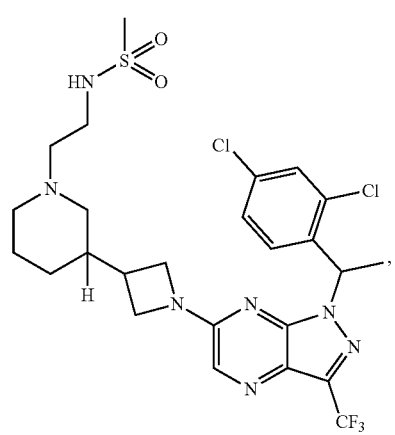
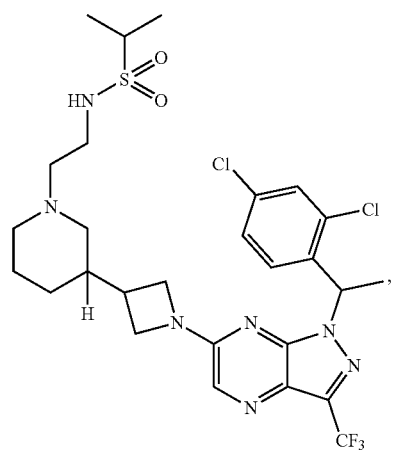
158
-continued
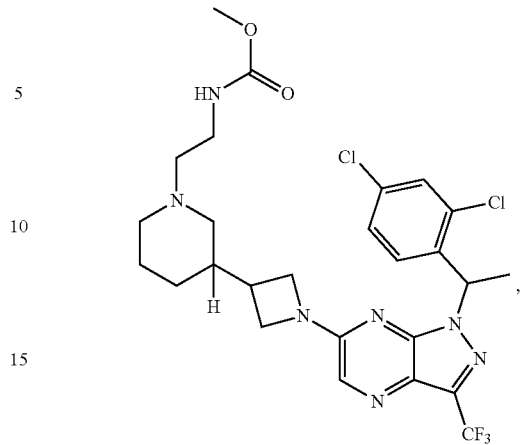
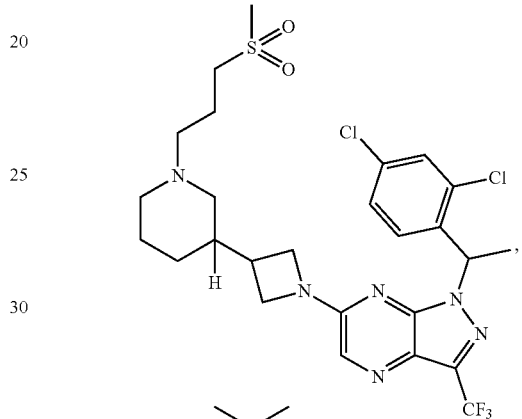
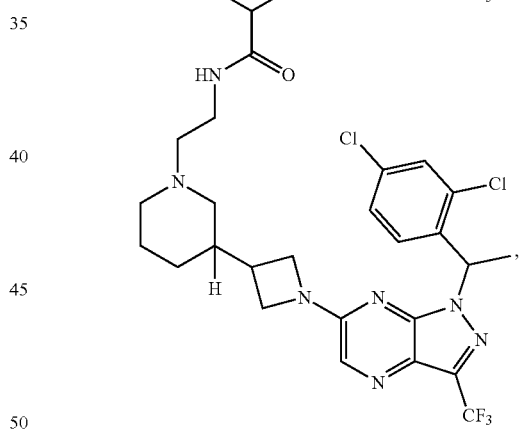
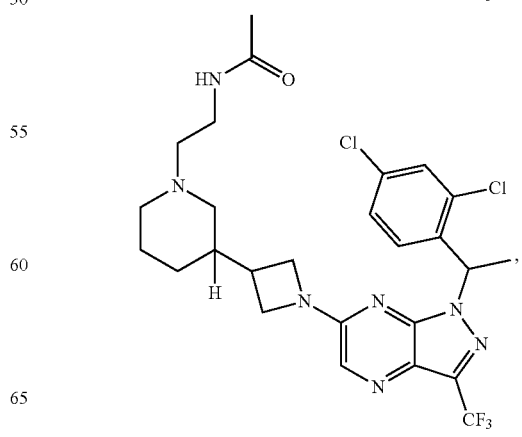

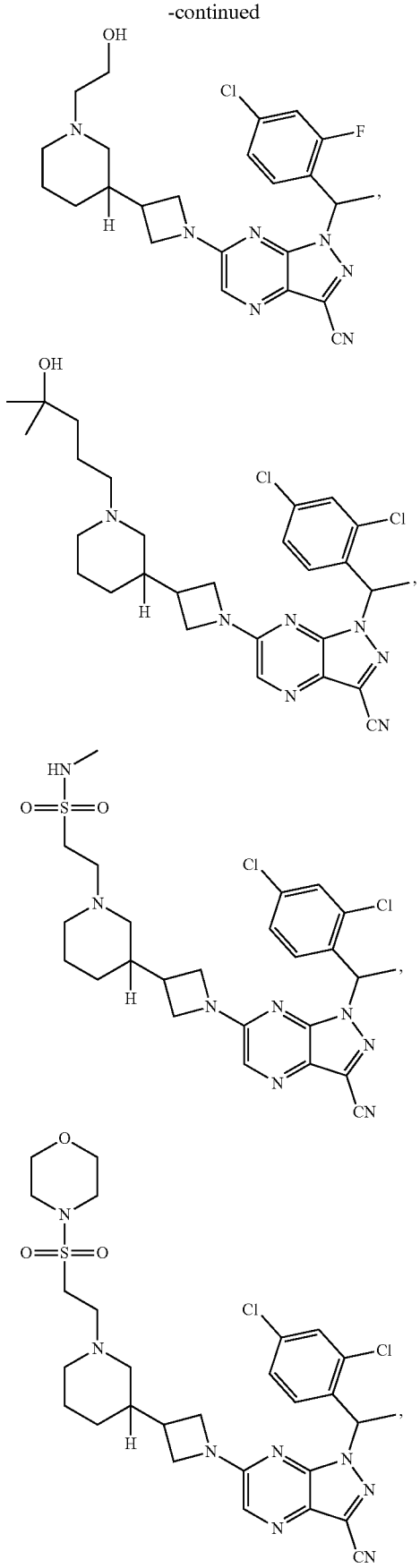
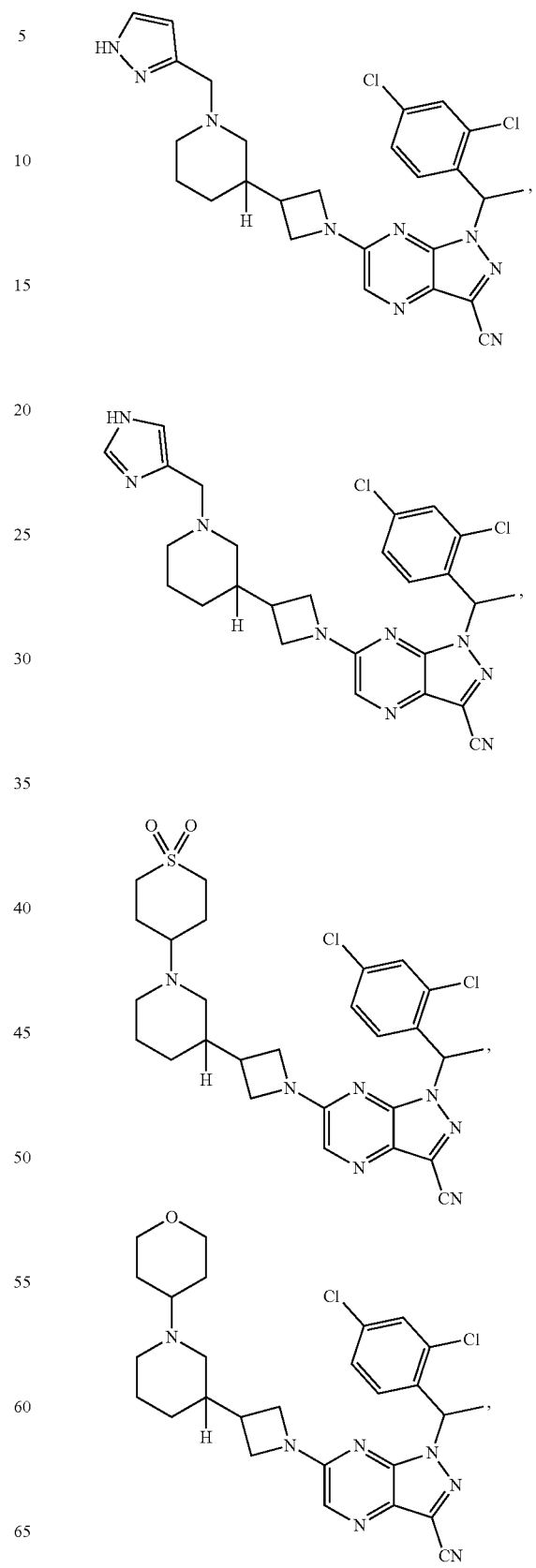

161
-continued
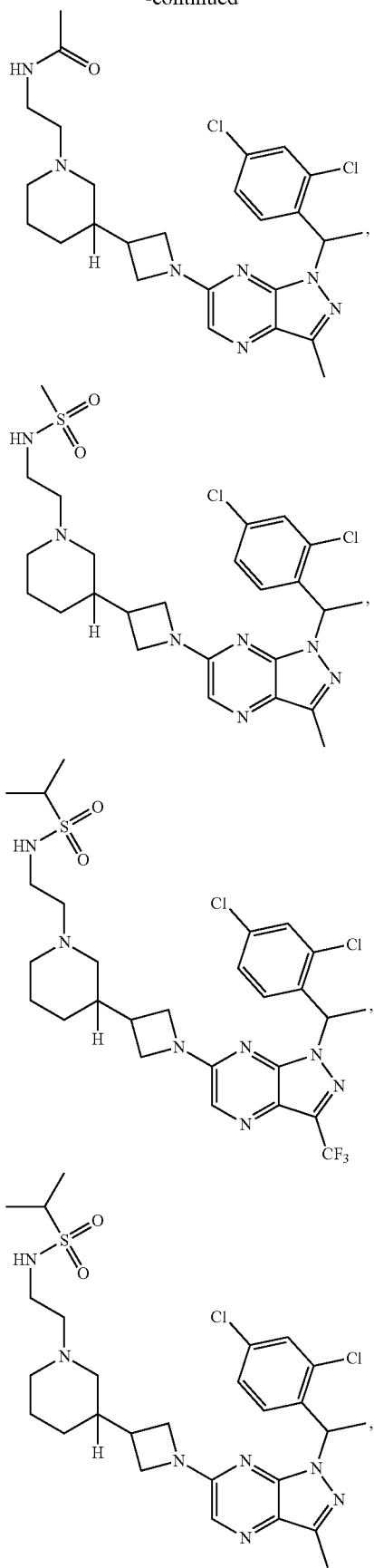
162
-continued
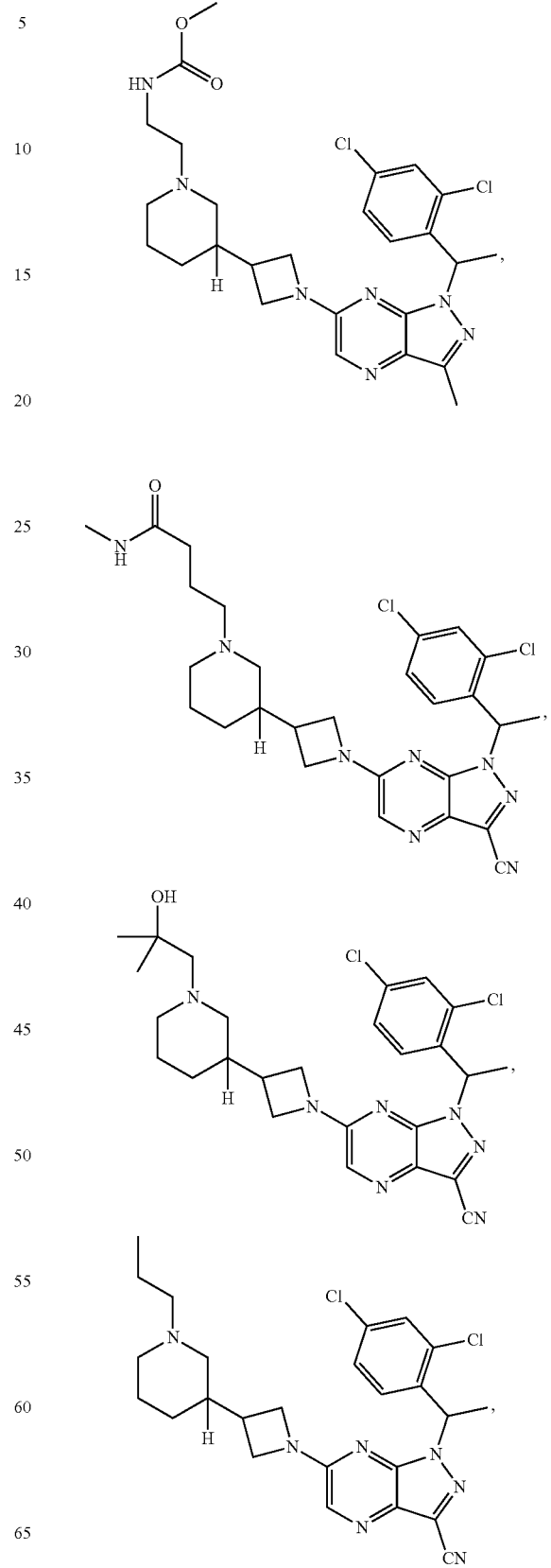

163
-continued
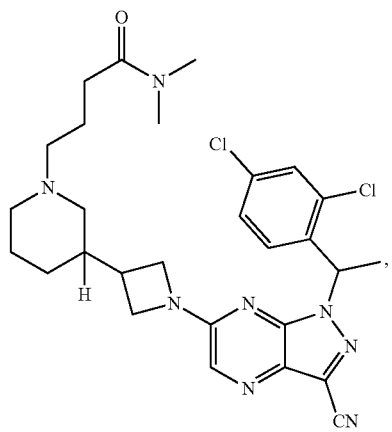
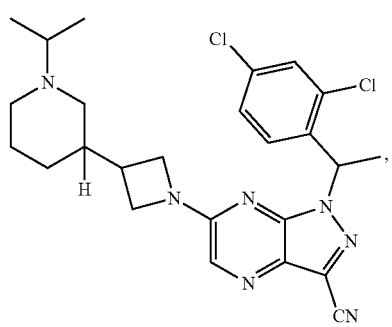
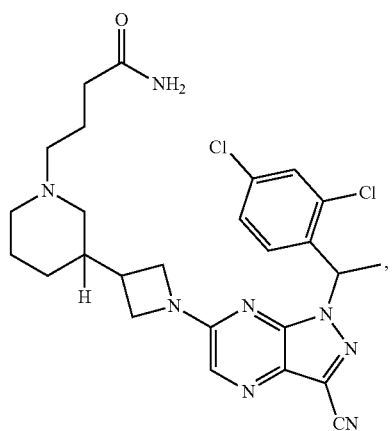
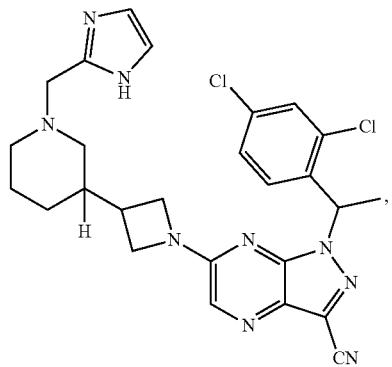
164
-continued
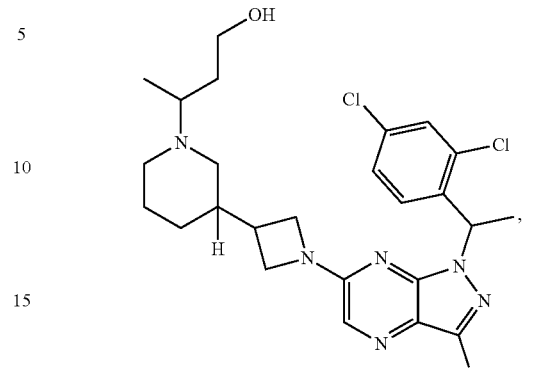
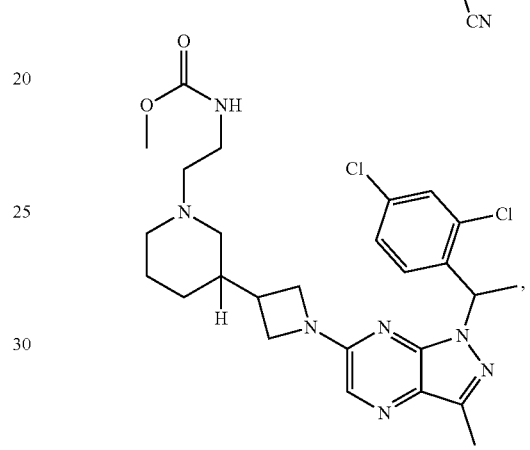
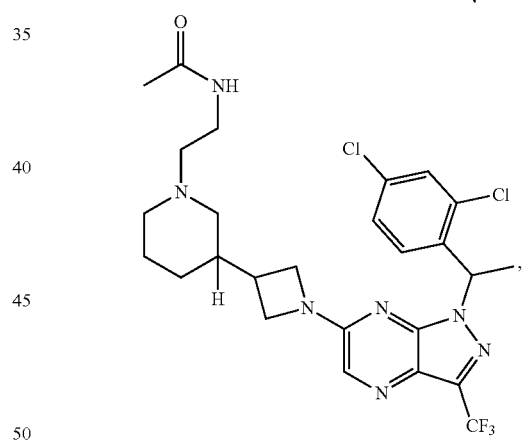
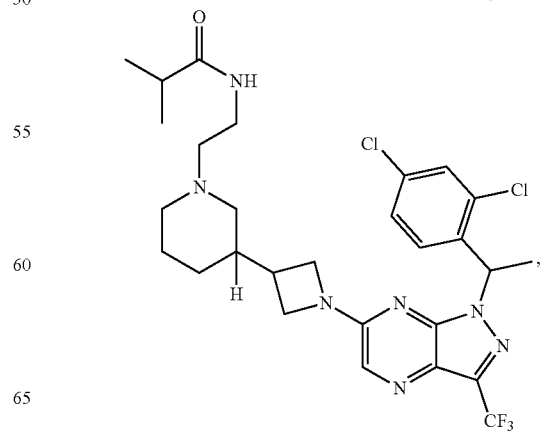

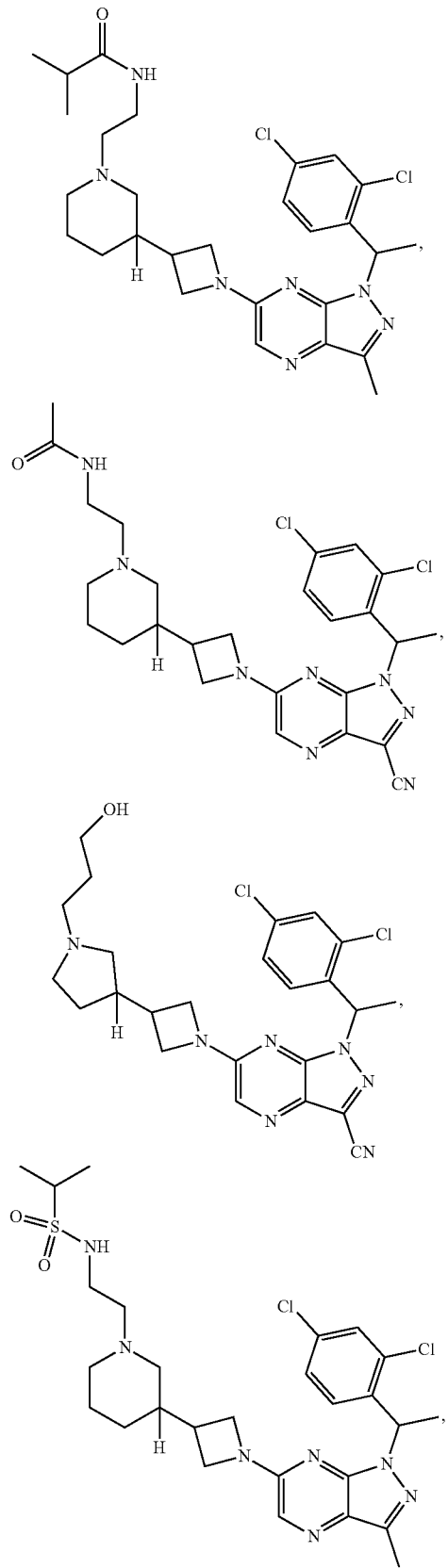
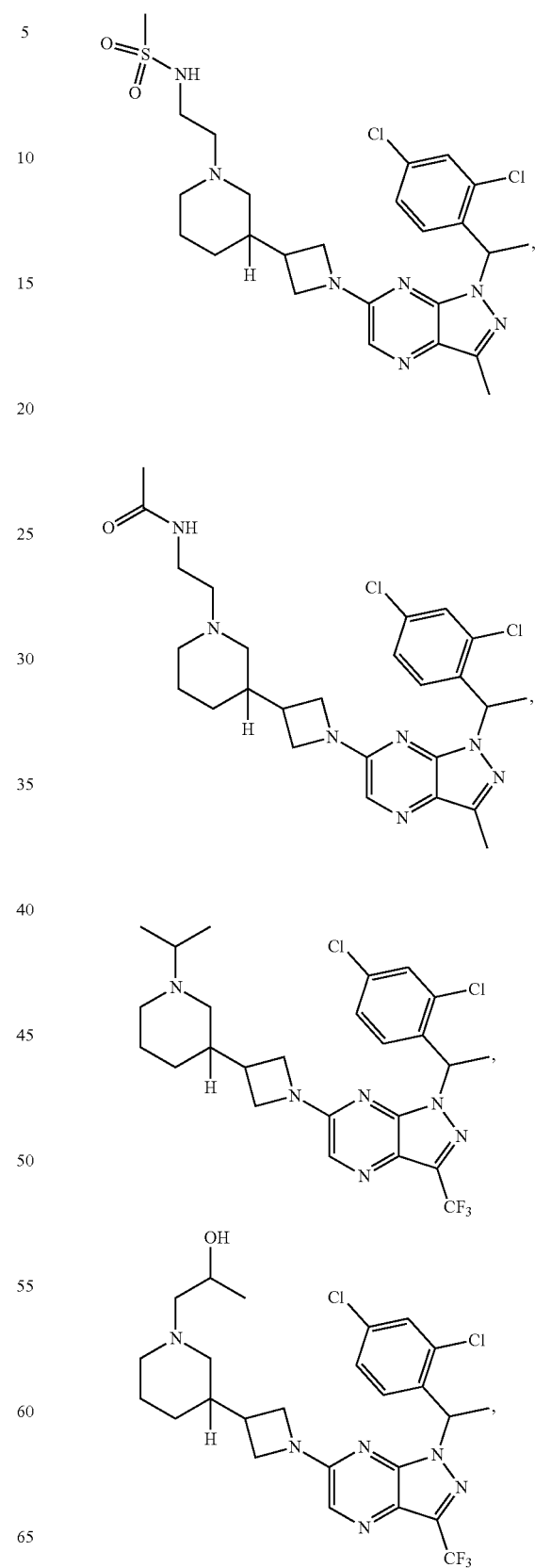

-continued

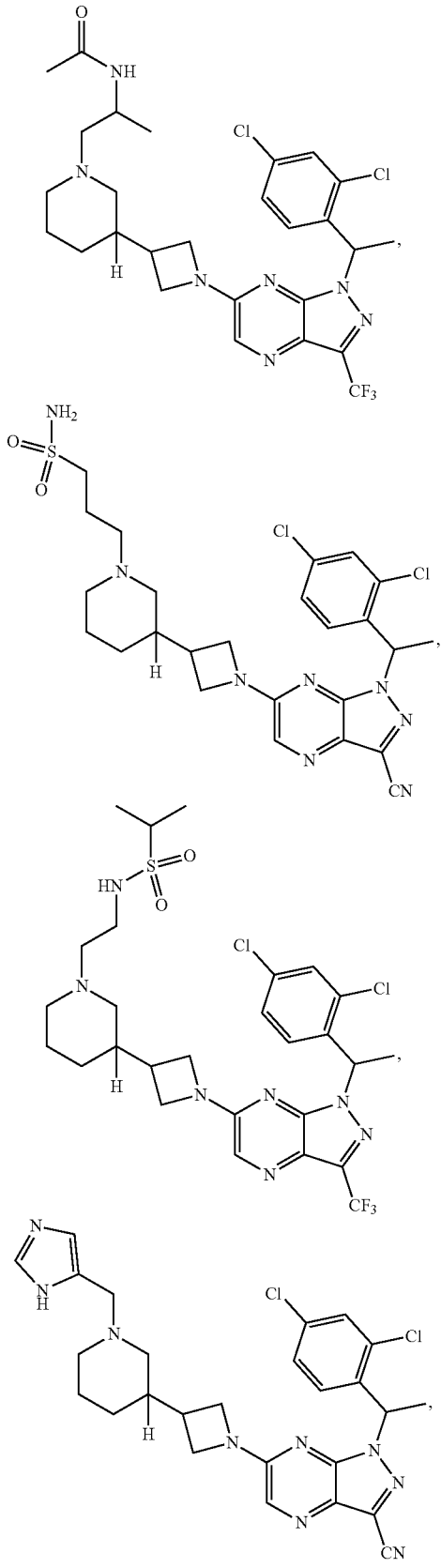

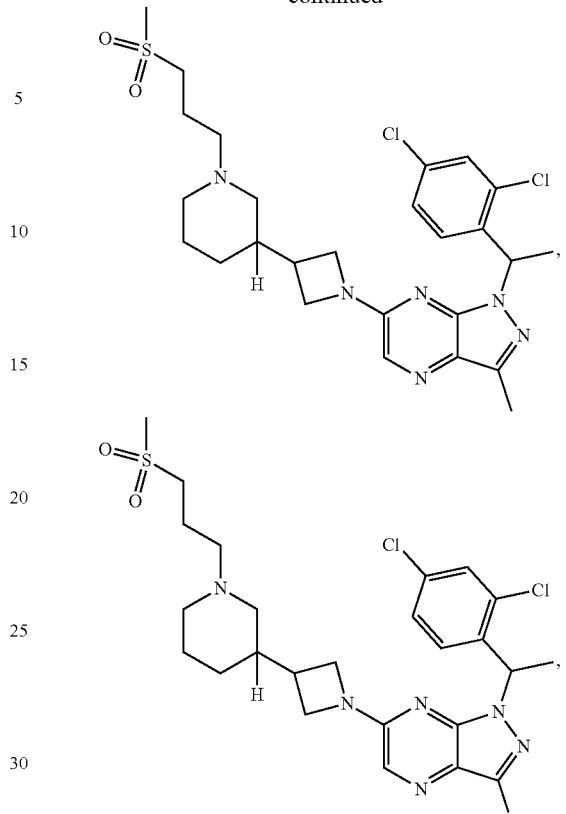

or pharmaceutically acceptable salts thereof.

Embodiment P3

A method of treating a malignancy that is positive for Epstein Barr Virus (EBV), the method comprising administering to a subject in need thereof a therapeutically effective amount of a compound of formula (II):

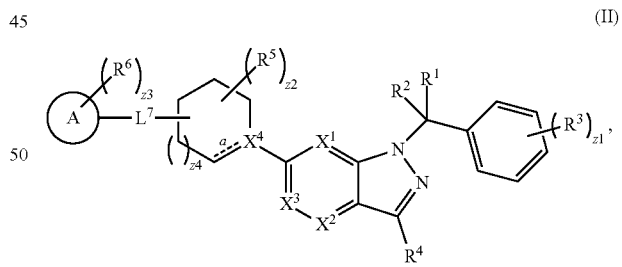

(II)

or a pharmaceutically acceptable salt thereof,
wherein:
A is a substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
z1 is an integer from 0 to 5;
z2 is an integer from 0 to 13;
z3 is an integer from 0 to 12;
z4 is an integer from 0 to 3;

⫤ is a single bond or double bond, wherein if ⫤ is a single bond, then $X^4$ is $CR^{11}$ or N, and if ⫤ is a double bond, then $X^4$ is C;

$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10.1}_3$, —$CHX^{10.1}_2$, —$CH_2X^{10.1}$, —CN, —$SO_{n10}R^{10A}$, —$SO_{v10}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m10}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11.1}_3$, —$CHX^{11.1}_2$, —$CH_2X^{11.1}$, —CN, —$SO_{n11}R^{11A}$, —$SO_{v11}NR^{11B}R^{11C}$, —$NHNR^{11B}R^{11C}$, —$ONR^{11B}R^{11C}$, —$NHC(O)NHNR^{11B}R^{11C}$, —$NHC(O)NR^{11B}R^{11C}$, —$N(O)_{m11}$, —$NR^{11B}R^{11C}$, —$C(O)R^{11D}$, —$C(O)OR^{11D}$, —$C(O)NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl;

n1, n2, n3, n4, n5, n6, n8, n9, n10 and n11 are independently an integer from 0 to 4;

m1, m2, m3, m4, m5, m6, m8, m9, m10, m11, v1, v2, v3, v4, v5, v6, v8, v9, v10, and v11 are independently 1 or 2; and $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, and $X^{11.1}$ are independently —Cl, —Br, —I or —F, wherein at least one of $X^1$, $X^2$, and $X^3$ is N.

Embodiment P4

The method of embodiment P3, wherein the compound is:

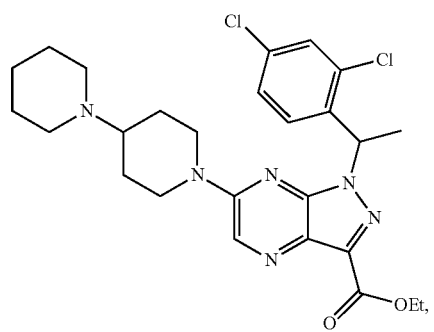

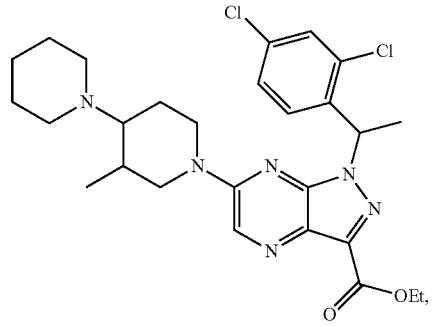

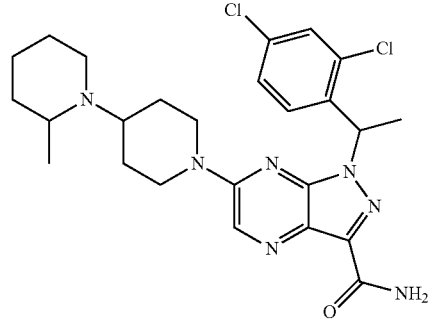

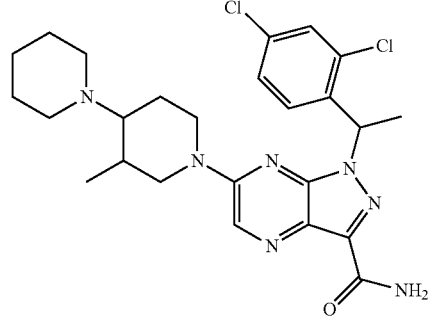

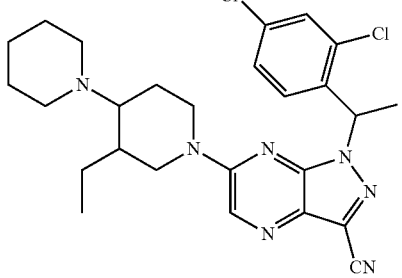

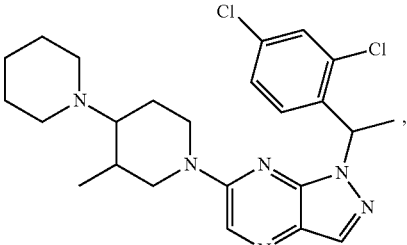

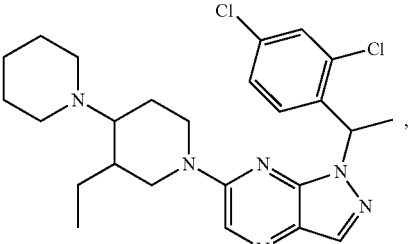

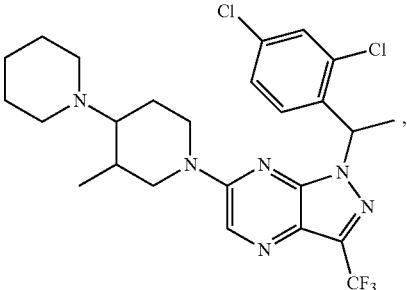

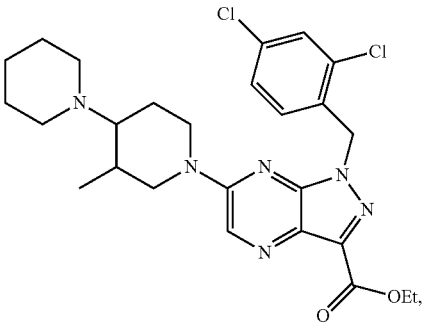

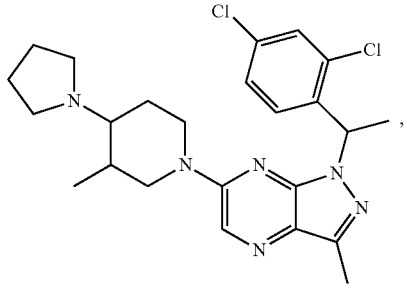

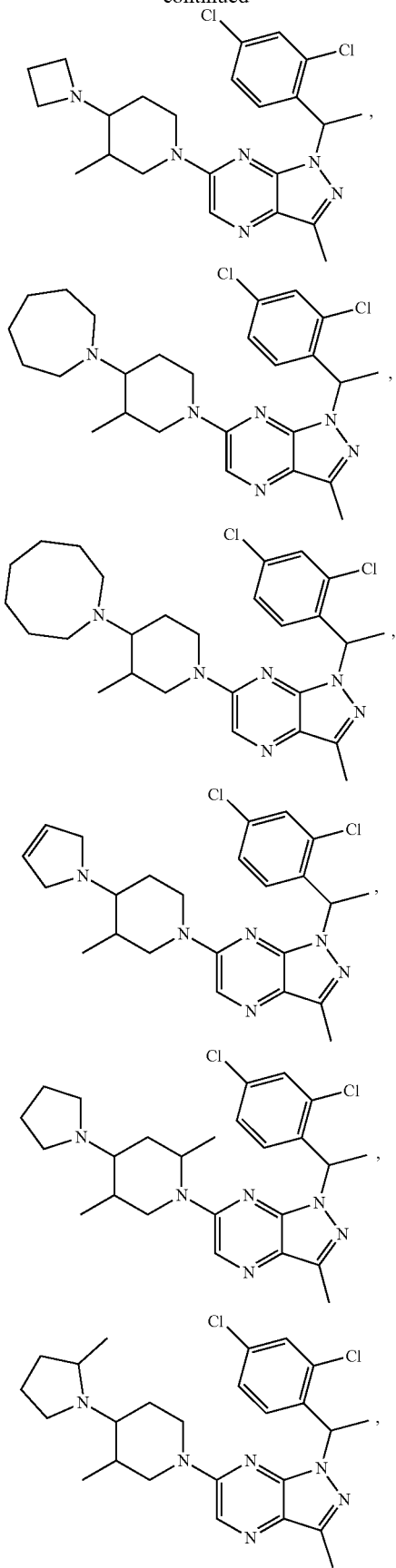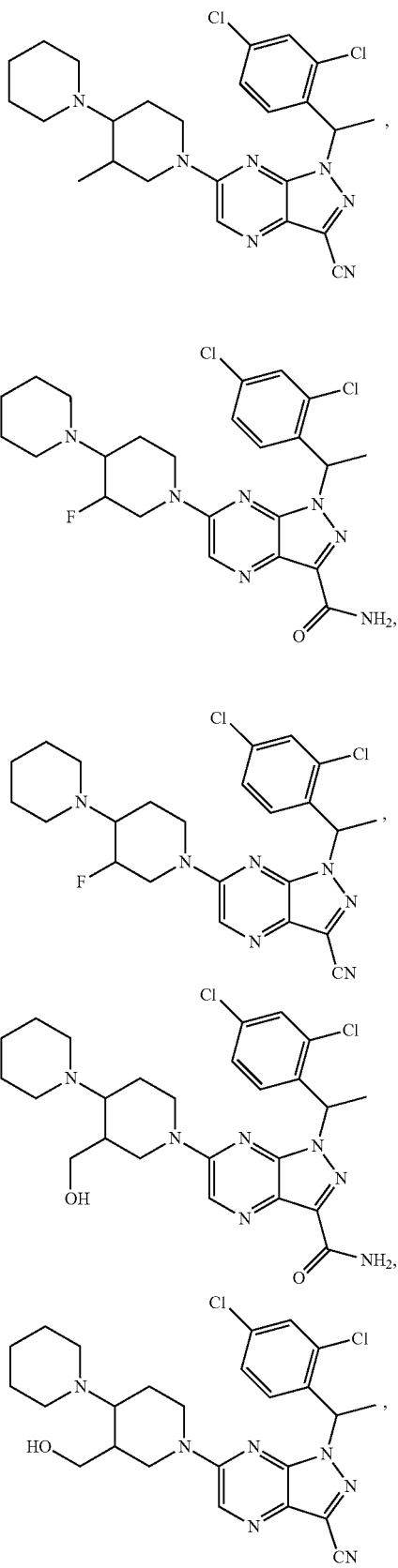

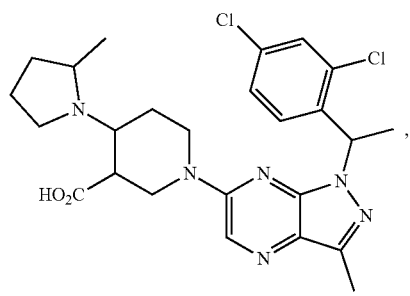
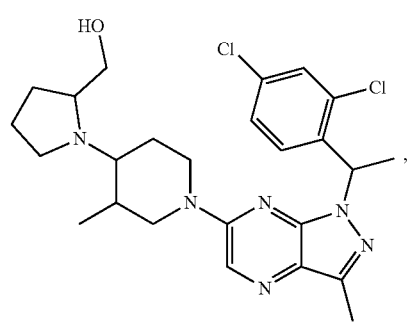
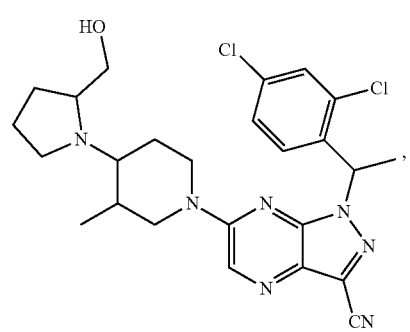
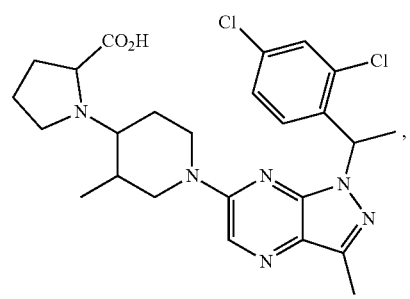
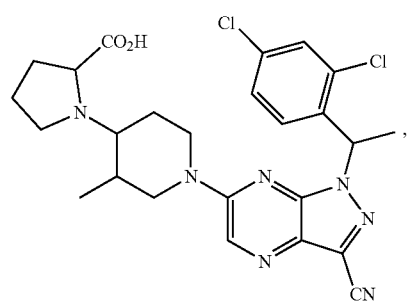
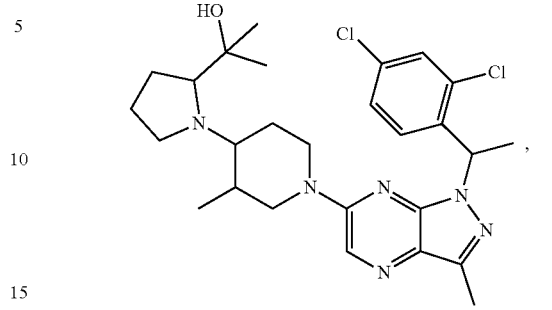
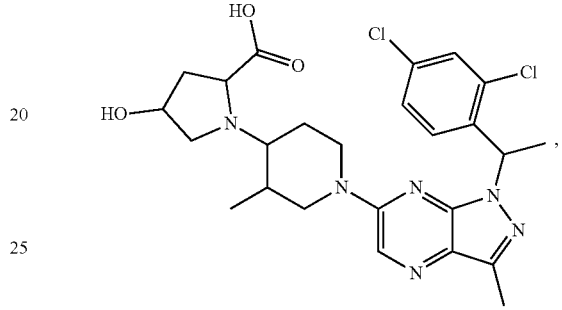
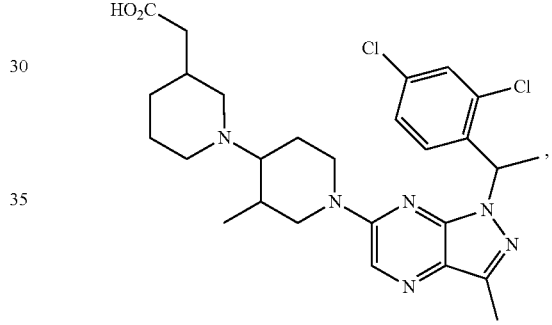
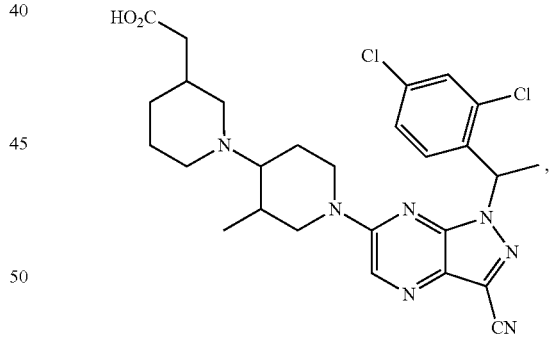
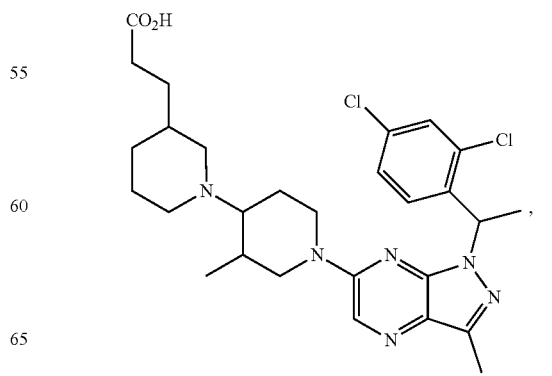

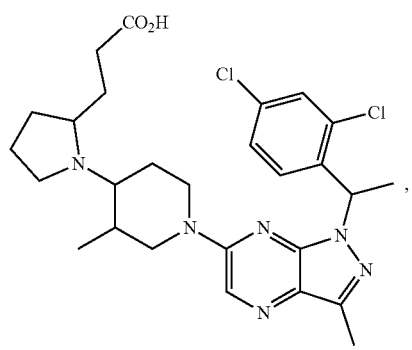
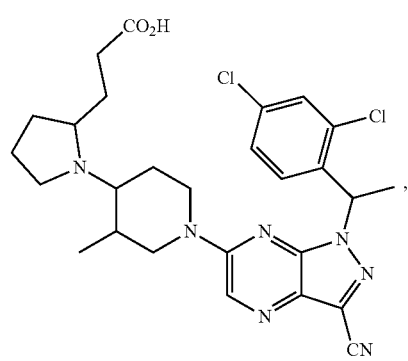
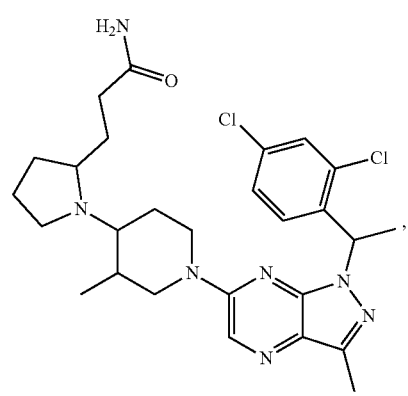
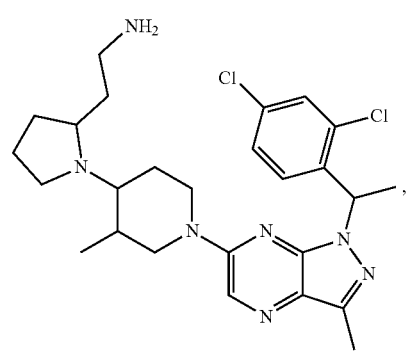
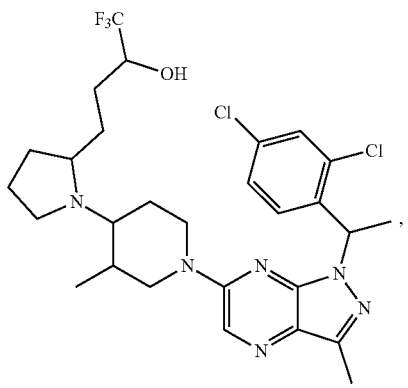
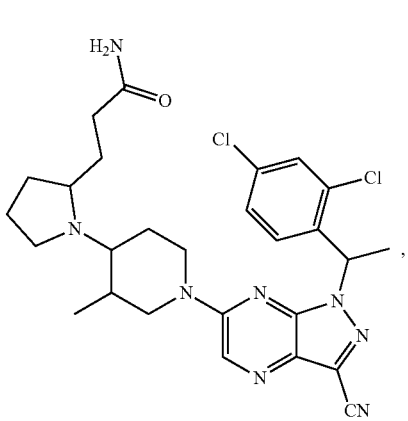
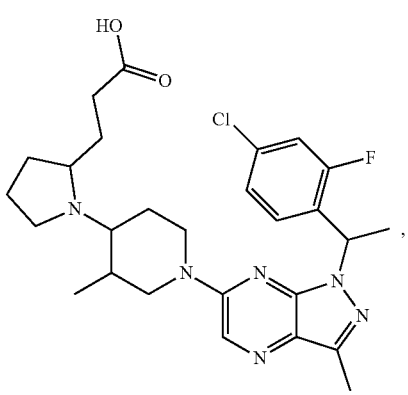
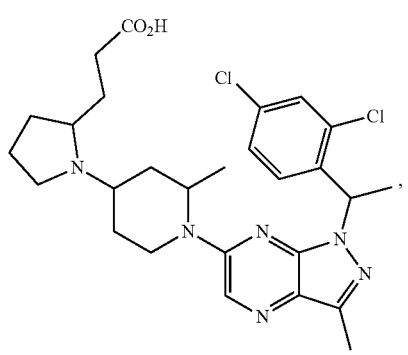

-continued
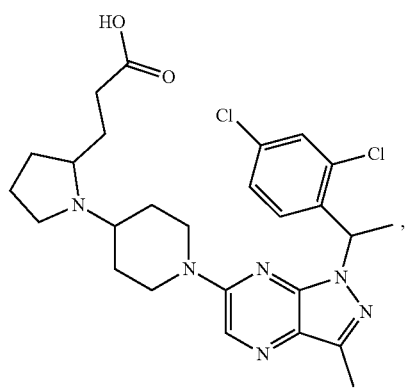
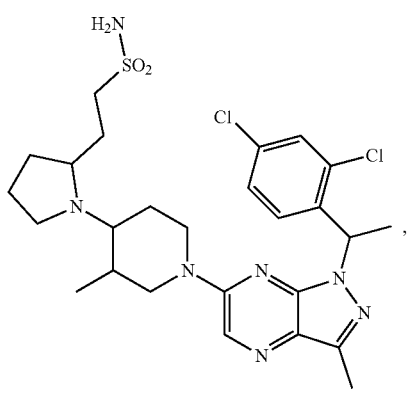
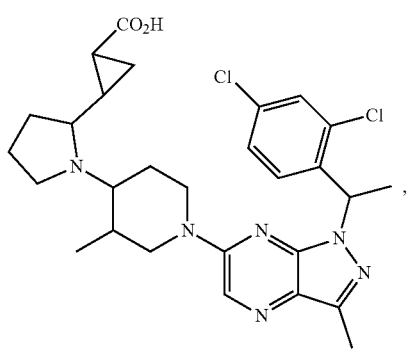
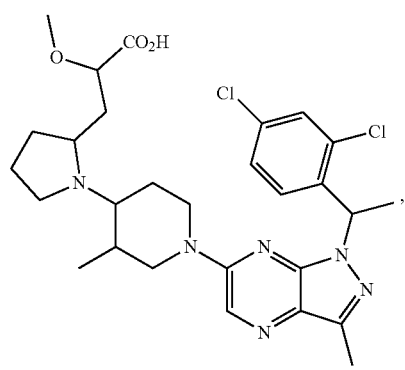
-continued
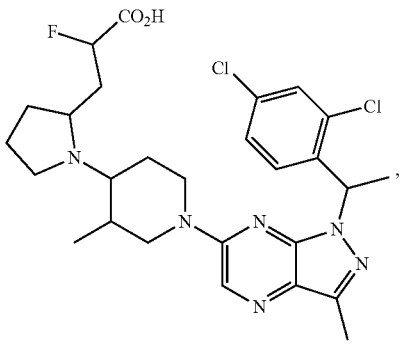
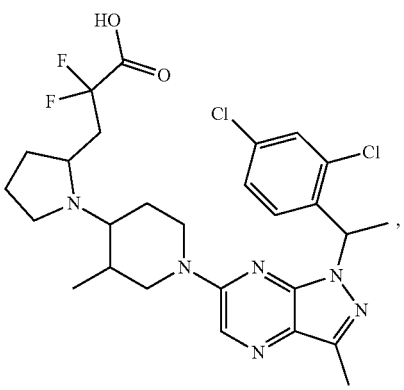
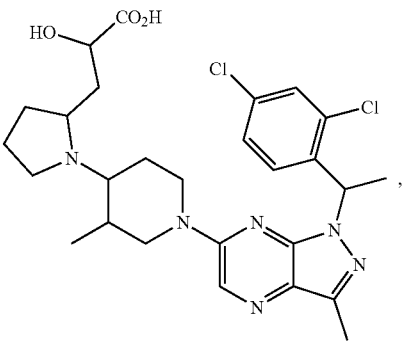
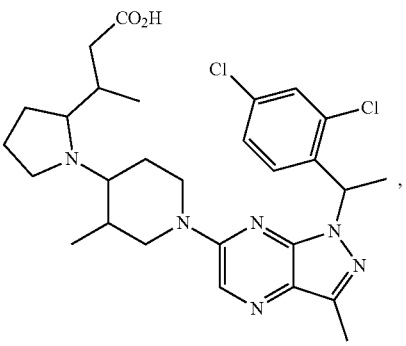
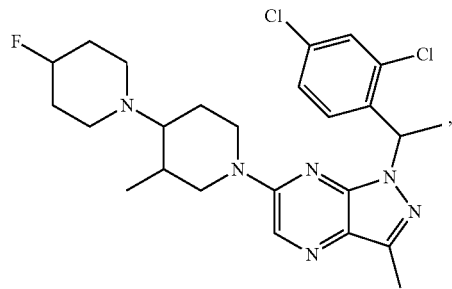

-continued
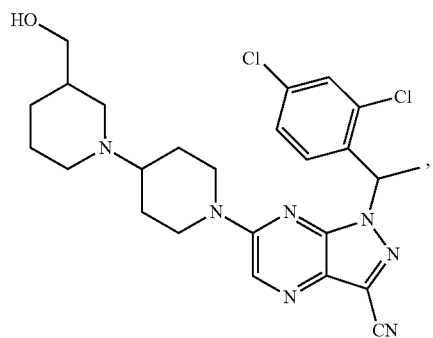
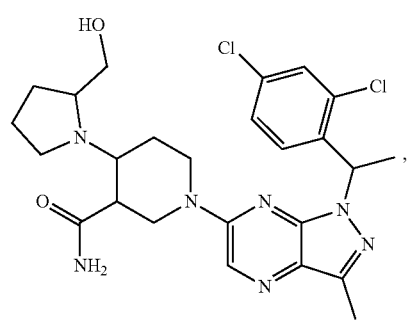
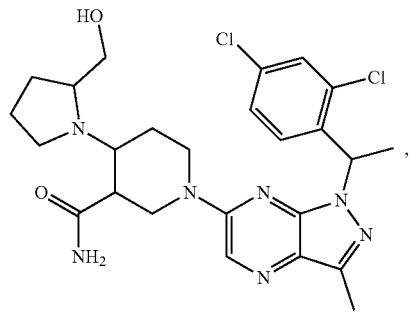
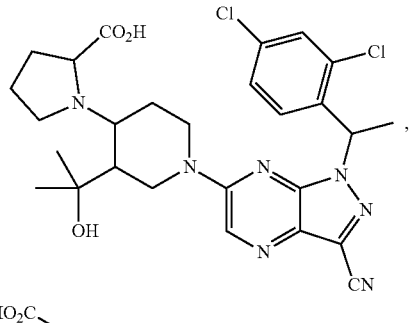
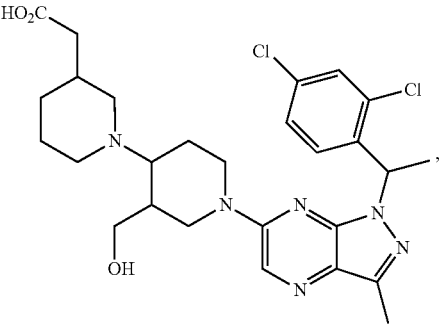
-continued
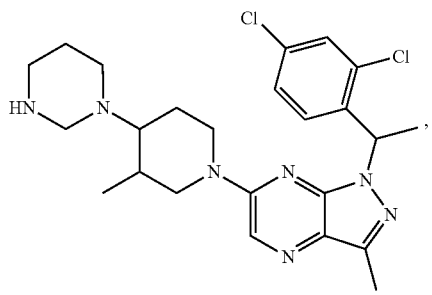
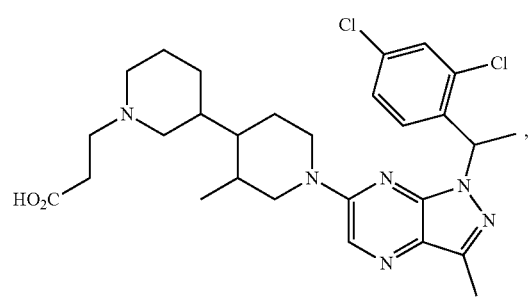
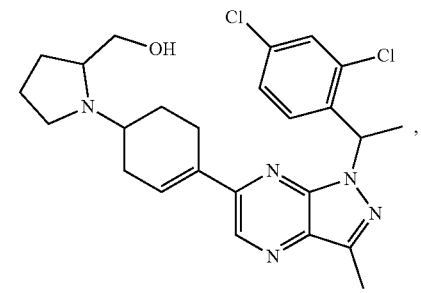
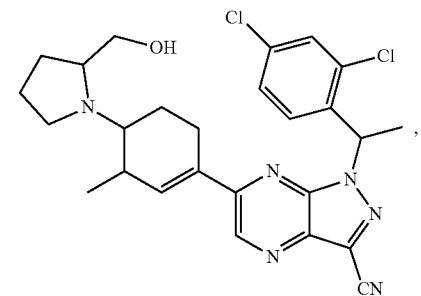
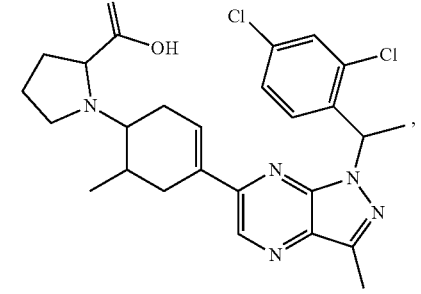

-continued
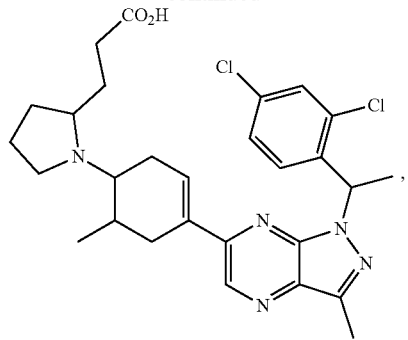
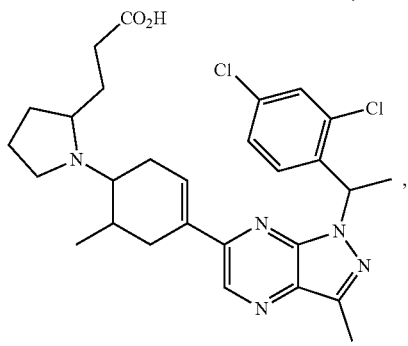
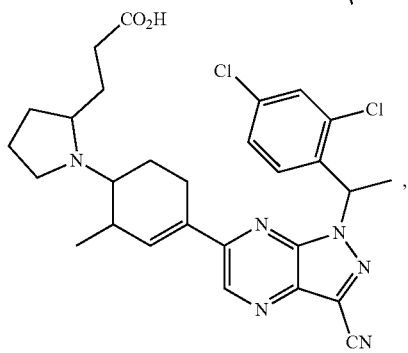
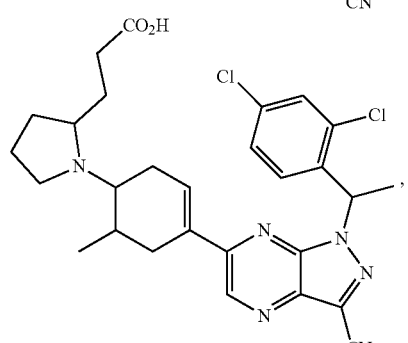
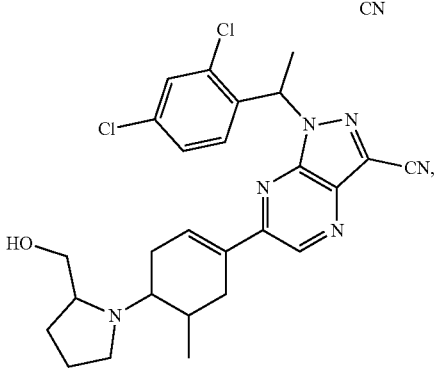
-continued
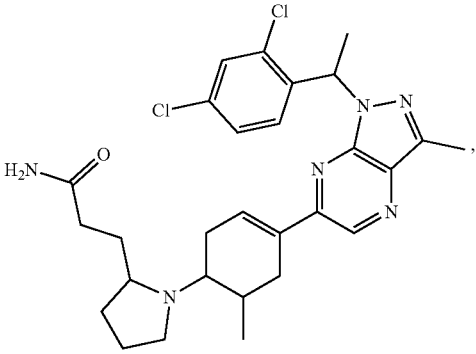
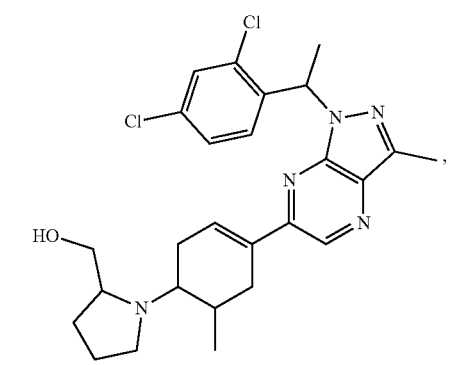
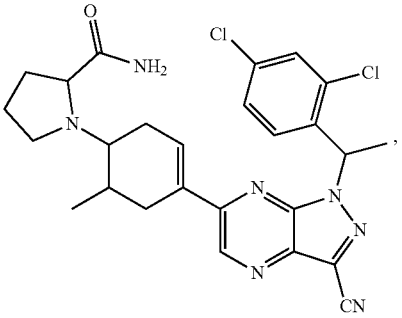
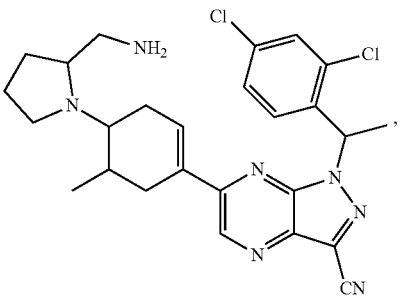
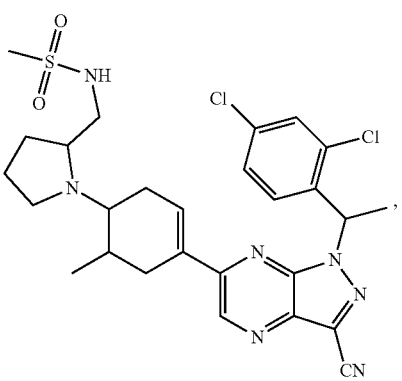

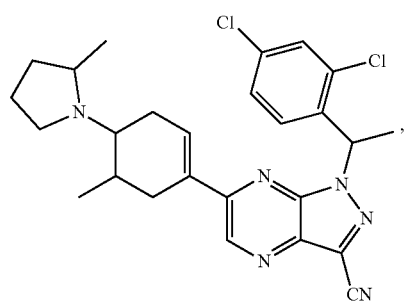
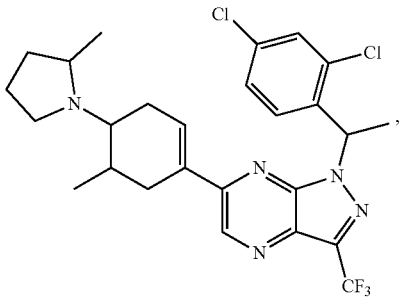
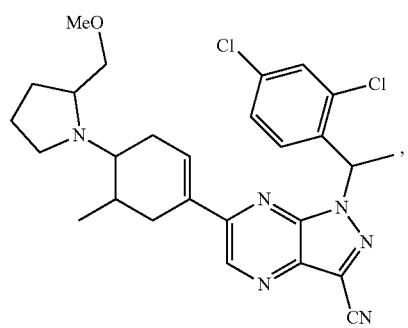
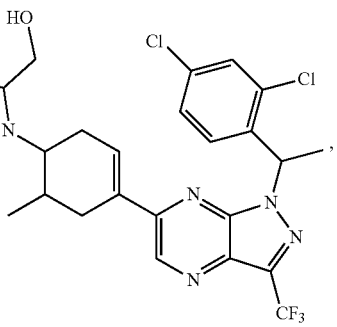
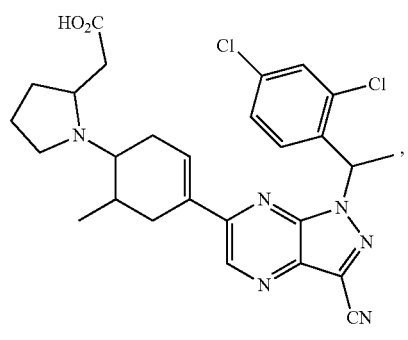
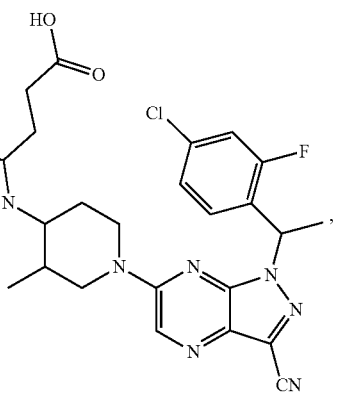
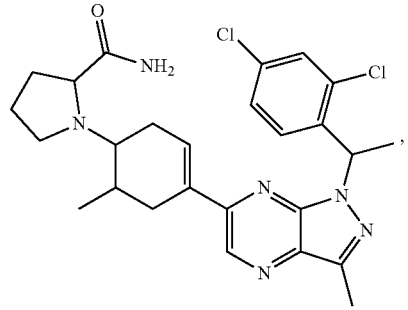
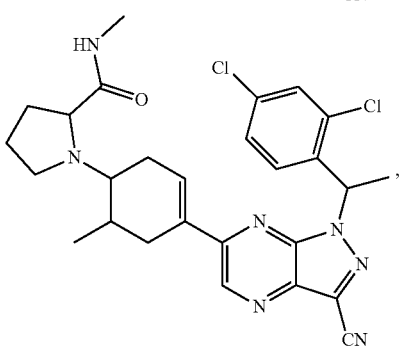
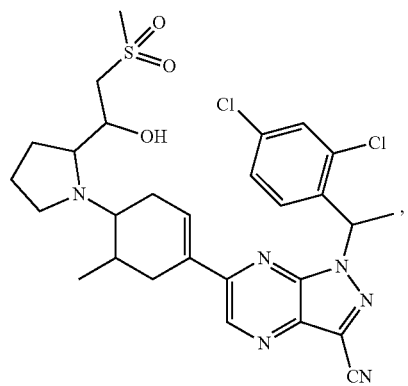
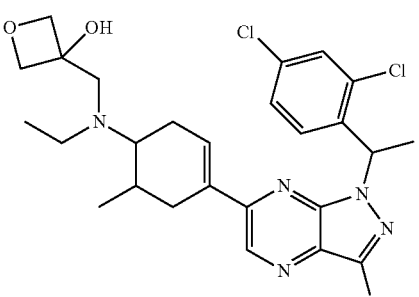
or pharmaceutically acceptable salts thereof.

Embodiment P5

A method of treating a malignancy that is positive for Epstein Barr Virus (EBV), the method comprising administering to a subject in need thereof a therapeutically effective amount of a compound of formula (III):

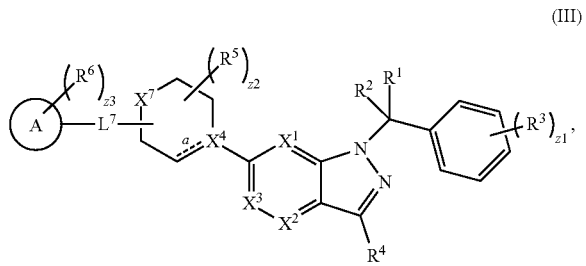

(III)

or a pharmaceutically acceptable salt thereof,
wherein:

A is substituted or unsubstituted cycloalkyl or substituted or unsubstituted heterocycloalkyl;

$X^1$ is $CR^8$ or N;

$X^2$ is $CR^9$ or N;

$X^3$ is $CR^{10}$ or N;

$X^4$ is C, $CR^{11}$ or N;

$X^7$ is $NR^7$ or N, wherein when $L^7$ is covalently bound to $X^7$, then $X^7$ is N;

n1, n2, n3, n4, n5, n6, n8, n9, n10, n11, and n17 are independently an integer from 0 to 4;

m1, m2, m3, m4, m5, m6, m8, m9, m10, m11, m17, v1, v2, v3, v4, v5, v6, v8, v9, v10, v11, and v17 are independently 1 or 2;

z1 is an integer from 0 to 5;

z2 is an integer from 0 to 8;

z3 is an integer from 0 to 12;

≐ is a single bond or double bond, wherein if ≐ is a single bond, then $X^4$ is $CR^{11}$ or N, and if ≐ is a double bond, then $X^4$ is C;

$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —NHC(O)$NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10.1}_3$, —CHX$^{10.1}_2$, —CH$_2$X$^{10.1}$, —CN, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11.1}_3$, —CHX$^{11.1}_2$, —CH$_2$X$^{11.1}$, —CN, —SO$_{n11}$R$^{11A}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m11}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17.1}_3$, —CHX$^{17.1}_2$, —CH$_2$X$^{17.1}$, —CN, —SO$_{n17}$R$^{17A}$, —SO$_{v17}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m17}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$ R$^{17A}$, R$^{17B}$, R$^{17C}$ and R$^{17D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$, R$^{4B}$ and R$^{4C}$, R$^{5B}$ and R$^{5C}$, R$^{6B}$ and R$^{6C}$, R$^{8B}$ and R$^{8C}$, R$^{9B}$ and R$^{9C}$, R$^{10B}$ and R$^{10C}$ R$^{11B}$ and R$^{11C}$ and R$^{17B}$ and R$^{17C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{8.1}$, X$^{9.1}$, X$^{10.1}$, X$^{11.1}$ and X$^{17.1}$ are independently —Cl, —Br, —I or —F, wherein at least one of X$^1$, X$^2$ and X$^3$ is N.

Embodiment P6

The method of embodiment P5, wherein the compound is:

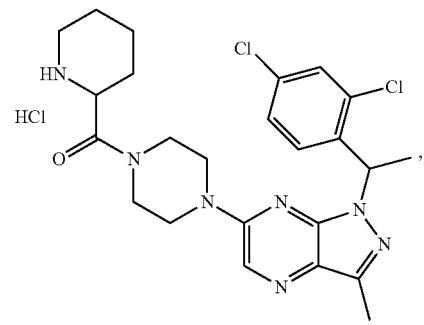

,

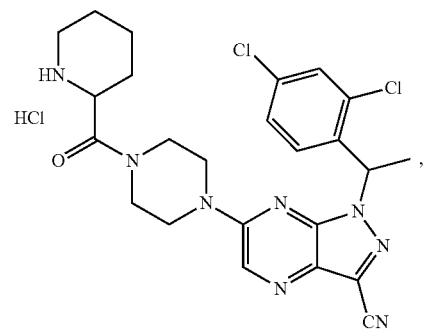

,

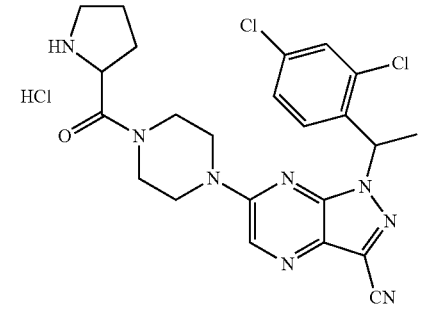

,

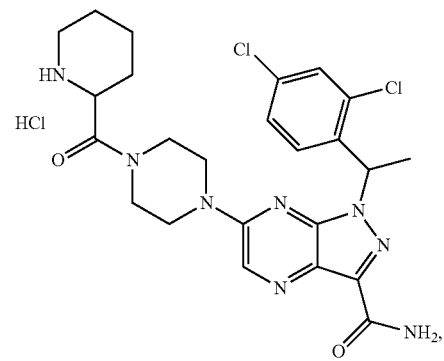

,

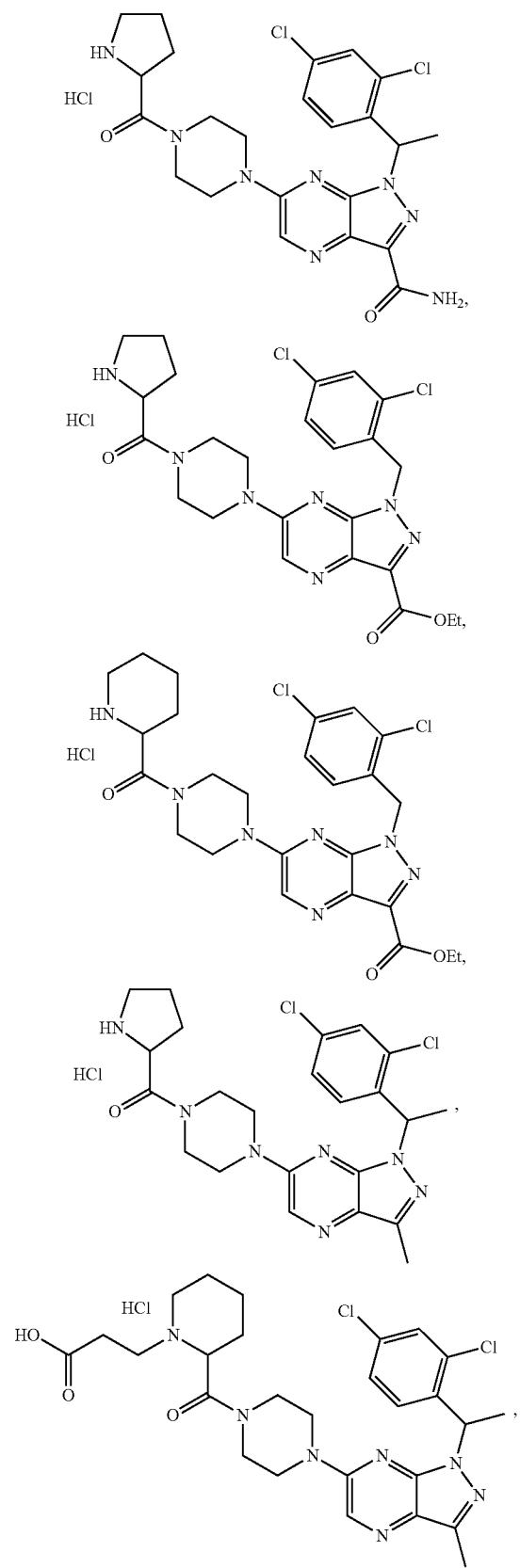
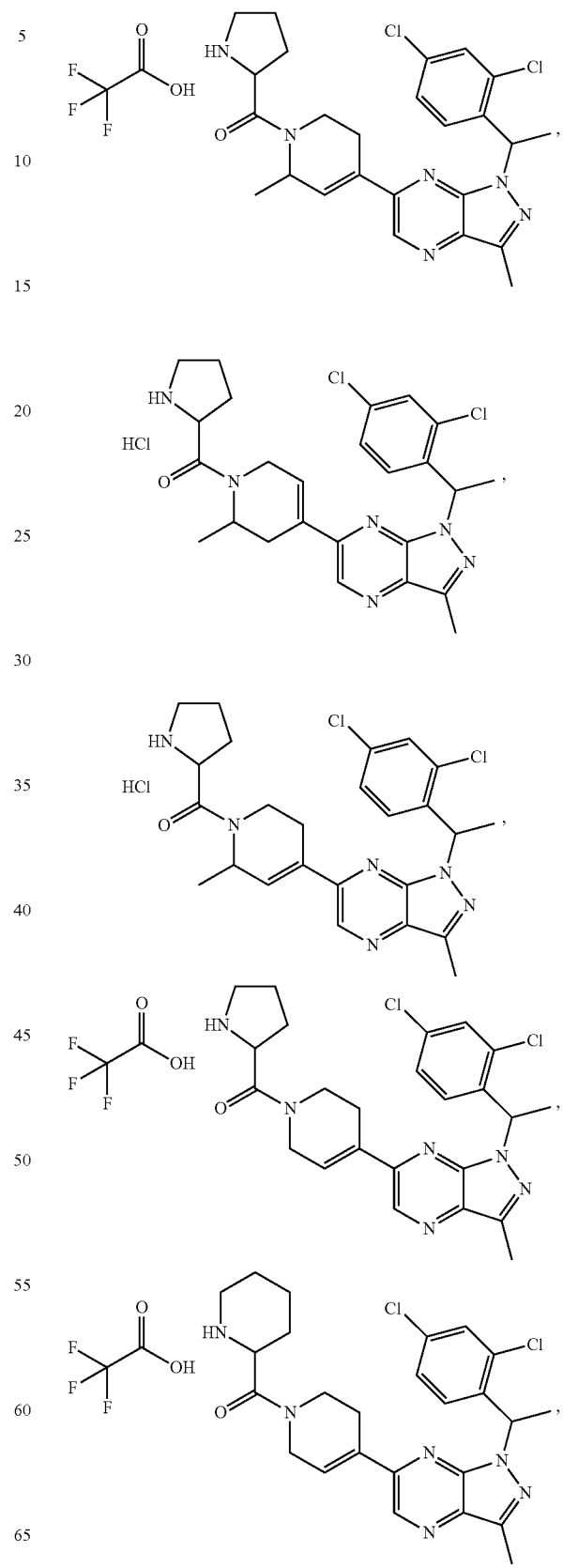

193
-continued
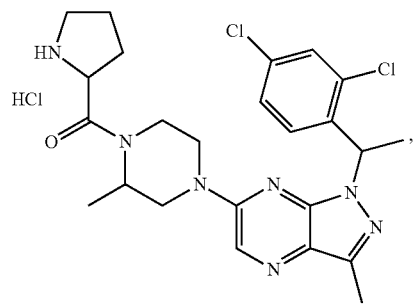
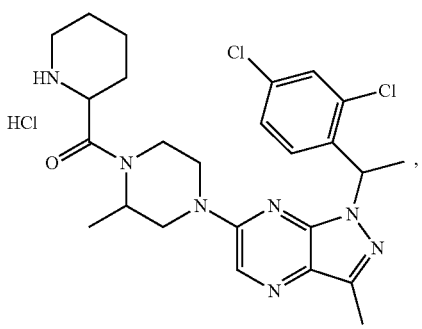
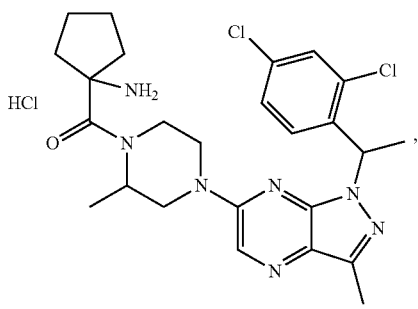
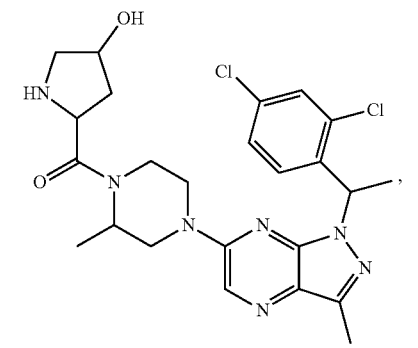
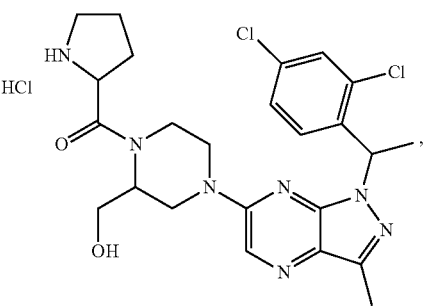
194
-continued
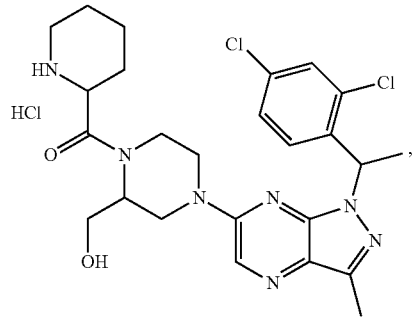
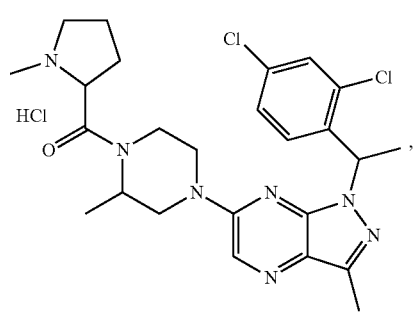
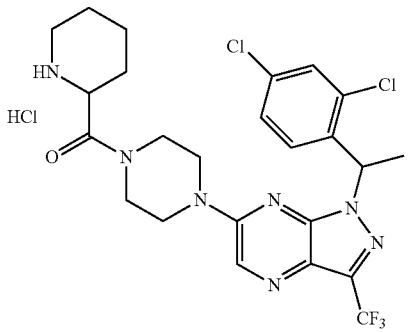
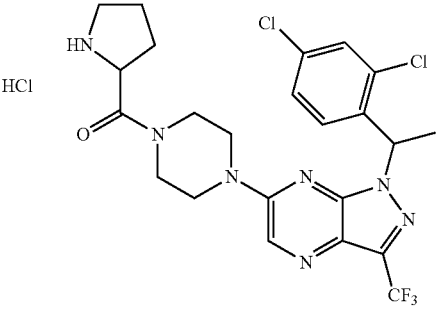
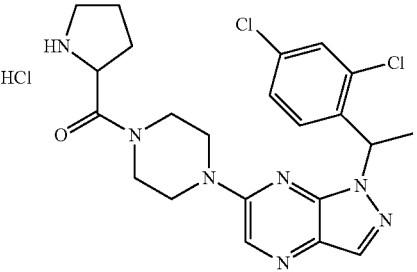

-continued

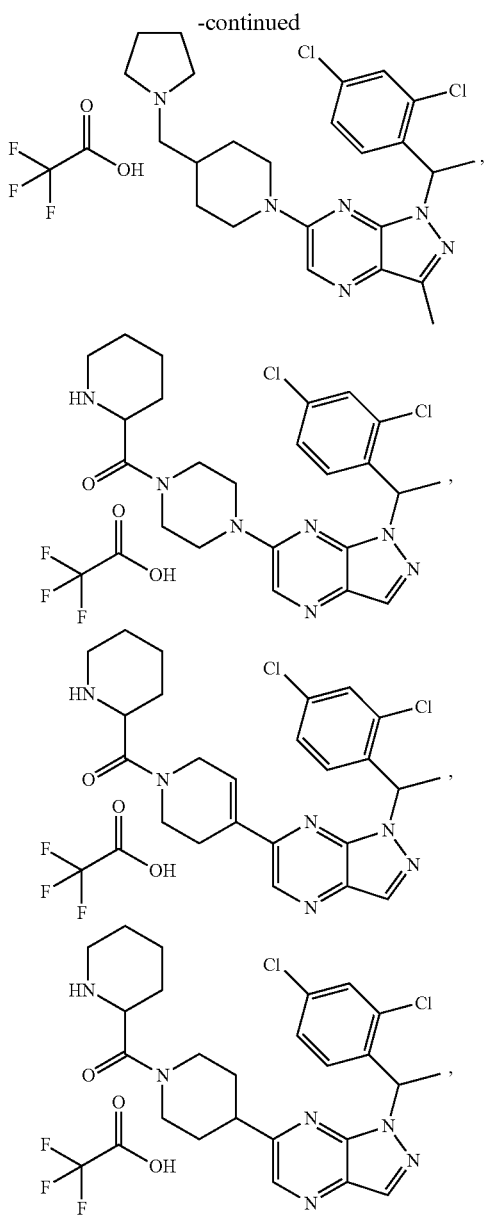

or pharmaceutically acceptable salts thereof.

Embodiment P7

The method of any one of embodiments P1 to P6, wherein the EBV positive malignancy is Burkitt lymphoma, Hodgkin's lymphoma, diffuse large B-cell lymphoma, NK/T-cell lymphoma, cutaneous T-cell lymphoma, nasopharyngeal carcinoma, gastric cancer, vulvar squamous cell carcinoma, salivary gland cancer, orbit choroidal melanoma, or adenocarcinoma consistent with pancreaticobiliary.

Embodiment P8

The method of embodiment P7 further comprising co-administering to a subject in need thereof a chemotherapeutic agent or anticancer agent.

Embodiment P9

The method of embodiment P8, wherein the chemotherapeutic agent or anticancer agent is an antiproliferative/ antineoplastic drug, an antimetabolite, an antitumor antibiotic, an antimitotic agent, a topoisomerase inhibitor, a cytostatic agent, an estrogen receptor down regulator, an antiandrogen, a LHRH antagonist or LHRH agonist, a progestogen, an aromatase inhibitor, an inhibitor of 5-alpha-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an antisense therapy agent, an anti-ras antisense agent, an gene therapy agent, an immunotherapeutic agent, or an antibody.

Embodiment P10

The method of embodiment P9, wherein the chemotherapeutic agent or anticancer agent is an anti-proliferative agent, a chemotherapeutic agent, an antimetabolite, an anti-microtubule agent, an alkylating agent, a platinum agent, an anthracycline, an antitumor antibiotic, a topoisomerase inhibitor, a purine antagonist, a pyrimidine antagonist, a cell maturing agent, a DNA repair enzyme inhibitor, an enzyme that prevents cell survival, a histone deacetylase inhibitor, a cytotoxic agent, a hormone, an antibody, an immuno-modulator, a Bcr-Abl kinase inhibitor, a hormone agonist or antagonist, partial agonist or partial antagonist, a kinase inhibitor, surgery, radiotherapy, an endocrine therapy, a biological response modifier, a hyperthermial agent, a cryotherapeutic agent, an immuomodulating agent, an agent to attenuate any adverse effects, a spindle poison, a podophyllotoxin, an antibiotic, or a nitrosourea.

Embodiment P11

The method of embodiment P10, wherein the antimetabolite is 5-fluoro uracil, methotrexate, azacitidine, decitabine, fludarabine or cytarabine.

Embodiment P12

The method of embodiment P10, wherein the antimicrotubule agent is a *vinca* alkaloid or a taxane.

Embodiment P13

The method of embodiment P10, wherein the alkylating agent is mechlorethamine, chlorambucil, cyclophosphamide, melphalan, carmustine, lomustine, ifosfamide, carmustine, busulfan, cyclophosphamide, dacarbazine, ifosfamide, bischloroethylnitrosurea or hydroxyurea.

Embodiment P14

The method of embodiment P10, wherein the platinum agent is cisplatin, carboplatin, oxaliplatin, satraplatin (JM-216) or CI-973.

Embodiment P15

The method of embodiment P9, wherein the chemotherapeutic agent or anticancer agent is an antibody.

Embodiment P16

The method of embodiment P9, wherein the chemotherapeutic agent or anticancer agent is an immunomodulating agent.

Embodiment P17

Use of the compound of any one of embodiment P1 to P6 to treat a malignancy that is positive for Epstein Barr Virus (EBV).

Embodiment P18

Use of the compound of any one of embodiment P1 to P6 in the manufacture of a medicament to treat a malignancy that is positive for Epstein Barr Virus (EBV).

FURTHER EMBODIMENTS

Embodiment 1

A method of treating a malignancy that is positive for Epstein Barr Virus (EBV), the method comprising administering to a subject in need thereof a therapeutically effective amount of a compound of formula (I):

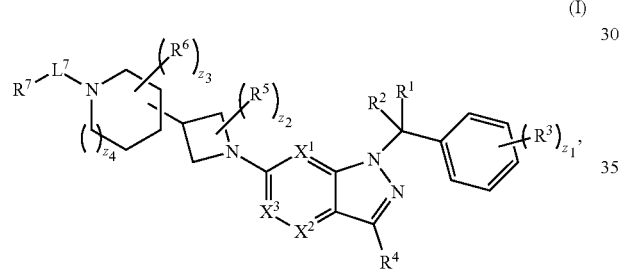

or a pharmaceutically acceptable salt thereof, wherein:

$X^1$ is $CR^8$ or N;
$X^2$ is $CR^9$ or N;
$X^3$ is $CR^{10}$ or N;
n1, n2, n3, n4, n5, n6, n7, n8, n9 and n10 are independently an integer from 0 to 4;
m1, m2, m3, m4, m5, m6, m7, m8, m9, m10, v1, v2, v3, v4, v5, v6, v7, v8, v9 and v10 are independently 1 or 2;
z1 is an integer from 0 to 5;
z2 is an integer from 0 to 2;
z3 is an integer from 0 to 11;
z4 is an integer from 0 to 2;
$L^7$ is a bond, —O—, —S—, —$NR^{7.2B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —NHC(O)$NHNR^{1B}R^{1C}$, —NHC(O)$NR^{1B}R^{1C}$, —N(O)$_{m1}$, —$NR^{1B}R^{1C}$, —C(O)$R^{1D}$, —C(O)$OR^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NHNR^{2B}R^{2C}$, —$ONR^{2B}R^{2C}$, —NHC(O)$NHNR^{2B}R^{2C}$, —NHC(O)$NR^{2B}R^{2C}$, —N(O)$_{m2}$, —$NR^{2B}R^{2C}$, —C(O)$R^{2D}$, —C(O)$OR^{2D}$, —C(O)$NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, —$CX^{3.1}_3$, —$CHX^{3.1}_2$, —$CH_2X^{3.1}$, —CN, —$N_3$, —$SO_{n3}R^{3A}$, —$SO_{v3}NR^{3B}R^{3C}$, —$NHNR^{3B}R^{3C}$, —$ONR^{3B}R^{3C}$, —NHC(O)$NHNR^{3B}R^{3C}$, —NHC(O)$NR^{3B}R^{3C}$, —N(O)$_{m3}$, —$NR^{3B}R^{3C}$, —C(O)$R^{3D}$, —C(O)$OR^{3D}$, —C(O)$NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^4$ is hydrogen, halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —$NHNR^{4B}R^{4C}$, —$ONR^{4B}R^{4C}$, —NHC(O)$NHNR^{4B}R^{4C}$, —NHC(O)$NR^{4B}R^{4C}$, —N(O)$_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^5$ is independently hydrogen, halogen, oxo, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)$OR^{5D}$, —C(O)$NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^6$ is independently hydrogen, halogen, oxo, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —N(O)$_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^7$ is hydrogen, halogen, —$CX^{7.1}_3$, —$CHX^{7.1}_2$, —$CH_2X^{7.1}$, —CN, —$N_3$, —$SO_{n7}R^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7B}$C(O)R$^{7D}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^8$ is hydrogen, halogen, —CX$^{8.1}_3$, —CHX$^{8.1}_2$, —CH$_2$X$^{8.1}$, —CN, —N$_3$, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}_3$, —CHX$^{9.1}_2$, —CH$_2$X$^{9.1}$, —CN, —N$_3$, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10.1}_3$, —CHX$^{10.1}_2$, —CH$_2$X$^{10.1}$, —CN, —N$_3$, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$ and R$^{10D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$ and R$^{10C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$ and X$^{10.1}$ are independently —Cl, —Br, —I or —F, wherein at least one of X$^1$, X$^2$ and X$^3$ is N.

Embodiment 2

The method of embodiment 1, wherein the compound is:

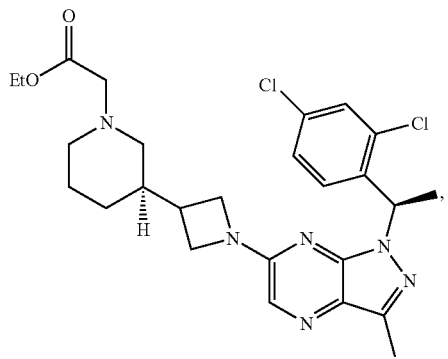

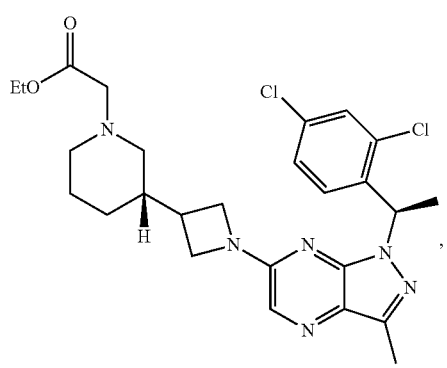

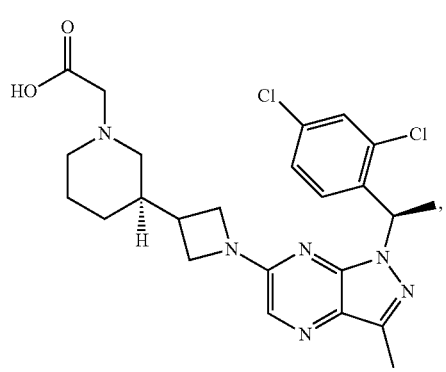

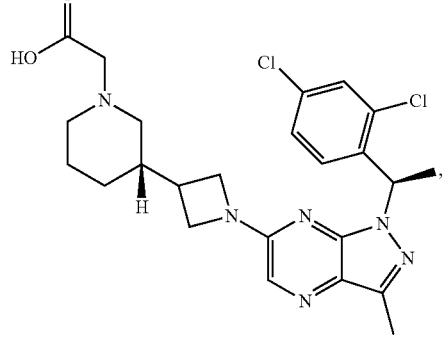

201
-continued
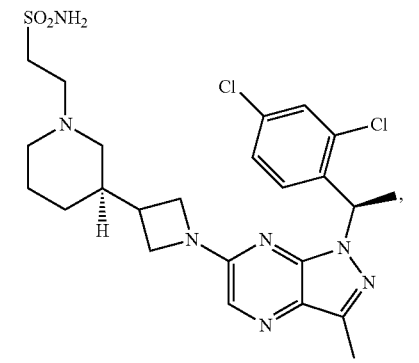
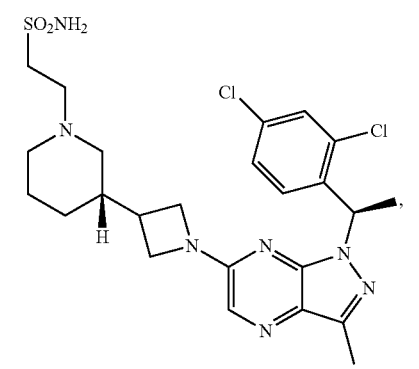
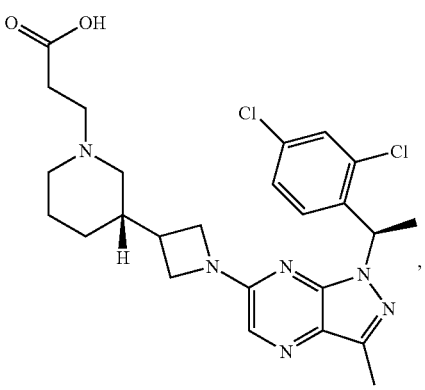
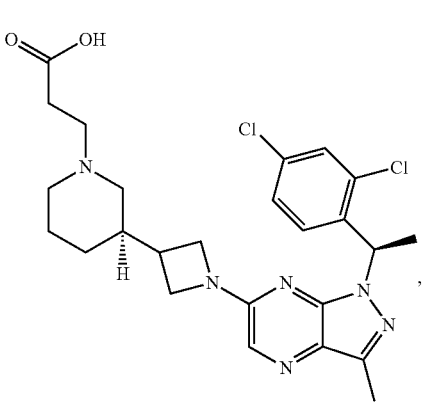
202
-continued
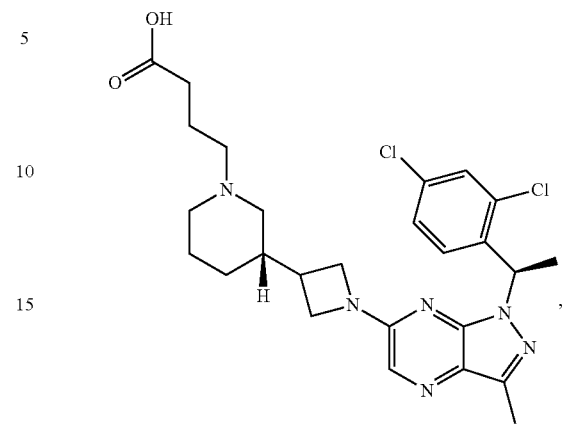
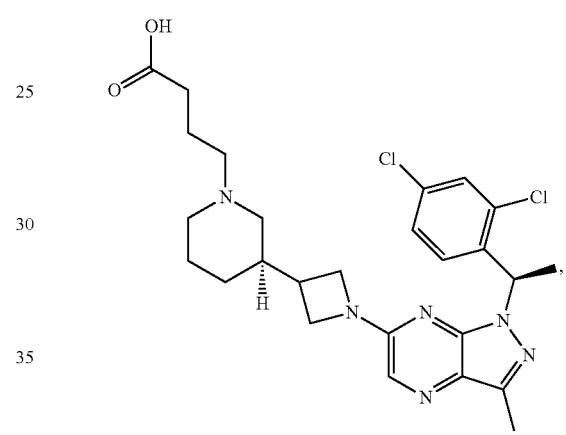
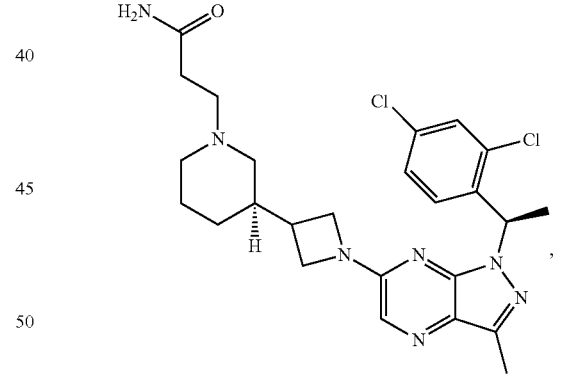
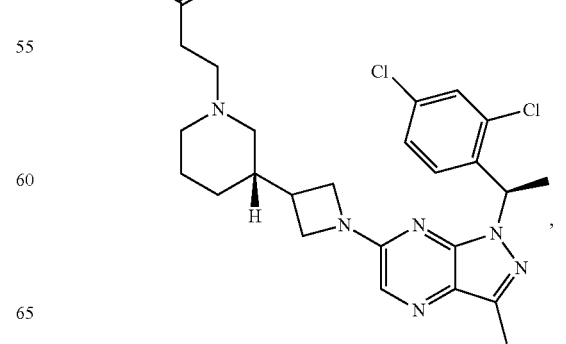

203
-continued
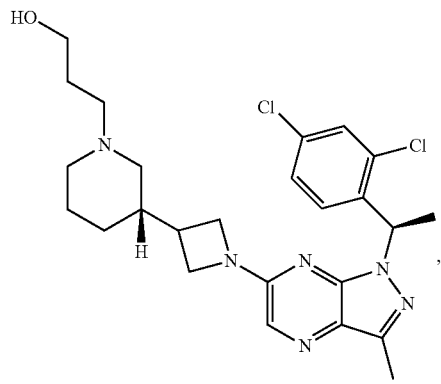
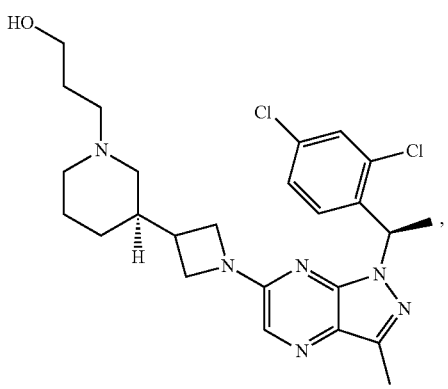
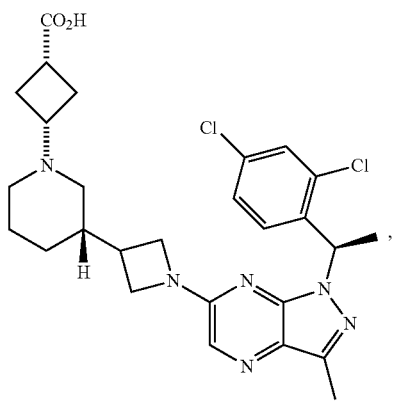
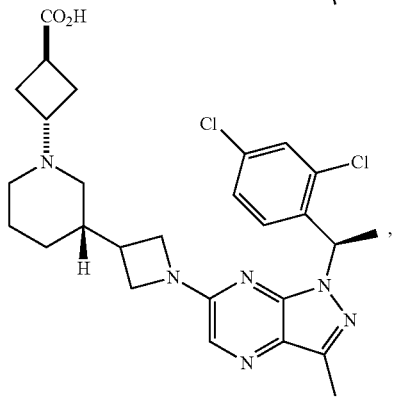
204
-continued
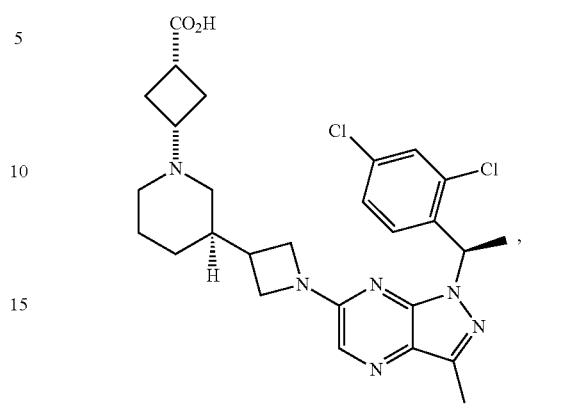
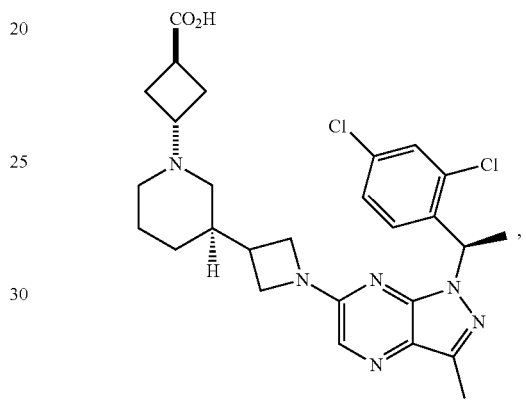
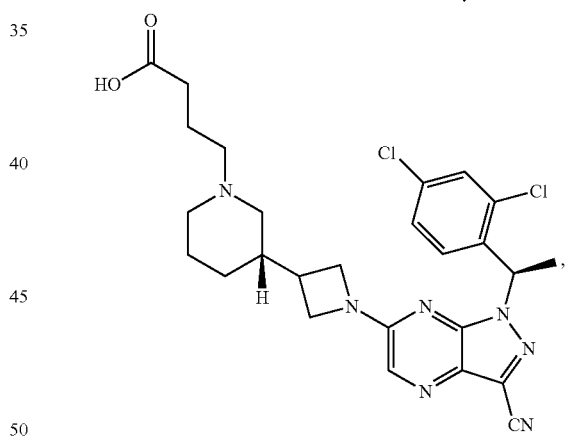
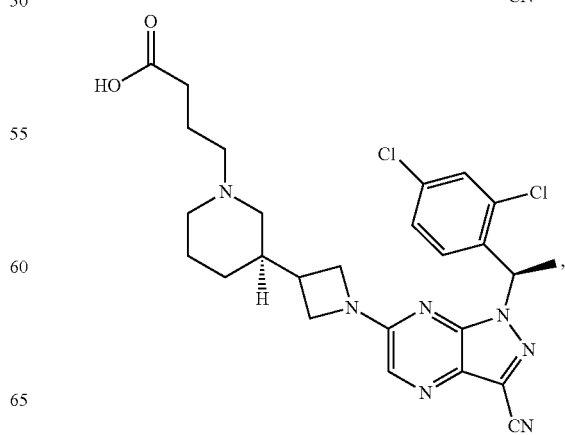

205
-continued
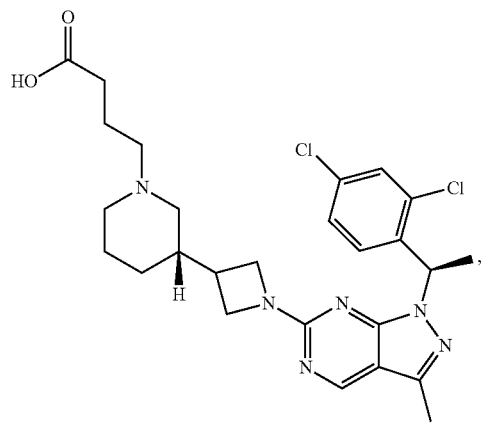
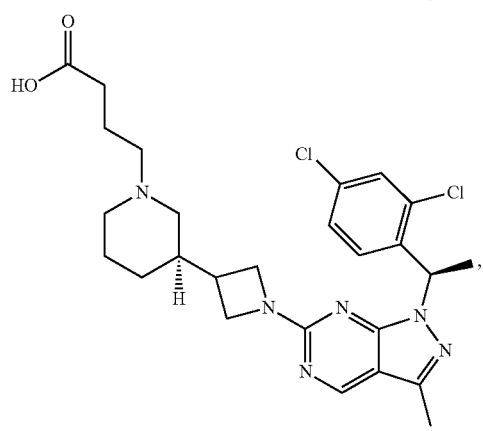
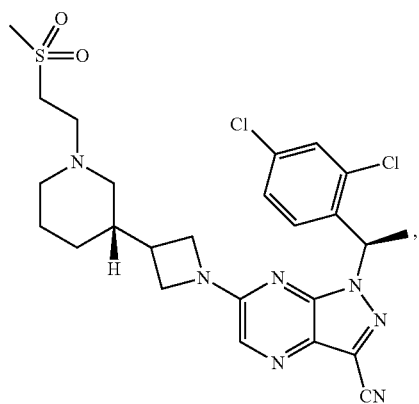
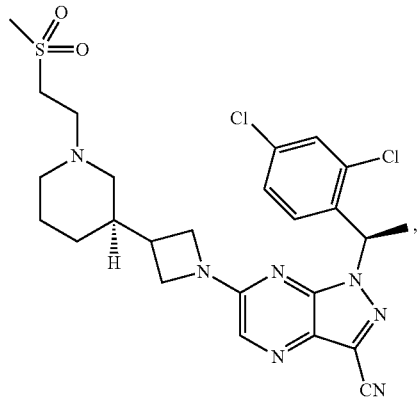
206
-continued
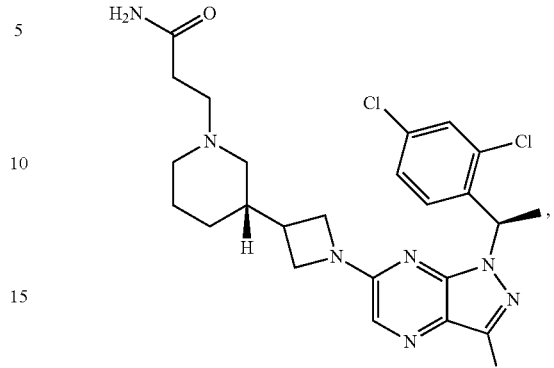
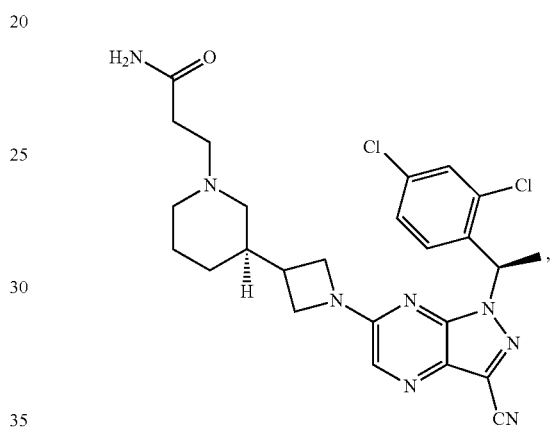
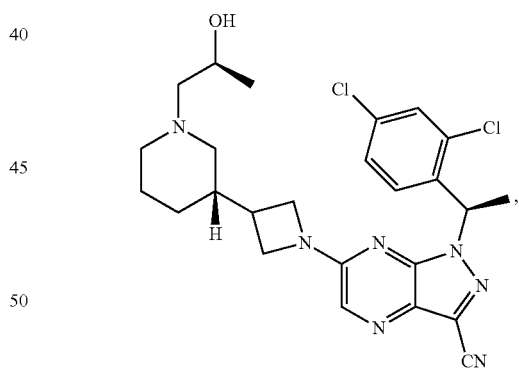
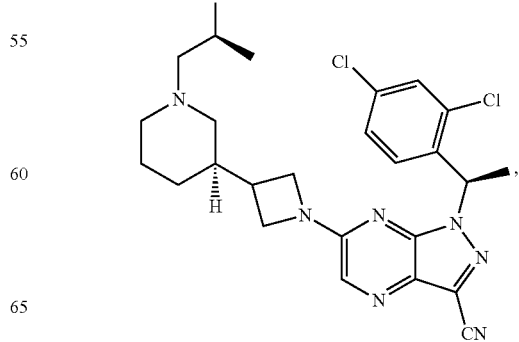

207
-continued
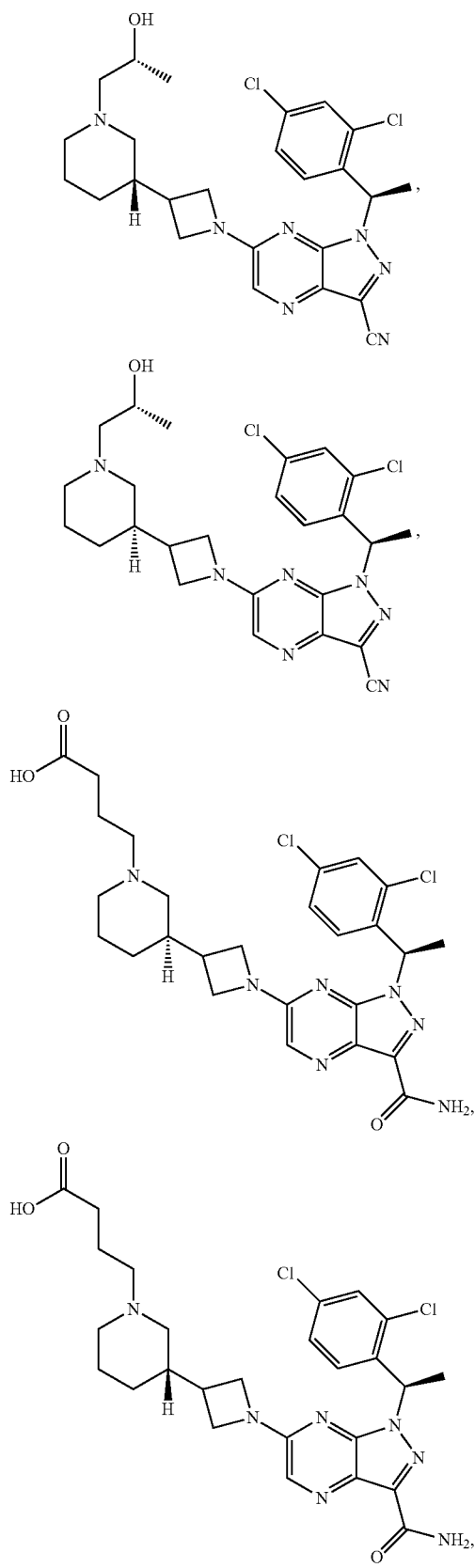
208
-continued
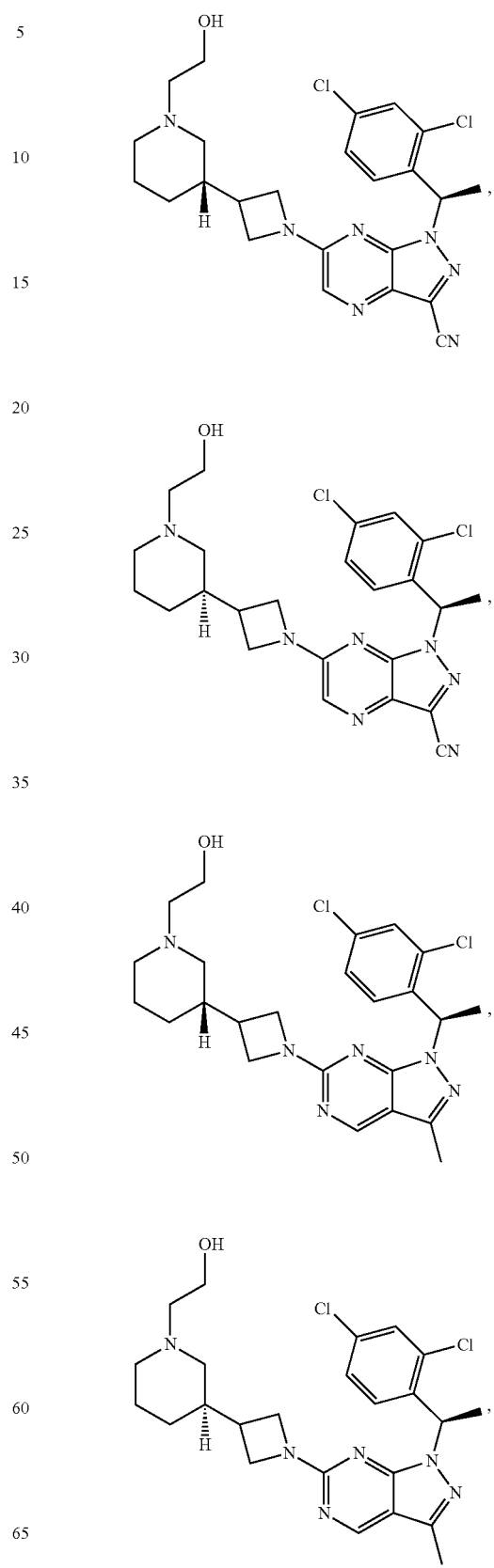

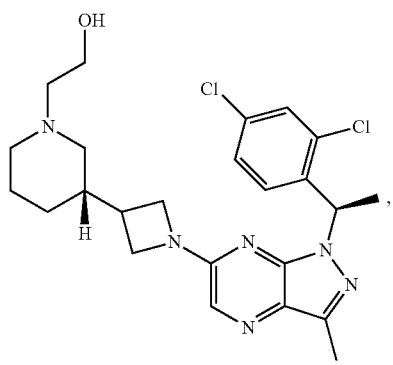
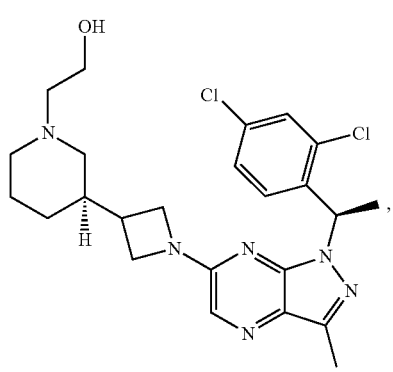
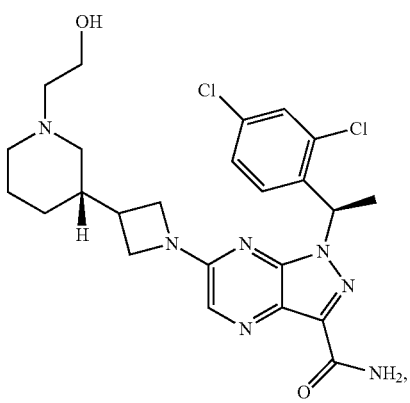
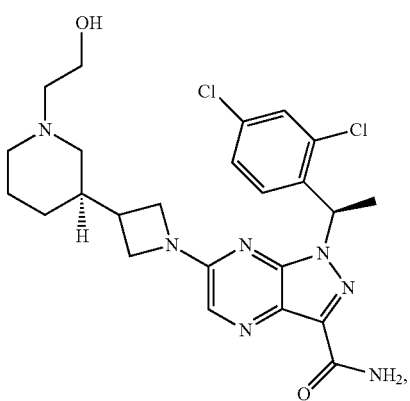
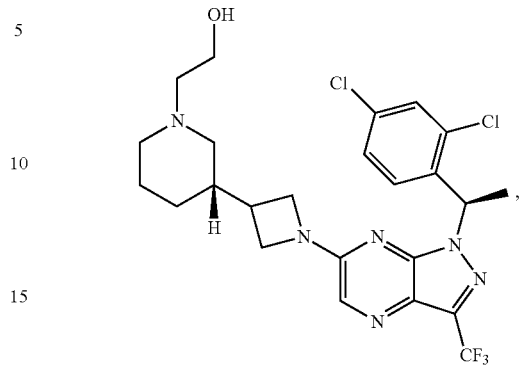
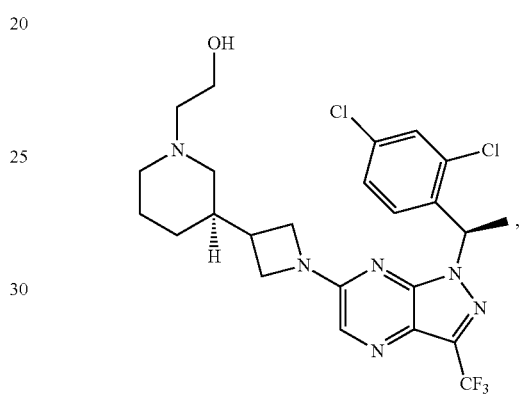
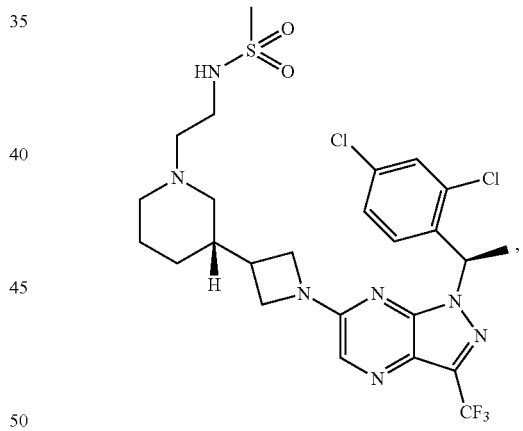
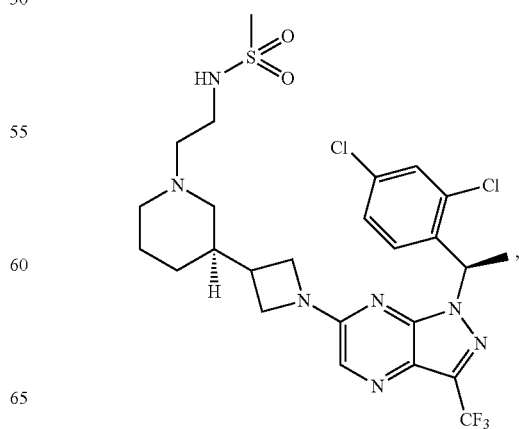

211
-continued
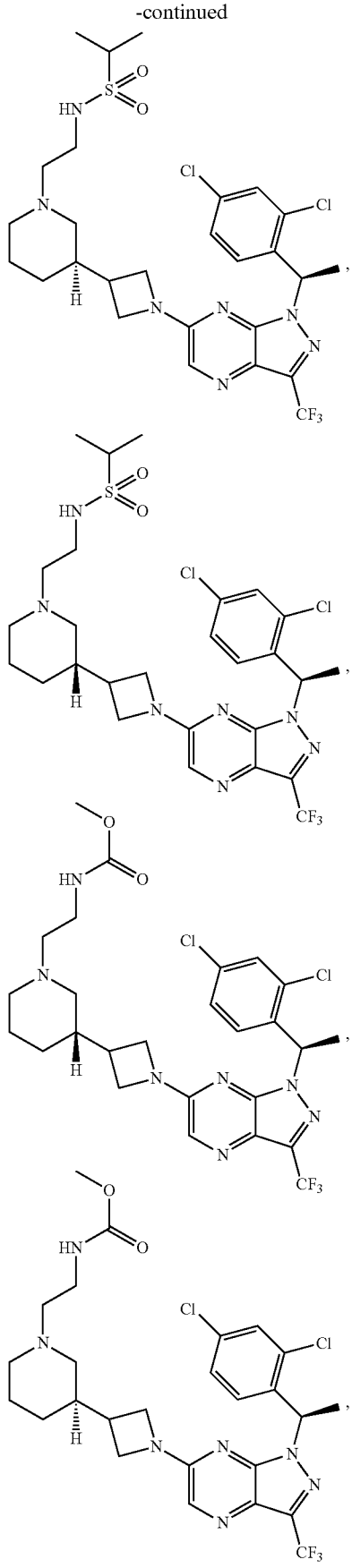
212
-continued
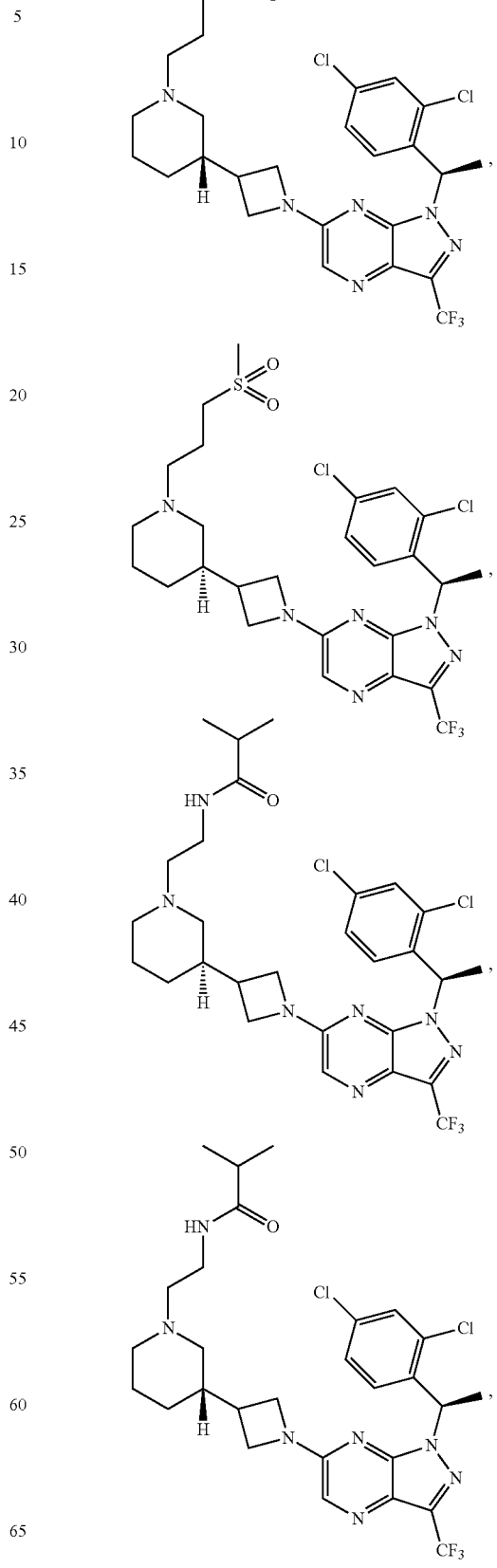

213
-continued
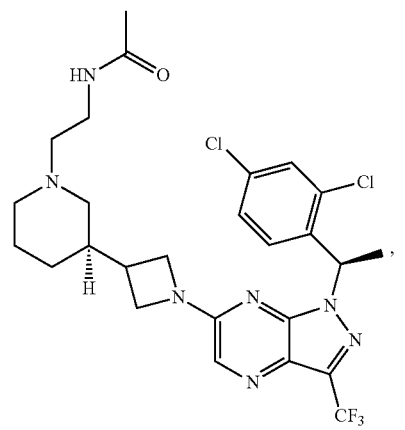
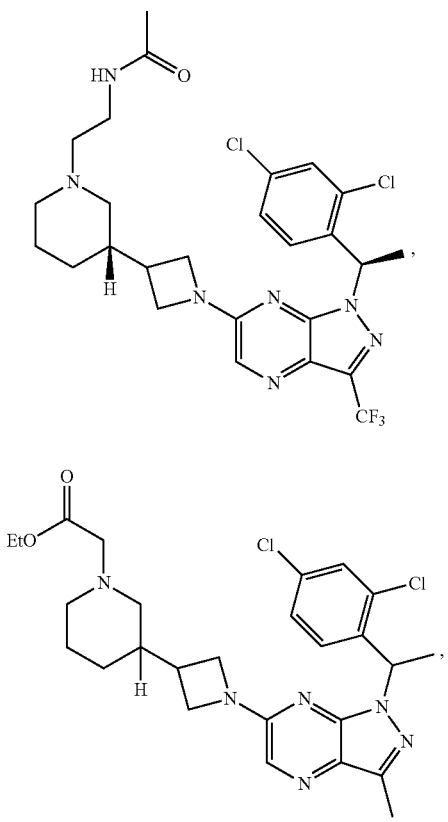
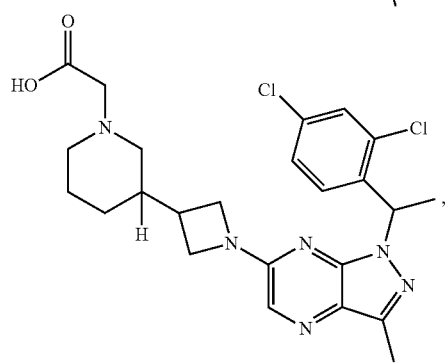
214
-continued
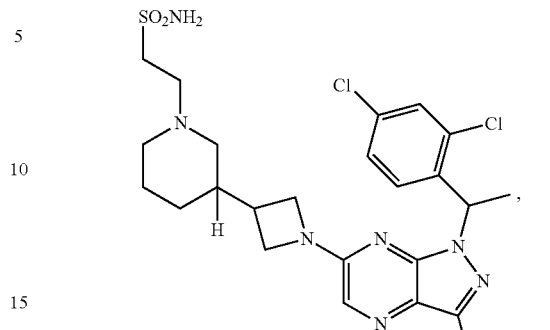
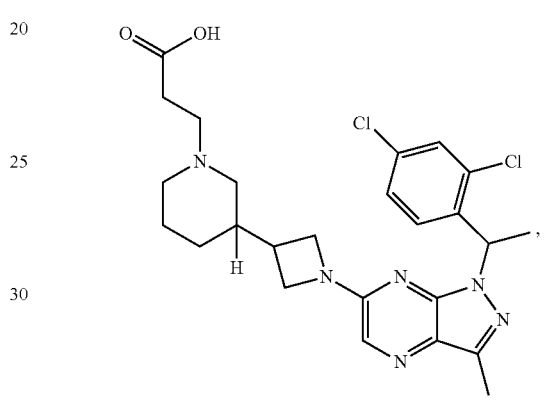
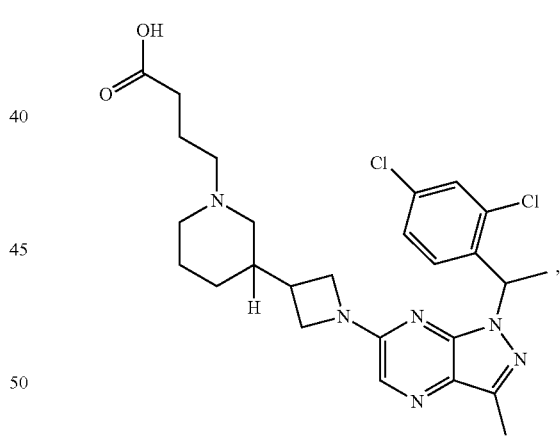
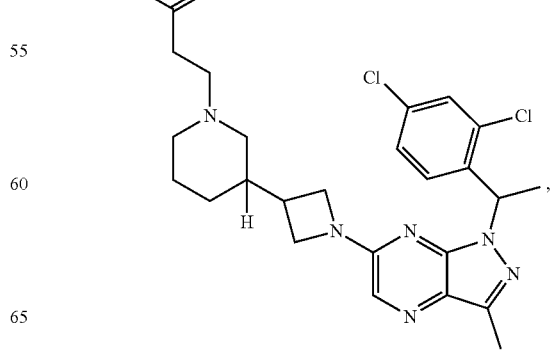

-continued
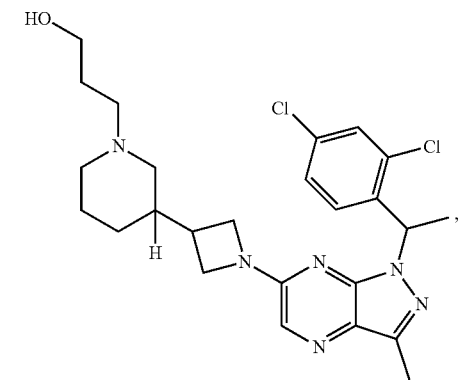
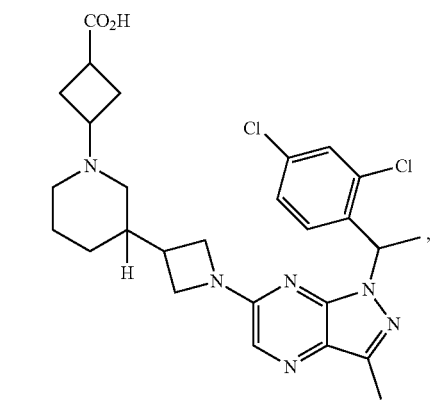
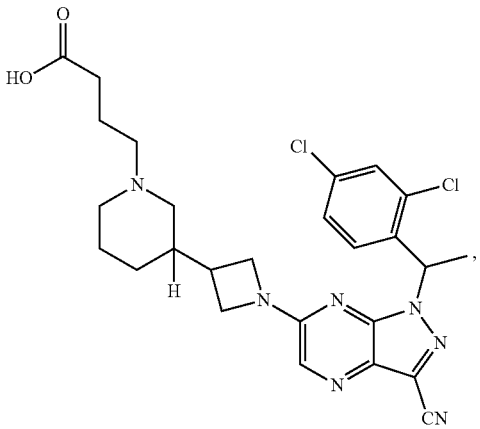
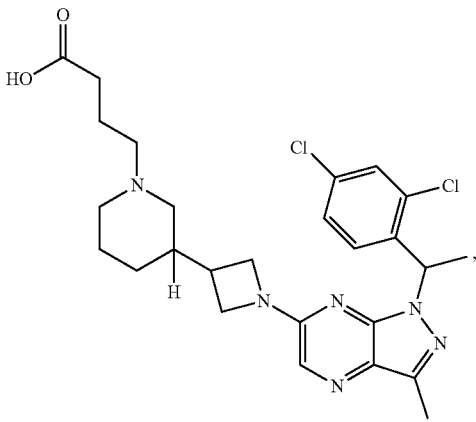
-continued
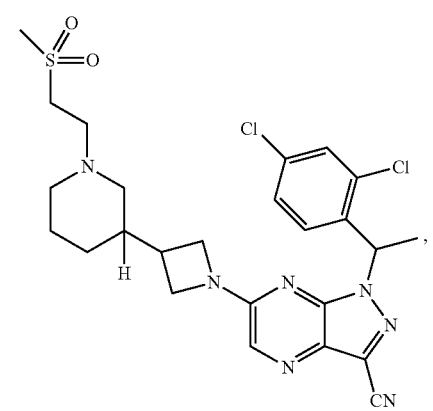
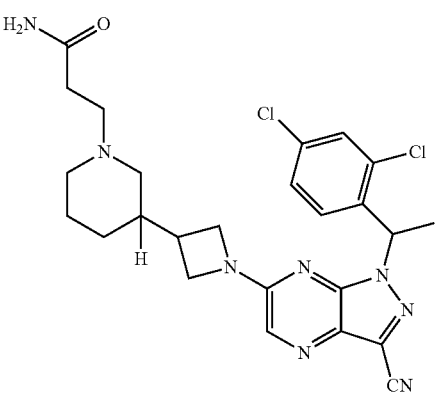
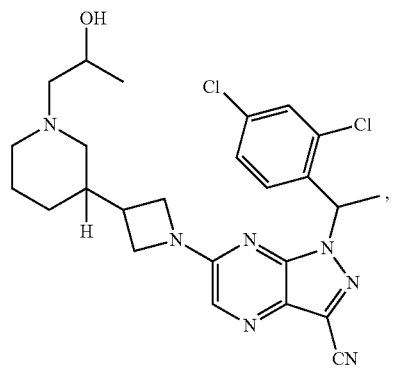
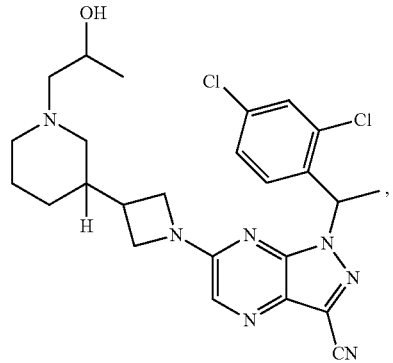

217
-continued
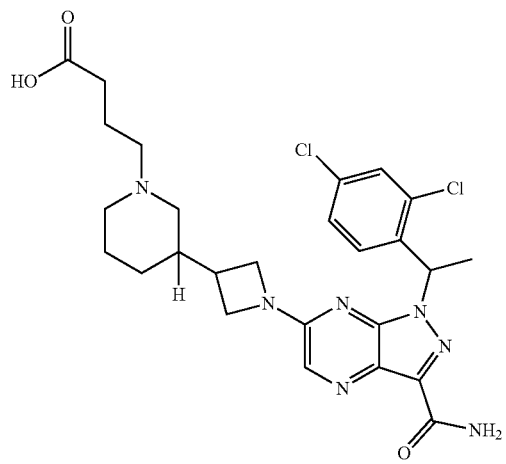
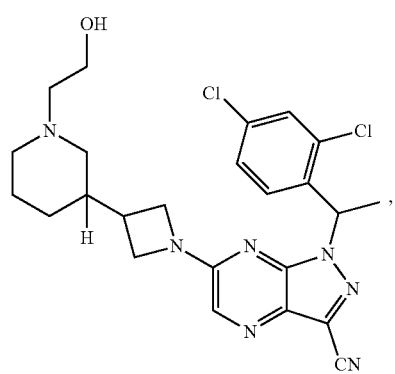
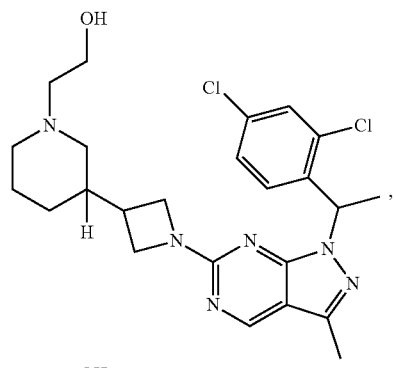
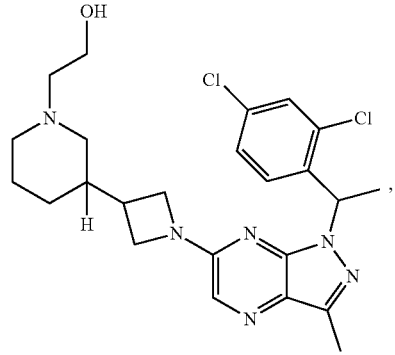
218
-continued
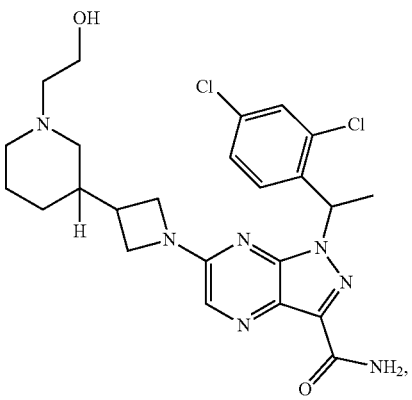
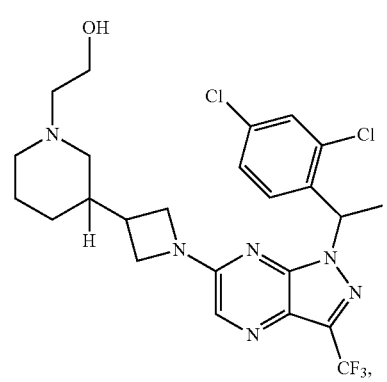
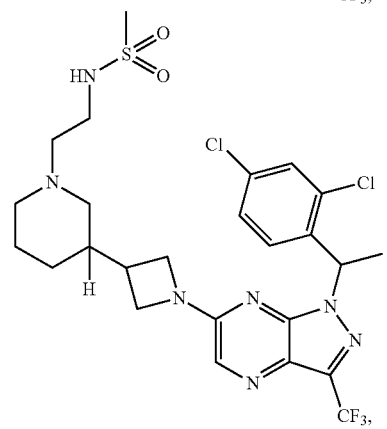
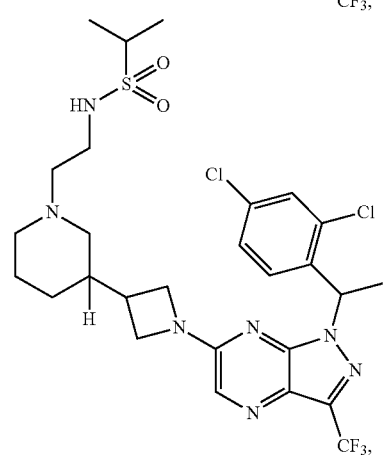

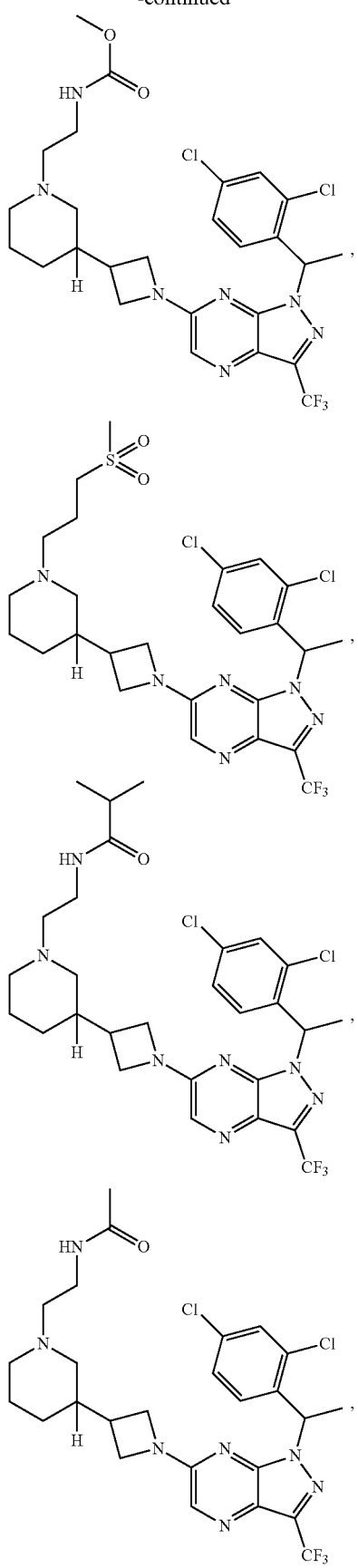
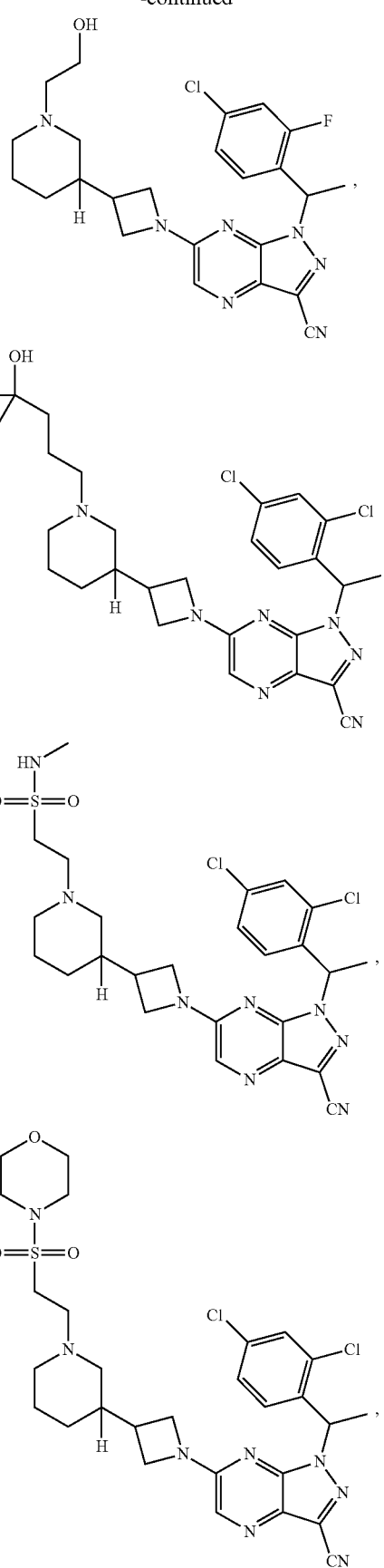

221
-continued
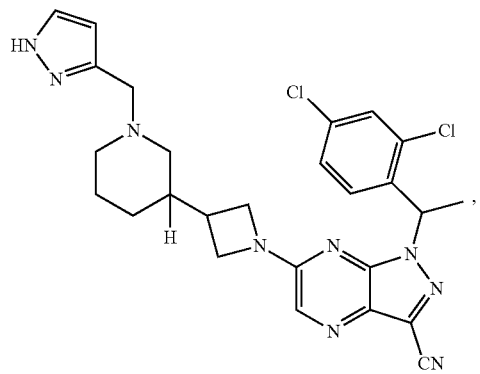
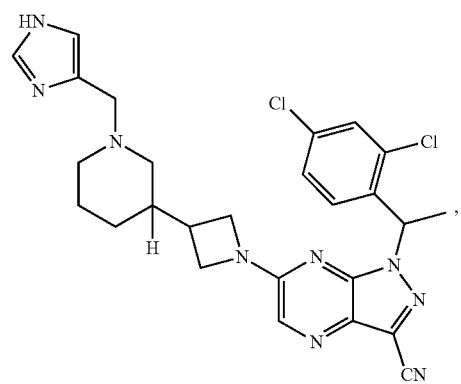
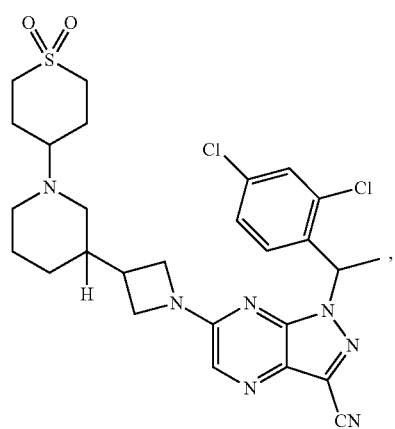
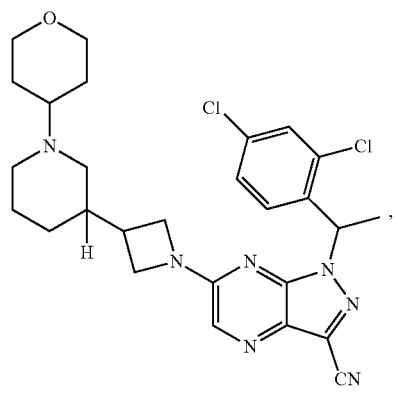
222
-continued
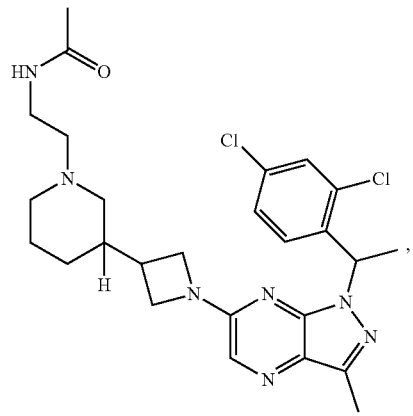
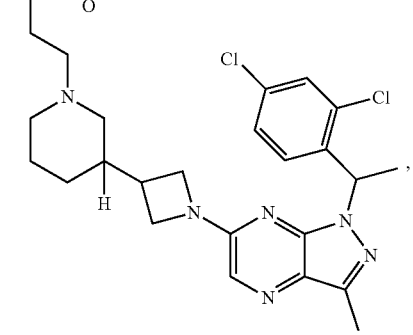
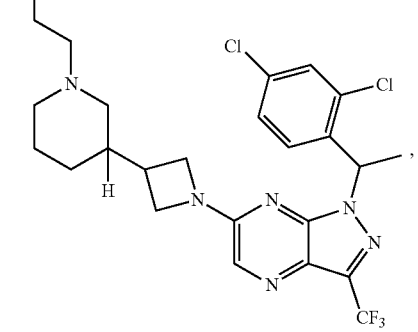

223
-continued
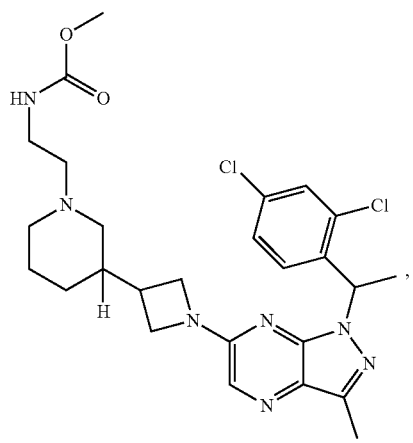
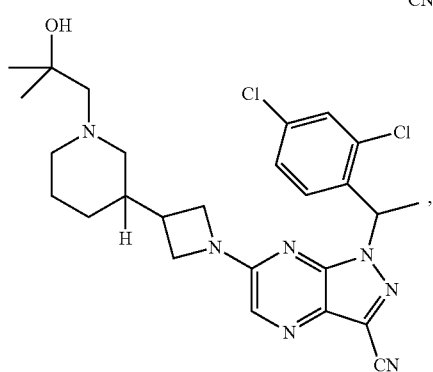
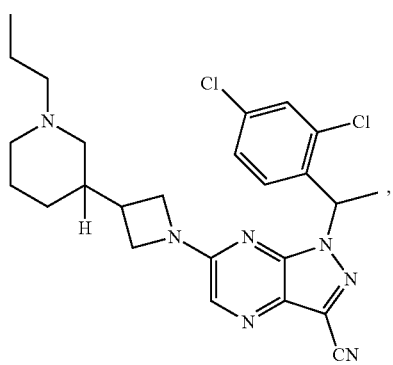
224
-continued
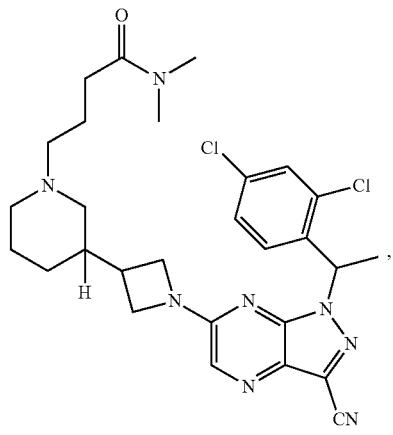
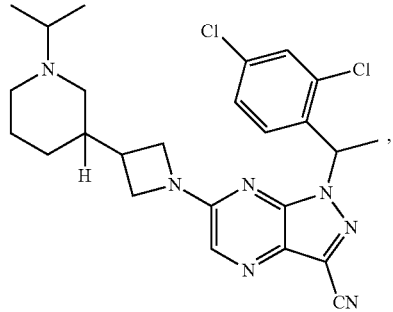
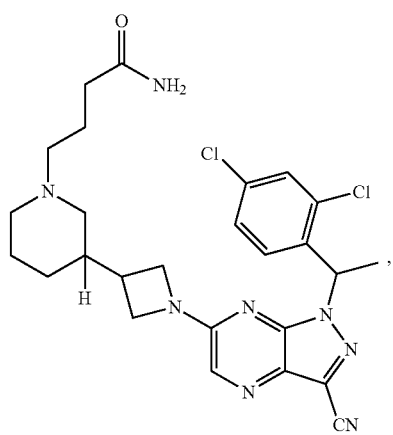
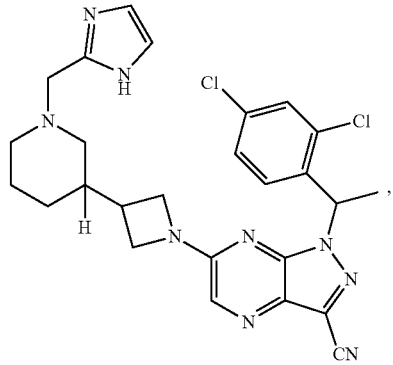

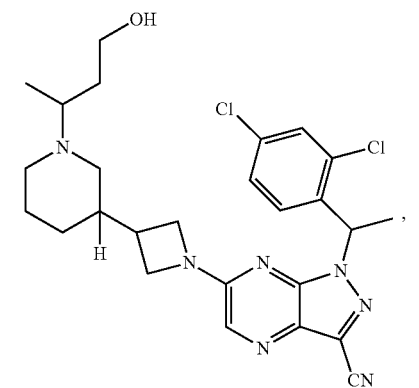
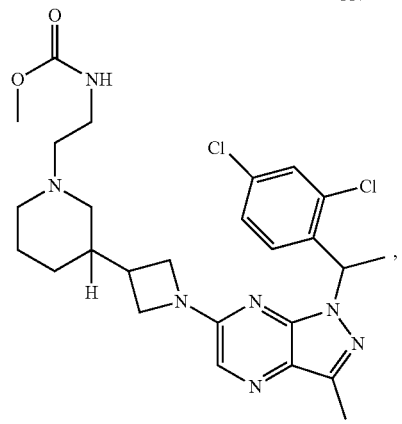
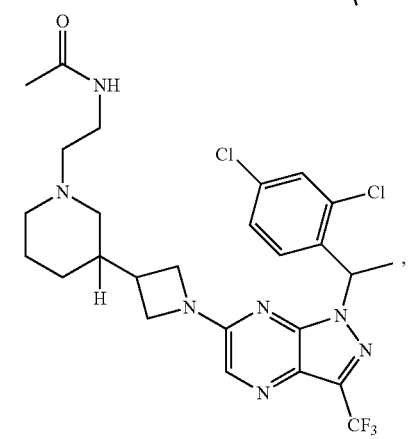
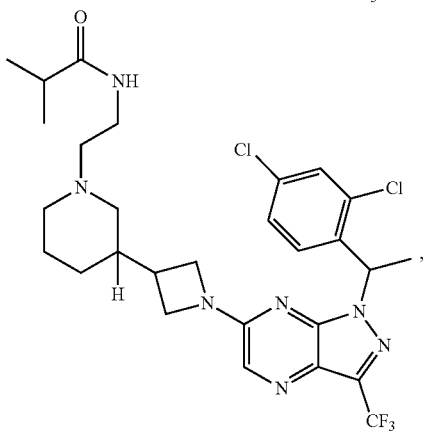
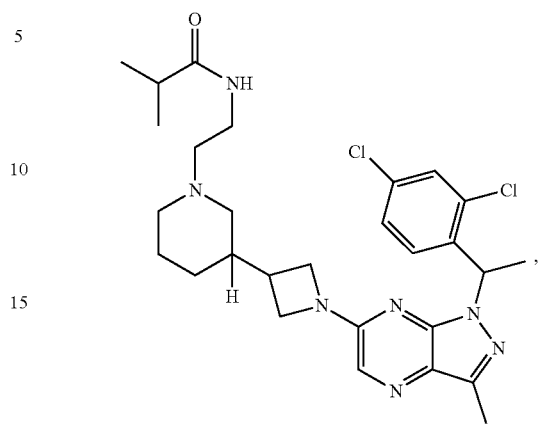
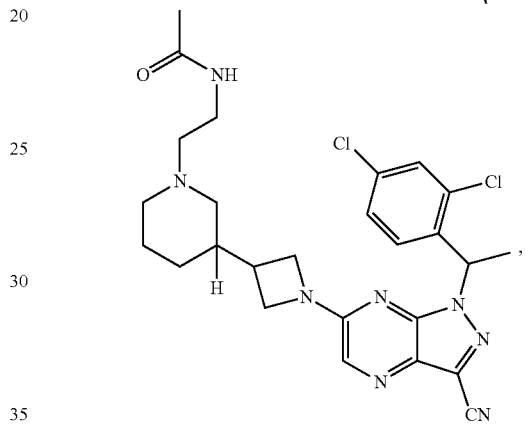
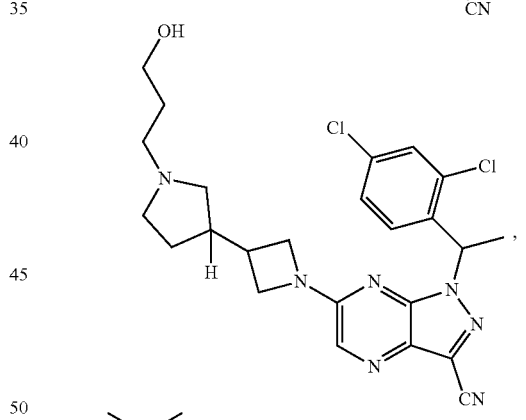
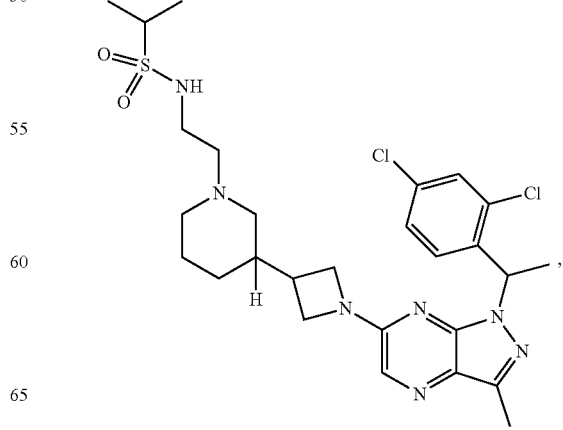

227
-continued
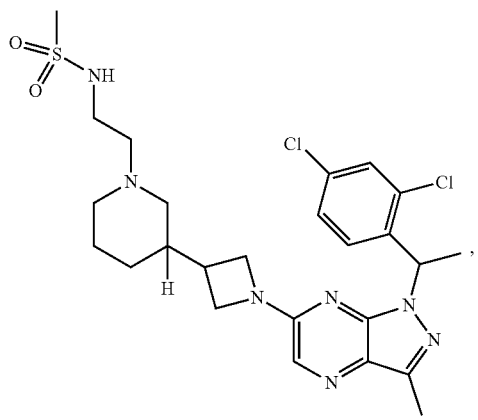
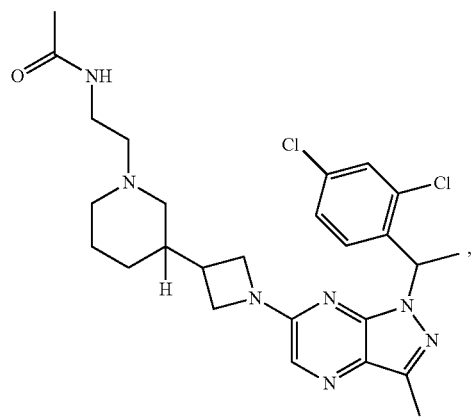
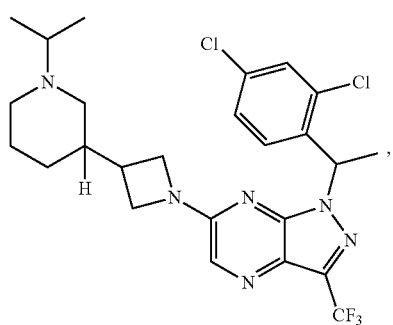
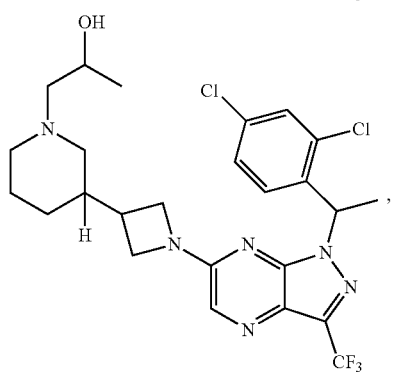
228
-continued
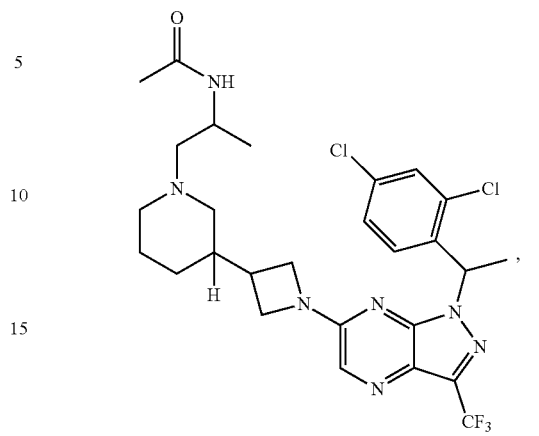
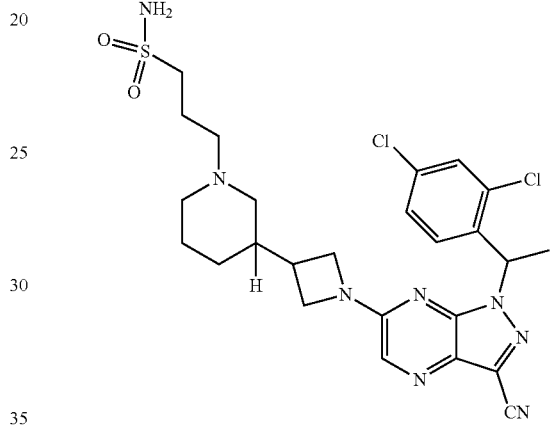
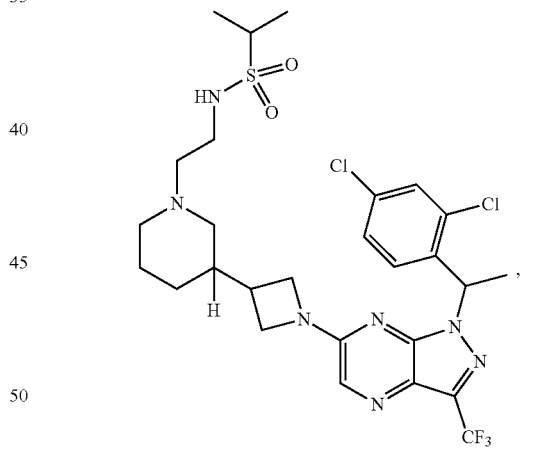
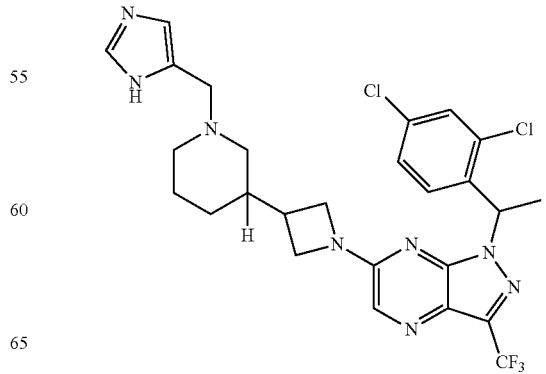

-continued

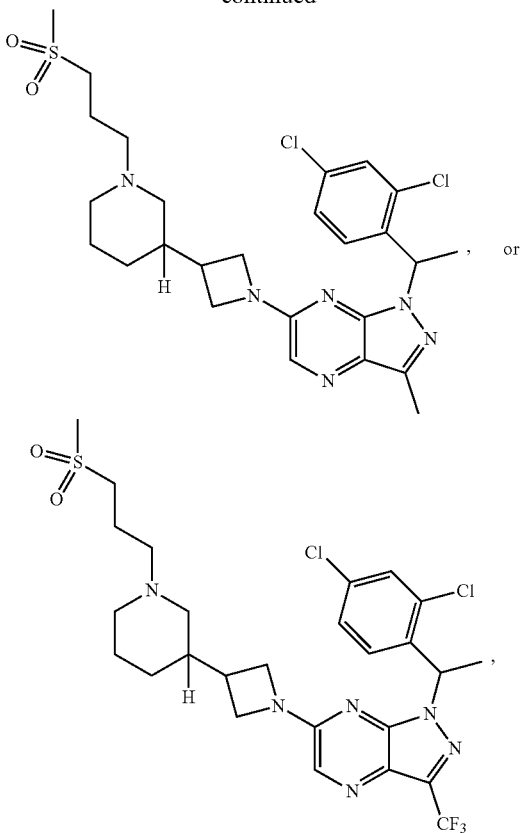

or a pharmaceutically acceptable salt thereof.

Embodiment 3

A method of treating a malignancy that is positive for Epstein Barr Virus (EBV), the method comprising administering to a subject in need thereof a therapeutically effective amount of a compound of formula (II):

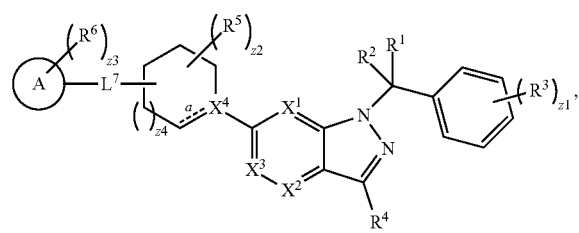

(II)

or a pharmaceutically acceptable salt thereof,
wherein:
A is a substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
z1 is an integer from 0 to 5;
z2 is an integer from 0 to 13;
z3 is an integer from 0 to 12;
z4 is an integer from 0 to 3;

⸺ is a single bond or double bond, wherein if ⸺ is a single bond, then $X^4$ is $CR^{11}$ or N, and if ⸺ is a double bond, then $X^4$ is C;

$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$NR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —CN, —$SO_{n6}R^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^8$ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10.1}_3$, —CHX$^{10.1}_2$, —CH$_2$X$^{10.1}$, —CN, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11.1}_3$, —CHX$^{11.1}_2$, —CH$_2$X$^{11.1}$, —CN, —SO$_{n11}$R$^{11A}$, —SO$_{v11}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m11}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$ and R$^{11D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$ and R$^{1C}$, R$^{2B}$ and R$^{2C}$, R$^{3B}$ and R$^{3C}$, R$^{4B}$ and R$^{4C}$, R$^{5B}$ and R$^{5C}$, R$^{6B}$ and R$^{6C}$, R$^{8B}$ and R$^{8C}$, R$^{9B}$ and R$^{9C}$, R$^{10B}$ and R$^{10C}$, R$^{11B}$ and R$^{11C}$ substituents bonded to the same nitrogen atom may optionally be joined to form a substituted or unsubstituted heterocycloalkyl or substituted or unsubstituted heteroaryl;

n1, n2, n3, n4, n5, n6, n8, n9, n10 and n11 are independently an integer from 0 to 4;

m1, m2, m3, m4, m5, m6, m8, m9, m10, m11, v1, v2, v3, v4, v5, v6, v8, v9, v10, and v11 are independently 1 or 2; and X$^{1.1}$, X$^{2.1}$, X$^{3.1}$, X$^{4.1}$, X$^{5.1}$, X$^{6.1}$, X$^{8.1}$, X$^{9.1}$, X$^{10.1}$, and X$^{11.1}$ are independently —Cl, —Br, —I or —F, wherein at least one of X$^1$, X$^2$, and X$^3$ is N.

Embodiment 4

The method of embodiment 3, wherein the compound is:

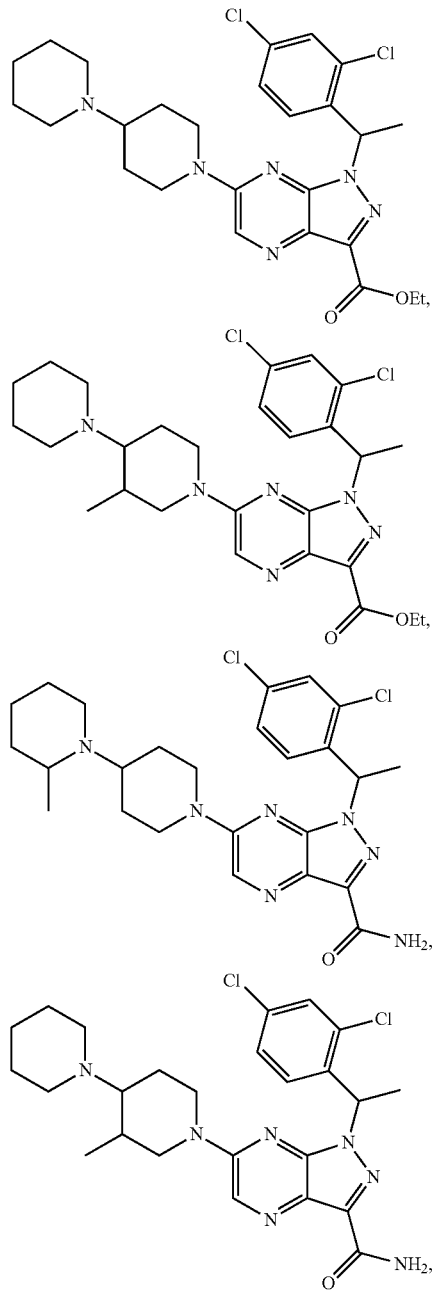

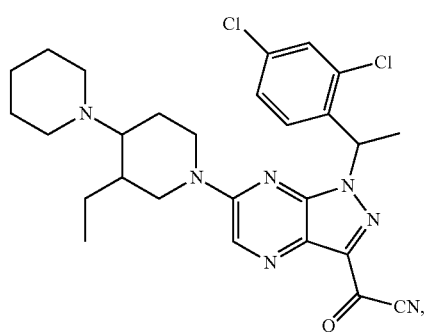
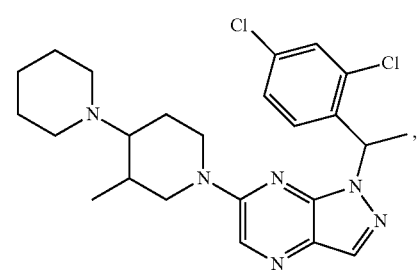
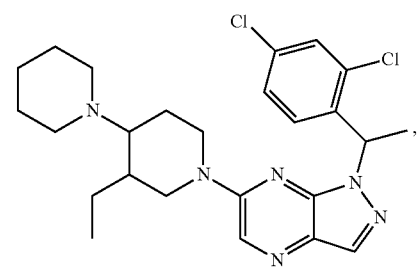
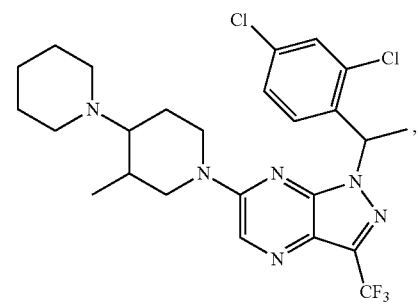
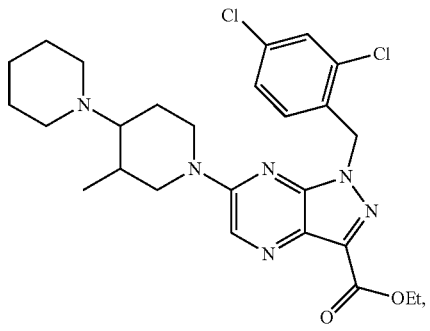
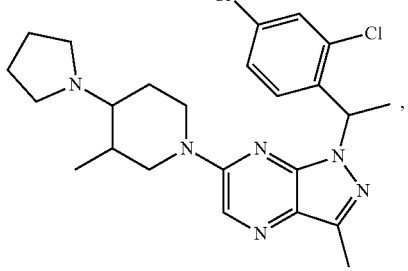
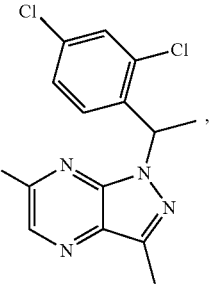
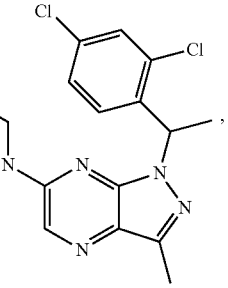
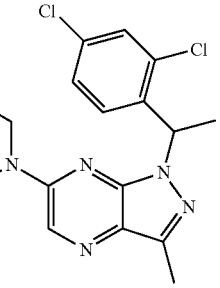
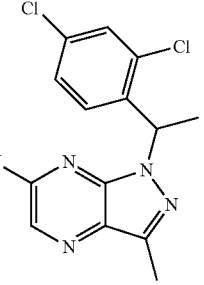
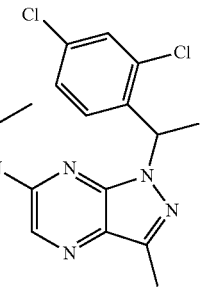

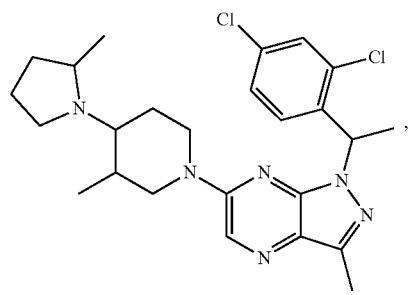
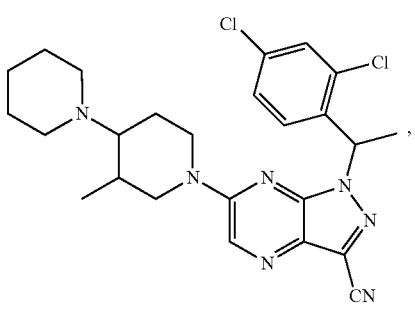
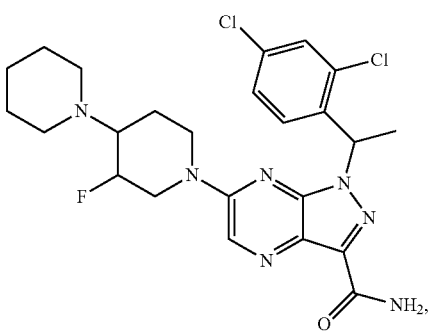
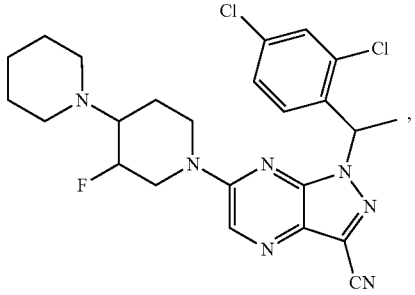
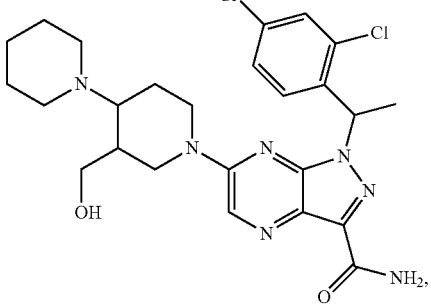
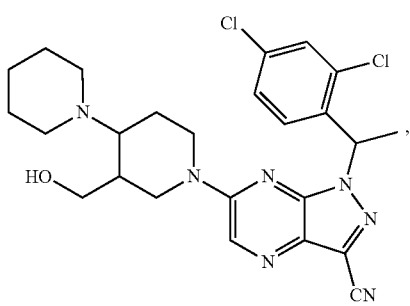
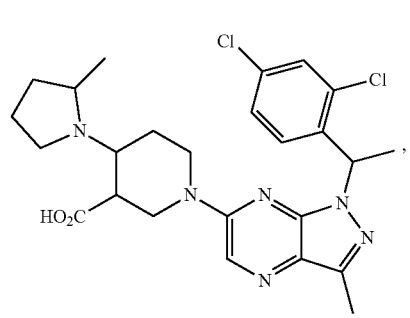
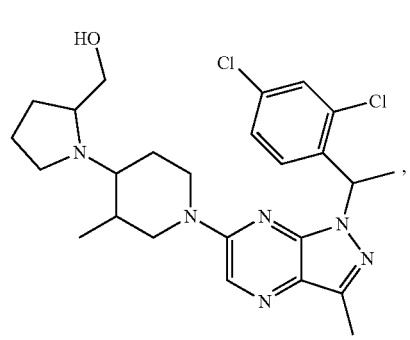
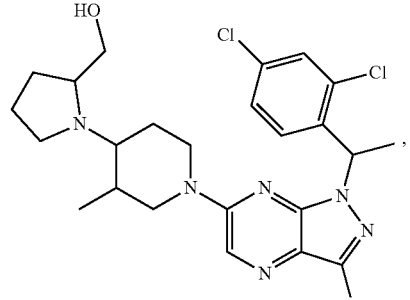
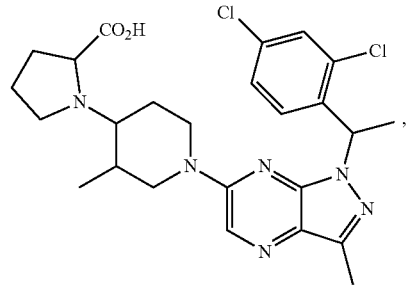

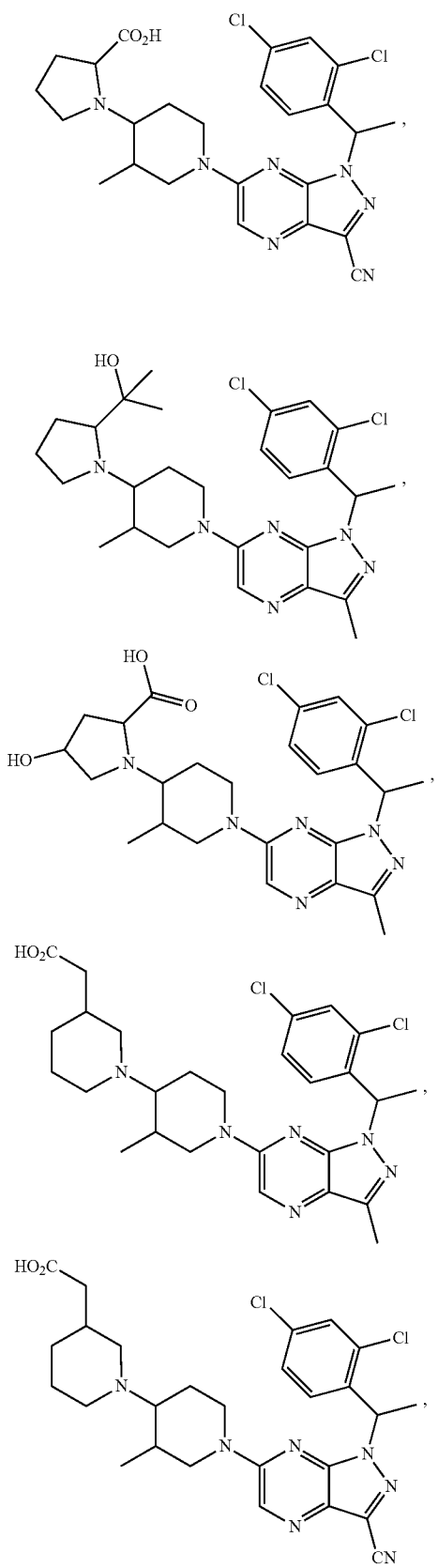
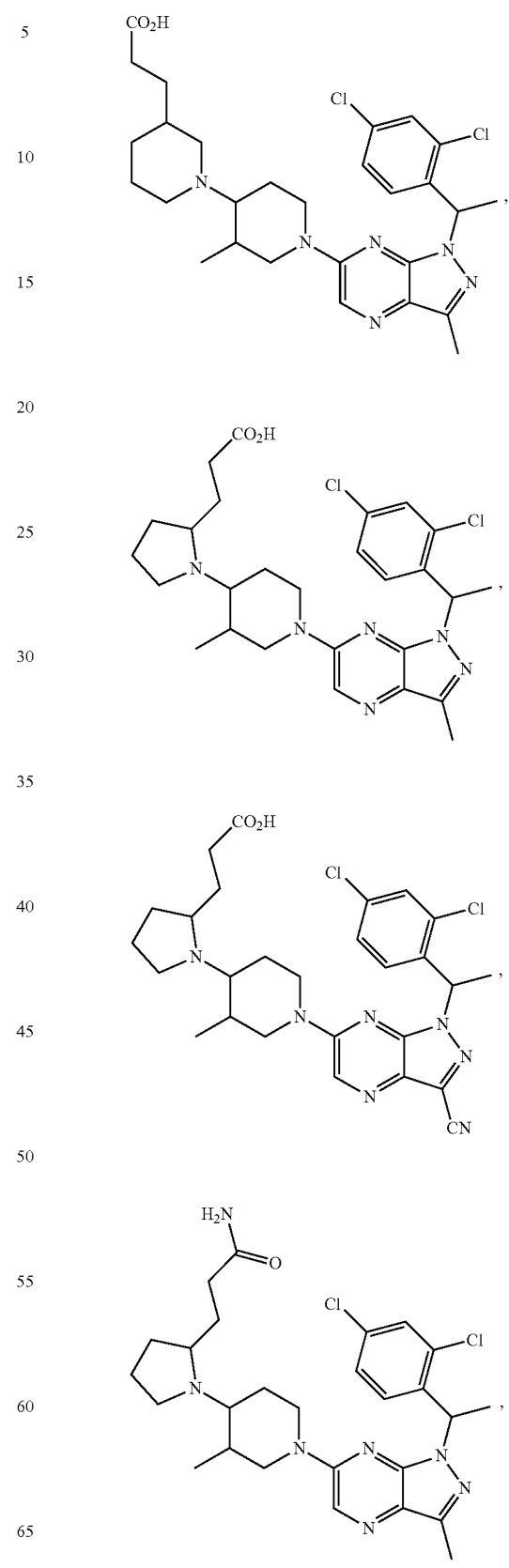

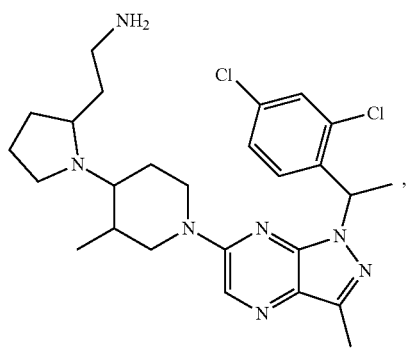
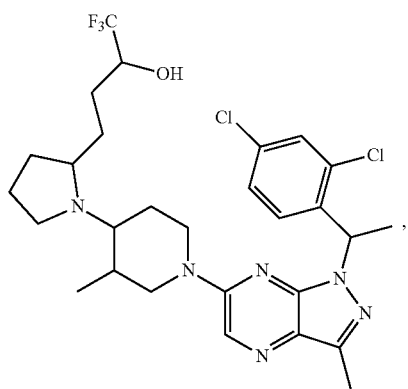
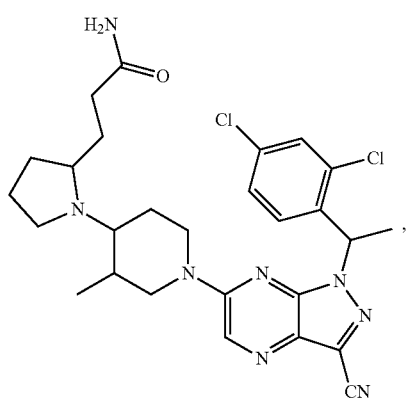
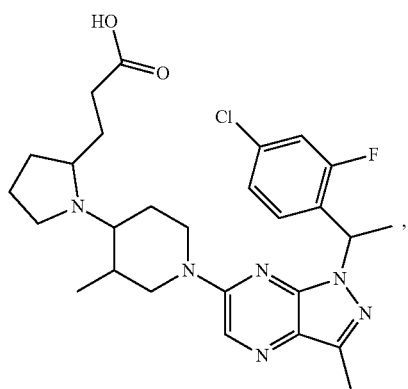
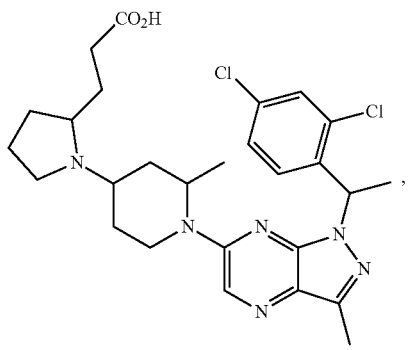
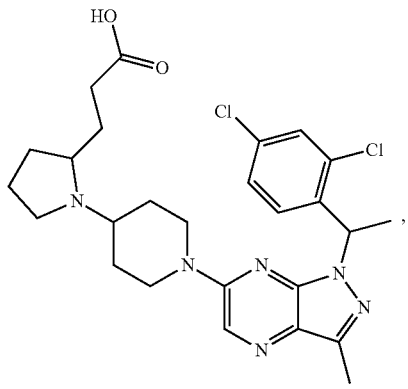
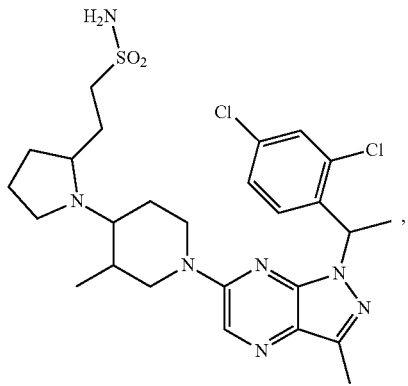
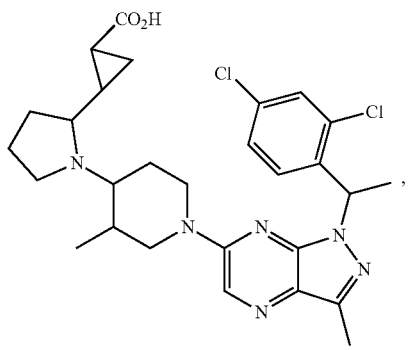

241
-continued
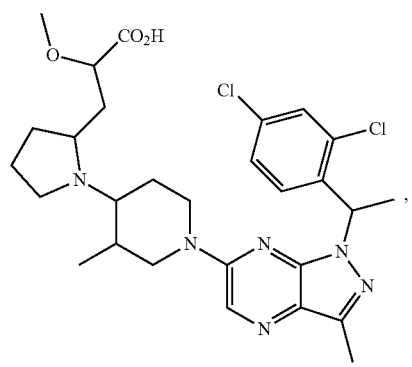
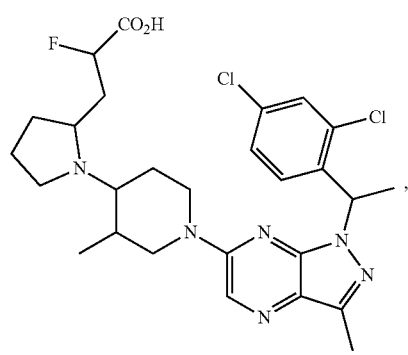
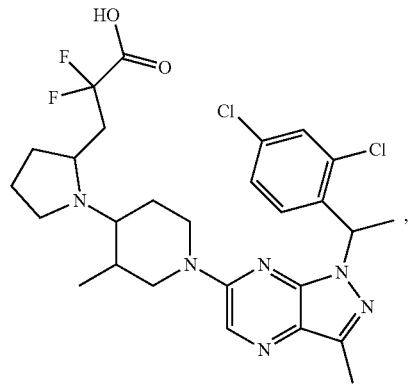
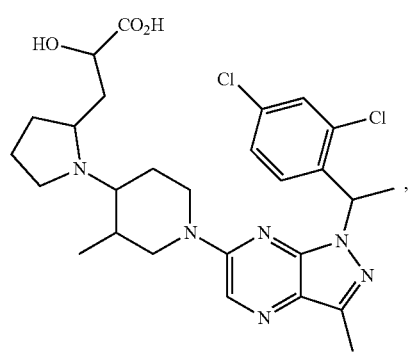
242
-continued
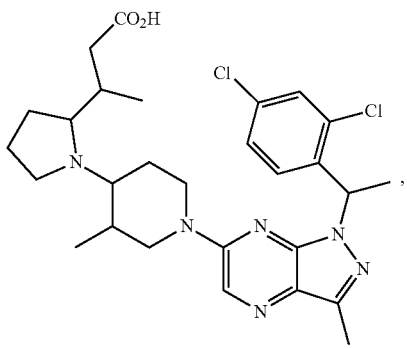
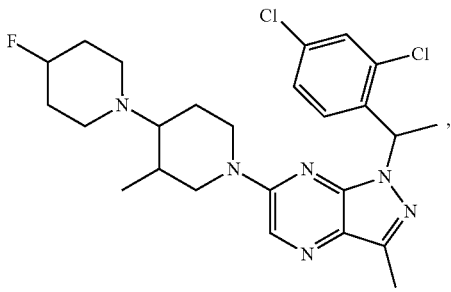
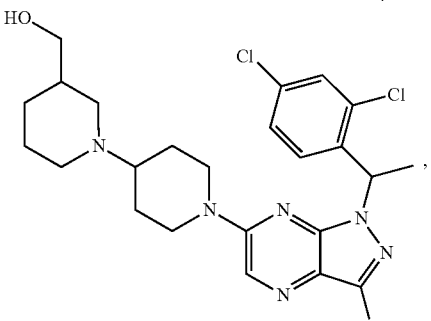
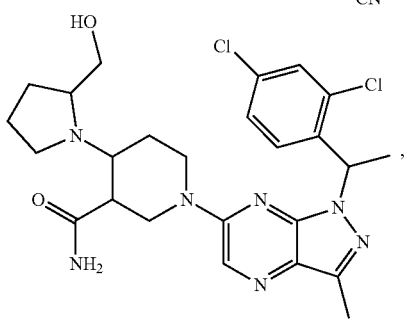
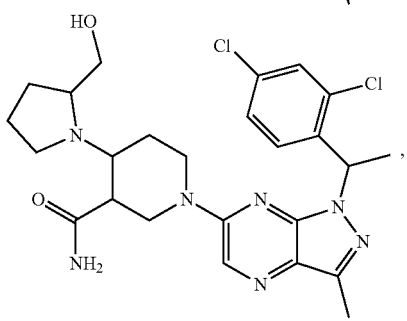

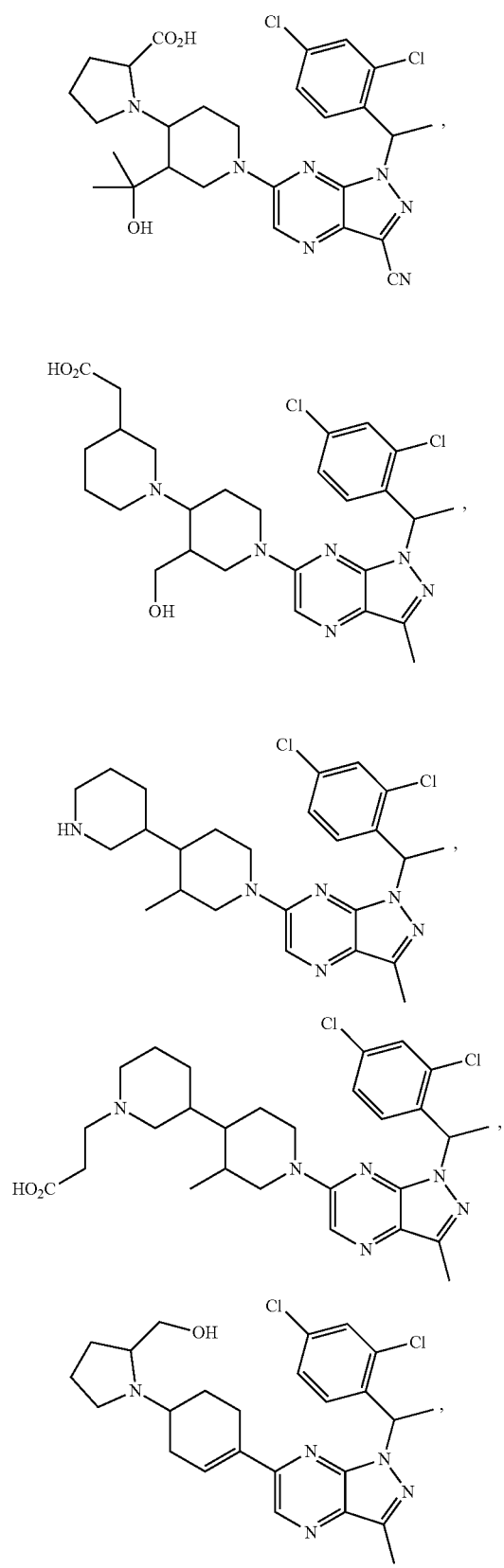
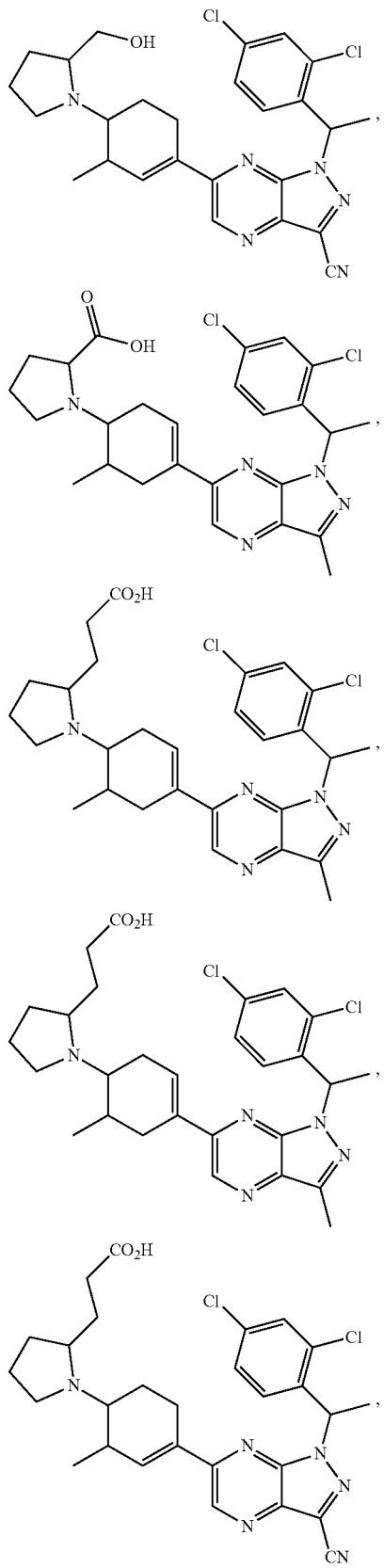

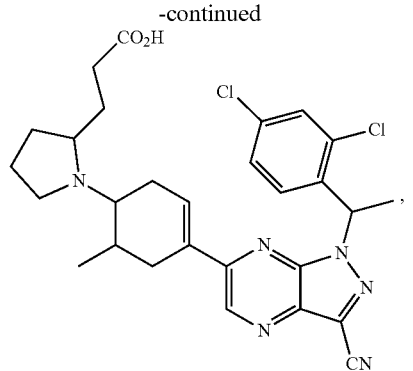
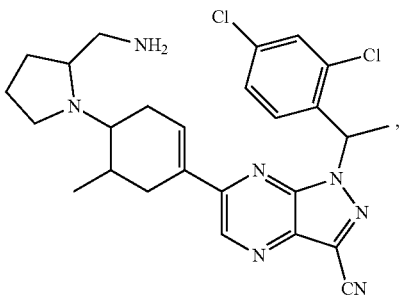
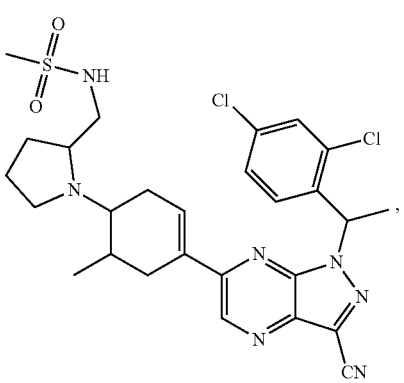
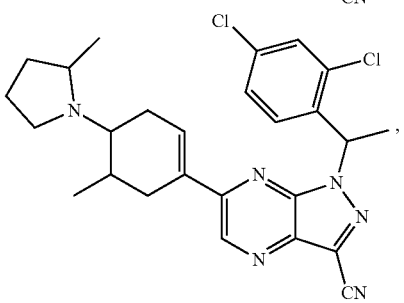
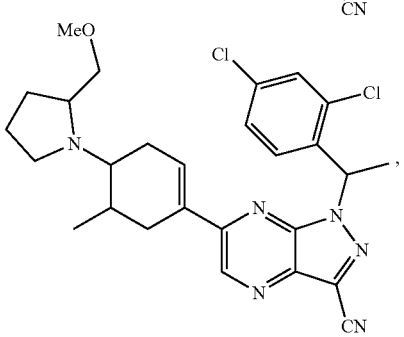
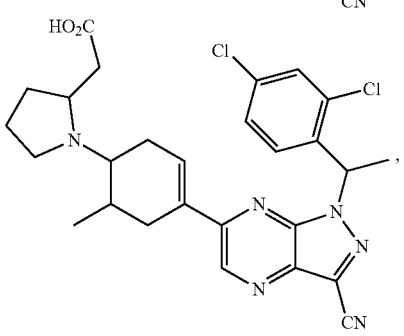

247
-continued

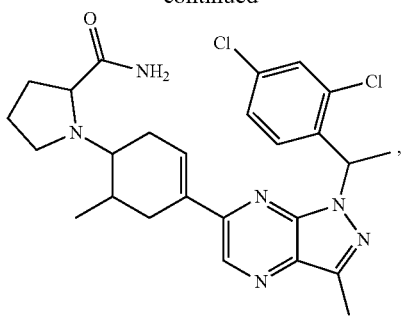

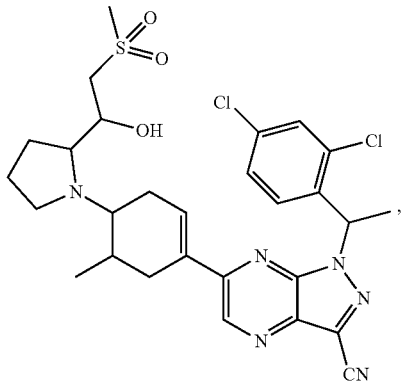

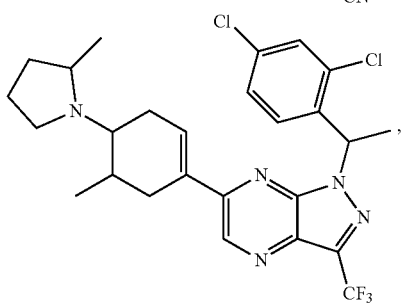

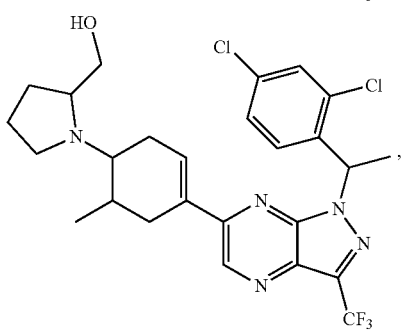

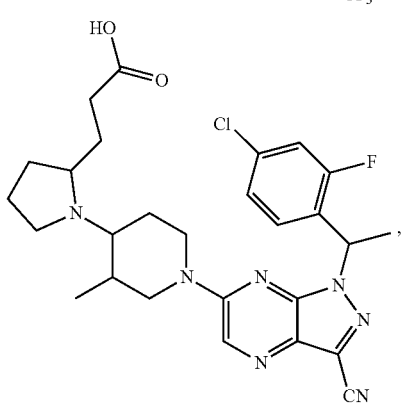

248
-continued

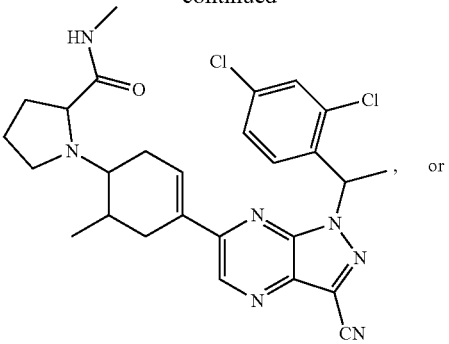

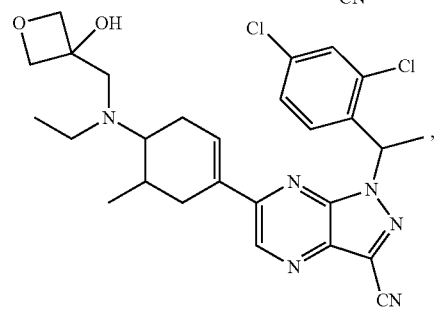

or a pharmaceutically acceptable salt thereof.

Embodiment 5

A method of treating a malignancy that is positive for Epstein Barr Virus (EBV), the method comprising administering to a subject in need thereof a therapeutically effective amount of a compound of formula (III):

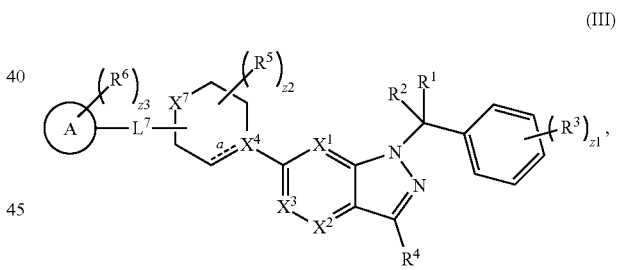

(III)

or a pharmaceutically acceptable salt thereof,
wherein:
A is substituted or unsubstituted cycloalkyl or substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
$X^7$ is $NR^{17}$ or N, wherein when $L^7$ is covalently bound to $X^7$, then $X^7$ is N;
n1, n2, n3, n4, n5, n6, n8, n9, n10, n11, and n17 are independently an integer from 0 to 4;
m1, m2, m3, m4, m5, m6, m8, m9, m10, m11, m17, v1, v2, v3, v4, v5, v6, v8, v9, v10, v11, and v17 are independently 1 or 2;
z1 is an integer from 0 to 5;
z2 is an integer from 0 to 8;
z3 is an integer from 0 to 12;

≐ is a single bond or double bond, wherein if ≐ is a single bond, then $X^4$ is $CR^{11}$ or N, and if ≐ is a double bond, then $X^4$ is C;

$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{10B}R^{10C}$, —NHC(O)$NHNR^{1B}R^{1C}$, —NHC(O)$NR^{1B}R^{1C}$, —N(O)$_{m1}$, —$NR^{1B}R^{1C}$, —C(O)$R^{1D}$, —C(O)$OR^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —NHC(O)$NHNR^{2B}R^{2C}$, —NHC(O)$NR^{2B}R^{2C}$, —N(O)$_{m2}$, —$NR^{2B}R^{2C}$, —C(O)$R^{2D}$, —C(O)$OR^{2D}$, —C(O)$NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —NHC(O)$NHNR^{3B}R^{3C}$, —NHC(O)$NR^{3B}R^{3C}$, —N(O)$_{m3}$, —$NR^{3B}R^{3C}$, —C(O)$R^{3D}$, —C(O)$OR^{3D}$, —C(O)$NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —NHC(O)$NHNR^{4B}R^{4C}$, —NHC(O)$NR^{4B}R^{4C}$, —N(O)$_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)$OR^{5D}$, —C(O)$NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —N(O)$_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —N(O)$_{m8}$, —$NR^{8B}R^{8C}$, —C(O)$R^{8D}$, —C(O)$OR^{8D}$, —C(O)$NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —NHC(O)$NHNR^{9B}R^{9C}$, —NHC(O)$NR^{9B}R^{9C}$, —N(O)$_{m9}$, —$NR^{9B}R^{9C}$, —C(O)$R^{9D}$, —C(O)$OR^{9D}$, —C(O)$NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10.1}_3$, —$CHX^{10.1}_2$, —$CH_2X^{10.1}$, —CN, —$SO_{n10}R^{10A}$, —$SO_{v10}NR^{10B}R^{10C}$, —$NHNR^{10B}R^{10C}$, —$ONR^{10B}R^{10C}$, —NHC(O)$NHNR^{10B}R^{10C}$, —NHC(O)$NR^{10B}R^{10C}$, —N(O)$_{m10}$, —$NR^{10B}R^{10C}$, —C(O)$R^{10D}$, —C(O)$OR^{10D}$, —C(O)$NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11.1}_3$, —$CHX^{11.1}_2$, —$CH_2X^{11.1}$, —CN, —$SO_{n11}R^{11A}$, —$SO_{v11}NR^{11B}R^{11C}$, —$NHNR^{11B}R^{11C}$, —$ONR^{11B}R^{11C}$, —NHC(O)$NHNR^{11B}R^{11C}$, —NHC(O)$NR^{11B}R^{11C}$, —N(O)$_{m11}$, —$NR^{11B}R^{11C}$, —C(O)$R^{11D}$, —C(O)$OR^{11D}$, —C(O)$NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —$CX^{17.1}_3$, —$CHX^{17.1}_2$, —$CH_2X^{17.1}$, —CN, —$SO_{n17}R^{17A}$, —$SO_{v17}NR^{17B}R^{17C}$, —$NHNR^{17B}R^{17C}$, —$ONR^{17B}R^{17C}$, —NHC(O)$NHNR^{17B}R^{17C}$, —NHC(O)$NR^{17B}R^{17C}$, —N(O)$_{m17}$, —$NR^{17B}R^{17C}$, —C(O)$R^{17D}$, —C(O)$OR^{17D}$, —C(O)$NR^{17B}R^{17C}$, —$OR^{17A}$, —$NR^{17B}SO_2R^{17A}$, —$NR^{17B}C(O)R^{17D}$, —$NR^{17B}C(O)OR^{17D}$, —$NR^{17B}OR^{17D}$, —$OCX^{17.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$ $R^{17A}$, $R^{17B}$, $R^{17C}$ and $R^{17D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$ $R^{11B}$ and $R^{11C}$ and $R^{17B}$ and $R^{17C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, $X^{11.1}$ and $X^{17.1}$ are independently —Cl, —Br, —I or —F, wherein at least one of $X^1$, $X^2$ and $X^3$ is N.

Embodiment 6

The method of embodiment 5, wherein the compound is:

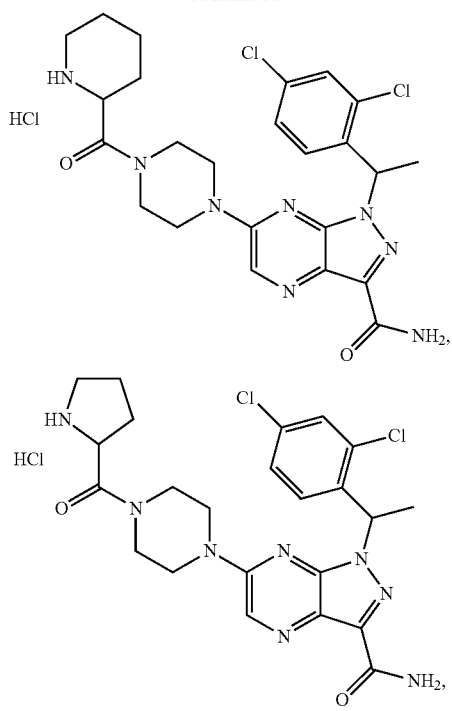

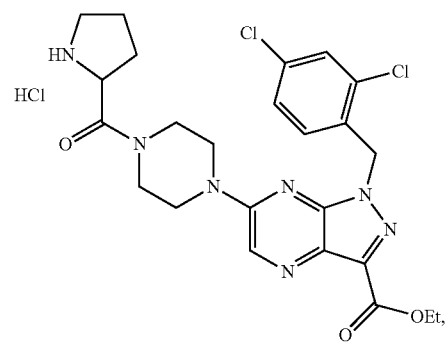

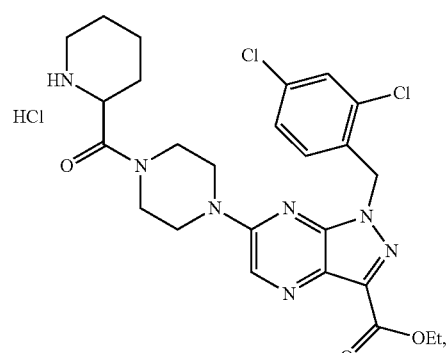

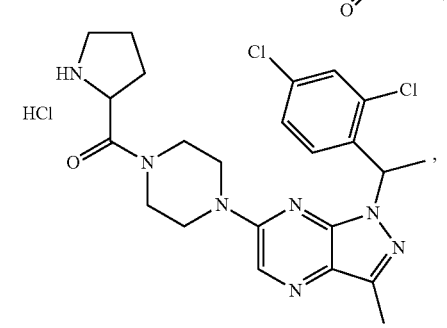

253
-continued
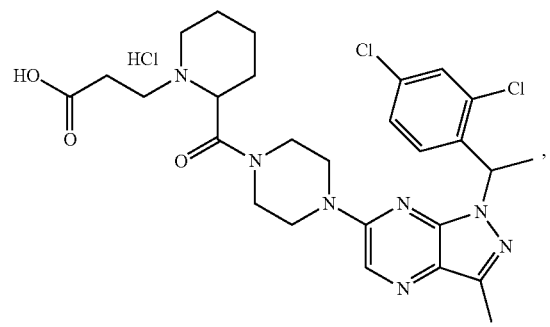
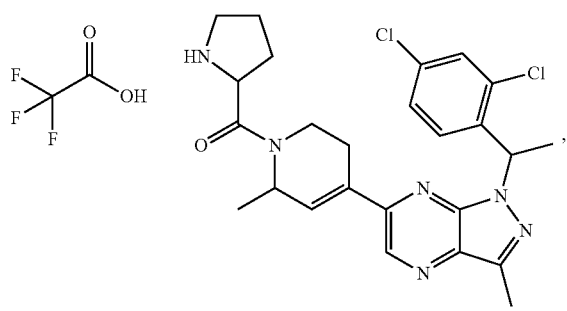
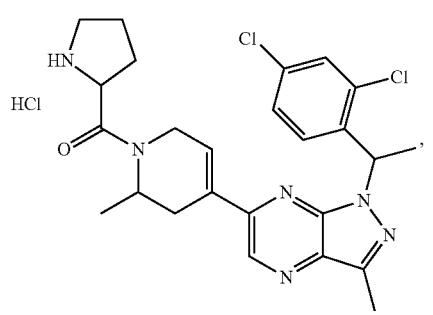
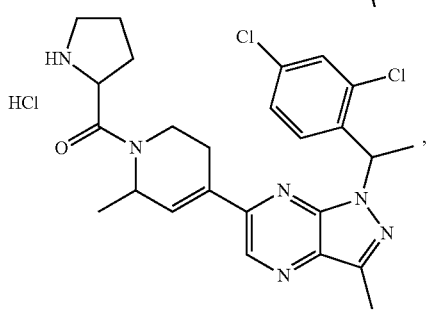
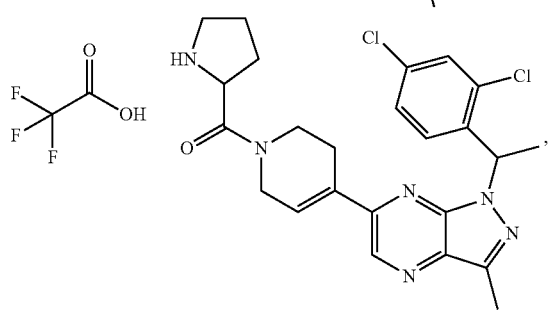
254
-continued
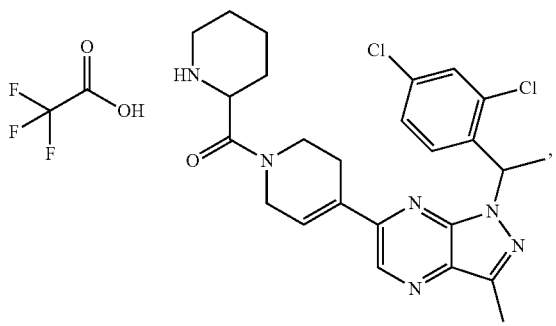
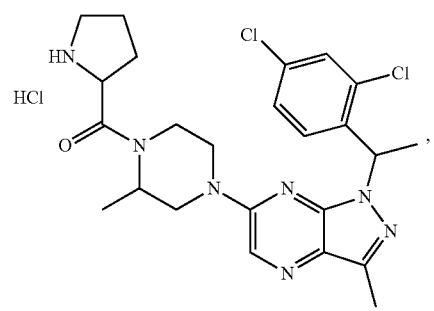
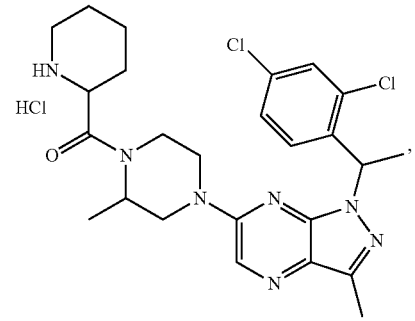
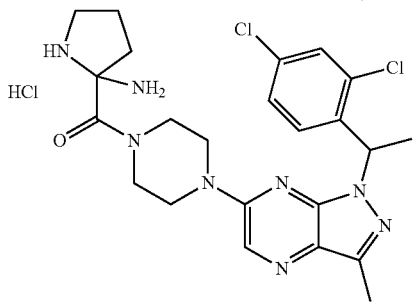
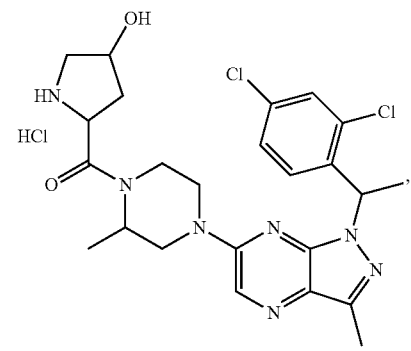

255
-continued
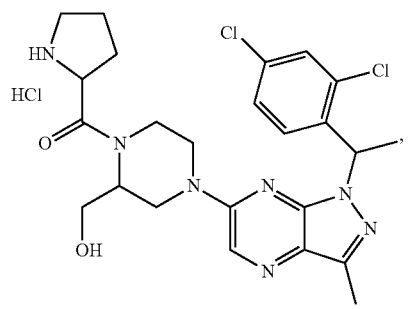
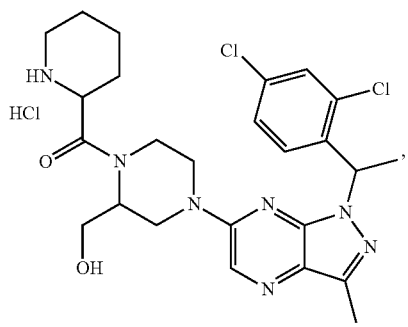
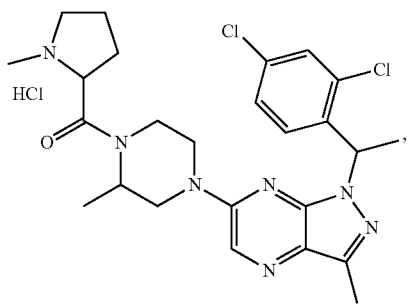
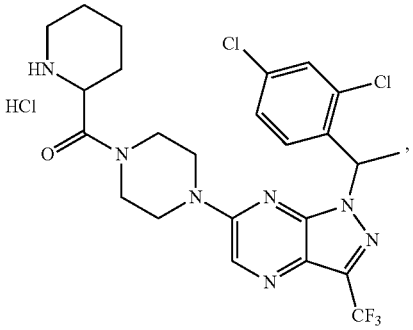
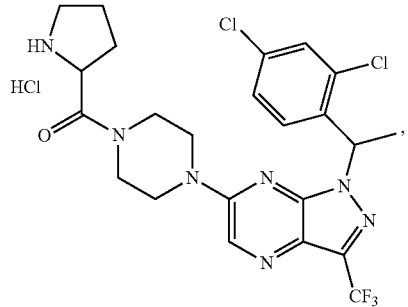
256
-continued
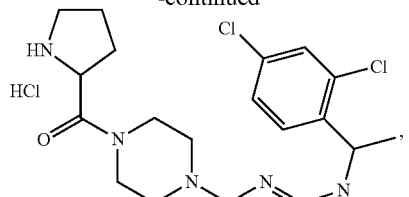
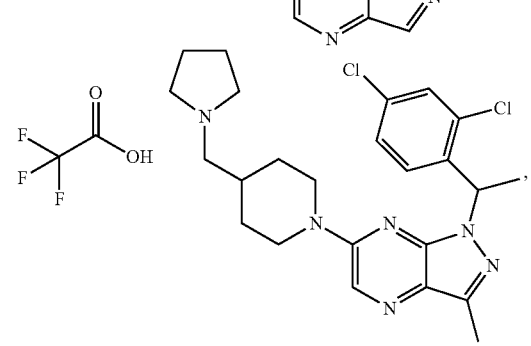
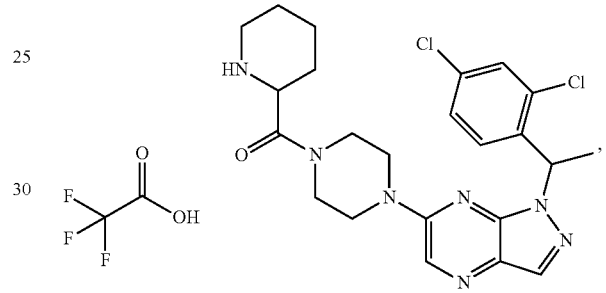
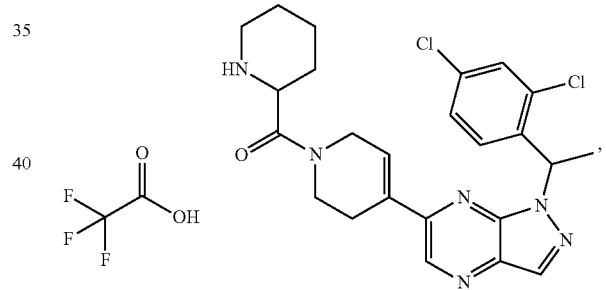
or
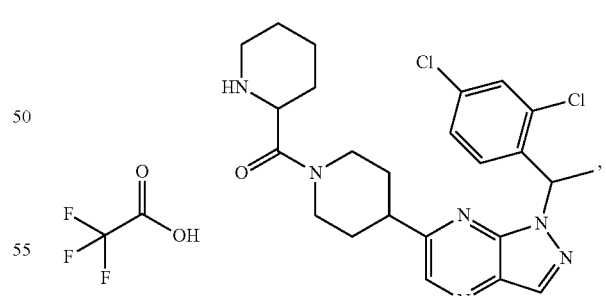
or a pharmaceutically acceptable salt thereof.
Embodiment 7
A method of treating a malignancy that is positive for Epstein Barr Virus (EBV), the method comprising administering to a subject in need thereof a therapeutically effective amount of a compound of formula (IV):

(IV)

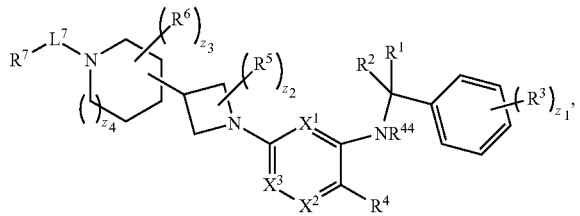

or a pharmaceutically acceptable salt thereof,
wherein:
$X^1$ is $CR^8$ or N;
$X^2$ is $CR^9$ or N;
$X^3$ is $CR^{10}$ or N;
n1, n2, n3, n4, n5, n6, n7, n8, n9, n10, and n44 are independently an integer from 0 to 4;
m1, m2, m3, m4, m5, m6, m7, m8, m9, m10, v1, v2, v3, v4, v5, v6, v7, v8, v9, v10, and v44 are independently 1 or 2;
z1 is an integer from 0 to 5;
z2 is an integer from 0 to 4;
z3 is an integer from 0 to 11;
z4 is an integer from 0 to 2;
$L^7$ is a bond, —O—, —S—, —$NR^{7.2B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, —$OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^2$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, —$OCH_2X^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently halogen, —$CX^{3.1}_3$, —$CHX^{3.1}_2$, —$CH_2X^{3.1}$, —CN, —$N_3$, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, —$OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^4$ is hydrogen, halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, —$OCH_2X^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or when $X^2$ is $CR^9$, then $R^4$ and $R^9$ may optionally be joined to form a substituted or unsubstituted cycloalkyl, substituted or unsubstituted heterocycloalkyl, substituted or unsubstituted aryl, or substituted or unsubstituted heteroaryl;
$R^5$ is independently halogen, oxo, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, —$OCH_2X^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^6$ is independently halogen, oxo, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, —$OCH_2X^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^7$ is hydrogen, halogen, —$CX^{7.1}_3$, —$CHX^{7.1}_2$, —$CH_2X^{7.1}$, —CN, —$N_3$, —$SO_{n7}R^{7A}$, —$SO_{v7}NR^{7B}R^{7C}$, —$NHNR^{7B}R^{7C}$, —$ONR^{7B}R^{7C}$, —$NHC(O)NHNR^{7B}R^{7C}$, —$NHC(O)NR^{7B}R^{7C}$, —$N(O)_{m7}$, —$NR^{7B}R^{7C}$, —$C(O)R^{7D}$, —$C(O)OR^{7D}$, —$C(O)NR^{7B}R^{7C}$, —$OR^{7A}$, —$NR^{7B}SO_2R^{7A}$, —$NR^{7B}C(O)R^{7D}$, —$NR^{7B}C(O)OR^{7D}$, —$NR^{7B}OR^{7D}$, —$OCX^{7.1}_3$, —$OCHX^{7.1}_2$, —$OCH_2X^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
$R^8$ is hydrogen, halogen, —$CX^{8.1}_3$, —$CHX^{8.1}_2$, —$CH_2X^{8.1}$, —CN, —$N_3$, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C (O)R$^{8D}$, —NR$^{8B}$C(O)OR$^{8D}$, —NR$^{8B}$OR$^{8D}$, —OCX$^{8.1}_3$, —OCHX$^{8.1}_2$, —OCH$_2$X$^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}_3$, —CHX$^{9.1}_2$, —CH$_2$X$^{9.1}$, —CN, —N$_3$, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, —OCH$_2$X$^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or when X$^2$ is CR$^9$, then R$^4$ and R$^9$ may optionally be joined to form a substituted or unsubstituted cycloalkyl, substituted or unsubstituted heterocycloalkyl, substituted or unsubstituted aryl, or substituted or unsubstituted heteroaryl; or when X$^2$ is CR$^9$ and X$^3$ is CR$^{10}$, then R$^9$ and R$^{10}$ may optionally be joined to form a substituted or unsubstituted cycloalkyl, substituted or unsubstituted heterocycloalkyl, or unsubstituted aryl, or substituted or unsubstituted heteroaryl;

R$^{10}$ is hydrogen, halogen, —CX$^{10.1}_3$, —CHX$^{10.1}_2$, —CH$_2$X$^{10.1}$, —CN, —N$_3$, —SO$_{n10}$R$^{10A}$, —SO$_{v10}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m10}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{1B}$SO$_2$R$^{1A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, —OCH$_2$X$^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or when X$^2$ is CR$^9$ and X$^3$ is CR$^{10}$, then R$^9$ and R$^{10}$ may optionally be joined to form a substituted or unsubstituted cycloalkyl, substituted or unsubstituted heterocycloalkyl, or unsubstituted aryl, or substituted or unsubstituted heteroaryl;

R$^{44}$ is hydrogen, —CX$^{44.1}_3$, —CHX$^{44.1}_2$, —CH$_2$X$^{44.1}$, —SO$_{n44}$R$^{44A}$, —SO$_{v44}$NR$^{44B}$R$^{44C}$, —C(O)R$^{44D}$, —C(O)OR$^{44D}$, —C(O)NR$^{44B}$R$^{44C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{7.2B}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{44A}$, R$^{44B}$, R$^{44C}$, and R$^{44D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{44B}$, and R$^{44C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, and X$^{44.1}$ are independently —Cl, —Br, —I or —F; wherein at least one of X$^1$, X$^2$ and X$^3$ is N.

Embodiment 8

The method of Embodiment 7, wherein the compound is:

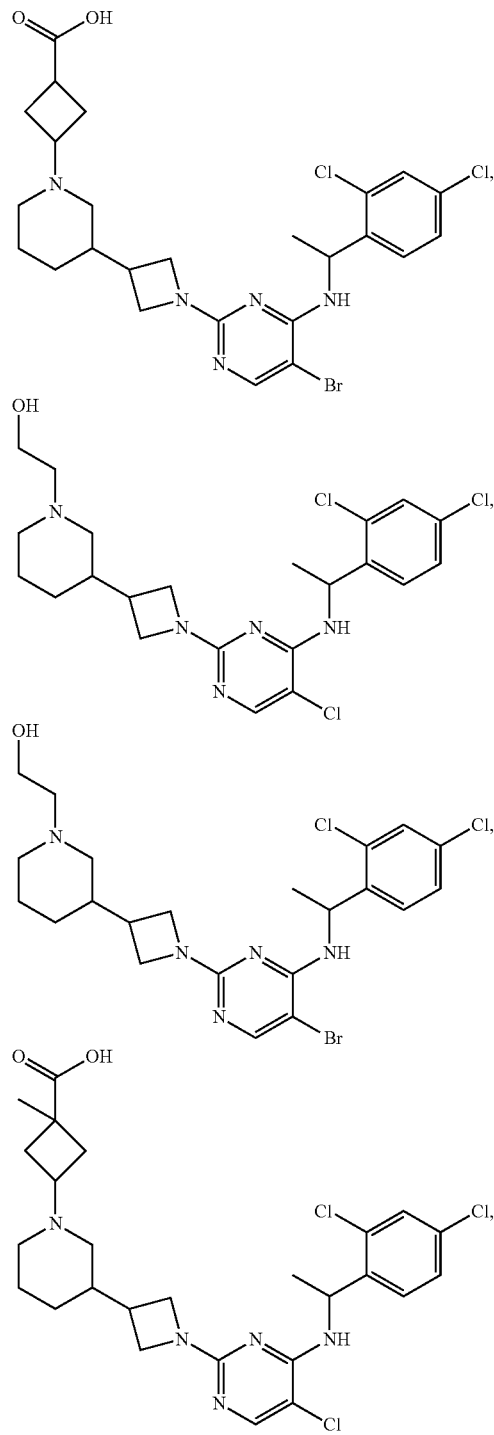

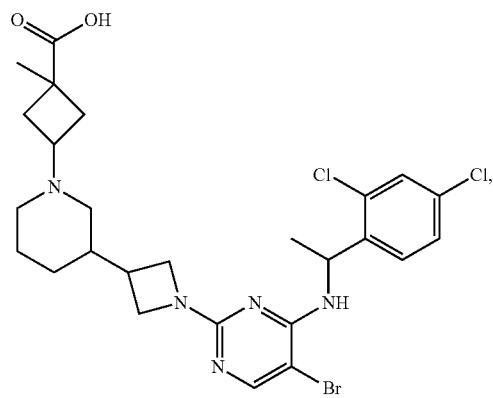
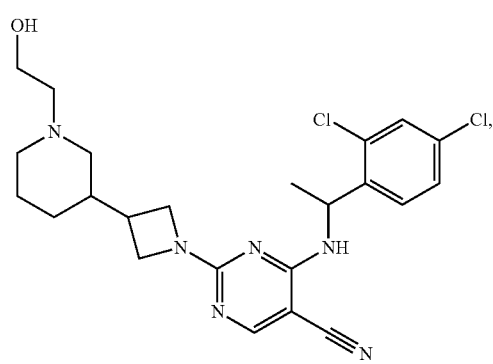
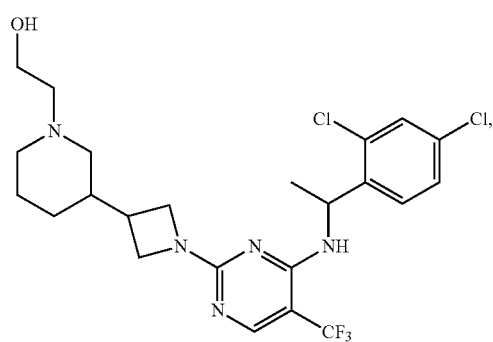
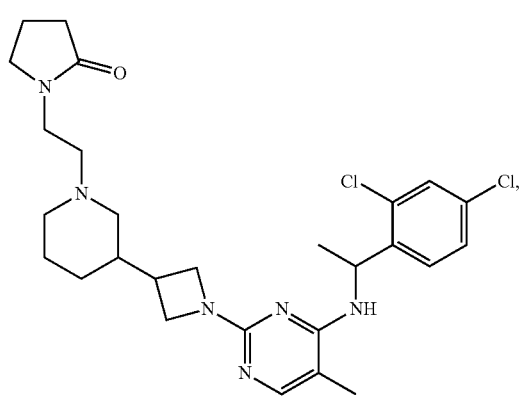
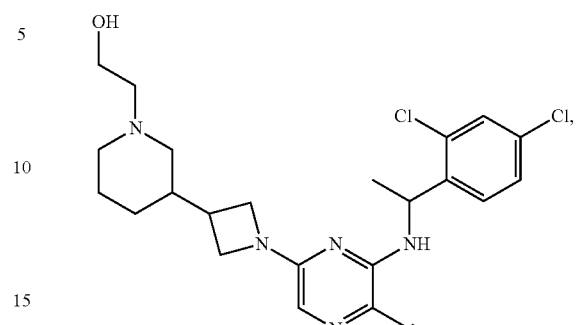
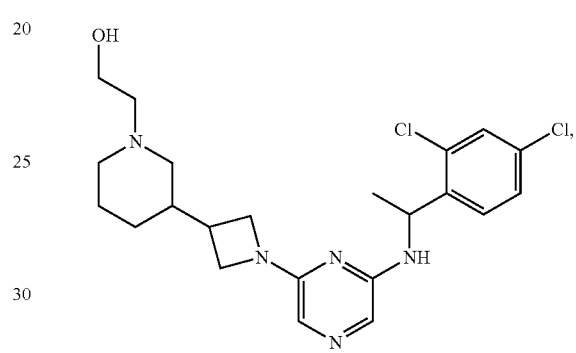
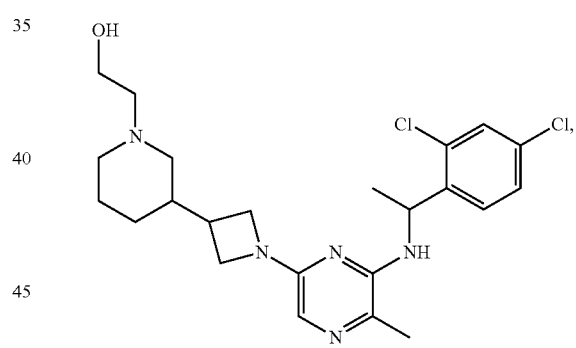
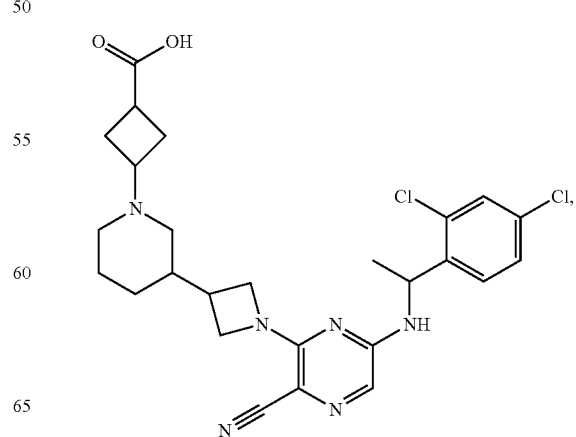

263
-continued
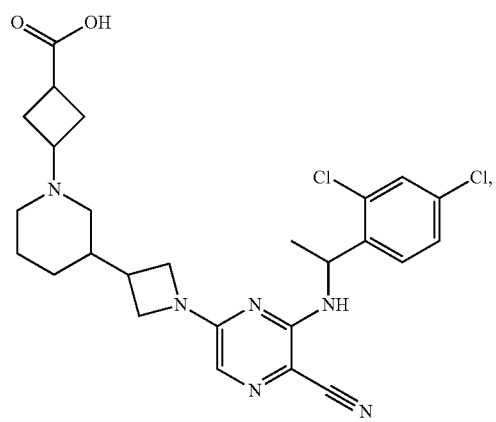
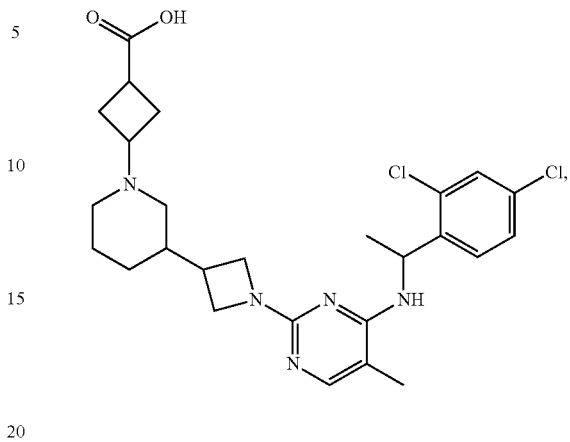
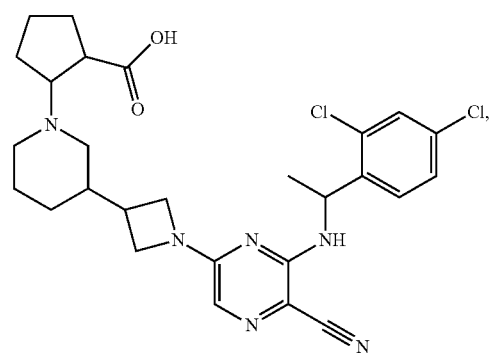
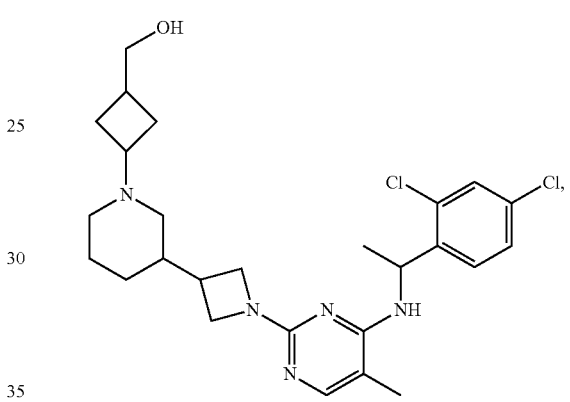
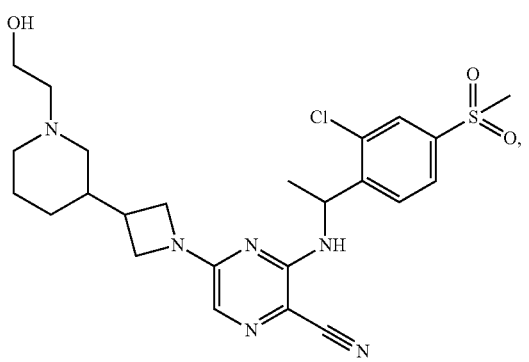
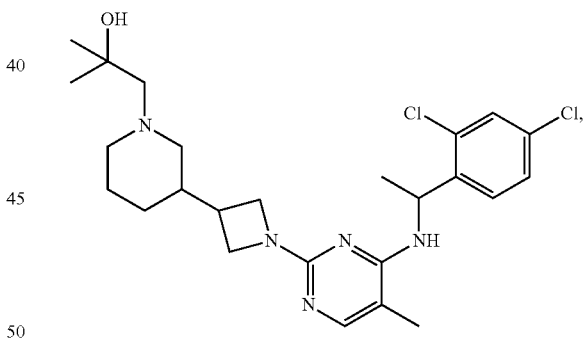
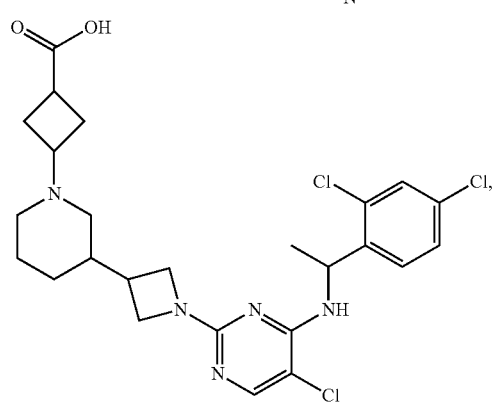
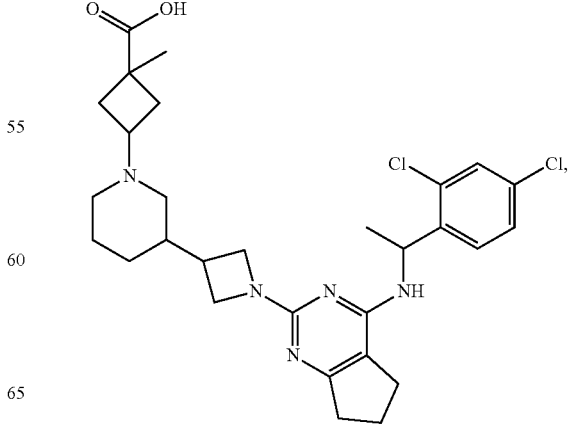
264
-continued 265
-continued
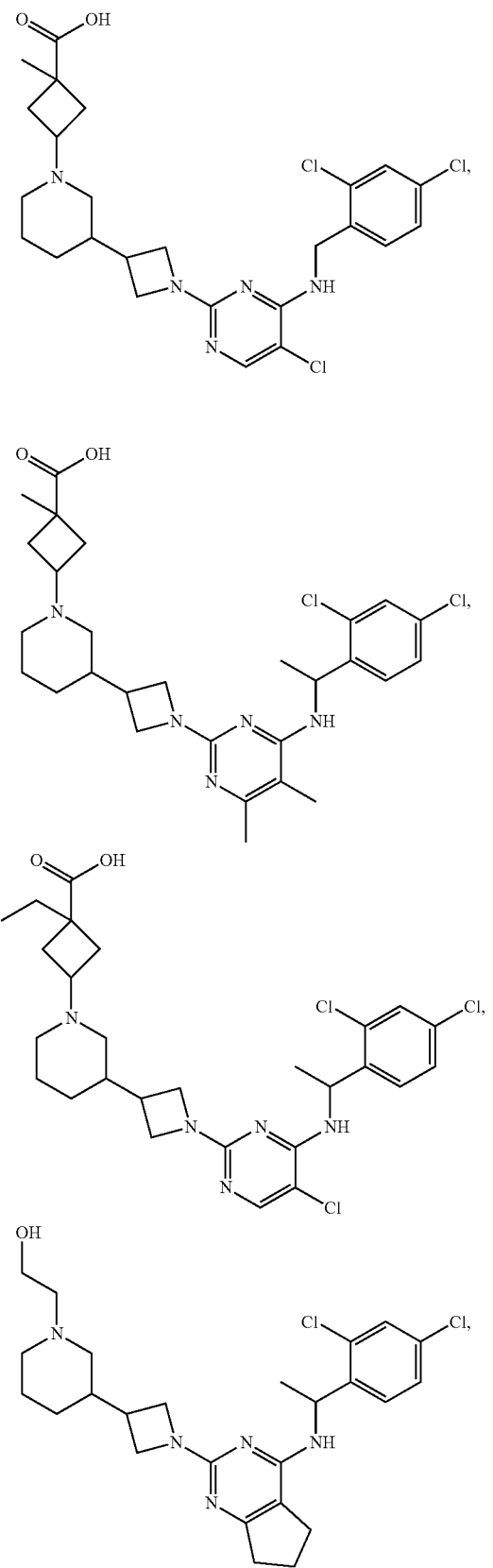
266
-continued
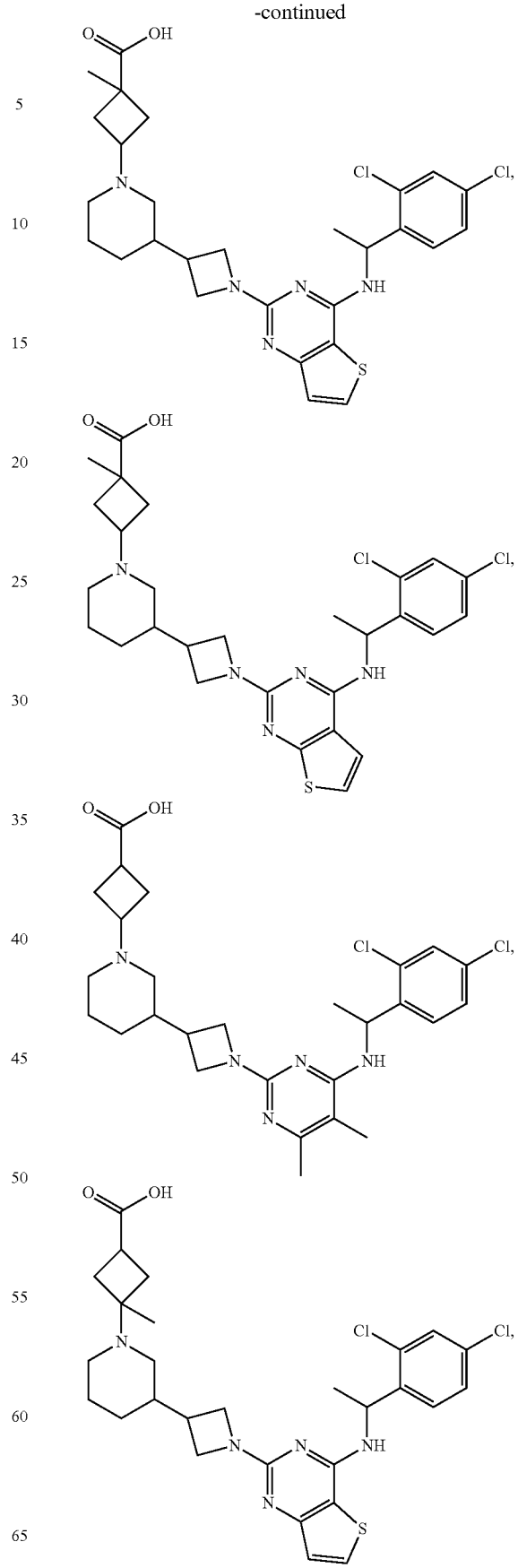

267
-continued
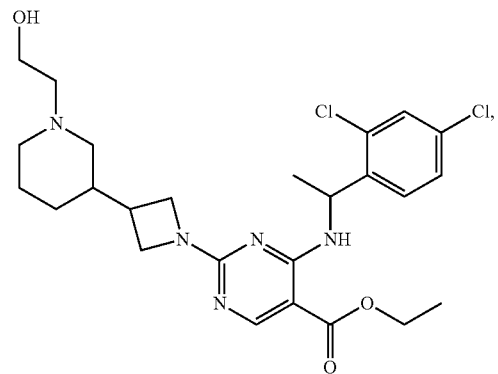
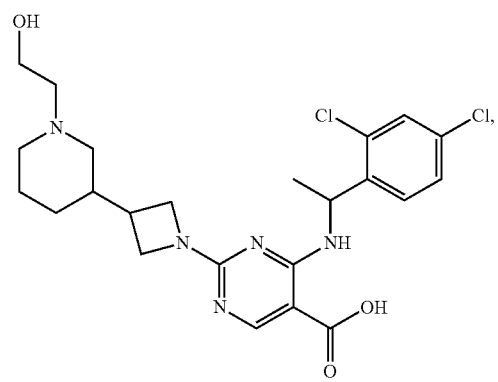
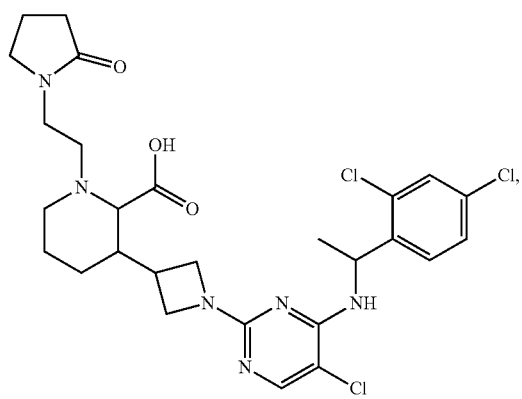
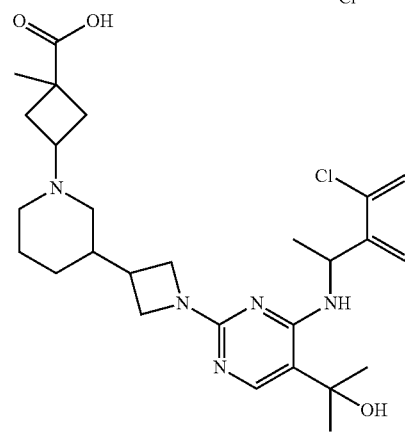
268
-continued
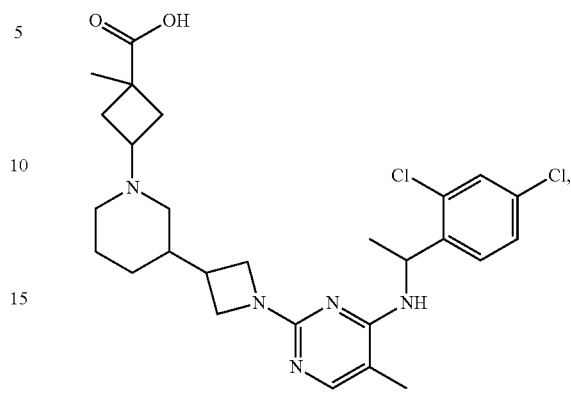
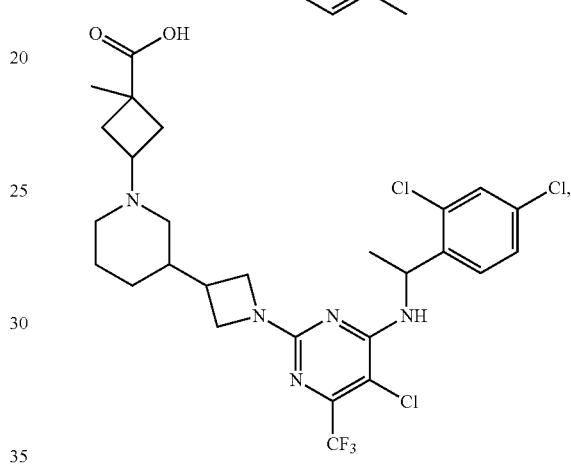

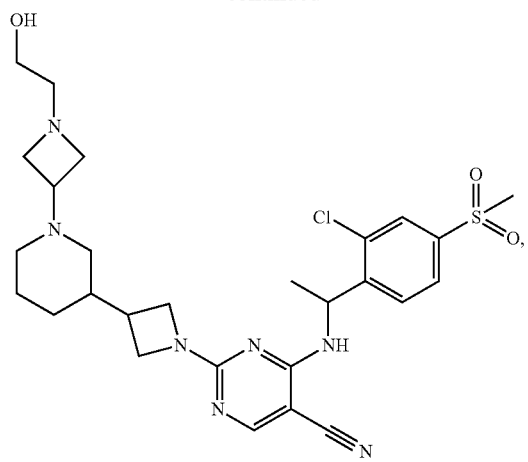
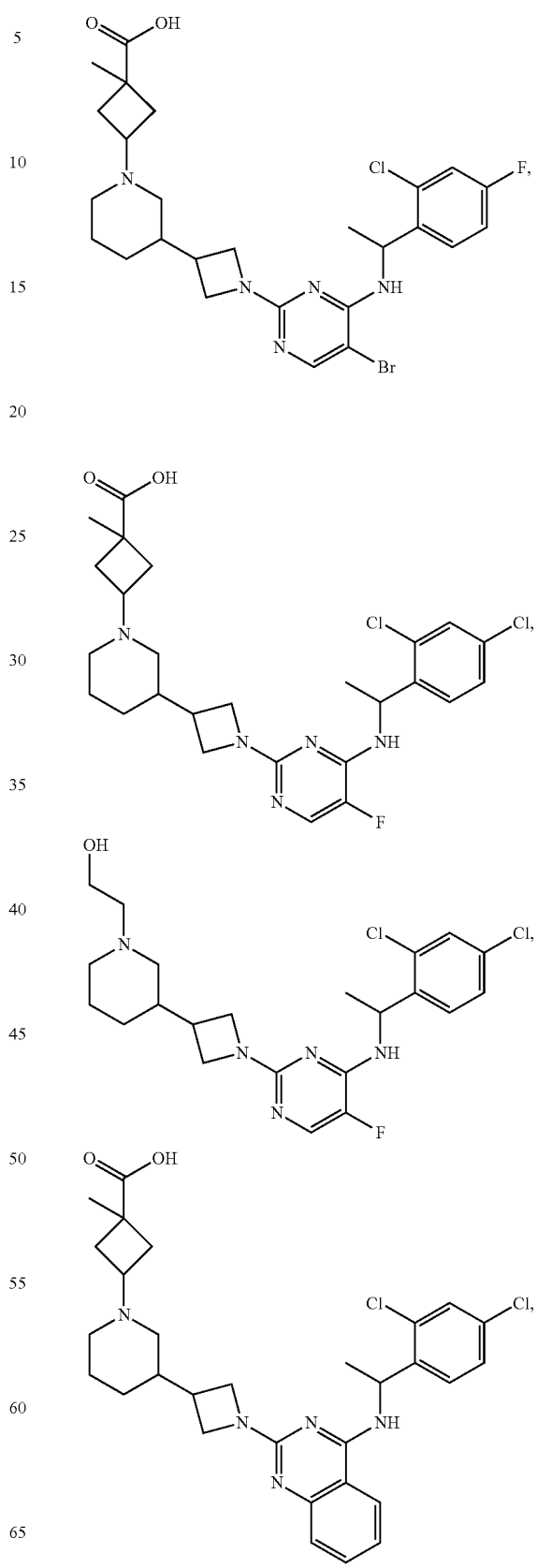

-continued

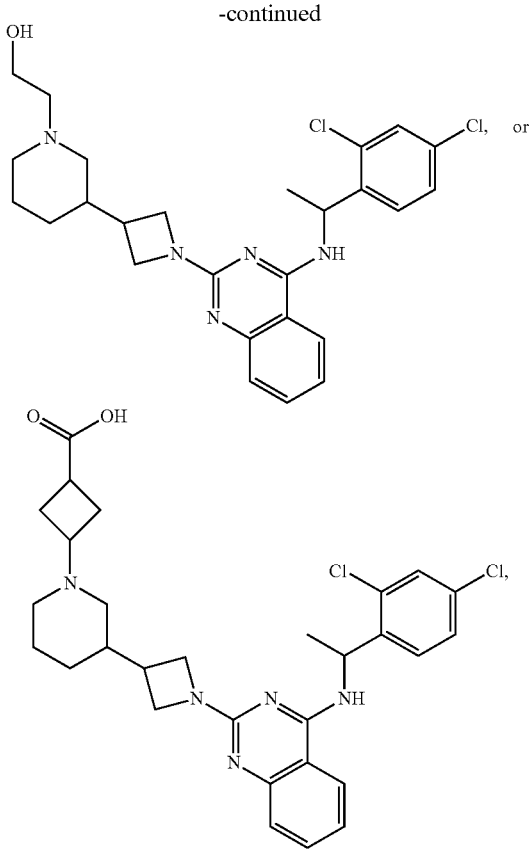

or a pharmaceutically acceptable salt thereof.

Embodiment 9

A method of treating a malignancy that is positive for Epstein Barr Virus (EBV), the method comprising administering to a subject in need thereof a therapeutically effective amount of a compound of formula (V):

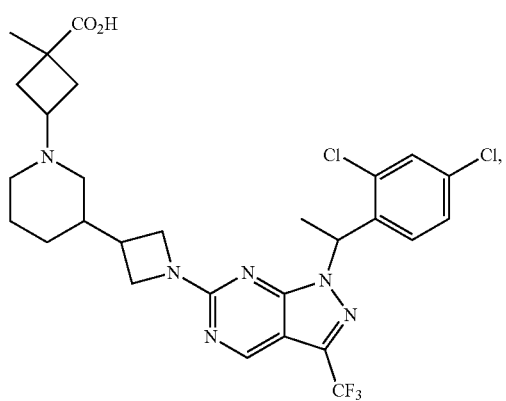

(V)

or a pharmaceutically acceptable salt thereof.

Embodiment 10

The method of any one of embodiments 1 to 9, wherein the EBV positive malignancy is Burkitt's lymphoma, Hodgkin's lymphoma, diffuse large B-cell lymphoma, NK/T-cell lymphoma, cutaneous T-cell lymphoma, nasopharyngeal carcinoma, gastric cancer, vulvar squamous cell carcinoma, salivary gland cancer, orbit choroidal melanoma, or adenocarcinoma consistent with pancreaticobiliary.

Embodiment 11

The method of embodiment 10, further comprising co-administering to a subject in need thereof a chemotherapeutic agent or anticancer agent.

Embodiment 12

The method of embodiment 11, wherein the chemotherapeutic agent or anticancer agent is an antiproliferative/antineoplastic drug, an antimetabolite, an antitumor antibiotic, an antimitotic agent, a topoisomerase inhibitor, a cytostatic agent, an estrogen receptor down regulator, an antiandrogen, a LHRH antagonist or LHRH agonist, a progestogen, an aromatase inhibitor, an inhibitor of 5-alpha-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an antisense therapy agent, an anti-ras antisense agent, an gene therapy agent, an immunotherapeutic agent, or an antibody.

Embodiment 13

The method of embodiment 12, wherein the chemotherapeutic agent or anticancer agent is an anti-proliferative agent, a chemotherapeutic agent, an antimetabolite, an anti-microtubule agent, an alkylating agent, a platinum agent, an anthracycline, an antitumor antibiotic, a topoisomerase inhibitor, a purine antagonist, a pyrimidine antagonist, a cell maturing agent, a DNA repair enzyme inhibitor, an enzyme that prevents cell survival, a histone deacetylase inhibitor, a cytotoxic agent, a hormone, an antibody, an immuno-modulator, a Bcr-Abl kinase inhibitor, a hormone agonist or antagonist, partial agonist or partial antagonist, a kinase inhibitor, surgery, radiotherapy, an endocrine therapy, a biological response modifier, a hyperthermial agent, a cryotherapeutic agent, an immuomodulating agent, an agent to attenuate any adverse effects, a spindle poison, a podophyllotoxin, an antibiotic, or a nitrosourea.

Embodiment 14

The method of embodiment 13, wherein the antimetabolite is 5-fluoro uracil, methotrexate, azacitidine, decitabine, fludarabine or cytarabine.

Embodiment 15

The method of embodiment 13, wherein the antimicrotubule agent is a vinca alkaloid or a taxane.

Embodiment 16

The method of embodiment 13, wherein the alkylating agent is mechlorethamine, chlorambucil, cyclophosphamide, melphalan, carmustine, lomustine, ifosfamide, carmustine, busulfan, cyclophosphamide, dacarbazine, ifosfamide, bischloroethylnitrosurea or hydroxyurea.

Embodiment 17

The method of embodiment 13, wherein the platinum agent is cisplatin, carboplatin, oxaliplatin, satraplatin (JM-216) or CI-973.

Embodiment 18

The method of embodiment 12, wherein the chemotherapeutic agent or anticancer agent is an antibody.

Embodiment 19

The method of embodiment 12, wherein the chemotherapeutic agent or anticancer agent is an immunomodulating agent.

Embodiment 20

Use of the compound of any one of embodiments 1 to 9 to treat a malignancy that is positive for Epstein Barr Virus (EBV).

Embodiment 21

Use of the compound of any one of embodiments 1 to 9 in the manufacture of a medicament to treat a malignancy that is positive for Epstein Barr Virus (EBV).

Embodiment 22

A method of treating a malignancy that is positive for Epstein Barr Virus (EBV), the method comprising administering to a subject in need thereof a therapeutically effective amount of a C—C chemokine receptor type 4 (CCR4) modulator.

Embodiment 23

The method of embodiment 22, wherein the CCR4 modulator is a compound disclosed in Hobbs et al, US 2012/0015932; Cheshire et al, US 2010/0144759; Cheshire et al, US 2008/0293742; Cheshire US 2006/0189613; Mete et al, US 2006/0128723; Harrison et al, US 2006/0122195; Habashita et al, US 2006/0004010; Collins et al, US 2004/0039035; Collins et al, US 2003/0018022; Collins et al, US 2002/0173524; Dairaghi et al, US 2002/0132836; U.S. Pat. Nos. 5,300,498; 6,509,357; US 2003/149018; WO 01/005758; WO 03/051876; WO 97/042174; WO 2006/101456; WO 2007/065683; WO 2007/065924; WO 2007/115231; WO 2008/045529; WO 2008/094575; WO 2008/094602; WO 2010/118367; and WO 2013/082429.

Embodiment 24

The method of embodiment 22, wherein the CCR4 modulator is an antibody.

Embodiment 25

The method of embodiment 24, wherein the CCR4 modulating antibody is one disclosed in Marasco et al. US 2017/0290911; Lin et al. US 2017/0088627; Marasco et al. US 2016/0185865; Ishii et al. US 2015/0147321; Shitara et al. US 2013/0295045; Wu et al. US 2007/0031896; Shitara et al. US 2007/0020263; and Iida et al. US 2005/0287138.

INCORPORATION BY REFERENCE

All disclosures (e.g., patents, publications, and web pages) referenced throughout this specification are incorporated by reference in their entireties.

The present disclosure has been described in connection with certain embodiments and examples; however, unless otherwise indicated, the claims should not be unduly limited to such specific embodiments and examples disclosed.

What is claimed is:

1. A method of treating a malignancy that is positive for Epstein Barr Virus (EBV), the method comprising administering to a subject in need thereof a therapeutically effective amount of a compound of formula (I):

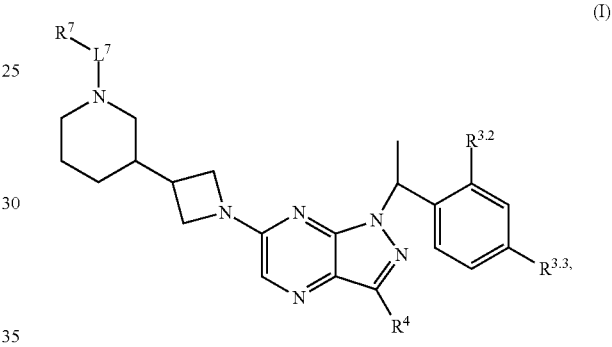

or a pharmaceutically acceptable salt thereof, wherein:
  $L^7$ is a bond, unsubstituted alkylene or unsubstituted heteroalkylene;
  $R^{3.2}$ and $R^{3.3}$ are independently halogen;
  $R^4$ is $-CX^{4.1}{}_3$, $-CN$, or unsubstituted $C_1$-$C_4$ alkyl;
  $R^7$ is hydrogen, $-C(O)R^{7D}$, $-C(O)NR^{7B}R^{7C}$, $OR^{7A}$, $-NR^{7B}C(O)R^{7D}$, substituted or unsubstituted alkyl or substituted or unsubstituted heteroalkyl;
  $R^{7A}$, $R^{7B}$, $R^{7C}$, and $R^{7D}$ are independently hydrogen or substituted or unsubstituted alkyl; and
  $X^{4.1}$ is $-Cl$, $-Br$, $-I$ or $-F$.

2. The method of claim 1, wherein the compound is:

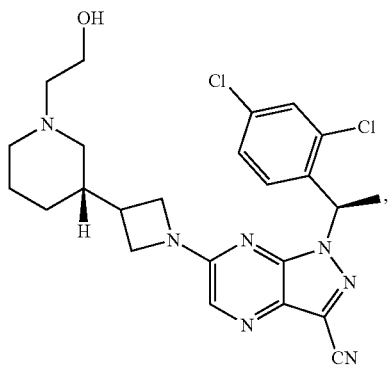

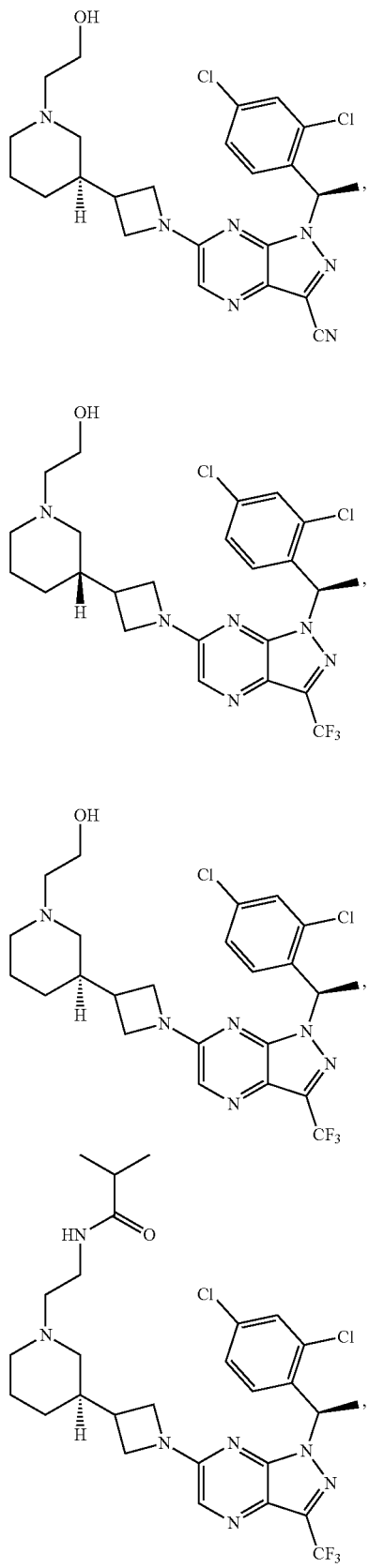
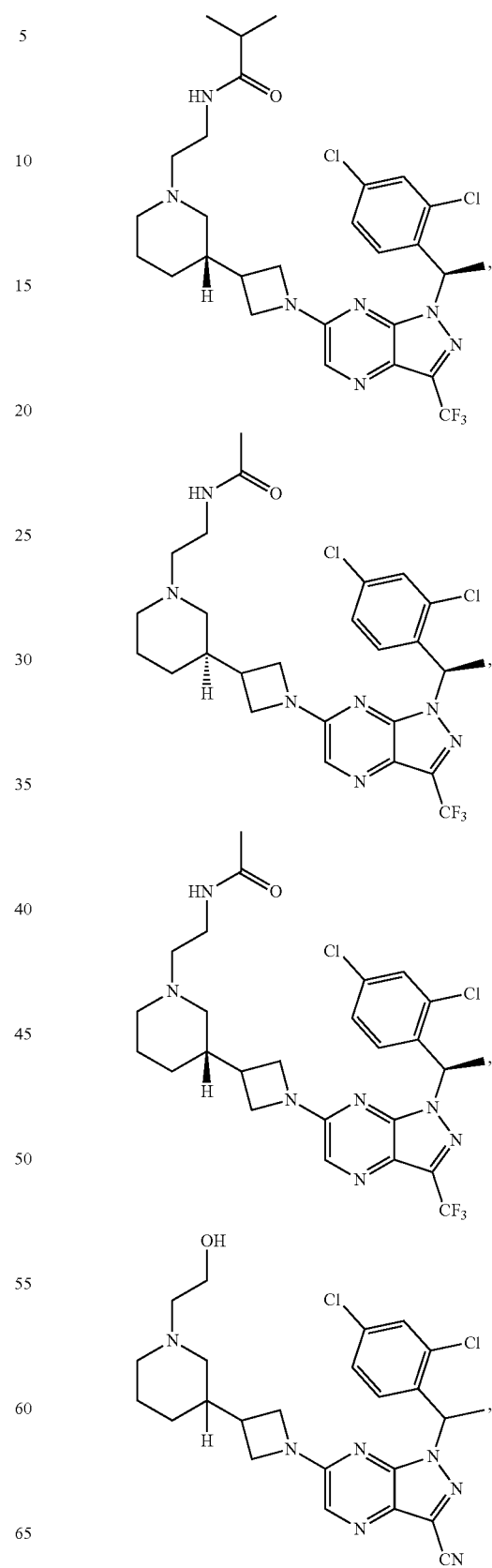

-continued

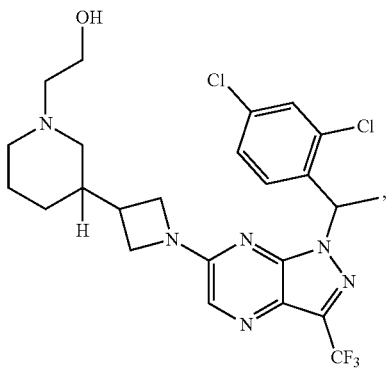

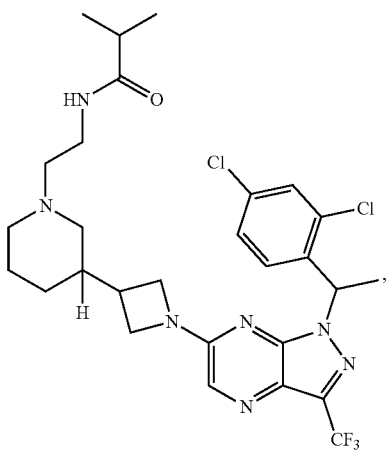

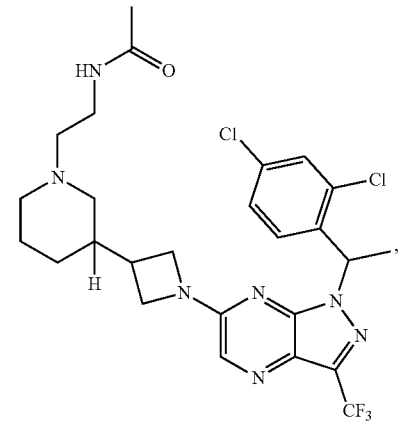

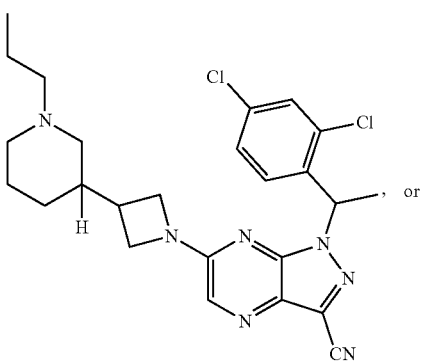

-continued

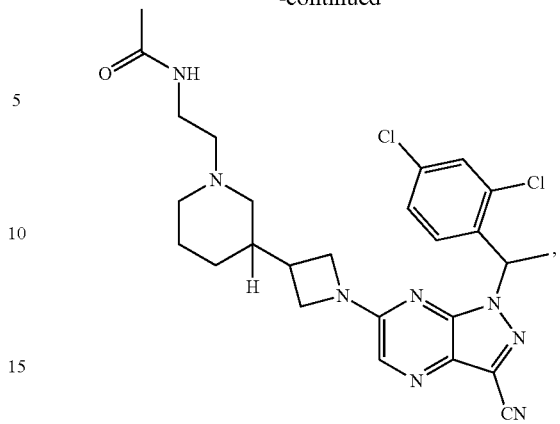

or a pharmaceutically acceptable salt thereof.

3. The method of claim 1, wherein the EBV positive malignancy is Burkitt's lymphoma, Hodgkin's lymphoma, diffuse large B-cell lymphoma, NK/T-cell lymphoma, cutaneous T-cell lymphoma, nasopharyngeal carcinoma, gastric cancer, vulvar squamous cell carcinoma, salivary gland cancer, orbit choroidal melanoma, or adenocarcinoma consistent with pancreaticobiliary.

4. The method of claim 3, further comprising co-administering to a subject in need thereof a chemotherapeutic agent or anticancer agent.

5. The method of claim 4, wherein the chemotherapeutic agent or anticancer agent is an antiproliferative/antineoplastic drug, an antimetabolite, an antitumor antibiotic, an antimitotic agent, a topoisomerase inhibitor, a cytostatic agent, an estrogen receptor down regulator, an antiandrogen, a LHRH antagonist or LHRH agonist, a progestogen, an aromatase inhibitor, an inhibitor of 5-alpha-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an antisense therapy agent, an anti-ras antisense agent, an gene therapy agent, an immunotherapeutic agent, or an antibody.

6. The method of claim 5, wherein the chemotherapeutic agent or anticancer agent is an anti-proliferative agent, a chemotherapeutic agent, an antimetabolite, an antimicrotubule agent, an alkylating agent, a platinum agent, an anthracycline, an antitumor antibiotic, a topoisomerase inhibitor, a purine antagonist, a pyrimidine antagonist, a cell maturing agent, a DNA repair enzyme inhibitor, an enzyme that prevents cell survival, a histone deacetylase inhibitor, a cytotoxic agent, a hormone, an antibody, an immuno-modulator, a Bcr-Abl kinase inhibitor, a hormone agonist or antagonist, partial agonist or partial antagonist, a kinase inhibitor, surgery, radiotherapy, an endocrine therapy, a biological response modifier, a hyperthermial agent, a cryotherapeutic agent, an immuomodulating agent, an agent to attenuate any adverse effects, a spindle poison, a podophyllotoxin, an antibiotic, or a nitrosourea.

7. The method of claim 6, wherein the antimetabolite is 5-fluoro uracil, methotrexate, azacitidine, decitabine, fludarabine or cytarabine.

8. The method of claim 6, wherein the antimicrotubule agent is a vinca alkaloid or a taxane.

9. The method of claim 6, wherein the alkylating agent is mechlorethamine, chlorambucil, cyclophosphamide, melphalan, carmustine, lomustine, ifosfamide, busulfan, dacarbazine, bischloroethylnitrosurea or hydroxyurea.

10. The method of claim 6, wherein the platinum agent is cisplatin, carboplatin, oxaliplatin, satraplatin (JM-216) or CI-973.

11. The method of claim 5, wherein the chemotherapeutic agent or anticancer agent is an antibody.

12. The method of claim 5, wherein the chemotherapeutic agent or anticancer agent is an immunomodulating agent.

13. Use of the compound of claim 1 to treat a malignancy that is positive for Epstein Barr Virus (EBV), wherein the use comprises administering to a subject in need thereof a therapeutically effective amount of the compound of formula (I).

14. The method of claim 1, wherein $R^4$ is $-CX^{4.1}_3$, $-CN$, or methyl.

15. The method of claim 5, wherein the chemotherapeutic agent is pembrolizumab.

* * * * *